US009611287B2

(12) United States Patent
Myers et al.

(10) Patent No.: US 9,611,287 B2
(45) Date of Patent: Apr. 4, 2017

(54) TRIOXACARCINS AND USES THEREOF

(71) Applicant: President and Fellows of Harvard College, Cambridge, MA (US)

(72) Inventors: Andrew G. Myers, Boston, MA (US); Nicholas E. Hill, Arlington, VA (US); Jakub Svenda, Cambridge, MA (US); Robert T. Yu, Somerville, MA (US); Daniel J. Smaltz, Cambridge, MA (US); Thomas Magauer, Steyr (AT)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/811,559

(22) Filed: Jul. 28, 2015

(65) Prior Publication Data

US 2016/0355537 A1    Dec. 8, 2016

Related U.S. Application Data

(63) Continuation of application No. 13/636,263, filed as application No. PCT/US2011/029343 on Mar. 22, 2011, now Pat. No. 9,102,697.

(60) Provisional application No. 61/316,139, filed on Mar. 22, 2010.

(51) Int. Cl.
| C07H 17/04 | (2006.01) |
| C07H 15/24 | (2006.01) |
| C07H 15/26 | (2006.01) |
| C07D 493/22 | (2006.01) |

(52) U.S. Cl.
CPC .......... C07H 17/04 (2013.01); C07D 493/22 (2013.01); C07H 15/24 (2013.01); C07H 15/26 (2013.01)

(58) Field of Classification Search
None
See application file for complete search history.

(56) References Cited

U.S. PATENT DOCUMENTS

| 4,270,537 A | 6/1981 | Romaine |
| 4,355,023 A | 10/1982 | Ehrlich et al. |
| 4,459,291 A | 7/1984 | Shirahata et al. |
| 4,470,925 A | 9/1984 | Auditore-Hargreaves |
| 4,511,560 A | 4/1985 | Tomita et al. |
| 4,596,556 A | 6/1986 | Morrow et al. |
| 4,626,503 A | 12/1986 | Lee et al. |
| 4,790,824 A | 12/1988 | Morrow et al. |
| 4,816,567 A | 3/1989 | Cabilly et al. |
| 4,886,499 A | 12/1989 | Cirelli et al. |
| 4,940,460 A | 7/1990 | Casey, I. et al. |
| 4,941,880 A | 7/1990 | Burns |
| 4,946,778 A | 8/1990 | Ladner et al. |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,202,238 A | 4/1993 | Fell et al. |
| 5,204,244 A | 4/1993 | Fell et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,399,163 A | 3/1995 | Peterson et al. |
| 5,417,662 A | 5/1995 | Hjertman et al. |
| 5,466,220 A | 11/1995 | Brenneman |
| 5,480,381 A | 1/1996 | Weston |

(Continued)

FOREIGN PATENT DOCUMENTS

| JP | 58-065293 A | 4/1983 |
| JP | 63-135389 A | 6/1988 |

(Continued)

OTHER PUBLICATIONS

International Search Report and Written Opinion for PCT/US2011/029343, mailed Jul. 22, 2011.
International Preliminary Report on Patentability for PCT/US2011/029343, mailed Oct. 4, 2012.
International Search Report and Written Opinion for PCT/US2013/071924, mailed Feb. 6, 2014.
International Preliminary Report on Patentability for PCT/US2013/071924, mailed Jun. 4, 2015.
Anelli et al., Fast and selective oxidation of primary alcohols to aldehydes or to carboxylic acids and of secondary alcohols to ketones mediated by oxoammonium salts under two-phase conditions. J Org Chem. 1987;52(12):2559-2562.

(Continued)

Primary Examiner — Traviss C McIntosh, III
(74) Attorney, Agent, or Firm — Wolf, Greenfield & Sacks, P.C.

(57) ABSTRACT

The present invention relates to trioxacarcin compounds of the formula:

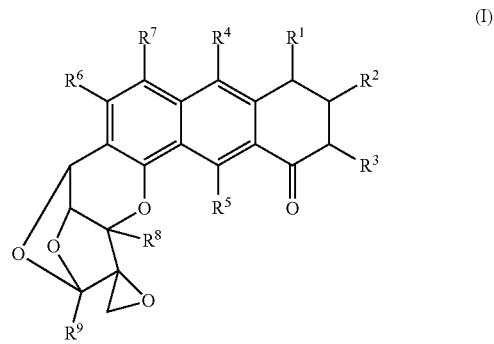

or pharmaceutically acceptable forms thereof; wherein $R^1$, $R^2$, $R^3$, $R^4$, $R^5$, $R^6$, $R^7$, $R^8$, and $R^9$ are as defined herein. The present invention also provides processes for preparing such compounds and intermediates thereto; pharmaceutical compositions comprising such compounds; and methods of use and treatment.

20 Claims, 19 Drawing Sheets

(56) References Cited

U.S. PATENT DOCUMENTS

| | | | |
|---|---|---|---|
| 5,503,627 | A | 4/1996 | McKinnon et al. |
| 5,520,639 | A | 5/1996 | Peterson et al. |
| 5,527,288 | A | 6/1996 | Gross et al. |
| 5,565,354 | A | 10/1996 | Ostberg |
| 5,567,610 | A | 10/1996 | Borrebaeck et al. |
| 5,569,189 | A | 10/1996 | Parsons |
| 5,569,825 | A | 10/1996 | Lonberg et al. |
| 5,599,302 | A | 2/1997 | Lilley et al. |
| 5,649,912 | A | 7/1997 | Peterson |
| 5,704,911 | A | 1/1998 | Parsons |
| 5,893,397 | A | 4/1999 | Peterson et al. |
| 5,993,412 | A | 11/1999 | Deily et al. |
| 9,102,697 | B2 * | 8/2015 | Myers ............... C07H 17/04 |
| 2011/0165155 | A1 | 7/2011 | Agresta et al. |
| 2013/0150314 | A1 | 6/2013 | Myers et al. |
| 2015/0297747 | A1 | 10/2015 | Myers et al. |

FOREIGN PATENT DOCUMENTS

| | | |
|---|---|---|
| JP | 63-135390 A | 6/1988 |
| JP | 63-135391 A | 6/1988 |
| WO | WO 97/13537 A1 | 4/1997 |
| WO | WO 97/37705 A1 | 10/1997 |
| WO | WO 99/34850 A1 | 7/1999 |
| WO | WO 2005/080549 A2 | 9/2005 |
| WO | WO 2011/119549 A1 | 9/2011 |

OTHER PUBLICATIONS

Boeckman et al., Catechol Boron Halides: Mild and Selective Reagents for Cleavage of Common Protecting Groups. Tetrahedron Lett. 1985;26:1411-14.

Bondar et al., Pectenotoxin-2 synthetic studies. 2. Construction and conjoining of ABC and DE Eastern hemisphere subtargets. Org Lett. Apr. 28, 2005;7(9):1813-6.

Brubaker et al., A practical, enantioselective synthetic route to a key precursor to the tetracycline antibiotics. Org Lett. Aug. 30, 2007;9(18):3523-5. Epub Aug. 11, 2007.

Brzezinski et al., The Asymmetric Baylis—Hillman Reaction. J Am Chem Soc. 1997;119(18):4317-4318.

Cassidy et al., Phase I clinical study of LL-D49194 alpha 1 with retrospective pharmacokinetic investigations in mice and humans. The EORTC ECTG. Cancer Chemother Pharmacol. 1993;31(5):395-400.

Collum et al., Synthesis of the polyether antibiotic monensin. 2. Preparation of intermediates. J Am Chem Soc. 1980;102(6):2118-2120.

Dimond, Antibody-Drug Conjugates Stage a Comeback. GEN Genetic Engineering & Biotechnology News. Mar 10, 2010. 3 pages. Accessed at http://www.genengnews.com/insight-and-intelligenceand153/antibody-drug-conjugates-stage-a-comeback/77899350.

Drewes et al., Facile Diastereoselective Synthesis of 2,6-Dialkyl-5-methylene-1,3-dioxan-4-ones via α-Activated Vinyl Esters. Chem Ber. 1990;123:1447-48.

Ducry et al., Antibody-drug conjugates: linking cytotoxic payloads to monoclonal antibodies. Bioconjug Chem. Jan. 2010;21(1):5-13. doi: 10.1021/bc9002019.

Fitzner et al., Formation of gutingimycin: analytical investigation of trioxacarcin A-mediated alkylation of dsDNA. Anal Bioanal Chem. Feb. 2008;390(4):1139-47. Epub Jan. 22, 2008.

Fujimoto et al., Antitumor activity of trioxacarcin C. J Antibiot (Tokyo). Sep. 1983;36(9):1216-21.

Garegg et al., Synthesis of Methyl 2,6-Dideoxy-3-C-methyl-α-L-xylo-hexopyranoside ("Methyl-α-Axenoside"). Acta Chemica Scandinavica B. 1975;29:507-12.

Hill et al., Anhydrous tert-butyl hydroperoxide in toluene: the preferred reagent for applications requiring dry TBHP. J Org Chem. 1983;48(20):3607-3608.

Kato et al., Fluorescence study on the nyctinasty of *Phyllanthus urinaria* L. using novel-fluorescence-labeled probe compounds. Tetrahedron. 2006;62:7307-18.

Kovtun et al., Antibody-drug conjugates designed to eradicate tumors with homogeneous and heterogeneous expression of the target antigen. Cancer Res. Mar. 15, 2006;66(6):3214-21.

Kovtun et al., Cell killing by antibody-drug conjugates. Cancer Lett. Oct. 8, 2007;255(2):232-40. Epub Jun. 5, 2007.

Kraus et al., An Annelation Route to Quinones. Tetrahedron Lett. 1978;19(26):2263-66.

Le Pecq et al., A new fluorometric method for RNA and DNA determination. Anal Biochem. Oct. 1966;17(1):100-7.

Lim et al., A method for the preparation of differentiated trans-1,2-diol derivatives with enantio- and diastereocontrol. J Am Chem Soc. Apr. 29, 2009;131(16):5763-5.

Magauer et al., Component-based syntheses of trioxacarcin A, DC-45-A1 and structural analogues. Nat Chem. Oct. 2013;5(10):886-93.

Maiese et al., LL-D49194 antibiotics, a novel family of antitumor agents: taxonomy, fermentation and biological properties. J Antibiot (Tokyo). Mar. 1990;43(3):253-8.

Marshall et al., Synthesis of Protected Carbohydrate Derivatives Through Homologation of Threose and Erythrose Derivatives with Chiral .gamma.-Alkoxy Allylic Stannanes. J Org Chem. 1994;59(12):3413-3420.

Maskey et al., Anti-cancer and antibacterial trioxacarcins with high anti-malaria activity from a marine Streptomycete and their absolute stereochemistry. J Antibiot (Tokyo). Dec. 2004;57(12):771-9.

Maskey et al.. Gutingimycin: a highly complex metabolite from a marine streptomycete. Angew Chem Int Ed Engl. Feb. 27, 2004;43(10):1281-3.

Mattes et al., Mechanism of DNA strand breakage by piperidine at sites of N7-alkylguanines. Biochim Biophys Acta. Oct. 16, 1986;868(1):71-6.

Oppolzer et al., Enantioselective Addition of (Z)- and (E)-Alkenylzinc Bromides to Aldehydes: Asymmetric Synthesis of Sec-Allylalcohols. Tetrahedron Lett. 1991;32:5777-80.

Pangborn et al., Safe and Convenient Procedure for Solvent Purification. Organometallics. 1996;15(5):1518-1520.

Pfoh et al., Crystal structure of trioxacarcin A covalently bound to DNA. Nucleic Acids Res. Jun. 2008;36(10):3508-14. Epub May 3, 2008.

Pröpper et al., Crystalline guanine adducts of natural and synthetic trioxacarcins suggest a common biological mechanism and reveal a basis for the instability of trioxacarcin A. Bioorg Med Chem Lett. Sep. 15, 2014;24(18):4410-3. doi: 10.1016/j.bmcl.2014.08.016.

Schinzer et al., Syntheses of (−)-Epothilone B. J Chem—Euro J. 1999;5:2492-500.

Sharpless et al., Metal-Catalyzed, Highly Selective Oxygenations of Olefins and Acetylenes with tert-Butyl Hydroperoxide. Practical Considerations and Mechanisms. Aldrichimica Acta. 1979;12:63-74.

Smaltz et al., Diastereoselective additions of allylmetal reagents to free and protected syn-α,β-dihydroxyketones enable efficient synthetic routes to methyl trioxacarcinoside A. Org Lett. Apr. 6, 2012;14(7):1812-5. Epub Mar. 9, 2012.

Still et al., Rapid chromatographic technique for preparative separations with moderate resolution. J Org Chem. 1978;43(14):2923-2925.

Suami et al., Synthesis of Methyl α-Trioxacarcinoside B. Chem Lett. 1982:1245-48.

Suami et al., Synthetic Studies on Methyl α-Trioxacarcinoside B. Bull Chem Soc Jpn. 1983;56:1431-34.

Švenda et al., A multiply convergent platform for the synthesis of trioxacarcins. Proc Natl Acad Sci U S A. Apr. 26, 2011;108(17):6709-14. Epub Jan. 18, 2011.

Svenda et al., Anti-selective epoxidation of methyl alpha-methylene-beta-tert-butyldimethylsilyloxycarboxylate esters. Evidence for stereospecific oxygen atom transfer in a nucleophilic epoxidation process. Org Lett. Jun. 4, 2009;11(11):2437-40.

Tamaoki et al., Trioxacarcins, novel antitumor antibiotics. II. Isolation, physico-chemical properties and mode of action. J Antibiot (Tokyo). Dec. 1981;34(12):1525-30.

Teicher et al., Antibody conjugate therapeutics: challenges and potential. Clin Cancer Res. Oct. 15, 2011;17(20):6389-97. doi: 10.1158/1078-0432.CCR-11-1417.

(56) References Cited

OTHER PUBLICATIONS

Tomita et al., Trioxacarcins, Novel Antitumor Antibiotics. I. Producing Organism, Fermentation and Biological Activities. J Antibiotics. 1981;34(12):1520-24.
Wahl et al., Improved radioimaging and tumor localization with monoclonal F(ab')2. J Nucl Med. Apr. 1983;24(4):316-25.
Williams et al., A New General Method of Preparation of N-Methoxy-N-Methylamides. Applications in Direct Conversion of an Ester to a Ketone. Tetrahedron. 1995;36:5461-64.
Yu et al., Improved procedure for the oxidative cleavage of olefins by OsO4-NaIO4. Org Lett. Sep. 16, 2004;6(19):3217-9.
U.S. Appl. No. 13/636,263, filed Jan. 17, 2013, Andrew G. Myers.
U.S. Appl. No. 14/647,198, filed May 26, 2015, Andrew G. Myers.
PCT/US2011/029343, Jul. 22, 2011, International Search Report and Written Opinion.
PCT/US2011/029343, Oct. 4, 2012, International Preliminary Report on Patentability.
PCT/US2013/071924, Feb. 6, 2014, International Search Report and Written Opinion.
PCT/US2013/071924, Jun. 4, 2015, International Preliminary Report on Patentability.

\* cited by examiner

Trioxacarcin scaffold

Dideoxy trioxacarcin scaffold

Synthetically Viable Variants of the Aldehyde Coupling Partner

DNA oligo = ds(AATTACGTAATT) (SEQ ID 1)

Buffer = 10 mM $Na_2NPO_4/NaH_2PO_4$, 100 mmol NaCl

Aglycone = DC-45-A2
Dia. Aglycone = iso-DC-45-A2

SEQUENCE LISTING

<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: Synthetic Polynucleotide

<400> SEQUENCE: 1
aattacgtaa tt                                                          12

TRIOXACARCINS AND USES THEREOF

RELATED APPLICATIONS

This application is a continuation of and claims priority under 35 U.S.C. §120 to U.S. patent application U.S. Ser. No. 13/636,263, filed Jan. 17, 2013, now U.S. Pat. No. 9,102,697, which is a national stage filing under 35 U.S.C. §371 of international PCT application, PCT/US2011/029343, filed Mar. 22, 2011, which claims priority under 35 U.S.C. §119(e) to U.S. provisional application, U.S. Ser. No. 61/316,139, filed Mar. 22, 2010, each of which is incorporated herein by reference.

GOVERNMENT SUPPORT

This invention was made with U.S. government support under CA047148 and GM007598 awarded by the National Institutes of Health and under CHE-0749566 awarded by the National Science Foundation. The U.S. government has certain rights in the invention.

BACKGROUND OF THE INVENTION

Natural products that bind and often covalently modify duplex DNA figure prominently in chemotherapy for human cancers. The trioxacarcins are a new class of DNA-modifying natural products with antiproliferative effects. The trioxacarcins were first described in 1981 by Tomita and coworkers (Tomita et al., *J. Antibiotics,* 34(12):1520-1524, 1981; Tamaoki et al., *J. Antibiotics* 34(12):1525-1530, 1981; Fujimoto et al., *J. Antibiotics* 36(9):1216-1221, 1983). Trioxacarcin A, B, and C were isolated by Tomita and coworkers from the culture broth of *Streptomyces bottropensis* DO-45 and shown to possess anti-tumor activity in murine models as well as gram-positive antibiotic activity. Subsequent work led to the discovery of other members of this family. Trioxacarcin A is a powerful anticancer agent with subnanmolar $IC_{70}$ values against lung (LXFL 529L, H-460), mammary (MCF-7), and CNS (SF-268) cancer cell lines. The trioxacarcins have also been shown to have antimicrobial activity (e.g., anti-bacterial and anti-malarial activity) (see, e.g., Maskey et al., *J. Antibiotics* (2004) 57:771-779).

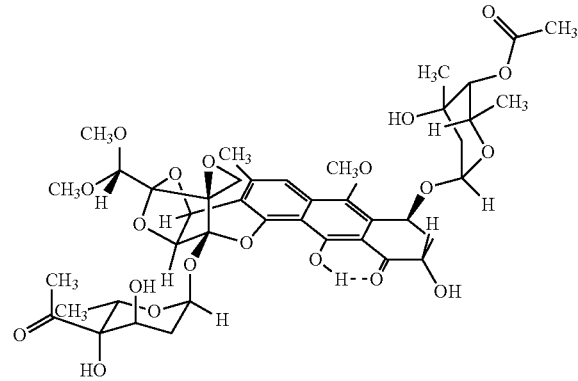

trioxacarcin A

An X-ray crystal structure of trioxacarcin A bound to N-7 of a guanidylate residue in a duplex DNA oligonucleotide substrate has provided compelling evidence for a proposed pathyway of DNA modification that proceeds by duplex intercalation and alkylation (Pfoh et al., *Nucleic Acids Research* 36(10):3508-3514, 2008).

All trioxacarcins appear to be derivatives of the aglycone, which is itself a bacterial isolate referred to in the patent literature as DC-45-$A_2$. U.S. Pat. No. 4,459,291, issued Jul. 10, 1984, describes the preparation of DC-45-$A_2$ by fermentation. DC-45-$A_2$ is the algycone of trioxacarcins A, B, and C and is prepared by the acid hydrolysis of the fermentation products trioxacarcins A and C or the direct isolation from the fermentation broth of *Streptomyces bottropensis*.

Based on the biological activity of the trioxacarcins, a fully synthetic route to these compounds would be useful in exploring the biological and chemical activity of known trioxacarcin compounds and intermediates thereto, as well as aid in the development of new trioxacarcin compounds with improved biological and/or chemical properties.

SUMMARY OF THE INVENTION

The present invention provides a fully synthetic route to trioxacarcins and analogues thereof. The provided synthesis provides the fully synthetic aglycone DC-45-$A_2$, which is differentially protected allowing for the selective glycosylation of the alcohol functionalities of the molecule. The synthesis of DC-45-$A_2$ is provided by an enantioselective, convergent approach. Three components of similar complexity are assembled at a late stage to generate the differentially protected aglycone. A late stage, complexity generating dipolar cycloaddition is used to create four of the seven stereogenic centers of the molecule. Removal of the orthogonal protecting groups furnishes DC-45-$A_2$. The inventive synthesis not only provides naturally occurring trioxacarcins but can also be used to prepare unnatural analogs with different glycosylation or other functionalities at the alcohol moieties. Being a total synthesis, it also provides for other analogs not previously accessable by semi-synthetic routes. For example, variants of the A, B, and/or C ring may be prepared by the inventive processes. Such compounds may have greater potency than natural trioxacarcins.

In one aspect, the present invention provides synthetic methology for preparing trioxacarcins and various analogs thereof. The inventive methology allows for the preparation of analogs of trioxacarcins that were previously not available from natural sources or semi-synthetic approaches.

In another aspect, the present invention provides novel trioxacarcin analogs. Compounds of the present invention, either novel trioxacarcins and/or intermediates thereto, may be useful in the treatment of proliferative diseases, diabetic retinopathy, inflammatory diseases, autoimmune diseases, or infectious diseases. These compounds may also be used as research tools to modify DNA.

For example, in one aspect, provided is a compound of the Formula (I):

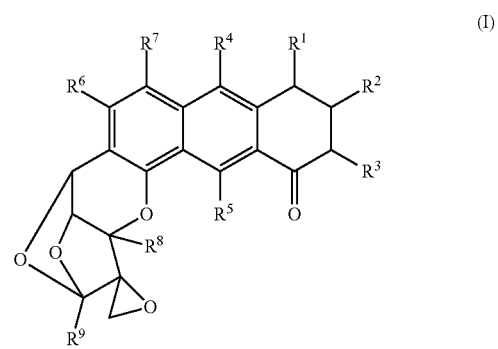

or a pharmaceutically acceptable form thereof; wherein $R^1$, $R^2$, $R^3$, $R^4$, $R^5$, $R^6$, $R^7$, $R^8$, and $R^9$ are as defined herein.

In certain embodiments, the compound is of the formula:

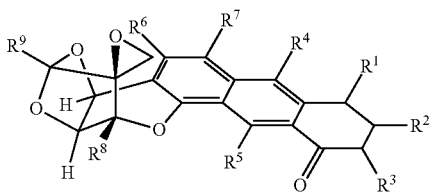

or a pharmaceutically acceptable form thereof.

In certain embodiments, the compound is of the formula:

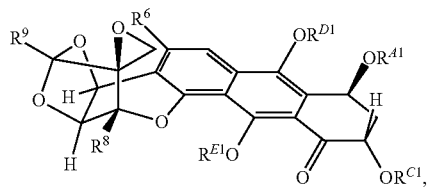

or a pharmaceutically acceptable form thereof.

In certain embodiments, the compound is of formula:

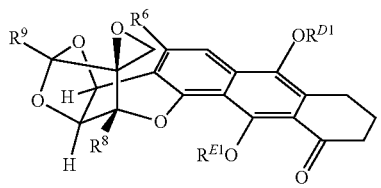

or a pharmaceutically acceptable form thereof.

In certain embodiments, the compound is of the formula:

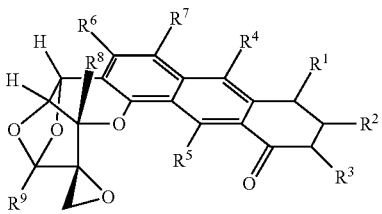

or a pharmaceutically acceptable form thereof.

In certain embodiments, $R^1$ is hydrogen. In certain embodiments, $R^1$ is —$OR^{A1}$ or —OH, wherein $R^{A1}$ is not hydrogen. In certain embodiments, $R^1$ is —$OR^{A1}$, wherein $R^{A1}$ is a carbohydrate. In certain embodiments, the carbohydrate is of the formula:

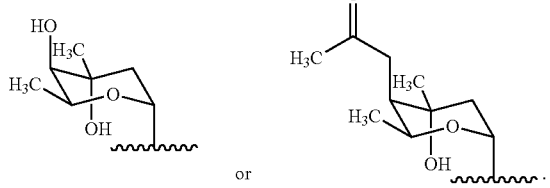

In certain embodiments, $R^2$ is hydrogen.

In certain embodiments, $R^3$ is hydrogen. In certain embodiments, $R^3$ is —$OR^{C1}$, wherein $R^{C1}$ is not hydrogen. In certain embodiments, $R^3$ is —OH. In certain embodiments, $R^3$ is —$OR^{C1}$, wherein $R^{C1}$ is a carbohydrate.

In certain embodiments, each of $R^1$, $R^2$, and $R^3$ are hydrogen.

In certain embodiments, $R^4$ is —OH or —$OR^{D1}$ wherein $R^{D1}$ is not hydrogen. In certain embodiments, $R^4$ is —$OR^{D1}$, wherein $R^{D1}$ is hydrogen or $C_{1-6}$ alkyl. In certain embodiments, $R^4$ is —$OCH_3$.

In certain embodiments, $R^5$ is —OH or —$OR^{E1}$, wherein $R^{E1}$ is not hydrogen. In certain embodiments, $R^5$ is —OH.

In certain embodiments, $R^6$ is $C_{1-6}$ alkyl. In certain embodiments, $R^6$ is —$CH_3$.

In certain embodiments, $R^7$ is hydrogen.

In certain embodiments, both $R^2$ and $R^7$ are hydrogen.

In certain embodiments, R is —OH. In certain embodiments, R is —$OR^{H1}$, wherein $R^{H1}$ is not hydrogen. In certain embodiments, $R^{H1}$ is $C_{1-6}$ alkyl. In certain embodiments, $R^{H1}$ is a carbohydrate. In certain embodiments, the carbohydrate is of the formula:

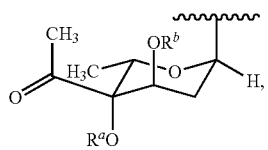

wherein $R^a$ and $R^b$ are independently selected from hydrogen; carbohydrate; an oxygen protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl.

In certain embodiments, $R^9$ is —$C(R^{J2})_3$. In certain embodiments, $R^9$ is —$CH(OR^{J3})_2$. In certain embodiments, the two —$OR^{J3}$ are the same. In certain embodiments, the two —$OR^{J3}$ are different. In certain embodiments, $R^9$ is —$CH(OR^{J3})_2$, wherein one —$OR^{J3}$ is —O—$C_{1-6}$ alkyl, and the other —$OR^{J3}$ is —O-carbohydrate. In certain embodiments, $R^9$ is —$CH(OR^{J3})_2$, wherein one —$OR^{J3}$ is —$OCH_3$, and the other —$OR^{J3}$ is —O-carbohydrate. In certain embodiments, $R^9$ is —$CH(OCH_3)_2$.

In another aspect, provided is a method of preparing a compound of Formula (I), the method comprising providing a cycloadduct of the formula:

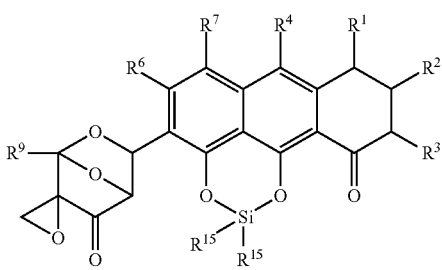

or salt thereof, wherein $R^{15}$ is as defined herein; and deprotecting the cycloadduct to provide a compound of the Formula (I), or a pharmaceutically acceptable form thereof, wherein $R^5$ and $R^8$ are —OH.

In certain embodiments, the cycloadduct is prepared by providing a silacycle of the formula:

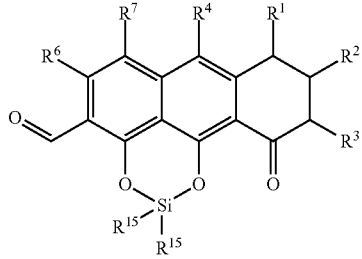

or salt thereof, and reacting the silacycle with a diazoketone of formula:

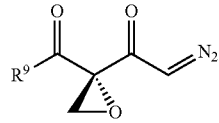

or salt thereof.

Alternatively, in certain embodiments, the cycloadduct is prepared by providing a silacycle of the formula:

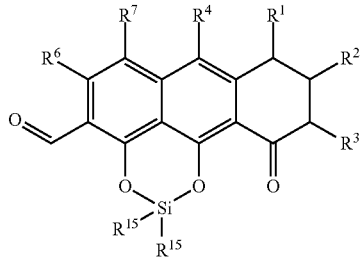

or salt thereof, and reacting the silacycle with a halohydrin ketone of formula:

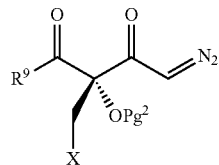

or salt thereof, wherein $Pg^2$ is hydrogen, alkyl, or an oxygen protecting group and X is a leaving group; to provide a compound of the formula:

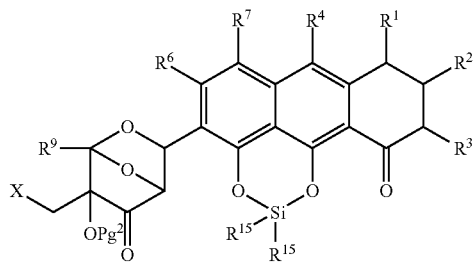

or salt thereof; optionally deprotecting $Pg^2$ when $Pg^2$ is alkyl or an oxygen protecting group; and cyclizing to form the cycloadduct or salt thereof.

In certain embodiments, the cycloadduct is any one of the formula:

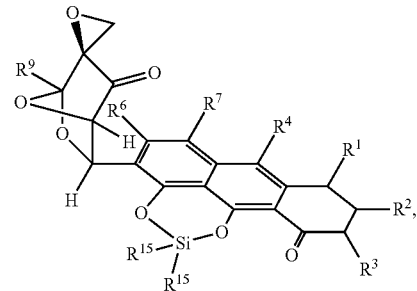

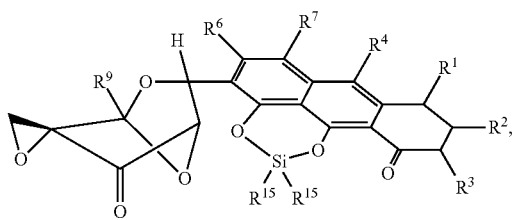

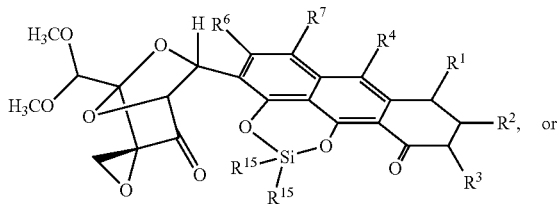

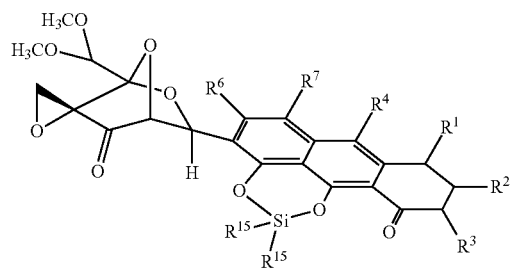

or salt thereof.

In certain embodiments, the silacycle is prepared by providing an aldehyde of the formula:

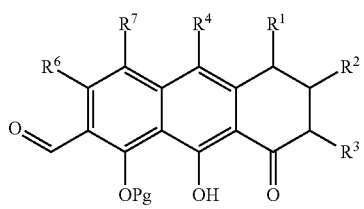

or salt thereof, wherein Pg is hydrogen, alkyl, or an oxygen-protecting group; deprotecting the aldehyde to provide a diol of the formula:

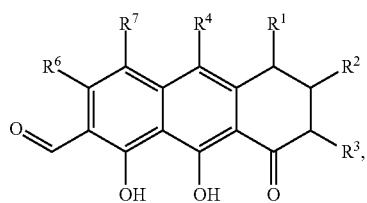

or salt thereof; and treating the diol with a silyl reagent of the formula $Si(R^{15})G_2$ wherein G is a leaving group.

In certain embodiments, the aldehyde is prepared by providing an anthrone of the formula:

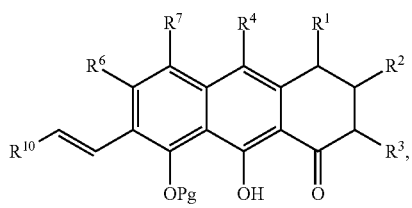

or salt thereof, wherein $R^{10}$ is defined herein; and oxidatively cleaving the alkenyl side chain of the anthrone to provide the aldehyde or salt thereof.

In certain embodiments, the anthrone is prepared by providing an enone of the formula:

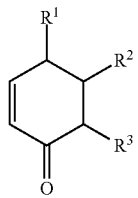

or salt thereof; and providing a cyanophthalide of formula:

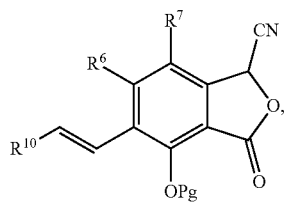

or salt thereof, and reacting the enone and the cyanophthalide together to provide the anthrone or salt thereof.

In certain embodiments, the invention provides compounds with modifications at $R^1$, $R^2$, and/or $R^3$ as compared to the natural products. For example, different carbohydrates, esters, ethers, etc. may be placed at these sites based on the synthetic approach described herein. As would be appreciated by one of skill in the art, other positions as identified in the generic structure above may also be modified based on the synthetic approach described herein.

In another aspect, the present invention provides a method of treating a disease, disorder or condition selected from the group consisting of proliferative diseases, diabetic retinopathy, inflammatory diseases, autoimmune diseases, and infectious diseases, comprising administering to a subject an effective amount of a compound of Formula (I) or pharmaceutically acceptable form thereof. In certain embodiments, the proliferative disease is a cancer. In certain embodiments, the infectious disease is a bacterial, fungal, or parasitic infection. In certain embodiments, the parasitic infection is malaria.

DEFINITIONS

Chemical Definitions

Definitions of specific functional groups ad chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Certain compounds of the present invention can comprise one or more asymmetric centers, and thus can exist in various isomeric forms, e.g., enantiomers and/or diastereomers. The compounds provided herein can be in the form of an individual enantiomer, diastereomer or geometric isomer, or can be in the form of a mixture of stereoisomers, including racemic mixtures and mixtures enriched in one or more stereoisomer. In certain embodiments, the compounds of the invention are enantiopure compounds. In certain other embodiments, mixtures of stereoisomers are provided.

Furthermore, certain compounds, as described herein may have one or more double bonds that can exist as either the cis or trans, or the E or Z isomer, unless otherwise indicated. The invention additionally encompasses the compounds as individual isomers substantially free of other isomers, and alternatively, as mixtures of various isomers, e.g., racemic mixtures of E/Z isomers or mixtures enriched in one E/Z isomer.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

The terms "enantiomerically enriched," "enantiomerically pure" and "non-racemic," as used interchangeably herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, more preferably at least 75% by weight, and even more preferably at least 80% by weight. In some embodiments, the enrichment can be much greater than 80% by weight, providing a "substantially enantiomerically enriched," "substantially enantiomerically pure" or a "substantially non-racemic" preparation, which refers to preparations of compositions which have at least 85% by weight of one enantiomer relative to other enantiomer, more preferably at least 90% by weight, and even more preferably at least 95% by weight. In preferred embodiments, the enantiomerically enriched composition has a higher potency with respect to therapeutic utility per unit mass than does the racemic mixture of that composition.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972).

"Independently selected": The term "independently selected" is used herein to indicate that the R groups can be identical or different.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_1$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic," as used herein, includes both saturated and unsaturated, straight chain (i.e., unbranched), branched, acyclic, cyclic, or polycyclic aliphatic hydrocarbons, containing 1-20 carbon atoms and which are optionally substituted with one or more functional groups. As will be appreciated by one of ordinary skill in the art, "aliphatic" is intended herein to include, but is not limited to, alkyl, alkenyl, alkynyl, and carbocycyl (e.g., cycloalkyl, cycloalkenyl, and cycloalkynyl) moieties. Thus, as used herein, the term "aliphatic" includes straight, branched and cyclic groups.

The term "heteroaliphatic," as used herein, refers to an aliphatic group, as defined herein, which further includes 1 or more (e.g., 1, 2, 3, or 4) heteroatoms (e.g., oxygen, sulfur, nitrogen, boron, silicon, phosphorus) in the parent chain. As will be appreciated by one of ordinary skill in the art, "heteroaliphatic" is intended herein to include, but is not limited to, heteroalkyl, heteroalkenyl, heteroalkynyl, and heterocyclyl moieties. Thus, as used herein, the term "heteroaliphatic" includes straight, branched and cyclic groups.

As used herein, alone or as part of another group, "alkyl" refers to a monoradical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Other alkyl groups include, but are not limited to, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$— cyclohexyl. Unless otherwise specified, each instance of an alkyl group is independently unsubstituted (an "unsubstituted alkyl") or substituted (a "substituted alkyl") with one or more substituents (e.g., 1, 2, 3, 4, or 5 substituents). In certain embodiments, the alkyl group is an unsubstituted $C_{1-10}$ alkyl (e.g., —$CH_3$). In certain embodiments, the alkyl group is a substituted $C_{1-10}$ alkyl.

The term "heteroalkyl," as used herein, refers to an alkyl group, as defined herein, which further includes 1 or more (e.g., 1, 2, 3, or 4) heteroatoms (e.g., oxygen, sulfur, nitrogen, boron, silicon, phosphorus) in the parent chain.

The term "haloalkyl" denotes an alkyl group, as defined above, having one, two, or three halogen atoms attached thereto and is exemplified by such groups as chloromethyl, bromoethyl, trifluoromethyl, and the like.

"Perhaloalkyl" as defined herein refers to an alkyl group having from 1 to 20 carbon atoms wherein all of the hydrogen atoms are each independently replaced halogen, e.g., selected from fluoro, bromo, chloro or iodo ("$C_{1-20}$ perhaloalkyl"). In some embodiments, the alkyl moiety has 1 to 10 carbon atoms ("$C_{1-10}$ perhaloalkyl"). In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are each replaced with fluoro. In some embodiments, all of the hydrogen atoms are each replaced with chloro. Examples of perhaloalkyl groups include —$CF_3$, —$CF_2CF_3$, —$CF_2CF_2CF_3$, —$CCl_3$, —$CFCl_2$, —$CF_2Cl$ and the like.

As used herein, alone or as part of another group, "alkenyl" refers to a monoradical of a straight-chain or branched hydrocarbon group having from 2 to 20 carbon atoms and one or more carbon-carbon double bonds ("$C_{2-20}$ alkenyl"). In some embodiments, an alkenyl group has 2 to 9 carbon atoms ("$C_{2-20}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$) and the like. Additional examples of alkenyl include heptenyl ($C_7$), octenyl ($C_8$), octatrienyl ($C_8$), and 1-methyl-2-buten-1-yl. Unless otherwise specified, each instance of an alkenyl group is independently unsubstituted (an "unsubstituted alkenyl") or substituted (a "substituted alkenyl") with one or more substituents (e.g., 1, 2, 3, 4, or 5 substituents). In certain embodiments, the alkenyl group is an unsubstituted $C_{2-10}$ alkenyl. In certain embodiments, the alkenyl group is a substituted $C_{2-10}$ alkenyl.

The term "heteroalkenyl," as used herein, refers to an alkenyl group, as defined herein, which further includes 1 or more (e.g., 1, 2, 3, or 4) heteroatoms (e.g., oxygen, sulfur, nitrogen, boron, silicon, phosphorus) in the parent chain.

As used herein, alone or as part of another group, "alkynyl" refers to a monoradical of a straight-chain or branched hydrocarbon group having from 2 to 20 carbon atoms and one or more carbon-carbon triple bonds ("$C_{2-20}$ alkynyl"). In some embodiments, an alkynyl group has 2 to 9 carbon atoms ("$C_{2-20}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atom ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$) and the like. Examples of $C_{2-6}$ alkenyl groups include the aforementioned $C_{2-4}$ alkynyl groups as well as pentynyl ($C_5$), hexynyl ($C_6$) and the like. Additional examples of alkynyl include heptynyl ($C_7$), octynyl ($C_8$) and the like. Unless otherwise specified, each instance of an alkynyl group is independently unsubstituted (an "unsubstituted alkynyl") or substituted (a "substituted alkynyl") with one or more substituents (e.g., 1, 2, 3, 4, or 5 substituents). In certain embodiments, the alkynyl group is an unsubstituted $C_{2-10}$ alkynyl. In certain embodiments, the alkynyl group is a substituted $C_{2-10}$ alkynyl.

The term "heteroalkynyl," as used herein, refers to an alkynyl group, as defined herein, which further includes 1 or more (e.g., 1, 2, 3, or 4) heteroatoms (e.g., oxygen, sulfur, nitrogen, boron, silicon, phosphorus) in the parent chain.

As used herein, alone or as part of another group, "carbocyclyl" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$) and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$) and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents (e.g., 1, 2, 3, 4, or 5 substituents). In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents (e.g., 1, 2, 3, 4, or 5) substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, alone or as part of another group, "heterocyclyl" refers to a radical of a 3- to 14-membered non-aromatic ring system having ring carbon atoms and 1 to 4 ring heteroatoms, wherein each heteroatom is independently selected from nitrogen, oxygen and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocycyl ring, as defined above, is fused with one or more carbocycyl groups wherein the point of attachment is either on the carbocycyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. In some embodiments, a heterocyclyl group is a 5-10 membered non-aromatic ring system having ring carbon atoms and 1-4 ring heteroatoms, wherein each heteroatom is independently selected from nitrogen, oxygen and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen and sulfur ("5-6 membered heterocyclyl"). In some embodiments, the 5-6 membered heterocyclyl has 1-3 ring heteroatoms selected from nitrogen, oxygen and sulfur. In some embodiments, the 5-6 membered heterocyclyl has 1-2 ring heteroatoms selected from nitrogen, oxygen and sulfur. In some embodiments, the 5-6 membered heterocyclyl has 1 ring heteroatom selected from nitrogen, oxygen and sulfur. Exemplary 3-membered heterocyclyls containing 1 heteroatom include, without limitation, azirdinyl, oxiranyl, thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like. Unless otherwise specified, each instance of heterocyclyl is independently unsubstituted (an "unsubstituted heterocyclyl") or substituted (a "substituted heterocyclyl") with one or more substituents (e.g., 1, 2, 3, 4, or 5 substituents). In certain embodiments, the heterocyclyl group is an unsubstituted 3-14 membered heterocyclyl. In certain embodiments, the heterocyclyl group is a substituted 3-14 membered heterocyclyl.

As used herein, alone or as part of another group, "aryl" refers to a radical of a monocyclic or polycyclic (e.g., bicyclic or tricyclic) aromatic ring system (e.g., having 6, 10 or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents (e.g., 1, 2, 3, 4, or 5 substituents). In certain embodiments, the aryl group is an unsubstituted $C_{6-14}$ aryl. In certain embodiments, the aryl group is a substituted $C_{6-14}$ aryl.

"Aralkyl" is a subset of "aliphatic" and refers to an aliphatic group, as defined herein, substituted by an aryl group, as defined herein, wherein the point of attachment is on the aliphatic moiety.

As used herein, alone or as part of another group, "heteroaryl" refers to a radical of a 5-14 membered monocyclic or polycyclic (e.g., bicyclic or tricyclic) aromatic ring system (e.g., having 6, 10 or 14π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocycyl or heterocycyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or on the heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl and the like) the point of attachment can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen and sulfur ("5-6 membered heteroaryl"). In some embodiments, the 5-6 membered heteroaryl has 1-3 ring heteroatoms selected from nitrogen, oxygen and sulfur. In some embodiments, the 5-6 membered heteroaryl has 1-2 ring heteroatoms selected from nitrogen, oxygen and sulfur. In some embodiments, the 5-6 membered heteroaryl has 1 ring heteroatom selected from nitrogen, oxygen and sulfur. Exemplary 5-membered heteroaryls containing 1 heteroatom include, without limitation, pyrrolyl, furanyl and thiophenyl. Exemplary 5-membered heteroaryls containing 2 heteroatoms include, without limitation, imidazolyl, pyrazolyl, oxazolyl, isoxazolyl, thiazolyl, and isothiazolyl. Exemplary 5-membered heteroaryls containing 3 heteroatoms include, without limitation, triazolyl, oxadiazolyl, thiadiazolyl. Exemplary 5-membered heteroaryls containing 4 heteroatoms include, without limitation, tetrazolyl. Exemplary 6-membered heteroaryls containing 1 heteroatom include, without limitation, pyridinyl. Exemplary 6-membered heteroaryls containing 2 heteroatoms include, without limitation, pyridazinyl, pyrimidinyl and pyrazinyl. Exemplary 6-membered heteroaryls containing 3 or 4 heteroatoms include, without limitation, triazinyl and tetrazinyl, respectively. Exemplary 7 membered heteroaryls containing 1 heteroatom include, without limitation, azepinyl, oxepinyl and thiepinyl. Exemplary 5,6-bicyclic heteroaryls include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryls include, without limitation, naphthyridinyl, pteridinyl, quinolinyl, isoquinolinyl, cinnolinyl, quinoxalinyl, phthalazinyl and quinazolinyl. Exemplary tricyclic heteroaryls include, without limitation, phenanthridinyl, dibenzofuranyl, carbazolyl, acridinyl, phenothiazinyl, phenoxazinyl and phenazinyl. Unless otherwise specified, each instance of a heteroaryl group is independently unsubstituted (an "unsubstituted heteroaryl") or substituted (a "substituted heteroaryl") with one or more substituents (e.g., 1, 2, 3, 4, or 5 substituents). In certain embodiments, the heteroaryl group is an unsubstituted 5-14 membered heteroaryl. In certain embodiments, the heteroaryl group is a substituted 5-14 membered heteroaryl.

"Heteroaralkyl" is a subset of "aliphatic" and refers to an aliphatic group, as defined herein, substituted by a heteroaryl group, as defined herein, wherein the point of attachment is on the aliphatic moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

Aliphatic (e.g., alkyl, alkenyl, alkynyl, carbocyclyl), heteroaliphatic (e.g., heteroalkyl, heteroalkenyl, heteroalkynyl, heterocyclyl), aryl and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom etc.) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

Exemplary carbon atom substituents include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; acyl; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted.

Other exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3{}^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-14}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkynyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl) X, —NH$_3$$^+$X$^-$, —N(OC$_{1-6}$ alkyl)(C$_6$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_6$10 aryl, 3-10 membered heterocyclyl, 5-10 membered heteroaryl; or two geminal R$^{gg}$ substituents can be joined to form =O or =S; wherein X is a counterion.

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

The term "alkoxy" as used herein refers to a hydroxyl group wherein the oxygen atom directly attached to the parent molecule is substituted with an aliphatic group. In certain embodiments, alkoxy contains 1-20 alipahtic carbon atoms ($C_{1-20}$ alkoxy). In certain embodiments, alkoxy contains 1-10 alipahtic carbon atoms ($C_{1-10}$ alkoxy). In certain embodiments, alkoxy contains 1-8 alipahtic carbon atoms ($C_{1-8}$ alkoxy). In certain embodiments, alkoxy contains 1-6 alipahtic carbon atoms ($C_{1-6}$ alkoxy). In certain embodiments, alkoxy contains 1-4 alipahtic carbon atoms ($C_{1-4}$ alkoxy). Examples of alkoxy, include but are not limited to, methoxy, ethoxy, propoxy, isopropoxy, n-butoxy, tert-butoxy, neopentoxy, and n-hexoxy.

The term "aryloxy" refers to a hydroxyl group wherein the oxygen atom directly attached to the parent molecule is substituted with an aryl group.

The term "heteroaryloxy" refers to a hydroxyl group wherein the oxygen atom directly attached to the parent molecule is substituted with an heteroaryl group.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —$SR^{aa}$, —S=$SR^{cc}$, —SC(=S)$SR^{aa}$, —SC(=O)$SR^{aa}$, —SC(=O)$OR^{aa}$, and —SC(=O)$R^{aa}$, wherein $R^{aa}$ and $R^{cc}$ are as defined herein.

The term "alkylthio" refers to a thiol group wherein the sulfur atom directly attached to the parent molecule is substituted with an aliphatic group. In certain embodiments, alkylthio contains 1-20 alipahtic carbon atoms ($C_{1-20}$ alkylthio). In certain embodiments, alkylthio contains 1-10 alipahtic carbon atoms ($C_{1-10}$ alkylthio). In certain embodiments, alkylthio contains 1-8 alipahtic carbon atoms ($C_{1-8}$ alkylthio). In certain embodiments, alkylthio contains 1-6 alipahtic carbon atoms ($C_{1-6}$ alkylthio). In certain embodiments, alkylthio contains 1-4 alipahtic carbon atoms ($C_{1-4}$ alkylthio). Examples of alkylthio include, but are not limited to, methylthio, ethylthio, propylthio, isopropylthio, n-butylthio, and the like.

The term "arylthio" refers to a thiol group wherein the sulfur atom directly attached to the parent molecule is substituted with an aryl group.

The term "heteroarylthio" refers to a thiol group wherein the sulfur atom directly attached to the parent molecule is substituted with an heteroaryl group.

As used herein, the term, "amino" refers to the group —$NH_2$.

As used herein, the term "monosubstituted amino" refers to an amino group wherein the nitrogen atom directly attached to the parent molecule, or coordinated to an iron atom, is substituted with one hydrogen and one group other than hydrogen, and includes groups selected from —NH($R^{bb}$), —NHC(=O)$R^{aa}$, —$NHCO_2R^{aa}$, —NHC(=O)N($R^{bb}$)$_2$, —NHC(=$NR^{bb}$)N($R^{bb}$)$_2$, —$NHSO_2R^{aa}$, —NHP(=O)($OR^{cc}$)$_2$, and —NHP(=O)($NR^{bb}$)$_2$, wherein $R^{aa}$, $R^{bb}$ and $R^{cc}$ are as defined herein, and wherein $R^{bb}$ of the group —NH($R^{bb}$) is not hydrogen.

As used herein, the term "disubstituted amino" refers to an amino group wherein the nitrogen atom directly attached to the parent molecule is substituted with two groups other than hydrogen, and includes groups selected from —N($R^{bb}$)$_2$, —$NR^{bb}$C(=O)$R^{aa}$, —$NR^{bb}CO_2R^{aa}$, —$NR^{bb}$C(=O)N($R^{bb}$)$_2$, —$NR^{bb}$C(=$NR^{bb}$)N($R^{bb}$)$_2$, —$NR^{bb}SO_2R^{aa}$, —$NR^{bb}$P(=O)($OR^{cc}$)$_2$, and —$NR^{bb}$P(=O)($NR^{bb}$)$_2$, wherein $R^{aa}$, $R^{bb}$, and $R^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+$ $X^-$, wherein $R^{bb}$ and $X^-$ are as defined herein.

The term "alkylamino" refers to a group having the structure —NHR', wherein R' is aliphatic, as defined herein. In certain embodiments, the aliphatic group contains 1-20 aliphatic carbon atoms ("$C_{1-20}$alkylamino"). In certain other embodiments, the aliphatic group contains 1-10 aliphatic carbon atoms ("$C_{1-10}$alkylamino"). In yet other embodiments, the aliphatic group employed in the invention contain 1-8 aliphatic carbon atoms ("$C_{1-8}$alkylamino"). In still other embodiments, the aliphatic group contains 1-6 aliphatic carbon atoms ("$C_{1-6}$alkylamino"). In yet other embodiments, the aliphatic group contains 1-4 aliphatic carbon atoms ("$C_{1-4}$alkylamino"). Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each an aliphatic or heteroaliphatic group, as defined herein. R and R' may be the same or different in an dialkyamino moiety. In certain embodiments, each aliphatic group contains 1-20 aliphatic carbon atoms ("$C_{1-20}$dialkylamino"). In certain embodiments, each aliphatic group contains 1-10 aliphatic carbon atoms ("$C_{1-10}$dialkylamino"). In certain embodiments, each aliphatic group contains 1-8 aliphatic carbon atoms ("$C_{1-8}$dialkylamino"). In certain embodiments, each aliphatic group contains 1-6 aliphatic carbon atoms ("$C_{1-6}$dialkylamino"). In certain embodiments, each aliphatic group contains 1-4 aliphatic carbon atoms ("$C_{1-4}$dialkylamino"). Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

As used herein, the term "sulfonyl" refers to a group selected from —$SO_2$N($R^{bb}$)$_2$, —$SO_2R^{aa}$, and —$SO_2OR^{aa}$, wherein $R^{aa}$ and $R^{bb}$ are as defined herein.

As used herein, the term "sulfinyl" refers to the group —S(=O)$R^{aa}$, wherein $R^{aa}$ is as defined herein.

As used herein, the term "acyl" refers a group wherein the carbon directly attached to the parent molecule is $sp^2$ hybridized, and is substituted with an oxygen, nitrogen or sulfur atom, e.g., a group selected from ketones (—C(=O)$R^{aa}$), carboxylic acids (—$CO_2H$), aldehydes (—CHO), esters (—$CO_2R^{aa}$, —C(=O)$SR^{aa}$, —C(=S)$SR^{aa}$), amides (—C(=O)N($R^{bb}$)$_2$, —C(=O)$NR^{bb}SO_2R^{aa}$, —C(=S)N($R^{bb}$)$_2$), and imines (—C(=$NR^{bb}$)$R^{aa}$, —C(=$NR^{bb}$)$OR^{aa}$), —C(=$NR^{bb}$)N($R^{bb}$)$_2$), wherein $R^{aa}$ and $R^{bb}$ are as defined herein.

As used herein, the term "silyl" refers to the group —Si($R^{aa}$)$_3$, wherein $R^{aa}$ is as defined herein.

As used herein, alone or as part of another group, "halo" and "halogen" refer to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quarternary nitrogen atoms. If a nitrogen is quarternized, cationic nitrogen is complexed with a counterion to provide a neutral species. As used herein, a "counterion" is a negatively charged group associated with a positively charged quarternary amine in order to maintain electronic neutrality. Exemplary counterions include halide ions (e.g., F$^-$, Cl$^-$, Br$^-$, F$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-6}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

These and other exemplary substituents are described in more detail in the Detailed Description, Examples, and Claims. The invention is not intended to be limited in any manner by the above exemplary listing of substituents.

Protecting Groups (Pg)

One of ordinary skill in the art will appreciate that the synthetic methods, as described herein, utilize a variety of protecting groups. By the term "protecting group," as used herein, it is meant that a particular functional moiety, e.g., an oxygen, sulfur, or nitrogen atom, is temporarily blocked so that a reaction can be carried out selectively at another reactive site in a multifunctional compound. In certain embodiments, a protecting group reacts selectively in good yield to give a protected substrate that is stable to the projected reactions. In certain embodiments, a protecting group is selectively removable in good yield by readily available, preferably non-toxic reagents that do not attack the other functional groups. In certain embodiments, a protecting group forms an easily separable derivative (more preferably without the generation of new stereogenic centers). In certain embodiments, a protecting group has a minimum of additional functionality to avoid further sites of reaction. Nitrogen, oxygen, and sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

In certain embodiments, the substituent present on the nitrogen atom is an amino protecting group (also referred to herein as a "nitrogen protecting group"). Amino protecting groups include, but are not limited to, —OH, —OR, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein.

For example, amino protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Amino protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Amino protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Silyl (—Si(R$^{aa}$)$_3$) amino protecting groups include, but are not limited to, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS).

Other amino protecting groups include, but are not limited to, phenothiazinyl-(10)-carbonyl derivative, N'-p-toluenesulfonylaminocarbonyl derivative, N'-phenylaminothiocarbonyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Oxygen protecting groups (also referred to herein as "hydroxyl protecting groups") include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl; silyl (—Si(R$^{aa}$)$_3$) oxygen protecting groups [e.g., trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), and t-butylmethoxyphenylsilyl (TBMPS)], formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, tosylate (Ts), 9-(9-phenyl)xanthenyl, 9-(9-phenyl-10-oxo)anthryl, and 1,3-benzodithiolan-2-yl, benzisothiazolyl S,S-dioxido.

For protecting 1,2- or 1,3-diols, the oxygen protecting groups include, but are not limited to, methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

"Orthogonal" protecting groups or "differentially protected" refers to at least two protecting groups, as defined above and herein, wherein at least one protecting group is deprotected and the other protecting group(s) is (are) not under the deprotecting conditions employed. This type of selective deprotection is well-known in the art; see *Protecting Groups in Organic Synthesis*, T. W. Greene and P. G. M. Wuts, 3$^{rd}$ edition, John Wiley & Sons, 1999.

Exemplary nitrogen, oxygen, and thiol protecting groups are further described in the Description and in the Examples. However, it will be appreciated that the present invention is not intended to be limited to these protecting groups. Rather, a variety of additional equivalent protecting groups can be readily identified using the above criteria and utilized in the method of the present invention.

Other Definitions

As used herein, a "leaving group" is an art-understood term referring to a molecular fragment that departs with a pair of electrons in heterolytic bond cleavage, wherein the molecular fragment is an anion or neutral molecule. See, for example, Smith, March *Advanced Organic Chemistry* 6th ed. (501-502). Exemplary leaving groups include, but are not limited to, halo (e.g., chloro, bromo, iodo) and sulfonyl substituted hydroxyl groups (e.g., tosyl, mesyl, besyl).

As understood in the art, a "nucleophile" or "nucleophilic" refers to a group which forms a covalent bond to its reaction partner (the "electrophile" or "electrophilic") by donating both bonding electrons. Because nucleophilers donate electrons, they are by definition Lewis bases, and electrophiles are Lewis acids. All molecules and ions with a free pair of electrons can act as nucleophiles.

The term "carbohydrate" refers to a sugar or polymer of sugars. The terms "sugar," "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose. (e.g., 2'-fluororibose, deoxyribose, and hexose). Carbohydrates may exist in many different forms, for example, conformers, cyclic forms, acyclic forms, stereoisomers, tautomers, anomers, and isomers.

It will also be appreciated that certain of the compounds of the present invention can exist in free form, or where appropriate, as a pharmaceutically acceptable form thereof. According to the present invention, a pharmaceutically acceptable form includes, but is not limited to, pharmaceutically acceptable salts, pharmaceutically acceptable esters, salts of such esters, tautomers, and/or prodrugs. In certain embodiments, the pharmaceutically acceptable form thereof is a pharmaceutically acceptable salt.

The term "pharmaceutically acceptable salt" or "salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 66: 1-19, 1977; incorporated herein by reference. The salts can be prepared in situ during the final isolation and purification of the compounds of the invention, or separately by reacting the free base functionality with a suitable organic or inorganic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl moiety advantageously has not more than 6 carbon atoms. Examples of particular esters include formates, acetates, propionates, butyrates, acrylates, and ethylsuccinates. In certain embodiments, the esters are cleaved by enzymes such as esterases.

The term "pharmaceutically acceptable prodrug" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As used herein, the term "tautomer" refers to particular isomers of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridone-hydroxypyridine forms.

As used herein, an "epimer" of a compound of Formula (I) refers to the "iso" derivative of the compound, i.e., epimeric at C11, C12, and C13 of the trioxacarcin scaffold (see FIG. 1C for numbering).

The terms "polynucleotide," "nucleotide sequence," "nucleic acid," "nucleic acid molecule," "nucleic acid sequence," and "oligonucleotide" refer to a polymer of two or more nucleotides. The polynucleotides can be DNA, RNA, or derivatives or modified versions thereof. The polynucleotide may be single-stranded or double-stranded. The polynucleotide can be modified at the base moiety, sugar moiety, or phosphate backbone, for example, to improve stability of the molecule, its hybridization parameters, etc. The polynucleotide may comprise a modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine. The olynucleotide may comprise a modified sugar moiety (e.g., 2'-fluororibose, ribose, 2'-deoxyribose, 2'-O-methylcytidine, arabinose, and hexose), and/or a modified phosphate moiety (e.g., phosphorothioates and 5'-N-phosphoramidite linkages). A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA, and RNA-RNA hybrids, as well as "protein nucleic acids" (PNA) formed by conjugating bases to an amino acid backbone.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. Preferably, the non-human animal is a mammal. The non-human animal may be male or female and at any stage of development. A non-human animal may be a transgenic animal.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition, and which inhibits or reduces the severity of the disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. For example, the effective amount of a compound with anti-proliferative activity is the amount that results in a sufficient concentration to inhibit the proliferation of cells. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

BRIEF DESCRIPTION OF THE DRAWING

FIGS. 1A-1B show various members of the trioxacarcin family. FIG. 1C depicts the trioxacarcin molecular scaffold with carbons numbered.

FIG. 2A: retrosynthetic analysis an orthogonally protected trioxacarcin precursor (2) from epoxy diazo ketone (6), cyanophthalide (7) and cyclohexenone (8). FIG. 2B: general chemical scheme depicting the inventive method; FIG. 2C: Chemical synthesis of the three intermediates 6, 7, and 8. FIG. 2D: Convergent synthesis of DC-45-A2 from 6, 7, and 8.

FIG. 15 is provided as a black and white image, the co-localization of fluorescence shown in panels (ii) and (iii) represented in panel (iv) is still visible.

DETAILED DESCRIPTION OF CERTAIN EMBODIMENTS OF THE INVENTION

Figure 1A:
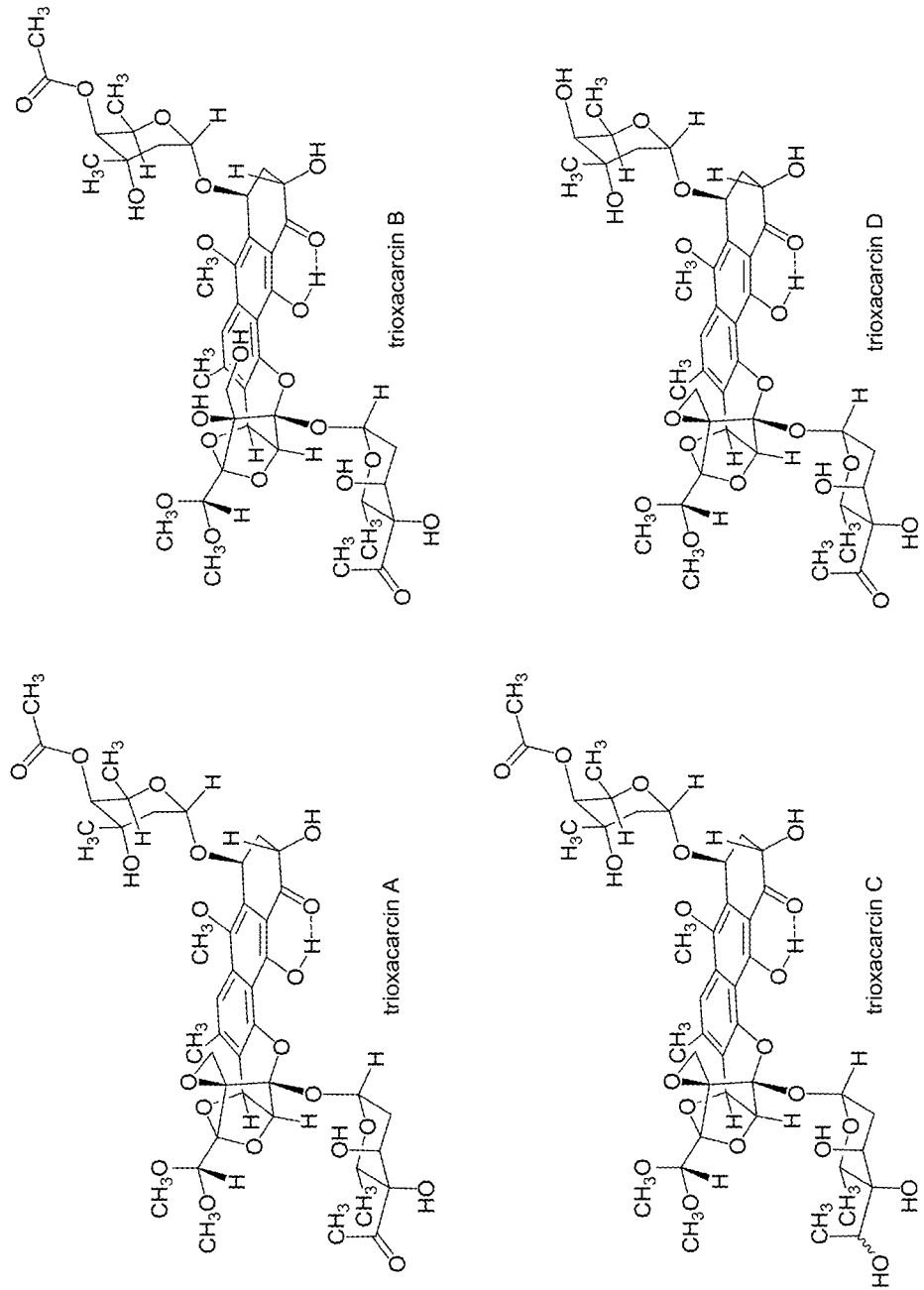
FIGS. 1A-1C.

The present invention is based at least in part upon the synthetic approach described herein for preparing trioxacarcins compounds.

Thus, the present invention provides the synthesis of a differentially protected form of the trioxacarcin aglycone DC-45-A$_2$, which may be used to prepare a variety of trioxacarcin analogues as described herein. The enantioselective, convergent synthesis of the trioxacarcin aglycone allows for the synthesis of analogs which could not have been isolated from natural sources or prepared by semisynthesis. Such analogues may be prepared for the purpose of developing compounds with improved anti-proliferative activity and/or improving pharmacological properties. Such compounds may find use in the treatment of proliferative diseases (e.g., cancer, benign tumors), diabetic retinopathy, inflammatory diseases, autoimmune diseases, or infectious diseases (e.g., bacterial infections, fungal infections, and parasitic infections, e.g., malaria). Given the inventive compounds' ability to bind and modify DNA, the inventive compounds may be used, for example, to cleave, tag, or alkylate nucleic acids in vivo or in vitro.

Compounds

The present invention provides novel trioxacarcin compounds and intermediates useful in the synthesis of trioxacarcins compounds.

For example, in one aspect, provided are trioxacarin compounds of the Formula (I):

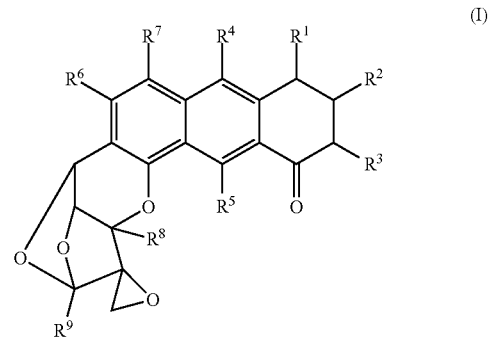

and pharmaceutically acceptable forms thereof;

wherein:

$R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{A1}$; —$C(=O)R^{A2}$; —$CO_2R^{A2}$; —$CN$; —$SCN$; —$SR^{A1}$; —$SOR^{A1}$; —$SO_2R^A$; —$NO_2$; —$N_3$; =O; =$N(R^{A2})$; =S; —$N(R^{A2})_2$; —$NR^{A2}C(=O)R^{A2}$; —$NR^{A2}C(=O)N(R^{A2})_2$; —$OC(=O)OR^{A1}$; —$OC(=O)R^{A2}$; —$OC(=O)N(R^{A2})_2$; —$NR^AC(=O)OR^{A1}$; or —$C(R^{A2})_3$; wherein each occurrence of $R^{A1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{A2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl (e.g., alkoxy; aryloxy; heteroaryloxy); substituted thiol (e.g., alkylthio; arylthio; heteroarylthio); amino; or substituted amino (e.g., alkylamino, dialkylamino), or two $R^{A2}$ groups are optionally joined to form a heterocyclyl or heteroaryl ring;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{B1}$; —$C(=O)R^{B2}$; —$CO_2R^{B2}$; —$CN$; —$SCN$; —$SR^{B1}$; —$SOR^{B1}$; —$SO_2R^{B2}$; —$NO_2$; —$N_3$; =O; =$N(R^{B2})$; =S; —$N(R^{B2})_2$; —$NR^{B2}C(=O)R^{B2}$; —$NR^{B2}C(=O)N(R^{B2})_2$; —$OC(=O)OR^{B1}$; —$OC(=O)R^{B2}$; —$OC(=O)N(R^{B2})_2$; —$NR^{B2}C(=O)OR^{B1}$; or —$C(R^{B2})_3$; wherein each occurrence of $R^{B1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{B2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl (e.g., alkoxy; aryloxy; heteroaryloxy); substituted thiol (e.g., alkylthio; arylthio; heteroarylthio); amino; or substituted amino (e.g., alkylamino, dialkylamino); or two $R^{B2}$ groups are optionally joined to form a heterocyclyl or heteroaryl ring;

$R^3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{C1}$; —$C(=O)R^{C2}$; —$CO_2R^{C1}$; —$CN$; —$SCN$; —$SR^{C1}$; —$SOR^{C1}$; —$SO_2R^{C2}$; —$NO_2$; —$N_3$; =O; =$N(R^{C2})$; =S; —$N(R^{C2})_2$; —$NHC(=O)R^{C2}$; —$NR^2C(=O)N(R^2)_2$; —$OC(=O)OR^{C1}$; —$OC(=O)R^{C2}$; —$OC(=O)N(R^{C2})_2$; —$NR^2C(=O)OR^{C1}$; or —$C(R^2)_3$; wherein each occurrence of $R^{C1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{C2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl (e.g., alkoxy; aryloxy; heteroaryloxy); substituted thiol (e.g., alkylthio; arylthio; heteroarylthio); amino; or substituted amino (e.g., alkylamino, dialkylamino); or two $R^{C2}$ groups are optionally joined to form a heterocyclyl or heteroaryl ring;

$R^4$ is hydrogen; halogen; cyclic or acyclubstituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{D1}$; —$C(=O)R^{D2}$; —$CO_2R^{D2}$; —$CN$; —$SCN$; —$SR^{D1}$; —$SOR^{D1}$; —$SO_2R^{D2}$; —$NO_2$; —$N_3$; —$N(R^{D2})_2$; —$NR^{D2}C(=O)R^{D2}$; —$NR^{D2}C(=O)N(R^{D2})_2$; —$OC(=O)OR^{D1}$; —$OC(=O)R^{D2}$; —$OC(=O)N(R^{D2})_2$; —$NR^{D2}C(=O)OR^{D1}$; or —$C(R^{D2})_3$; wherein each occurrence of $R^{D1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{D2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl (e.g., alkoxy; aryloxy; heteroaryloxy); substituted thiol (e.g., alkylthio; arylthio; heteroarylthio); amino; or substituted amino (e.g., alkylamino, dialkylamino); or two $R^{D2}$ groups are optionally joined to form a heterocyclyl or heteroaryl ring;

$R^5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{E1}$; —$C(=O)R^{E2}$; —$CO_2R^{E1}$; —$CN$; —$SCN$; —$SR^{E1}$; —$SOR^{E1}$; —$SO_2R^{E2}$; —$NO_2$; —$N_3$; —$N(R^{E2})_2$; —$NR^{E2}C(=O)R^{E2}$; —$NR^{E2}C(=O)N(R^{E2})_2$; —$OC(=O)OR^{E1}$; —$OC(=O)R^{E2}$; —$OC(=O)N(R^{E2})_2$; —$NR^{E2}C(=O)OR^{E1}$; or —$C(R^{E2})_3$; wherein each occurrence of $R^{E1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{E2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl (e.g., alkoxy; aryloxy; heteroaryloxy); substituted thiol (e.g., alkylthio; arylthio; heteroarylthio); amino; or substituted amino (e.g., alkylamino, dialkylamino); or two $R^{E2}$ groups are optionally joined to form a heterocyclyl or heteroaryl ring;

$R^6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $-OR^{F1}$; $-C(=O)R^{F2}$; $-CO_2R^{F1}$; $-CN$; $-SCN$; $-SR^{F1}$; $-SOR^{F1}$; $-SO_2R^{F2}$; $-NO_2$; $-N_3$; $-N(R^{F2})_2$; $-NR^{F2}C(=O)R^{F2}$; $-NR^{F2}C(=O)N(R^{F2})_2$; $-OC(=O)OR^{F1}$; $-OC(=O)R^{F2}$; $-OC(=O)N(R^{F2})_2$; $-NR^{F2}C(=O)OR^{F1}$; or $-C(R^{F2})_3$; wherein each occurrence of $R^{F1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{F2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl (e.g., alkoxy; aryloxy; heteroaryloxy); substituted thiol (e.g., alkylthio; arylthio; heteroarylthio); amino; or substituted amino (e.g., alkylamino, dialkylamino); or two $R^{F2}$ groups are optionally joined to form a heterocyclyl or heteroaryl ring;

$R^7$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $-OR^{G1}$; $-C(=O)R^{G2}$; $-CO_2R^{G1}$; $-CN$; $-SCN$; $-SR^{G1}$; $-SOR^{G1}$; $-SO_2R^{G2}$; $-NO_2$; $-N_3$; $-N(R^{G})_2$; $-NR^{G2}C(=O)R^{G2}$; $-NR^{G2}C(=O)N(R^{G2})_2$; $-OC(=O)OR^{G1}$; $-OC(=O)R^2$; $-OC(=O)N(R^{G2})_2$; $-NR^{G2}C(=O)OR^{G1}$; or $-C(R^{G2})_3$; wherein each occurrence of $R^{G1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{G2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl (e.g., alkoxy; aryloxy; heteroaryloxy); substituted thiol (e.g., alkylthio; arylthio; heteroarylthio); amino; or substituted amino (e.g., alkylamino, dialkylamino); or two $R^{G2}$ groups are optionally joined to form a heterocyclyl or heteroaryl ring;

$R^8$ is $-OR^{H1}$, wherein each occurrence of $R^{H1}$ is independently hydrogen, carbohydrate, an oxygen-protecting group, cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; or acyl;

$R^9$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $-OR^{I1}$; $-C(=O)R^2$; $-CO_2R^{I1}$; $-CN$; $-SCN$; $-SR^{I1}$; $-SOR^{I1}$; $-SO_2R^{I2}$; $-NO_2$; $-N_3$; $-N(R^{I2})_2$; $-NR^{I2}C(=O)R^{I2}$; $-NR^{I2}C(=O)N(R^{I2})_2$; $-OC(=O)OR^{I1}$; $-OC(=O)R^{I2}$; $-OC(=O)N(R^{I2})_2$; $-NR^{I2}C(=O)OR^{I1}$; or $-C(R^{I2})_3$; wherein each occurrence of $R^{I1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{I2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl (e.g., alkoxy; aryloxy; heteroaryloxy); substituted thiol (e.g., alkylthio; arylthio; heteroarylthio); amino; or substituted amino (e.g., alkylamino, dialkylamino); or two $R^{I2}$ groups are optionally joined to form a heterocyclyl or heteroaryl ring;

or $R^1$ and $R^2$ are optionally taken together with the intervening carbon atoms to form an optionally substituted cyclic moiety;

or $R^2$ and $R^3$ are optionally taken together with the intervening carbon atoms to form an optionally substituted cyclic moiety;

or $R^1$ and $R^4$ are optionally taken together with the intervening carbon atoms to form an optionally substituted cyclic moiety;

or $R^4$ and $R^7$ are optionally be taken together with the intervening carbon atoms to form an optionally substituted cyclic moiety;

or $R^6$ and $R^7$ are optionally be taken together with the intervening carbon atoms to form an optionally substituted cyclic moiety.

Figure 1B:
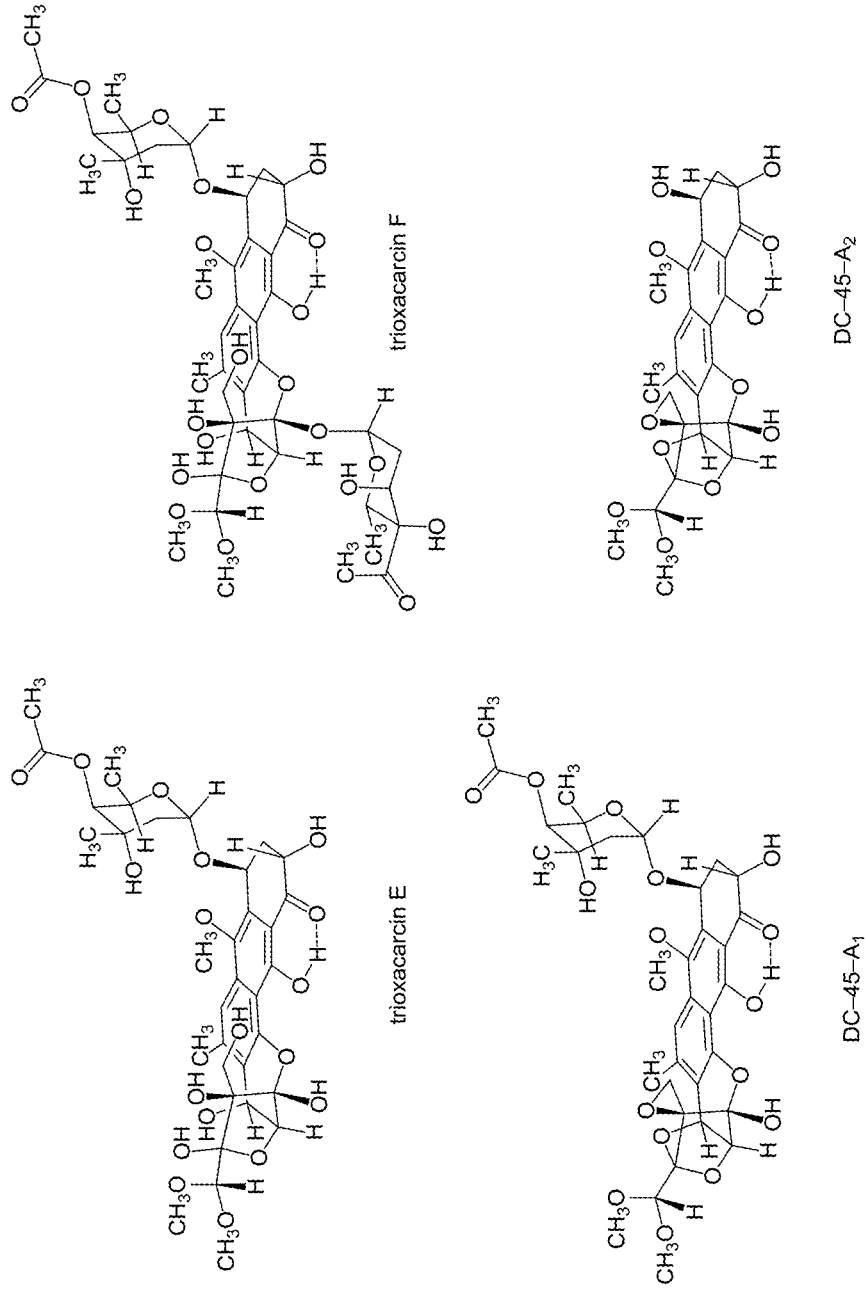

In certain embodiments, the inventive compound is not a naturally occurring trioxacarcin analog (e.g., as depicted in FIGS. 1A and 1B). In certain embodiments, the inventive compound is not a previously isolated and characterized, naturally occurring trioxacarcin analog. In certain embodiments, the inventive compound is not any of the compounds: trioxacarcin A, trioxacarcin B, trioxacarcin C, trioxacarcin D, trioxacarcin E, trioxacarcin F, gutingimycin, DC-45-A, DC-45-A$_1$, DC-45-A$_2$, DC-45-B$_1$, DC-45-B$_2$, LL-D49194α1, LL-D49194β1, LL-D49194β2, LL-D49194β3, LL-D49194γ, LL-D49194δ, LL-D49194ε, LL-D49194ξ, LL-D49194η, LL-D49194ω1, LL-D49194ω2, or LL-D49194ω3. In certain embodiments, the inventive compound is not a compound described in U.S. Pat. Nos. 4,459,291; 4,511,560; or 4,626,503, each of which is incorporated herein by reference.

As generally defined above, $R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $-OR^{A1}$; $-C(=O)R^{A2}$; $-CO_2R^{A2}$; $-CN$; $-SCN$; $-SR^{A1}$; $-SOR^{A1}$; $-SO_2R^A$; $-NO_2$; $-N_3$; $=O$; $=N(R^{A2})$; $=S$; $-N(R^{A2})_2$; $-NR^{A2}C(=O)R^{A2}$; $-NR^{A2}C(=O)N(R^{A2})_2$; $-OC(=O)OR^{A1}$; $-OC(=O)R^{A2}$; $-OC(=O)N(R^{A2})_2$; $-NR^{A}C(=O)OR^{A1}$; or $-C(R^{A2})_3$, or $R^1$ and $R^2$ are optionally taken together with the intervening carbon atoms to form an optionally substituted cyclic moiety.

In certain embodiments, $R^1$ is hydrogen.

In certain embodiments, $R^1$ is halogen. In certain embodiments, $R_1$ is fluorine.

In certain embodiments, $R_1$ is substituted or unsubstituted aliphatic. In some embodiments, $R_1$ is substituted or unsubstituted alkyl. In certain embodiments, $R_1$ is $C_1$-$C_6$ alkyl. In certain embodiments, $R_1$ is methyl. In certain embodiments, $R_1$ is ethyl. In certain embodiments, $R_1$ is propyl.

In certain embodiments, $R_1$ is substituted or unsubstituted aryl. In certain embodiments, $R_1$ is substituted or unsubstituted phenyl. In certain embodiments, $R_1$ is substituted phenyl. In certain embodiments, $R_1$ is unsubstituted phenyl.

In certain embodiments, $R_1$ is substituted or unsubstituted heteroaryl.

In certain embodiments, $R^1$ is —$OR^{A1}$. In certain embodiments, $R^1$ is —$OR^{A1}$, wherein $R^{A1}$ is hydrogen. In certain embodiments, $R^1$ is —$OR^{A1}$, wherein $R^{A1}$ is $C_{1-6}$ alkyl. In certain embodiments, $R^1$ is —$OR^{A1}$, wherein $R^{A1}$ is an oxygen-protecting group. In certain embodiments, $R^1$ is —$OR^{A1}$, wherein $R^{A1}$ is p-methoxybenzyl (PMB). In certain embodiments, $R^1$ is —$OR^{A1}$, wherein $R^{A1}$ is a silyl protecting group (e.g., TBS, TMS). In certain embodiments, $R^1$ is —$OR^{A1}$, wherein $R^{A1}$ is a carbohydrate. In certain embodiments, $R^1$ is —$OR^{A1}$, wherein $R^{A1}$ is selected from the group consisting of aldohexoses, deoxy sugars, and amino sugars. In certain embodiments, $R^1$ is —$OR^{A1}$, wherein $R^{A1}$ is selected from the group consisting of glucose, mannose, allose, altrose, gulose, idose, galactose, talose, glucosamine, rhamnose, fucose, and derivatives thereof. In certain embodiments, $R^1$ is —$OR^{A1}$, wherein $R^{A1}$ is a monosaccharide. In certain embodiments, $R^1$ is —$OR^{A1}$, wherein $R^{A1}$ is axenose or a derivative thereof.

In certain embodiments, $R^1$ is —$OR^{A1}$, wherein $R^{A1}$ is of the formula:

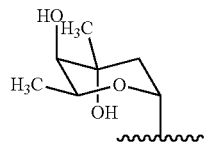

In certain embodiments, $R^1$ is —$OR^{A1}$, wherein $R^{A1}$ is trioxacarcinoase A or a derivative thereof.

In certain embodiments, $R^1$ is —$OR^{A1}$, wherein $R^A$ is of the formula:

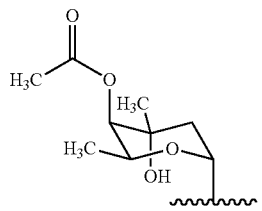

In certain embodiments, $R^1$ is —$OR^{A1}$, wherein $R^{A1}$ is a fluorinated derivative of axenose or trioxacarcinose A, wherein one or more hydrogen atoms has been replaced by fluorine. For example, in certain embodiments, $R^1$ is —$OR^{A1}$ and $R^{A1}$ is of one of the formulae:

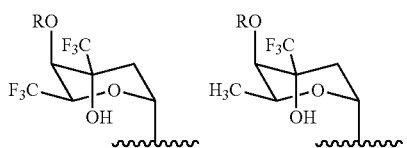

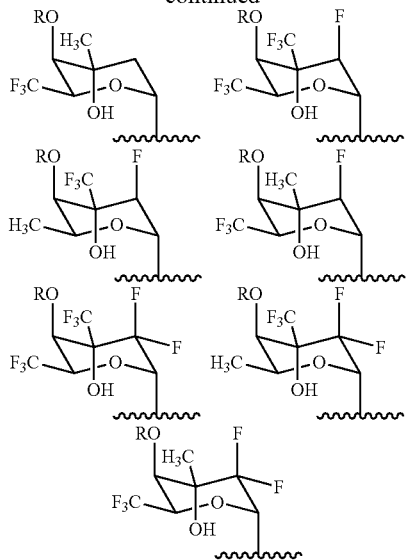

wherein each occurrence of R is independently hydrogen; an oxygen-protecting group; substituted or unsubstituted, branched or unbranched acyl; or $C_{1-6}$ alkyl.

In certain embodiments, $R^1$ is —$OR^{A1}$, wherein $R^{A1}$ is a disaccharide. In certain embodiments, $R^1$ is —$OR^{A1}$, wherein $R^{A1}$ is not a carbohydrate. In certain embodiments, $R^1$ is —$OR^{A1}$, wherein $R^{A1}$ is trisaccharide.

In certain embodiments, $R^1$ is —$OC(=O)R^{A1}$.

In certain embodiments, $R^1$ is —$C(=O)R^{A2}$. In certain embodiments, $R^1$ is acetyl (—$C(=O)CH_3$).

In certain embodiments, $R^1$ is —$N(R^{A2})_2$. In certain embodiments, $R^1$ is —$NHR^{A2}$.

In certain embodiments, $R^1$ is —$SR^{A1}$.

In certain embodiments, $R^1$ is =O.

As generally defined above, $R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{B1}$; —$C(=O)R^{B2}$; —$CO_2R^{B2}$; —CN; —SCN; —$SR^{B1}$; —$SOR^{B1}$; —$SO_2R^{B2}$; —$NO_2$; —$N_3$; =O; =$N(R^{B2})$; =S; —$N(R^{B2})_2$; —$NR^{B2}C(=O)R^{B2}$; —$NR^{B2}C(=O)N(R^{B2})_2$; —$OC(=O)OR^{B1}$; —$OC(=O)R^{B2}$; —$OC(=O)N(R^{B2})_2$; —$NR^{B2}C(=O)OR^{B1}$; or —$C(R^{B2})_3$, or $R^1$ and $R^2$ are optionally taken together with the intervening carbon atoms to form an optionally substituted cyclic moiety; or $R^2$ and $R^3$ are optionally taken together with the intervening carbon atoms to form an optionally substituted cyclic moiety.

In certain embodiments, $R^2$ is hydrogen.

In certain embodiments, $R^2$ is or $C_1$-$C_6$ aliphatic. In some embodiments, $R^2$ is substituted or unsubstituted alkyl. In certain embodiments, $R^2$ is $C_1$-$C_6$ alkyl. In certain embodiments, $R^2$ is methyl. In certain embodiments, $R^2$ is ethyl. In certain embodiments, $R^2$ is propyl. In certain embodiments, $R^2$ is butyl.

As generally defined above, $R^3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{C1}$; —$C(=O)R^{C2}$; —$CO_2R^{C1}$; —CN; —SCN; —$SR^{C1}$; —$SOR^{C1}$; —$SO_2R^{C2}$; —$NO_2$; —$N_3$; =O;

=N($R^{C2}$); =S; —N($R^{C2}$)$_2$; —NHC(=O)$R^{C2}$; —N$R^{C2}$C(=O)N($R^{C2}$)$_2$; —OC(=O)O$R^{C1}$; —OC(=O)$R^{C2}$; —OC(=O)N($R^{C2}$)$_2$; —N$R^{C2}$C(=O)O$R^{C1}$; or —C($R^{C2}$)$_3$; or $R^2$ and $R^3$ are optionally taken together with the intervening carbon atoms to form an optionally substituted cyclic moiety.

In certain embodiments, $R^3$ is hydrogen.

In certain embodiments, $R^3$ is halogen. In certain embodiments, $R^3$ is fluorine.

In certain embodiments, $R^3$ is substituted or unsubstituted aliphatic. In some embodiments, $R^3$ is substituted or unsubstituted alkyl. In certain embodiments, $R^3$ is $C_1$-$C_6$ alkyl. In certain embodiments, $R^3$ is methyl. In certain embodiments, $R^3$ is ethyl. In certain embodiments, $R^3$ is propyl.

In certain embodiments, $R^3$ is substituted or unsubstituted aryl. In certain embodiments, $R^3$ is substituted or unsubstituted phenyl. In certain embodiments, $R^3$ is substituted phenyl. In certain embodiments, $R^3$ is unsubstituted phenyl.

In certain embodiments, $R^3$ is substituted or unsubstituted heteroaryl.

In certain embodiments, $R^3$ is —O$R^{C1}$. In certain embodiments, $R^3$ is —O$R^{C1}$, wherein $R^{C1}$ is hydrogen. In certain embodiments, $R^3$ is —O$R^{C1}$, wherein $R^{C1}$ is $C_{1-6}$ alkyl. In certain embodiments, $R^3$ is —O$R^{C1}$, wherein $R^{C1}$ is an oxygen-protecting group. In certain embodiments, $R^3$ is —O$R^{C1}$, wherein $R^{C1}$ is p-methoxybenzyl (PMB). In certain embodiments, $R^3$ is —O$R^{C1}$, wherein $R^{C1}$ is a silyl protecting group (e.g., TBS, TMS). In certain embodiments, $R^3$ is —O$R^{C1}$, wherein $R^{C1}$ is a carbohydrate. In certain embodiments, $R^3$ is —O$R^{C1}$, wherein $R^{C1}$ is a monosaccharide. In certain embodiments, $R^3$ is —O$R^{C1}$, wherein $R^{C1}$ is selected from the group consisting of glucose, mannose, allose, altrose, gulose, idose, galactose, talose, glucosamine, rhamnose, fucose, and derivatives thereof. In certain embodiments, $R^3$ is —O$R^{C1}$, wherein $R^{C1}$ is a disaccharide. In certain embodiments, $R^3$ is —O$R^{CI}$, wherein $R^{C1}$ is trisaccharide. In certain embodiments, $R^3$ is —O$R^{C1}$, wherein $R^{C1}$ is not a carbohydrate.

In certain embodiments, $R^3$ is —OC(=O)$R^2$.

In certain embodiments, $R^3$ is —C(=O)$R^2$. In certain embodiments, $R^3$ is acetyl (—C(=O)CH$_3$).

In certain embodiments, $R^3$ is —N($R^{C2}$)$_2$. In certain embodiments, $R^3$ is —NH$R^{C2}$.

In certain embodiments, R is —S$R^{C1}$.

In certain embodiments, $R^2$ and $R^3$ are taken together with the intervening carbon atoms to form an optionally substituted cyclic moiety. In certain embodiments, $R^2$ and $R^3$ are taken together with the intervening carbon atoms to form an optionally substituted carbocyclic moiety. In certain embodiments, $R^2$ and $R^3$ are taken together with the intervening carbon atoms to form an optionally substituted aryl moiety. In certain embodiments, $R^2$ and $R^3$ are taken together with the intervening carbon atoms to form an optionally substituted heterocyclic moiety. In certain embodiments, $R^2$ and $R^3$ are taken together with the intervening carbon atoms to form an optionally substituted heteroaryl moiety.

As generally defined above, $R^4$ is hydrogen; halogen; cyclic or acyclubstituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —O$R^{D1}$; —C(=O)$R^{D2}$; —CO$_2R^{D2}$; —CN; —SCN; —S$R^{D1}$; SO$R^{D1}$; —SO$_2R^{D2}$; —NO$_2$; —N$_3$; —N($R^{D2}$)$_2$; —N$R^{D2}$C(=O)$R^{D2}$; —N$R^{D2}$C(=O)N($R^{D2}$)$_2$; —OC(=O)O$R^{D1}$; —OC(=O)$R^{D2}$; —OC(=O)N($R^{D2}$)$_2$; —N$R^{D2}$C(=O)O$R^{D1}$; or —C($R^{D2}$)$_3$; or $R^1$ and $R^4$ are optionally taken together with the intervening carbon atoms to form an optionally substituted cyclic moiety; or $R^4$ and $R^7$ are optionally be taken together with the intervening carbon atoms to form an optionally substituted cyclic moiety.

In certain embodiments, $R^4$ is hydrogen.

In certain embodiments, $R^4$ is halogen. In certain embodiments, $R^4$ is fluorine.

In certain embodiments, $R^4$ is substituted or unsubstituted aliphatic. In some embodiments, $R^4$ is substituted or unsubstituted alkyl. In certain embodiments, $R^4$ is $C_1$-$C_6$ alkyl. In certain embodiments, $R^4$ is methyl. In certain embodiments, $R^4$ is ethyl. In certain embodiments, $R^4$ is propyl.

In certain embodiments, $R^4$ is substituted or unsubstituted aryl. In certain embodiments, $R^4$ is substituted or unsubstituted phenyl. In certain embodiments, $R^4$ is substituted phenyl. In certain embodiments, $R^4$ is unsubstituted phenyl.

In certain embodiments, $R^4$ is substituted or unsubstituted heteroaryl.

In certain embodiments, $R^4$ is —O$R^{D1}$. In certain embodiments, $R^4$ is —O$R^{D1}$ wherein $R^{D1}$ is hydrogen (i.e., $R^4$ is —OH). In certain embodiments, $R^4$ is —O$R^{D1}$, wherein $R^{D1}$ is $C_{1-6}$ alkyl. In certain embodiments, $R^4$ is —OCH$_3$. In certain embodiments, $R^4$ is —O$R^{D1}$, wherein $R^{D1}$ is an oxygen-protecting group. In certain embodiments, $R^4$ is —O$R^{D1}$, wherein $R^{D1}$ is a silyl protecting group (e.g., TBS, TMS).

In certain embodiments, $R^4$ is —OC(=O)$R^{D2}$.

In certain embodiments, $R^4$ is —C(=O)$R^{D2}$. In certain embodiments, $R^4$ is acetyl (—C(=O)CH$_3$).

In certain embodiments, $R^4$ is —N($R^{D2}$)$_2$. In certain embodiments, $R^4$ is —NH$R^{D2}$.

In certain embodiments, $R^4$ is —S$R^{D1}$.

In certain embodiments, $R^1$ and $R^4$ are taken together with the intervening carbon atoms to form a cyclic moiety, which is optionally substituted.

As generally defined above, $R^5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —O$R^{E1}$; —C(=O)$R^{E2}$; —CO$_2R^{E1}$; —CN; —SCN; —S$R^{E1}$; —SO$R^{E1}$; —SO$_2R^{E2}$; —NO$_2$; —N$_3$; —N($R^{E2}$)$_2$; —N$R^{E2}$C(=O)$R^{E2}$; —N$R^{E2}$C(=O)N($R^{E2}$)$_2$; —OC(=O)O$R^{E1}$; —OC(=O)$R^{E2}$; —OC(=O)N($R^{E2}$)$_2$; —N$R^{E2}$C(=O)O$R^{E1}$; or —C($R^{E2}$)$_3$.

In certain embodiments, $R^5$ is hydrogen.

In certain embodiments, $R^5$ is halogen. In certain embodiments, $R^5$ is fluorine.

In certain embodiments, $R^5$ is substituted or unsubstituted aliphatic. In some embodiments, $R^5$ is substituted or unsubstituted alkyl. In certain embodiments, $R^5$ is $C_1$-$C_6$ alkyl. In certain embodiments, $R^5$ is methyl. In certain embodiments, $R^5$ is ethyl. In certain embodiments, $R^5$ is propyl.

In certain embodiments, $R^5$ is substituted or unsubstituted aryl. In certain embodiments, $R^5$ is substituted or unsubstituted phenyl. In certain embodiments, $R^5$ is substituted phenyl. In certain embodiments, $R^5$ is unsubstituted phenyl.

In certain embodiments, $R^5$ is substituted or unsubstituted heteroaryl.

In certain embodiments, $R^5$ is —O$R^{E1}$. In certain embodiments, $R^5$ is —OH. In certain embodiments, $R^5$ is —O$R^{E1}$, wherein $R^{E1}$ is $C_{1-6}$ alkyl. In certain embodiments, $R^5$ is —OCH$_3$. In certain embodiments, $R^5$ is —O$R^{E1}$, wherein $R^{E1}$ is an oxygen-protecting group. In certain embodiments, $R^5$ is —O$R^{E1}$, wherein $R^{E1}$ is a silyl protecting group (e.g., TBS, TMS).

In certain embodiments, $R^5$ is —OC(=O)$R^{E2}$.

In certain embodiments, $R^5$ is —C(=O)$R^{E2}$. In certain embodiments, $R^5$ is acetyl (—C(=O)CH$_3$).

In certain embodiments, $R^5$ is —N($R^{E2}$)$_2$. In certain embodiments, $R^5$ is —NH$R^{E2}$.

In certain embodiments, $R^5$ is —S$R^{E1}$.

As generally defined above, $R^6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —O$R^{F1}$; —C(=O)$R^{F2}$; —CO$_2R^{F1}$; —CN; —SCN; —S$R^{F1}$; —SO$R^{F1}$; —SO$_2R^{F2}$; —NO$_2$; —N$_3$; —N($R^{F2}$)$_2$; —N$R^{F2}$C(=O)$R^{F2}$; —N$R^{F2}$C(=O)N($R^{F2}$)$_2$; —OC(=O)O$R^{F1}$; —OC(=O)$R^{F2}$; —OC(=O)N($R^{F2}$)$_2$; —N$R^{F2}$C(=O)O$R^{F1}$; or —C($R^{F2}$)$_3$; or $R^6$ and $R^7$ are optionally be taken together with the intervening carbon atoms to form an optionally substituted cyclic moiety.

In certain embodiments, $R^6$ is hydrogen.

In certain embodiments, $R^6$ is halogen. In certain embodiments, $R^6$ is fluorine.

In certain embodiments, $R^6$ is substituted or unsubstituted aliphatic. In some embodiments, $R^6$ is substituted or unsubstituted alkyl. In certain embodiments, $R^6$ is $C_1$-$C_6$ alkyl. In certain embodiments, $R^6$ is methyl. In certain embodiments, $R^6$ is ethyl. In certain embodiments, $R^6$ is propyl.

In certain embodiments, $R^6$ is substituted or unsubstituted aryl. In certain embodiments, $R^6$ is substituted or unsubstituted phenyl. In certain embodiments, $R^6$ is substituted phenyl. In certain embodiments, $R^6$ is unsubstituted phenyl.

In certain embodiments, $R^6$ is substituted or unsubstituted heteroaryl.

In certain embodiments, $R^6$ is —O$R^{F1}$. In certain embodiments, $R^6$ is —OH. In certain embodiments, $R^6$ is —O$R^{F1}$, wherein $R^{F1}$ is $C_{1-6}$ alkyl. In certain embodiments, $R^6$ is —O$R^{F1}$, wherein $R^{F1}$ is an oxygen-protecting group. In certain embodiments, $R^6$ is —O$R^{F1}$ wherein $R^{F1}$ is p-methoxybenzyl (PMB). In certain embodiments, $R^6$ is —O$R^{F1}$, wherein $R^{F1}$ is a silyl protecting group (e.g., TBS, TMS). In certain embodiments, $R^6$ is —O$R^{F1}$, wherein $R^{F1}$ is a carbohydrate. In certain embodiments, $R^6$ is —O$R^{F1}$, wherein $R^{F1}$ is a monosaccharide. In certain embodiments, $R^6$ is —O$R^{F1}$, wherein $R^{F1}$ is selected from the group consisting of glucose, mannose, allose, altrose, gulose, idose, galactose, talose, glucosamine, rhamnose, fucose, and derivatives thereof. In certain embodiments, $R^6$ is —O$R^{F1}$, wherein $R^{F1}$ is a disaccharide. In certain embodiments, $R^6$ is —O$R^{F1}$, wherein $R^{F1}$ is trisaccharide.

In certain embodiments, $R^6$ is —OC(=O)$R^{F2}$.

In certain embodiments, $R^6$ is —C(=O)$R^{F2}$. In certain embodiments, $R^6$ is acetyl (—C(=O)CH$_3$).

In certain embodiments, $R^6$ is —N($R^{F2}$)$_2$. In certain embodiments, $R^6$ is —NH$R^{F2}$.

In certain embodiments, $R^6$ is —S$R^{F1}$.

As generally defined above, $R^7$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —O$R^{G1}$; —C(=O)$R^{G2}$; —CO$_2R^{G1}$; —CN; —SCN; —S$R^{G1}$; —SO$R^{G1}$; —SO$_2R^{G2}$; —NO$_2$; —N$_3$; —N($R^G$)$_2$; —N$R^{G2}$C(=O)$R^{G2}$; —N$R^{G2}$C(=O)N($R^{G2}$)$_2$; —OC(=O)O$R^{G1}$; —OC(=O)$R^{G2}$; —OC(=O)N($R^{G2}$)$_2$; —N$R^{G2}$C(=O)O$R^{G1}$; or —C($R^{G2}$)$_3$; or $R^4$ and $R^7$ are optionally be taken together with the intervening carbon atoms to form an optionally substituted cyclic moiety; or $R^6$ and $R^7$ are optionally be taken together with the intervening carbon atoms to form an optionally substituted cyclic moiety.

In certain embodiments, $R^7$ is hydrogen.

In certain embodiments, $R^7$ is halogen. In certain embodiments, $R^7$ is fluorine.

In certain embodiments, $R^7$ is substituted or unsubstituted aliphatic. In some embodiments, $R^7$ is substituted or unsubstituted alkyl. In certain embodiments, $R^7$ is $C_1$-$C_6$ alkyl. In certain embodiments, $R^7$ is methyl. In certain embodiments, $R^7$ is ethyl. In certain embodiments, $R^7$ is propyl.

In certain embodiments, $R^7$ is substituted or unsubstituted aryl. In certain embodiments, $R^7$ is substituted or unsubstituted phenyl. In certain embodiments, $R^7$ is substituted phenyl. In certain embodiments, $R^7$ is unsubstituted phenyl.

In certain embodiments, $R^7$ is substituted or unsubstituted heteroaryl.

In certain embodiments, R is —O$R^{G1}$. In certain embodiments, R is —OH. In certain embodiments, $R^7$ is —O$R^{G1}$, wherein $R^{G1}$ is $C_{1-6}$ alkyl. In certain embodiments, $R^7$ is —O$R^{G1}$, wherein $R^{G1}$ is an oxygen-protecting group. In certain embodiments, $R^7$ is —O$R^{G1}$ wherein $R^{G1}$ is p-methoxybenzyl (PMB). In certain embodiments, $R^7$ is —O$R^{G1}$, wherein $R^{G1}$ is a silyl protecting group (e.g., TBS, TMS). In certain embodiments, $R^7$ is —O$R^{G1}$, wherein $R^{G1}$ is a carbohydrate. In certain embodiments, $R^7$ is —O$R^{G1}$, wherein $R^{G1}$ is a monosaccharide. In certain embodiments, $R^7$ is —O$R^{G1}$, wherein $R^{G1}$ is selected from the group consisting of glucose, mannose, allose, altrose, gulose, idose, galactose, talose, glucosamine, rhamnose, fucose, and derivatives thereof. In certain embodiments, $R^7$ is —O$R^{G1}$, wherein $R^{G1}$ is a disaccharide. In certain embodiments, $R^7$ is —O$R^{G1}$, wherein $R^{G1}$ is trisaccharide.

In certain embodiments, $R^7$ is —OC(=O)$R^{G2}$.

In certain embodiments, $R^7$ is —C(=O)$R^{G2}$. In certain embodiments, $R^7$ is acetyl (—C(=O)CH$_3$).

In certain embodiments, $R^7$ is —N($R^{G2}$)$_2$. In certain embodiments, $R^7$ is —NH$R^{G2}$.

In certain embodiments, $R^7$ is —S$R^{G1}$.

As generally defined above, $R^8$ is —O$R^{H1}$, wherein each occurrence of $R^{H1}$ is independently hydrogen, carbohydrate, an oxygen-protecting group, cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; or acyl.

In certain embodiments, $R^8$ is —O$R^{H1}$. In certain embodiments, $R^8$ is —OH. In certain embodiments, $R^8$ is —O$R^{H1}$, wherein $R^{H1}$ is $C_{1-6}$ alkyl. In certain embodiments, $R^8$ is —O$R^{H1}$, wherein $R^{H1}$ is an oxygen-protecting group. In certain embodiments, $R^8$ is —O$R^{H1}$ wherein $R^{H1}$ is p-methoxybenzyl (PMB). In certain embodiments, $R^8$ is —O$R^{H1}$, wherein $R^{H1}$ is a silyl protecting group (e.g., TBS, TMS). In certain embodiments, R is —O$R^H$, wherein $R^H$ is a carbohydrate. In certain embodiments, $R^8$ is —O$R^{H1}$, wherein $R^{H1}$ is a monosaccharide. In certain embodiments, $R^8$ is —O$R^{H1}$, wherein $R^{H1}$ is selected from the group consisting of glucose, mannose, allose, altrose, gulose, idose, galactose, talose, glucosamine, rhamnose, fucose, and derivatives thereof. In certain embodiments, $R^8$ is —O$R^{H1}$, wherein $R^{H1}$ is trioxacarcinoase B or a derivative thereof.

In certain embodiments, $R^8$ is —O$R^{H1}$, wherein $R^{H1}$ is of the formula:

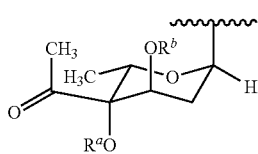

wherein $R^a$ and $R^b$ are independently selected from hydrogen; carbohydrate; an oxygen protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl. In certain embodiments, $R^a$ and $R^b$ are independently selected from hydrogen, an oxygen protecting group, or cyclic or acyclic, substituted or unsubstituted, branched or unbranched aliphatic. In certain embodiments, $R^a$ and $R^b$ are independently selected from hydrogen or an oxygen protecting group. In certain embodiments, $R^b$ is hydrogen and $R^a$ is an oxygen protecting group. In certain embodiments, $R^a$ is hydrogen and $R^b$ is an oxygen protecting group. In certain embodiments, $R^a$ is hydrogen and $R^b$ is —C(=O)CH$_3$ or —C(=)CH$_2$CH$_2$N$_3$. In certain embodiments, $R^a$ and $R^b$ are each hydrogen.

For example, in certain embodiments, wherein $R^a$ and $R^b$ are each hydrogen, $R^{H1}$ is of the formula:

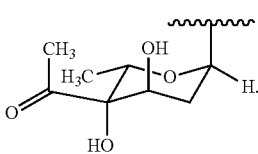

In certain embodiments, R is —OR$^{H1}$, wherein $R^{H1}$ is a fluorinated derivative of trioxacarcinose B, wherein one or more hydrogen atoms has been replaced by fluorine. For example, in certain embodiments, $R^8$ is —OR$^{H1}$ and $R^{H1}$ is of one of the formulae:

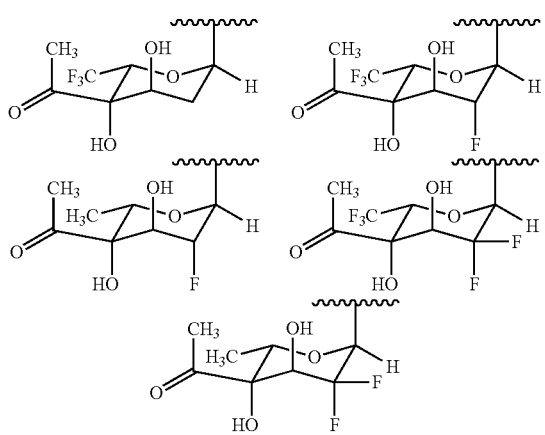

wherein each occurrence of R is independently hydrogen; an oxygen-protecting group; acyl; or $C_{1-6}$ alkyl.

In certain embodiments, $R^8$ is —OR$^{H1}$, wherein $R^{H1}$ is a disaccharide. In certain embodiments, $R^8$ is —OR$^{H1}$, wherein $R^{H1}$ is trisaccharide. In certain embodiments, $R^8$ is —OR$^{H1}$, wherein $R^{H1}$ is not a carbohydrate.

In certain embodiments, $R^{H1}$ is acyl, e.g., a group of the formula —C(=O)R$^{H2}$, wherein $R^{H2}$ is independently cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; alkoxy; aryloxy; alkylthio; arylthio; amino, alkylamino, dialkylamino, heteroaryloxy; or heteroarylthio.

As generally defined above, $R^9$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —OR$^{I1}$; —C(=O)R$^{I2}$; —CO$_2$R$^{I1}$; —CN; —SCN; —SR$^{I1}$; —SOR$^{I1}$; —SO$_2$R$^{I2}$; —NO$_2$; —N$_3$; —N(R$^{I2}$)$_2$; —NR$^{I2}$C(=O)R$^{I2}$; —NR$^{I2}$C(=O)N(R$^{I2}$)$_2$; —OC(=O)OR$^{I1}$; —OC(=O)R$^{I2}$; —OC(=O)N(R$^{I2}$)$_2$; —NR$^{I2}$C(=O)OR$^{I1}$; or —C(R$^{I2}$)$_3$.

In certain embodiments, $R^9$ is hydrogen.

In certain embodiments, $R^9$ is halogen. In certain embodiments, $R^9$ is fluorine.

In certain embodiments, $R^9$ is substituted or unsubstituted aliphatic. In some embodiments, $R^9$ is substituted or unsubstituted alkyl. In certain embodiments, $R^9$ is $C_1$-$C_6$ alkyl. In certain embodiments, $R^9$ is methyl. In certain embodiments, $R^9$ is ethyl. In certain embodiments, $R^9$ is propyl.

In certain embodiments, $R^9$ is —C(R$^{I2}$)$_3$. In certain embodiments, $R^9$ is —CH$_2$R$^{I2}$. In certain embodiments, $R^9$ is —CH(R$^{I2}$)$_2$. In certain embodiments, $R^9$ is —CH(R$^{I2}$)$_2$, wherein $R^I$ are different. In certain embodiments, $R^9$ is —CH(R$^{I2}$)$_2$, wherein $R^I$ are the same. In certain embodiments, $R^9$ is —CH(R$^{I2}$)$_2$, wherein each of $R^{I2}$ is independently hydrogen, alkyl, or alkyoxy. In certain embodiments, $R^9$ is —CH(R$^{I2}$)$_2$, wherein each of $R^I$ is independently alkyoxy. In certain embodiments, $R^9$ is —CH(R$^{I2}$)$_2$, wherein each of $R^{I2}$ is independently $C_1$-$C_6$ alkyoxy. For example, in certain embodiments, $R^9$ is —CH(OCH$_3$)$_2$.

In certain embodiments, $R^9$ is —CH(OR$^{I3}$)$_2$, wherein $R^{I3}$ is hydrogen, alkyl, aryl, heteroayl, or a carbohydrate. In certain embodiments, $R^9$ is —CH(OR$^{I3}$)$_2$, wherein the two —OR$^I$ are different. In certain embodiments, $R^9$ is —CH(OR$^{I3}$)$_2$, wherein the two —OR$^{I3}$ are the same. In certain embodiments, $R^9$ is —CH(OR$^{I3}$)$_2$, wherein one $R^{I3}$ is $C_{1-6}$ alkyl, and the other $R^{I3}$ is a carbohydrate. In certain embodiments, $R^9$ is —CH(OR$^{I3}$)$_2$, wherein one $R^{I3}$ is $C_{1-6}$ alkyl, and the other $R^{I3}$ is a monosaccharide or a disaccharide.

In certain embodiments, $R^9$ is —CH$_2$(OR$^{I3}$), wherein $R^{I3}$ is hydrogen, alkyl, aryl, heteroayl, or a carbohydrate.

In certain embodiments, $R^9$ is substituted or unsubstituted aryl. In certain embodiments, $R^9$ is substituted or unsubstituted phenyl. In certain embodiments, $R^9$ is substituted phenyl. In certain embodiments, $R^9$ is unsubstituted phenyl.

In certain embodiments, $R^9$ is substituted or unsubstituted heteroaryl.

In certain embodiments, In certain embodiments, $R^9$ is —OR$^1$. In certain embodiments, $R^9$ is —OR, wherein $R^{I1}$ is hydrogen. In certain embodiments, $R^9$ is —OR$^{I1}$, wherein $R^{I1}$ is $C_{1-6}$ alkyl. In certain embodiments, $R^9$ is —OR$^{I1}$, wherein $R^{I1}$ is an oxygen-protecting group. In certain embodiments, $R^9$ is —OR$^{I1}$, wherein $R^{I1}$ is p-methoxybenzyl (PMB). In certain embodiments, $R^9$ is —OR$^{I1}$, wherein $R^{I1}$ is a silyl protecting group (e.g., TBS, TMS). In certain embodiments, $R^9$ is —OR$^{I1}$, wherein $R^{I1}$ is a carbohydrate. In certain embodiments, $R^9$ is —OR$^{I1}$, wherein $R^{I1}$ is a monosaccharide. In certain embodiments, $R^9$ is —OR$^{I1}$, wherein $R^{I1}$ is selected from the group consisting of glucose, mannose, allose, altrose, gulose, idose, galactose, talose, glucosamine, rhamnose, fucose, and derivatives thereof. In certain embodiments, $R^9$ is —$OR^{J1}$, wherein $R^{J1}$ is a disaccharide. In certain embodiments, $R^9$ is —$OR^{J1}$, wherein $R^{J1}$ is a trisaccharide. In certain embodiments, $R^9$ is —$OR^{J1}$, wherein $R^{J1}$ is not a carbohydrate.

In certain embodiments, $R^9$ is —$OC(=O)R^{J2}$.

In certain embodiments, $R^9$ is —$C(=O)R^{J2}$. In certain embodiments, $R^9$ is acetyl (—$C(=O)CH_3$).

In certain embodiments, $R^9$ is —$N(R^{J2})_2$. In certain embodiments, $R^9$ is —$NHR^{J2}$.

In certain embodiments, $R^9$ is —$SR^{J2}$.

In certain embodiments, the compound of Formula (I) is a compound having the following stereochemistry, e.g., a compound of the Formula (II):

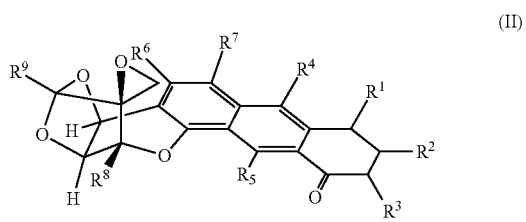

(II)

and pharmaceutically acceptable forms thereof.

Alternatively, in certain embodiments, the compound of Formula (I) is a compound having the following stereochemistry, e.g., a compound of the Formula (III):

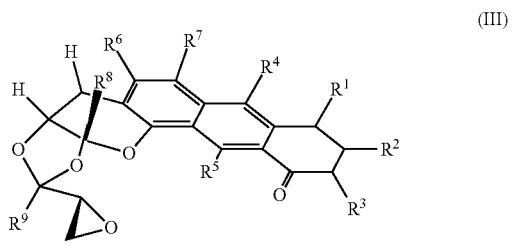

(III)

and pharmaceutically acceptable forms thereof.

Figure 1C:
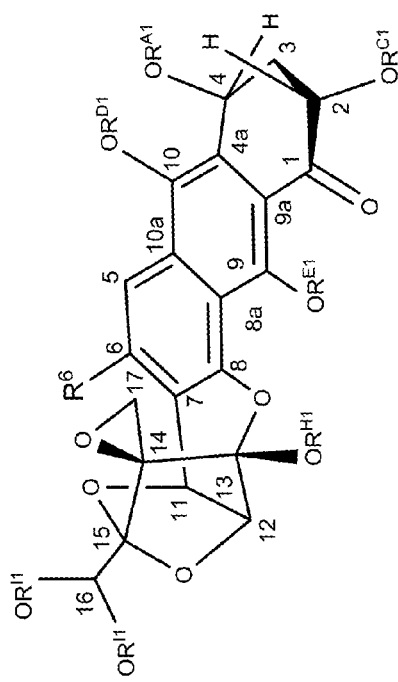
Figure 1C:
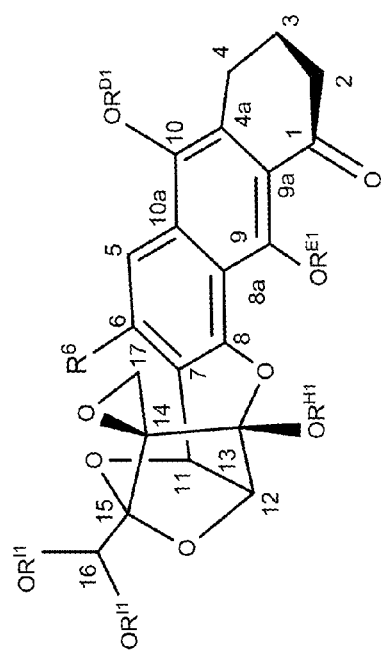

In certain embodiments, the compound of Formula (III) is an epimer of a compound of Formula (II). As used herein, an "epimer" of a compound of Formula (II) refers to the "iso" derivative of the compound, i.e., epimeric at C11, C12, and C13 of the trioxacarcin scaffold (see FIG. 1C for numbering).

In certain embodiments, the compound of Formula (II) is a compound of the Formula (II-a):

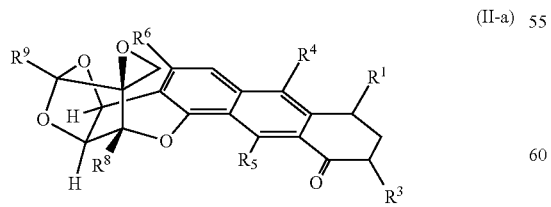

(II-a)

and pharmaceutically acceptable forms thereof.

In certain embodiments of Formula (II-a), $R^1$ is —$OR^{A1}$ wherein $R^{A1}$ is an oxygen protecting group, and $R^3$ is —OH. In certain embodiments, $R^3$ is —$OR^{C1}$ wherein $R^{C1}$ is an oxygen protecting group, and $R^1$ is —OH. In certain embodiments, $R^1$ is —$OR^{A1}$, $R^3$ is —$OR^{C1}$, and $R^{A1}$ and $R^{C1}$ are orthogonal oxygen protecting groups. In certain embodiments, $R^8$ is —$OR^{H1}$ and $R^{H1}$ is hydrogen or a carbohydrate. In certain embodiments, $R^8$ is —$OR^{H1}$ and $R^{H1}$ is a carbohydrate, and $R^1$ and $R^2$ are both —OH or orthogonal oxygen protecting groups.

In certain embodiments, the invention provides compounds of the Formula (II-b):

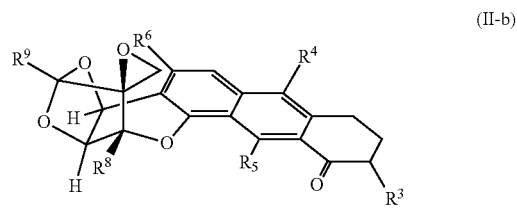

(II-b)

and pharmaceutically acceptable forms thereof.

In certain embodiments of Formula (II-b), $R^3$ is —$OR^{C1}$ wherein $R^{C1}$ is hydrogen or an oxygen protecting group. In certain embodiments, $R^8$ is —$OR^{H1}$ and $R^{H1}$ is hydrogen or a carbohydrate. In certain embodiments, R is —$OR^{H1}$ and $R^{H1}$ is a carbohydrate, and R is —OH or an oxygen protecting group.

In certain embodiments, the invention provides compounds of the Formula (II-c):

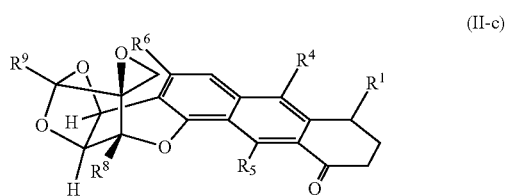

(II-c)

and pharmaceutically acceptable forms thereof.

In certain embodiments of Formula (II-c), $R^1$ is —$OR^{A1}$ wherein $R^{A1}$ is hydrogen or an oxygen protecting group. In certain embodiments, R is —$OR^{H1}$ and $R^{H1}$ is hydrogen or a carbohydrate. In certain embodiments, R is —$OR^{H}$ and $R^{H1}$ is a carbohydrate, and $R^1$ is —OH or an oxygen protecting group.

In certain embodiments, the invention provides compounds of the Formula (II-d):

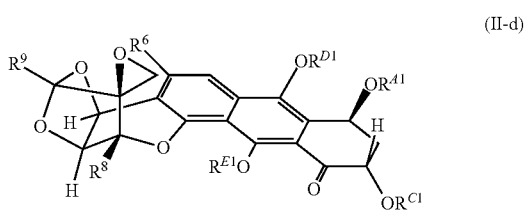

(II-d)

and pharmaceutically acceptable forms thereof.

In certain embodiments, the invention provides compounds of the Formula (II-e):

(II-e)

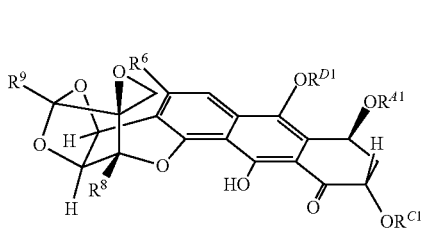

and pharmaceutically acceptable forms thereof.

In certain embodiments, the invention provides compounds of the Formula (II-f):

(II-f)

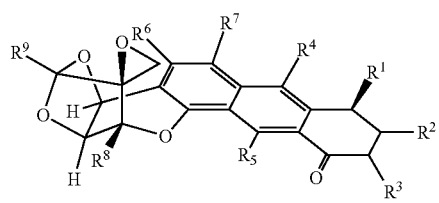

and pharmaceutically acceptable forms thereof.

In certain embodiments, the invention provides compounds of the Formula (II-g):

(II-g)

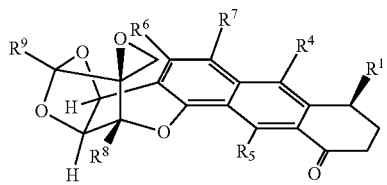

and pharmaceutically acceptable forms thereof.

In certain embodiments, the invention provides compounds of the Formula (I-h):

(II-h)

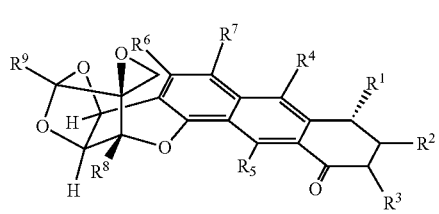

and pharmaceutically acceptable forms thereof.

In certain embodiments, the invention provides compounds of the Formula (II-i):

(II-i)

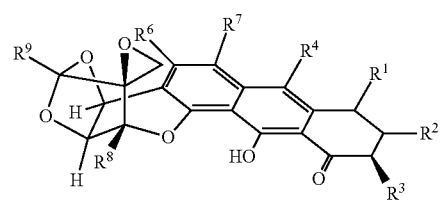

and pharmaceutically acceptable forms thereof.

In certain embodiments, the invention provides compounds of the Formula (II-j):

(II-j)

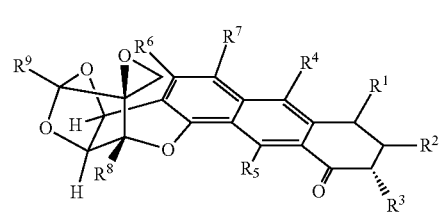

and pharmaceutically acceptable forms thereof.

In certain embodiments, the invention provides compounds of the Formula (II-k):

(II-k)

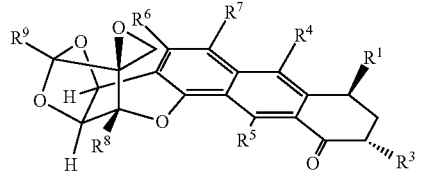

and pharmaceutically acceptable forms thereof.

In certain embodiments, the invention provides compounds of the Formula (II-l):

(II-l)

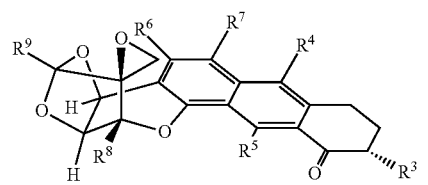

and pharmaceutically acceptable forms thereof.

In certain embodiments, the invention provides compounds of the Formula (II-m):

(II-m)

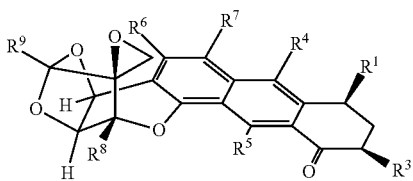

and pharmaceutically acceptable forms thereof.

In certain embodiments, the invention provides compounds of the Formula (II-n):

(II-n)

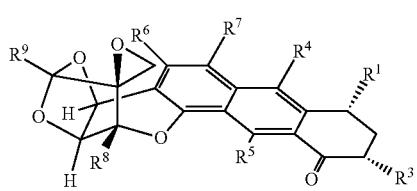

and pharmaceutically acceptable forms thereof.

In certain embodiments, the invention provides compounds of the Formula (II-o):

(II-o)

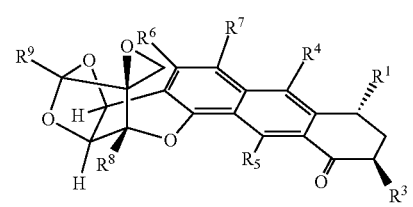

and pharmaceutically acceptable forms thereof.

In certain embodiments, the invention provides compounds of the Formula (II-p):

(II-p)

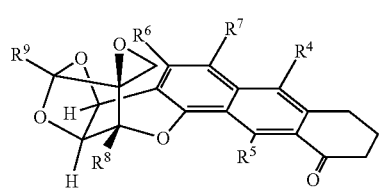

and pharmaceutically acceptable forms thereof.

In certain embodiments, the invention provides compounds of the Formula (II-q):

(II-q)

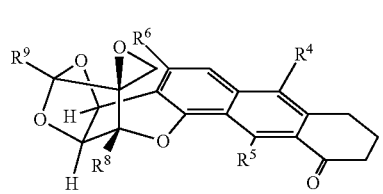

and pharmaceutically acceptable forms thereof.

In certain embodiments, the invention provides compounds of the Formula (II-r):

(II-r)

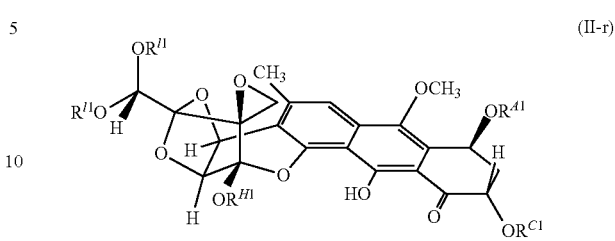

and pharmaceutically acceptable forms thereof.

In certain embodiments, the invention provides compounds of the Formula (II-s):

(II-s)

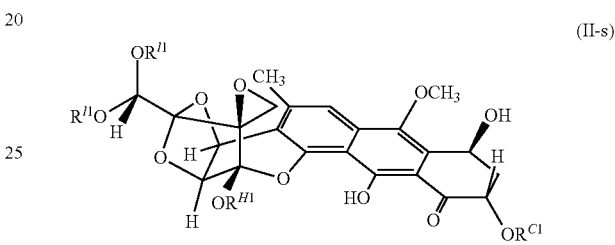

and pharmaceutically acceptable forms thereof, wherein $R^{C1}$ is not hydrogen.

In certain embodiments, the invention provides compounds of the Formula (II-t):

(II-t)

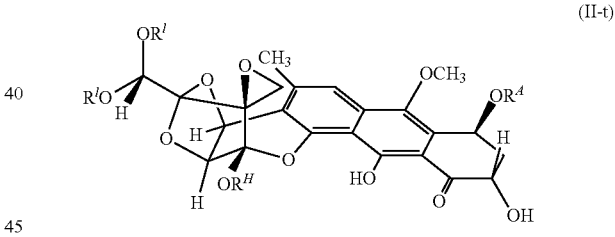

and pharmaceutically acceptable forms thereof, wherein $R^{A1}$ is not hydrogen.

In certain embodiments, the invention provides compounds of the Formula (II-u):

(II-u)

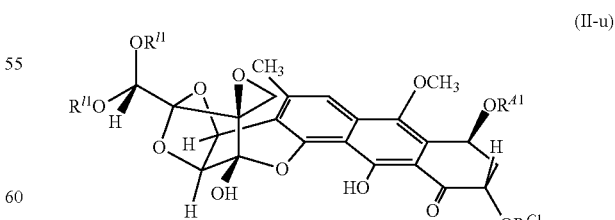

and pharmaceutically acceptable forms thereof, wherein $R^{A1}$ and/or $R^{C1}$ are not hydrogen.

In certain embodiments, the invention provides compounds of the Formula (II-v):

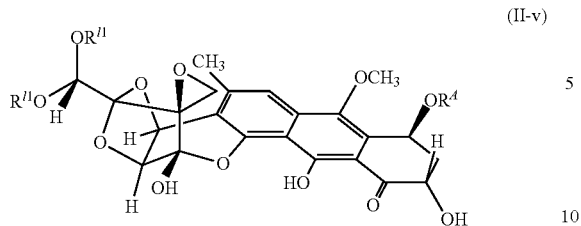

(II-v)

and pharmaceutically acceptable forms thereof, wherein $R^{A1}$ and/or $R^{C1}$ is not hydrogen.

In certain embodiments, the invention provides compounds of the Formula (II-w):

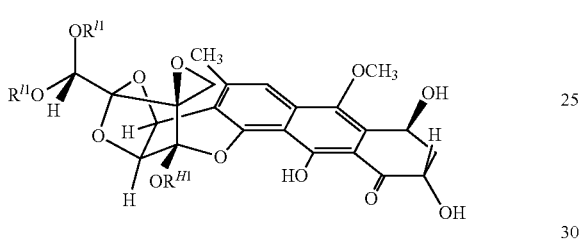

(II-w)

and pharmaceutically acceptable forms thereof, wherein $R^{AH}$ is not hydrogen.

Exemplary compounds of Formula (I) include, but are not limited to:

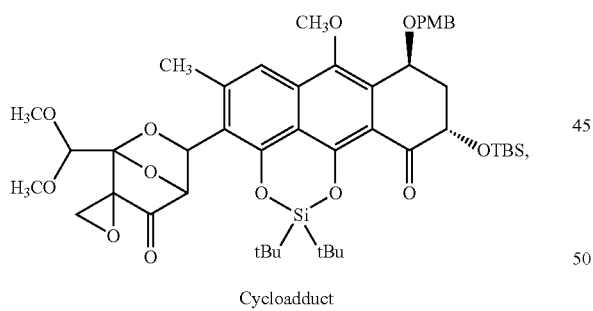

Cycloadduct

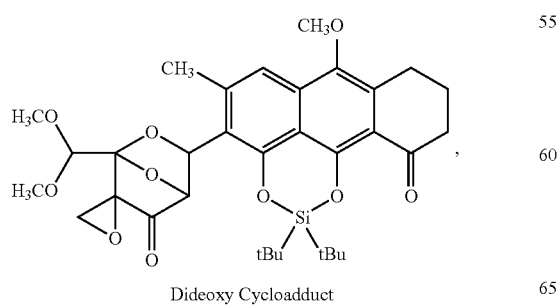

Dideoxy Cycloadduct

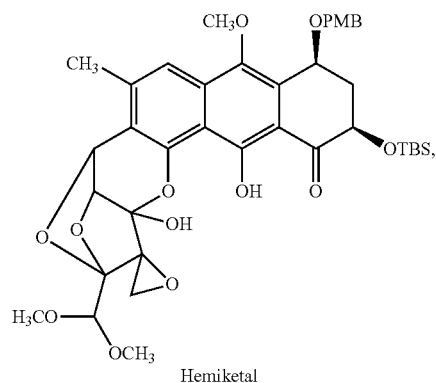

Hemiketal

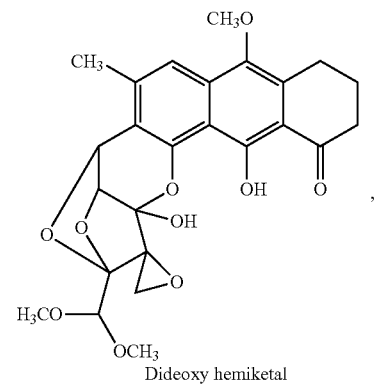

Dideoxy hemiketal

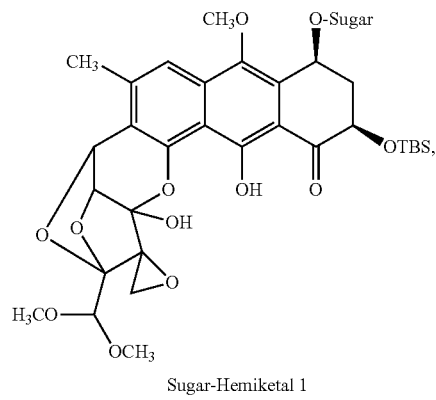

Sugar-Hemiketal 1

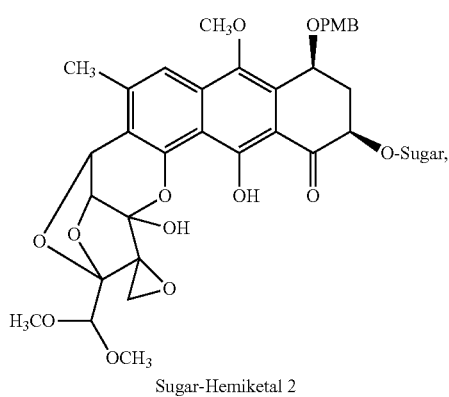

Sugar-Hemiketal 2

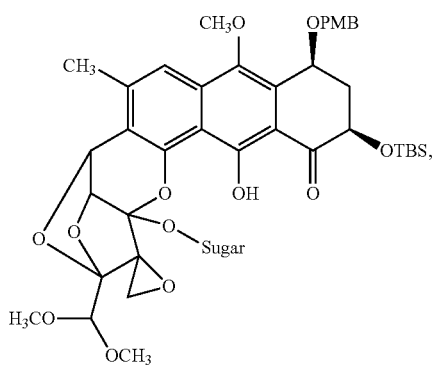
Sugar-Hemiketal 3
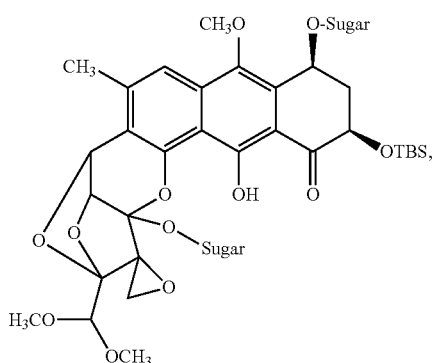
Sugar-Hemiketal 4
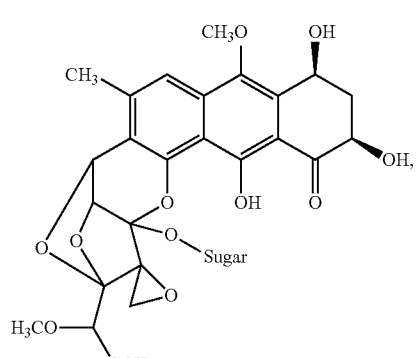
Sugar-Hemiketal 5
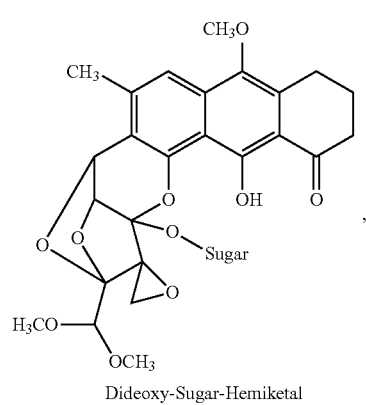
Dideoxy-Sugar-Hemiketal
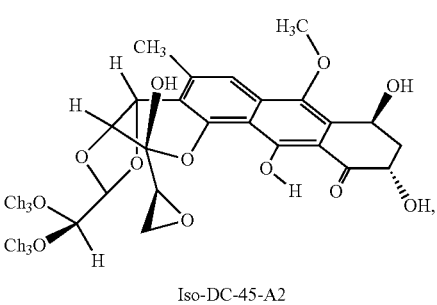
Iso-DC-45-A2
or salts thereof, wherein Sugar is a carbohydrate group as defined herein.
In certain embodiments, the cycloadduct is any one of the following stereoisomers:
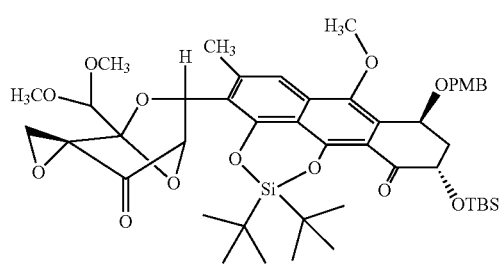
Exo cycloadduct 1
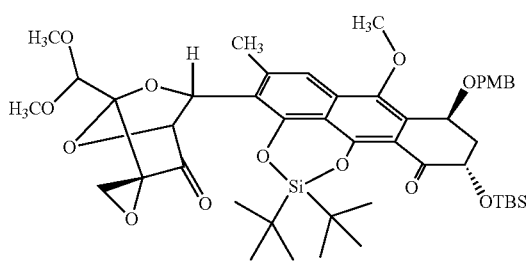
Endo cycloadduct 1
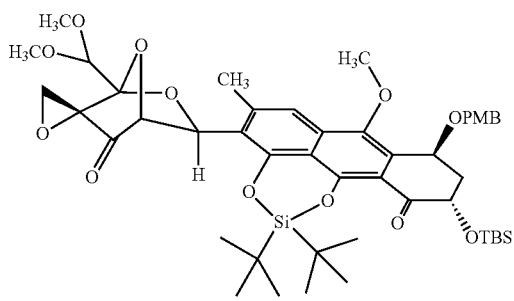
Exo cycloadduct 2

-continued

Endo cycloadduct 2

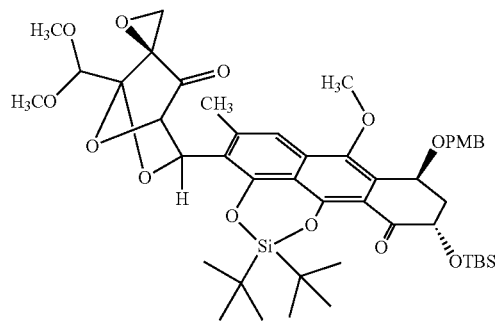

or salt thereof.

In certain embodiments, the hemiketal is any one of the following stereoisomers:

Endo 1 hemiketal

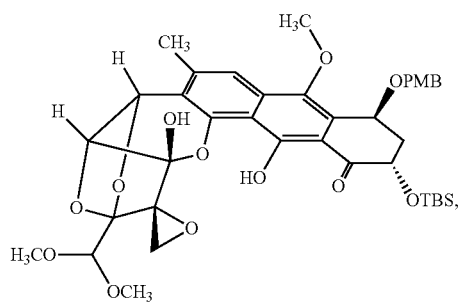

"Differentially protected iso-DC-45-A2"

Endo 2 hemiketal

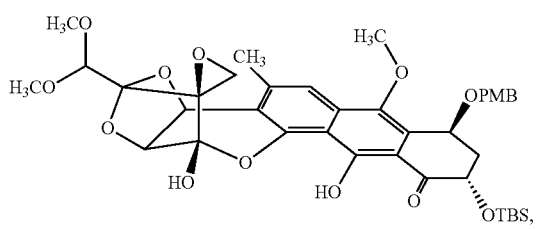

"Differentially protected DC-45-A2"

or salt thereof.

In certain embodiments, the dideoxy cycloadduct is any one of the following stereoisomers:

Dideoxy Exo cycloadduct 1

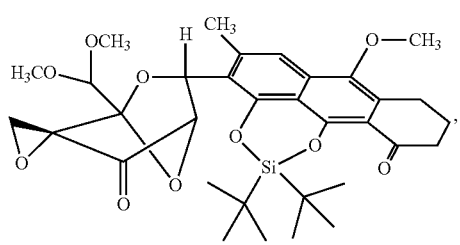

-continued

Dideoxy Endo cycloadduct 1

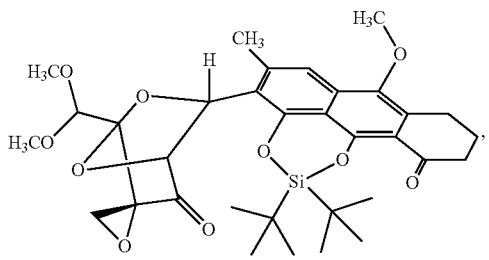

Dideoxy Exo cycloadduct 2

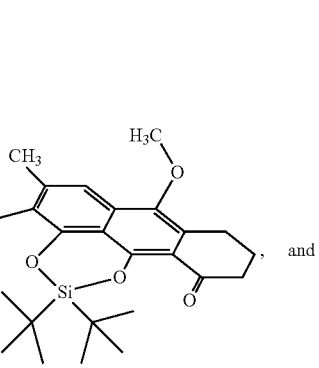

Dideoxy Endo cycloadduct 2

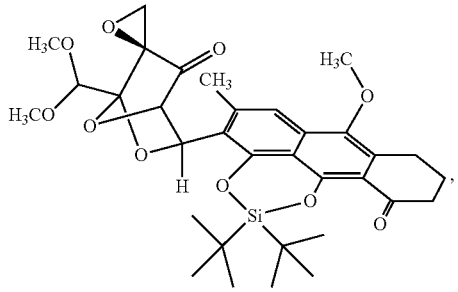

or salt thereof.

In certain embodiments, the dideoxy hemiketal is any one of the following stereoisomers:

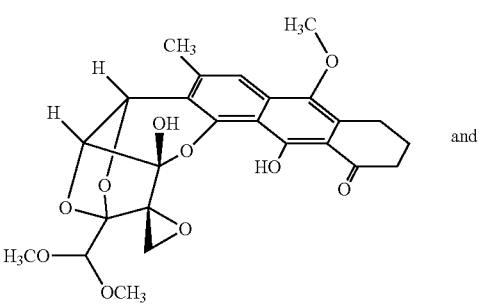

Dideoxy Endo 1 hemiketal
"Iso-Dideoxy-DC-45-A2"

-continued

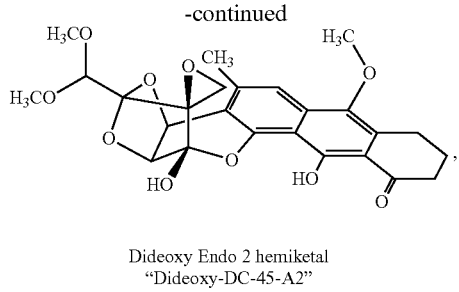

Dideoxy Endo 2 hemiketal
"Dideoxy-DC-45-A2", or salt thereof.

In certain embodiments, the Sugar-Hemiketal 1 is:

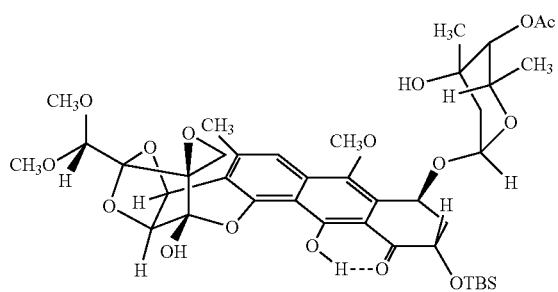

or salt thereof.

In certain embodiments, the Sugar-Hemiketal 3 is:

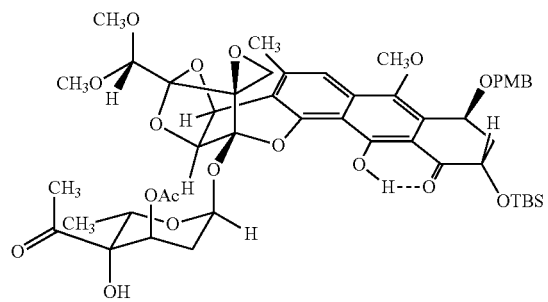

or salt thereof.

In certain embodiments, the Sugar-Hemiketal 4 is:

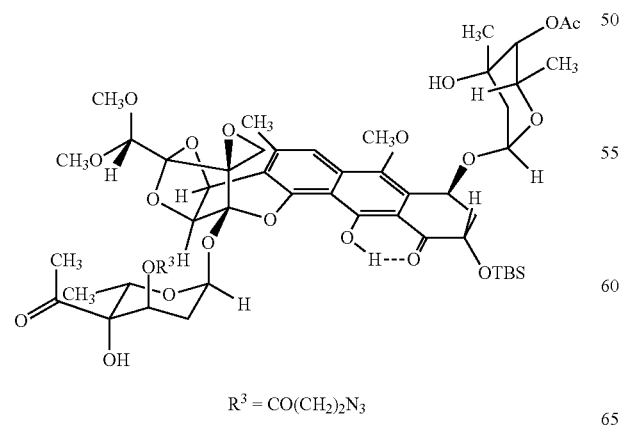

$R^3$ = CO(CH$_2$)$_2$N$_3$ or salt thereof.

In certain embodiments, the Sugar-Hemiketal 5 is:

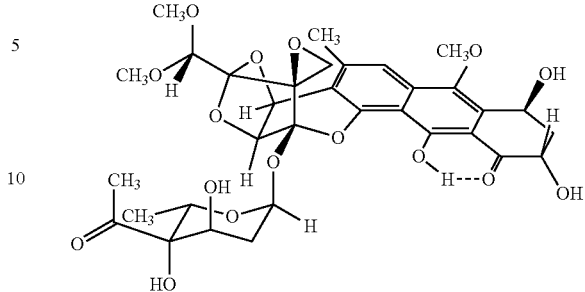

or salt thereof.

In certain embodiments, the Dideoxy-Sugar-Hemiketal is:

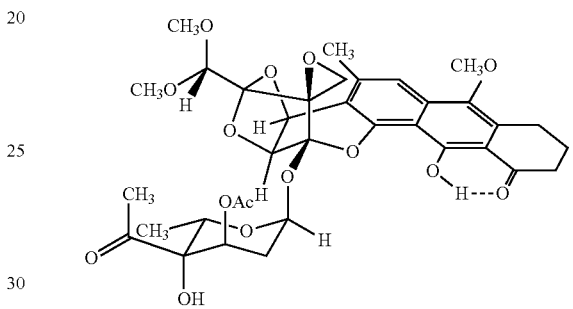

or salt thereof.

In yet another aspect, also provide is a compound of the Formula (IV):

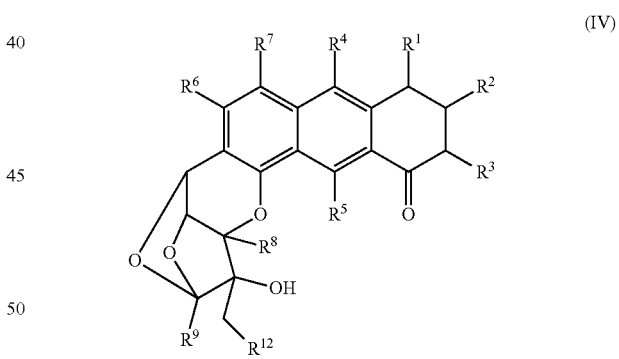

(IV)

wherein $R^1$, $R^2$, $R^3$, $R^4$, $R^5$, $R^6$, $R^7$, $R^8$, and $R^9$ are as defined herein, and $R^{12}$ is a polynucleotide; hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —OR$^{L1}$; —CN; —SCN; —SR$^{L1}$; —N$_3$; —N(R$^{L2}$)$_2$; —NR$^{L2}$C(=O)R$^{L2}$; —NR$^{L2}$C(=O)N(R$^{L2}$)$_2$; —OC(=O) OR$^{L1}$; —OC(=O)R$^{L2}$; —OC(=O)N(R$^{L2}$)$_2$; —NR$^{L2}$C (=O)OR$^{L1}$; or —C(R$^{L2}$)$_3$; wherein each occurrence of R$^{L1}$ is independently hydrogen, a protecting group, cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein occurrence of $R^{L2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; substituted hydroxyl (e.g., alkoxy; aryloxy; heteroaryloxy); substituted thiol (e.g., alkylthio; arylthio; heteroarylthio); amino; or substituted amino (e.g., alkylamino, dialkylamino); or two $R^{L2}$ groups are optionally joined to form a heterocyclyl or heteroaryl ring.

In certain embodiments, $R^{12}$ is hydrogen.

In certain embodiments, $R^{12}$ is halogen. In certain embodiments, $R^{12}$ is fluoro. In certain embodiments, $R^{12}$ is bromo. In certain embodiments, $R^{12}$ is chloro. In certain embodiments, $R^{12}$ is iodo.

In certain embodiments, $R^{12}$ is cyclic or acyclic, substituted or unsubstituted, branched or unbranched aliphatic.

In certain embodiments, $R^{12}$ is —$OR^{L1}$.

In certain embodiments, $R^{12}$ is —$SR^{L1}$.

In certain embodiments, $R^{12}$ is a polynucleotide.

In certain embodiments, R is —$N(R^{L2})_2$. In certain embodiments, $R^{12}$ comprises a guanine base. In certain embodiments, $R^{12}$ comprises guanine that is part of a strand of DNA. In certain embodiments, R is —$NH(R^{L2})$ wherein $R^{L2}$ is a heterocyclyl group; in such instance, in certain embodiments, R is selected from a guanine, adenine, or cytosine moiety. In certain embodiments, $R^{12}$ is a guanine moiety. In certain embodiments, the guanine, adenine, or cytosine moieties are optionally part of a strand of DNA.

In certain embodiments, $R^{12}$ is —$C(R^L)_3$.

In certain embodiments, the compound of Formula (IV) has any one of the following stereochemistry:

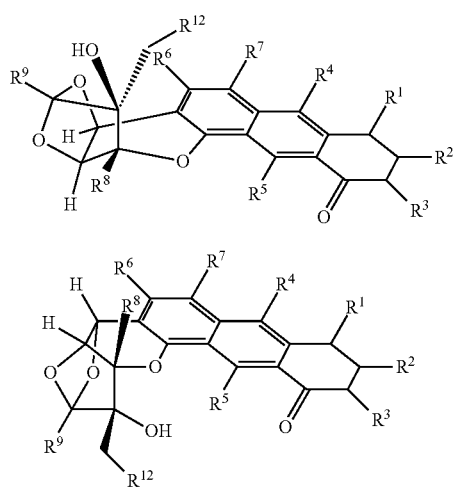

An exemplary compound of Formula (IV) includes, but is not limited to:

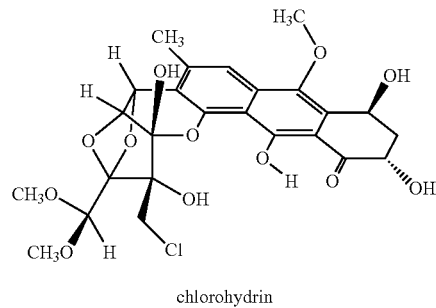

chlorohydrin or salt thereof.

Compounds of Formula (IV), (V) and (VI) may be generated by reaction of a compound of Formula (I), (II) or (III) with a nucleophile. For example, nucleophiles such as N7 of guanine of a DNA duplex are known to react with the epoxide moiety of trioxacarcin A to alkylate DNA. Therefore, in certain embodiments, a compound of Formula (I), (II) or (III) may react with a nucleophile in vivo or in vitro to form a compound of the Formula (IV), (V) and (VI), respectively.

Methods of Synthesis

The present invention provides methods of preparing trioxacarcins and analogs thereof. In certain embodiments, the present invention provides methods of synthesizing an inventive compound. In other embodiments, the present invention provides methods of synthesizing a trioxacarcin natural product (e.g., trioxacarcin A, trioxacarcin B, trioxacarcin C, trioxacarcin D, trioxacarcin E, trioxacarcin F, DC-45-$A_1$, DC-45-$A_2$). As would be appreciated by one of skill in the art, the synthetic methods described herein may be modified without departing from the scope of the present invention. For example, different starting materials, reagents, and/or conditions may be used in the inventive synthetic methods.

Figure 4:
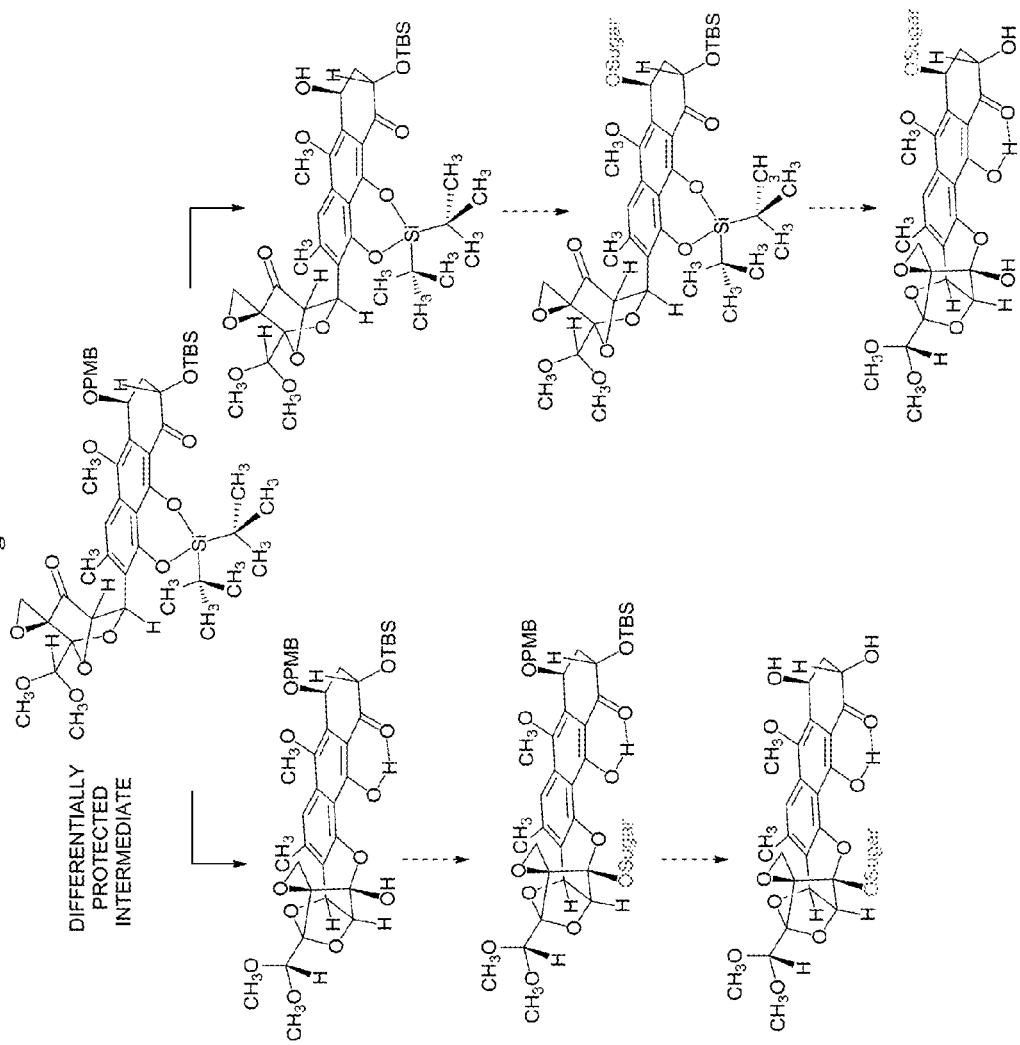
FIG. 4 shows glycosylation of differentially protected aglycones from endo cycloadduct (3).
Figure 5:
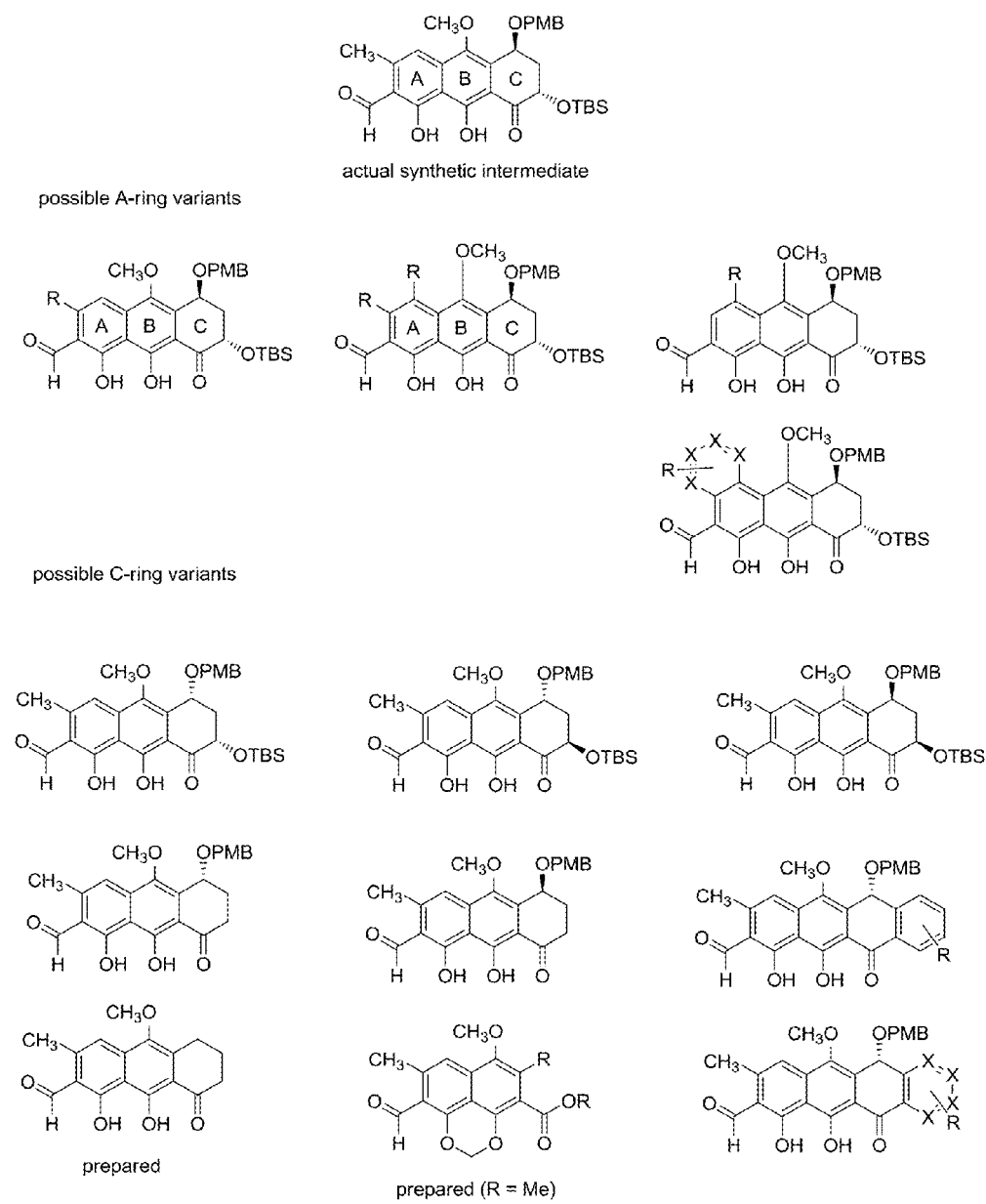
FIG. 5 shows exemplary variants of the aldehydes coupling partner.

In certain embodiments, the inventive compounds are prepared via a route as shown below and as exemplified in FIGS. 2A-2D. The three components of similar complexity, an enone, a cyanophthalide, and a diazoketone, are joined to form a 1,3-dipolar cycloadduct which upon deprotection undergoes spontaneous hemiketalization to form the trioxacarcin skeleton. A differentially protected form of the aglycone of trioxacarcins is then formed. Subsequent deprotection and reaction with an alkylating, glycosylating, or acylating reagent yields a trioxacarcin or an analog thereof. An exemplary scheme for differentially deprotecting and reacting two of the hydroxyl moieties of the trioxacarcin skeleton is shown in FIG. 4.

Figure 3:
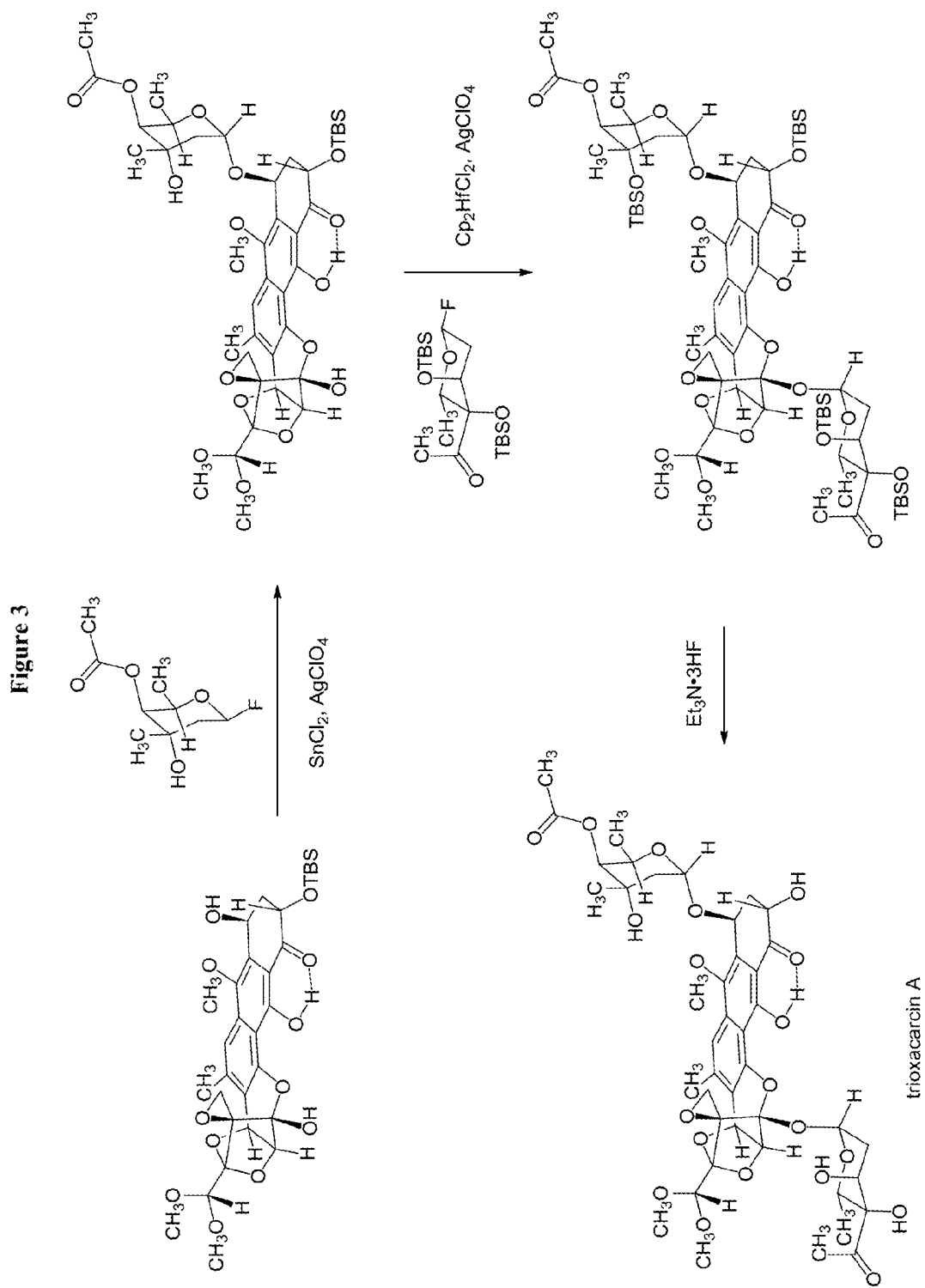
FIG. 3 shows an exemplary glycosylation sequence of DC-45-A2 to trioxacarcin A.

As shown in FIG. 3, the aglycone can be glycosylated in a few steps using known methods to yield trioxacarcin A or other trioxacarcins. In particular, positions 2, 4, and/or 13 may be glycosylated. As would be appreciated by one of skill in the art, other hydroxyl moieties of the trioxacarcin skeleton may also be glycosylated.

In certain embodiments, the invention provides a method of preparing an anthrone of formula:

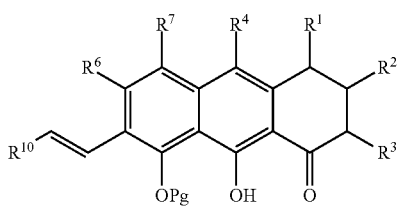

or salt thereof; wherein $R^1$, $R^2$, $R^3$, $R^4$, $R^6$, and $R^7$ are as defined above and herein;

$R^{10}$ is hydrogen; cyclic or acyclic, substituted or unsubstituted, branched or unbranched aliphatic; cyclic or acyclic, substituted or unsubstituted, branched or unbranched heteroaliphatic; acyl; substituted or unsubstituted, branched or unbranched aryl; substituted or unsubstituted, branched or unbranched heteroaryl; and Pg is hydrogen, alkyl, or an oxygen-protecting group;

comprising reacting an enone of formula:

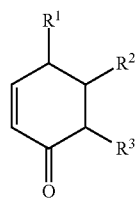

or salt thereof; with a cyanophthalide of formula:

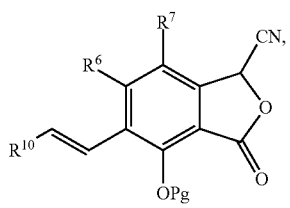

or salt thereof.

In certain embodiments, $R^7$ is hydrogen, e.g., to provide a cyanophthalide of the formula:

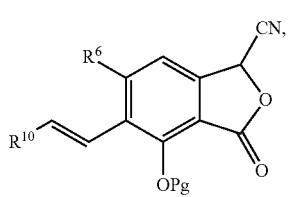

or salt thereof.

In certain embodiments, the enone is of the formula:

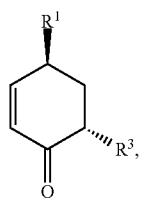

or salt thereof.

In certain embodiments, the invention provides a method of preparing an aldehyde of formula:

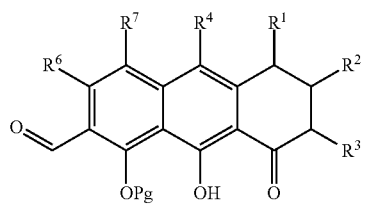

or salt thereof; wherein $R^1$, $R^2$, $R^3$, $R^4$, $R^6$, $R^7$, and Pg are as defined above; comprising oxidatively cleaving the alkenyl side chain of the anthrone of formula:

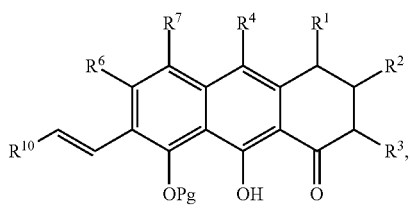

or salt thereof; wherein $R^{10}$ is as defined above.

In certain embodiments, the invention provides a method of preparing a silacycle of formula:

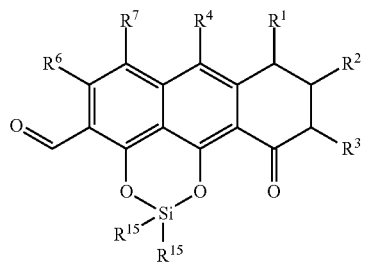

or salt thereof; comprising deprotecting the aldehyde of the formula:

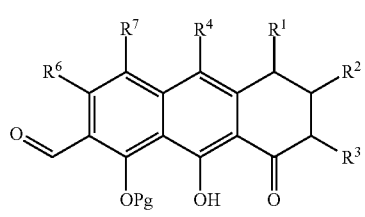

or salt thereof; to provide a diol of the formula:

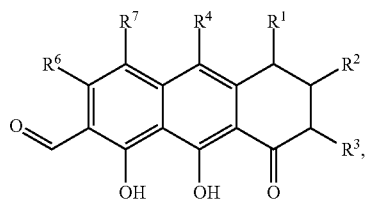

or salt thereof; and treating the diol with a silyl reagent of the formula $Si(R^{15})G_2$ wherein $R^{15}$ is an cyclic or acyclic, branched or unbranched, substituted or unsubstituted aliphatic, substituted or unsubstituted aryl, or substituted or unsubstituted heteroaryl, and G is a leaving group to provide the silacycle.

In certain embodiments, $R^{15}$ is branched or unbranched, substituted or unsubstituted aliphatic. In certain embodiments, $R^{15}$ is tBu. In certain embodiments, G is halogen. In certain embodiments, G is chloro.

In certain embodiments, the invention provides a method of preparing a cycloadduct of the Formula:

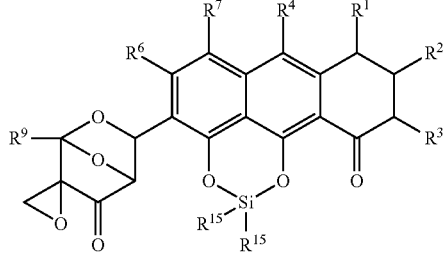

or salt thereof, wherein $R^1$, $R^2$, $R^3$, $R^4$, $R^6$, $R^7$, $R^9$, and $R^{15}$, are as defined above and herein; comprising reacting the silacycle of formula:

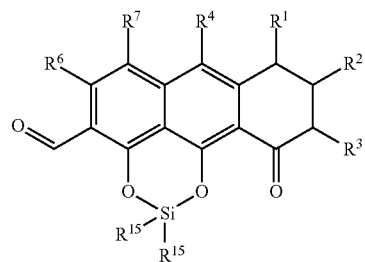

or salt thereof, with a diazoketone of formula:

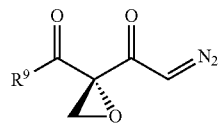

or salt thereof, wherein $R^9$ is as defined above and herein.

In certain embodiments, $R^9$ is —$CH(OR^{J1})_2$. In certain embodiments, both $R^{J1}$ are $C_{1-6}$ alkyl. In certain embodiments, both $R^{J1}$ are methyl. In certain embodiments, both $R^{J1}$ are oxygen-protecting groups.

In certain embodiments, the cycloadduct is a mixture of two, three, or four stereoisomers. For example, in certain embodiments, the cycloadduct is a mixture of any two, three or four stereoisomers:

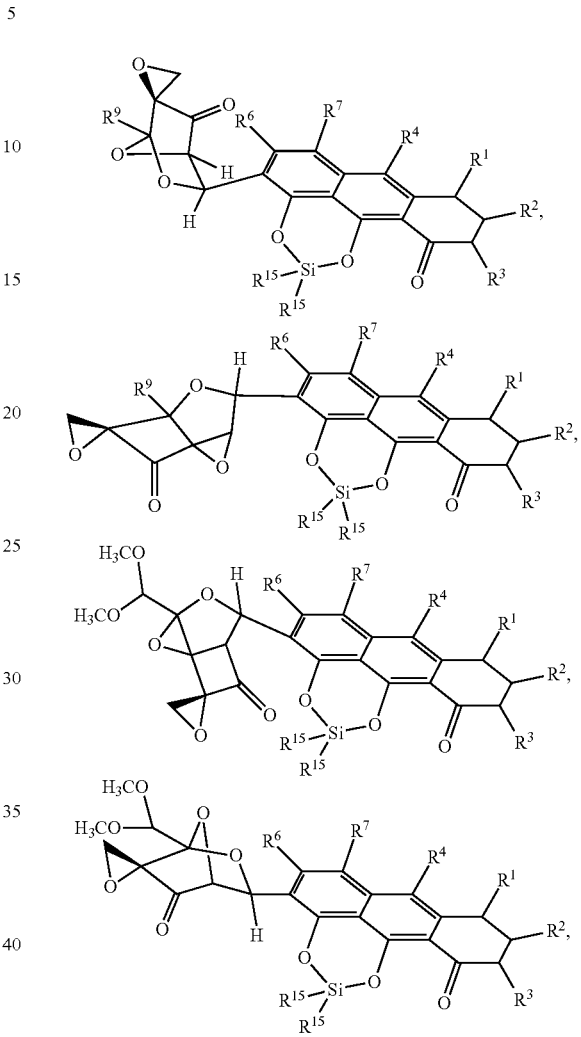

or salt thereof.

The stereoisomers may be isolated by standard methods known in the art. The conditions of the reaction and/or the starting materials may be modified to adjust the ratio of the four possible stereoisomers. For example, in certain embodiments, the reaction employs a rhodium catalyst. In certain embodiments, the reaction employs a copper catalyst.

Alternatively, instead of the diazoketone, a halohydrin may be used in the above inventive method, e.g., a halohydrin of the formula:

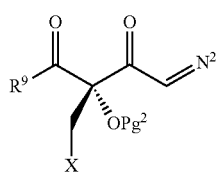

or salt thereof, wherein $R^9$ is as defined above and herein; X is a leaving group, and $Pg^2$ is independently hydrogen, alkyl, or an oxygen-protecting group.

For example, in certain embodiments, the invention provides a method of preparing a cycloadduct of the formula:

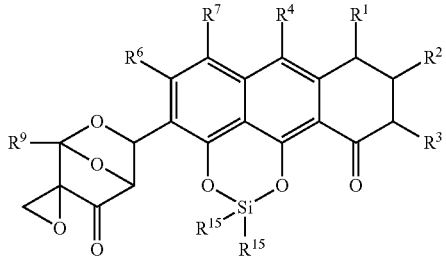

or salt thereof, wherein $R^1$, $R^2$, $R^3$, $R^4$, $R^6$, $R^7$, $R^9$, and $R^{15}$, are as defined above and herein; comprising:

reacting an aldehyde of formula:

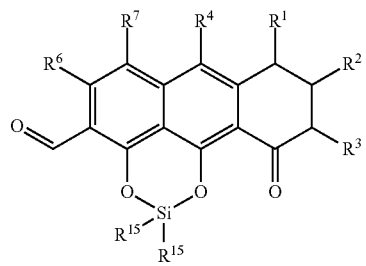

or salt thereof, with a halohydrin ketone of formula:

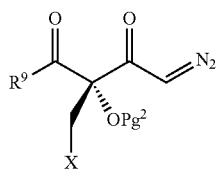

or salt thereof, wherein $R^9$ and $Pg^2$ are as defined above and X is a leaving group; to provide a cycloadduct of the formula:

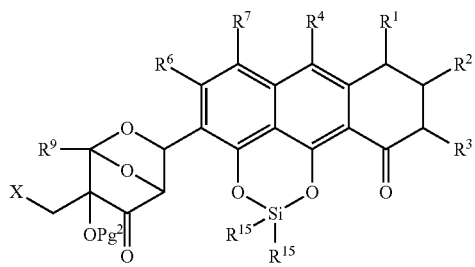

or salt thereof, and optionally deprotecting $Pg^2$ (i.e., in the instance when $Pg^2$ is alkyl or an oxygen protecting group) and cyclizing to form the epoxide, i.e., providing the cycloadduct of the formula:

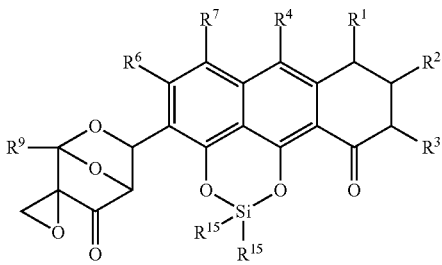

or salt thereof.

In certain embodiments, $R^9$ is —$CH(OR^{I1})_2$. In certain embodiments, both $R^I$ are $C_{1-6}$ alkyl. In certain embodiments, both $R^I$ are methyl. In certain embodiments, both $R^I$ are an oxygen-protecting group (e.g., a cyclic acetal). In certain embodiments, X is bromine, chlorine, or iodine. In certain embodiments, X is chlorine. In certain embodiments, X is —OTs. In certain embodiments, $Pg^2$ is a silyl-protecting group.

In certain embodiments, the step of cyclizing comprises deprotecting the protected hydroxyl group of the halohydrin to form an epoxide moiety. For example, in certain embodiments, the $PG^2$ is a silyl ether and the silyl group is removed by a source of fluoride anion (e.g., tetrabutylammonium fluoride (TBAF)) to provide an anion. In this instance, the anion attacks the group X to provide the epoxide moiety.

In certain embodiments, the invention provides methods for preparing a diazoketone of the formula:

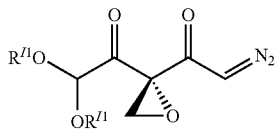

or salt thereof, wherein $R^{I1}$ is defined above and herein.

For example, in certain embodiments, the method comprises:

(a) epoxidizing a compound of formula:

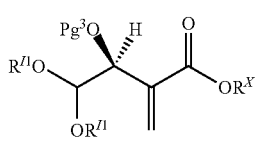

or salt thereof, wherein $R^{I1}$ is defined above and herein, $R^X$ is $C_{1-6}$ alkyl (e.g., methyl), and $Pg^3$ is an oxygen-protecting group (e.g., a silyl ether) to yield a compound of formula:

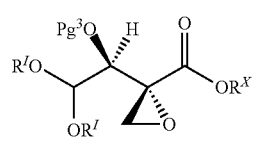

or salt thereof;

(b) forming the diazoketone of formula:

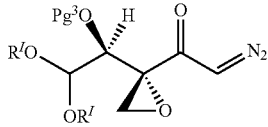

or salt thereof;

(c) deprotecting the protected hydroxyl group Pg³ to provide a compound of the formula:

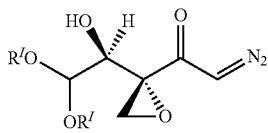

and (d) oxidizing the secondary alcohol to a ketone of formula:

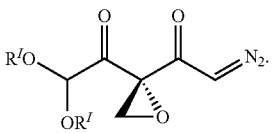

In certain embodiments, the step of epoxidizing is stereoselective.

In certain embodiments, the invention provides a method of preparing a compound of the Formula (I):

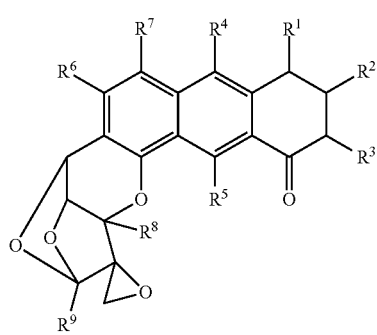

(I)

or a pharmaceutically acceptable form thereof, wherein $R^8$ and $R^5$ are —OH; comprising deprotecting the cycloadduct of the Formula:

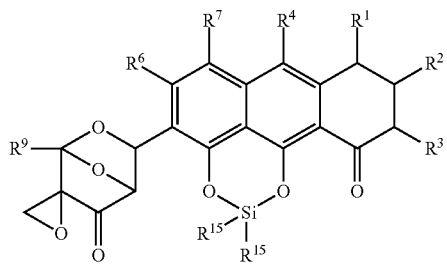

or salt thereof.

In certain embodiments, the compound of Formula (I) is of the Formula (I-a):

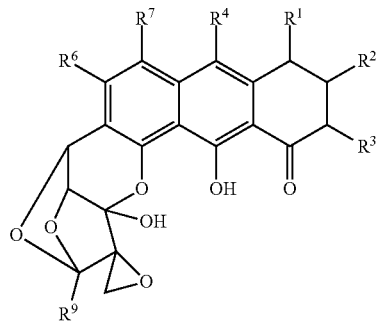

(I-a)

or a pharmaceutically acceptable form thereof.

In certain embodiments, the compound of Formula (I-a) has the following stereochemistry:

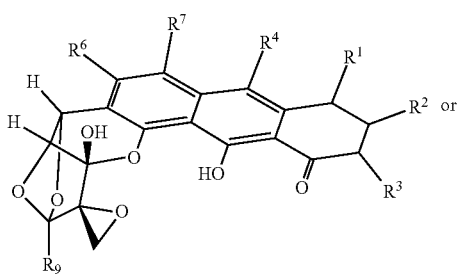

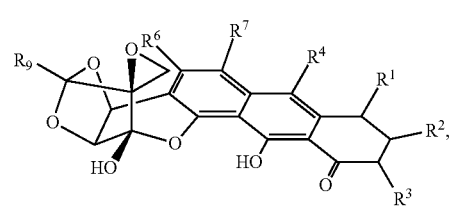

or a pharmaceutically acceptable form thereof.

In certain embodiments, the compound of the Formula (I-a) is of the formula:

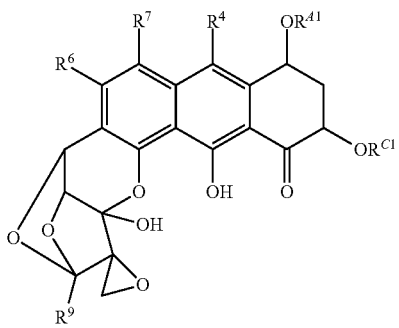

(I-b)

or a pharmaceutically acceptable form thereof.

In certain embodiments, the invention provides a method of preparing a compound of Formula (I-c):

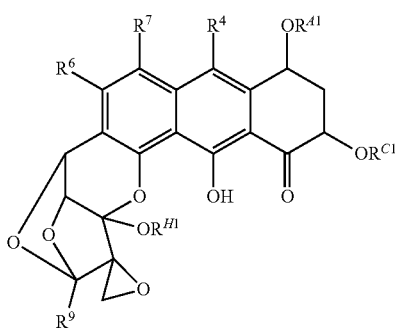

(I-c)

or a pharmaceutically acceptable form thereof; comprising reacting an electrophile $R^H$—Y with a compound of Formula (I-b):

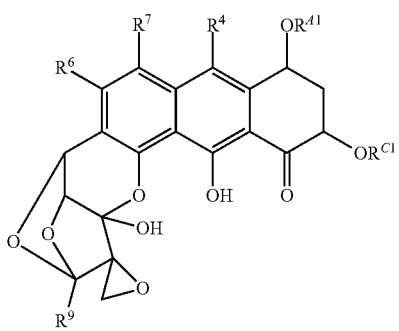

(I-b)

or a pharmaceutically acceptable form thereof; wherein Y is a leaving group. In certain embodiments, wherein $R^{H1}$ is a carbohydrate; an oxygen protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl, and Y is a leaving group. In certain embodiments, $R^{H1}$ is a carbohydrate.

In certain embodiments, the compound of the Formula (I-b) has the following stereochemistry:

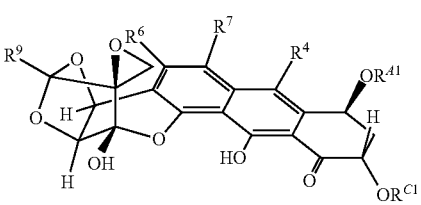

or a pharmaceutically acceptable form thereof.

In certain embodiments, the compound of Formula (I-c) has the following stereochemistry:

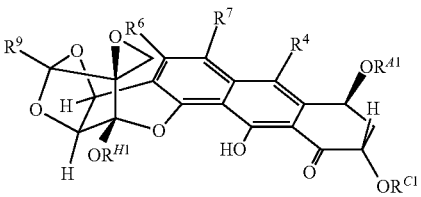

or a pharmaceutically acceptable form thereof.

In certain embodiments, the invention provides a method of preparing a compound of Formula (I-d):

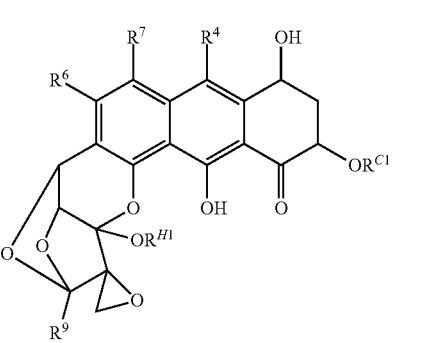

(I-d)

or a pharmaceutically acceptable form thereof; comprising selectively deprotecting a compound of Formula (I-c) or a pharmaceutically acceptable form thereof; wherein $R^{41}$ is an oxygen protecting group.

In certain embodiments, the compound of Formula (I-d) has the following stereochemistry:

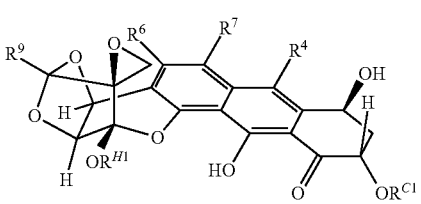

or a pharmaceutically acceptable form thereof.

The resulting alcohol at position 4 may then optionally be reacted with a electrophile. For example, in certain embodiments, the invention provides a method of preparing a compound of the Formula (I-e):

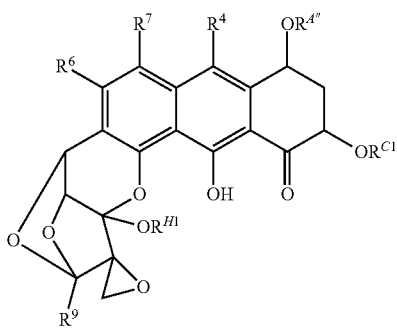

(I-e)

or a pharmaceutically acceptable form thereof;

comprising reacting a compound of the Formula (I-d) with an electrophile $R^{A''}$—Y, wherein $R^{A''}$ is a carbohydrate; an oxygen protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl, and Y is a leaving group. In certain embodiments, $R^{A''}$ is a carbohydrate.

In certain embodiments, the compound of Formula (I-e) has the following stereochemistry:

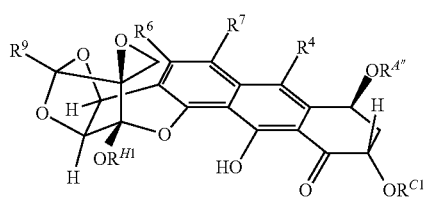

or a pharmaceutically acceptable form thereof.

In certain embodiments, the invention provides a method of preparing a compound of Formula (I-f):

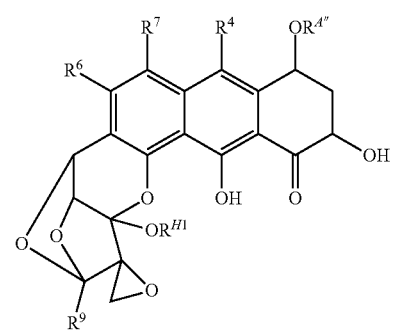

(I-f)

or a pharmaceutically acceptable form thereof; comprising selectively deprotecting a compound of Formula (I-c) or a pharmaceutically acceptable form thereof; wherein $R^{C1}$ is an oxygen protecting group.

In certain embodiments, the compound of Formula (I-f) has the following stereochemistry:

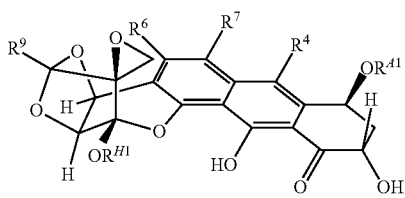

or a pharmaceutically acceptable form thereof.

The resulting hydroxyl moiety at position 2 may then optionally be reacted with an electrophile. For example, in certain embodiments, the invention provides a method of preparing a compound of Formula (I-g):

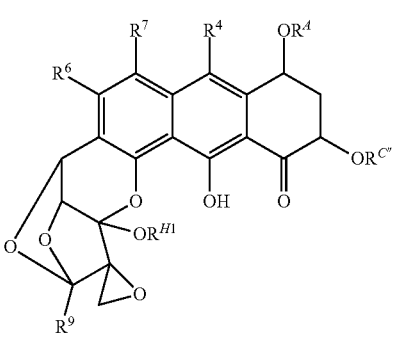

(I-g)

or a pharmaceutically acceptable form thereof; comprising reacting a compound of Formula (I-e) with an electrophile $R^{C''}$—Y, wherein $R^{C''}$ is a carbohydrate; an oxygen protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl, and Y is a leaving group. In certain embodiments, $R^{C''}$ is a carbohydrate.

In certain embodiments, the compound of Formula (I-g) has the following stereochemistry:

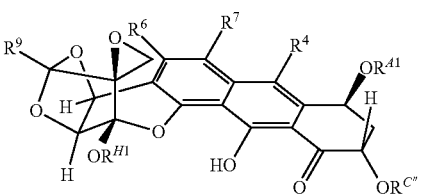

or a pharmaceutically acceptable form thereof.

Intermediates useful in the synthesis of the compounds described here may themselves have biological activity. The intermediates may be prepared via the synthetic routes described herein or via other synthetic routes based on knowledge in the art.

As will be appreciated by one of skill in this art, various modifications can be made to the starting materials and reagents used in the synthetic schemes described herein to provide trioxacarcins and trioxacarcin analogs of the present invention.

Pharmaceutical Compositions

In certain embodiments, the present invention provides a pharmaceutical composition comprising a compound of the present invention or a pharmaceutically acceptable form thereof, and a pharmaceutically acceptable excipient.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21$^{st}$ Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with the excipient and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered, by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* $21^{st}$ ed., Lippincott Williams & Wilkins, 2005.

Still further encompassed by the invention are pharmaceutical packs and/or kits. Pharmaceutical packs and/or kits provided may comprise a provided composition and a container (e.g., a vial, ampoule, bottle, syringe, and/or dispenser package, or other suitable container). In some embodiments, provided kits may optionally further include a second container comprising a suitable aqueous carrier for dilution or suspension of the provided composition for preparation of administration to a subject. In some embodiments, contents of provided formulation container and solvent container combine to form at least one unit dosage form.

Optionally, a single container may comprise one or more compartments for containing a provided composition, and/or appropriate aqueous carrier for suspension or dilution. In some embodiments, a single container can be appropriate for modification such that the container may receive a physical modification so as to allow combination of compartments and/or components of individual compartments. For example, a foil or plastic bag may comprise two or more compartments separated by a perforated seal which can be broken so as to allow combination of contents of two individual compartments once the signal to break the seal is generated. A pharmaceutical pack or kit may thus comprise such multi-compartment containers including a provided composition and appropriate solvent and/or appropriate aqueous carrier for suspension.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with additional therapy.

Methods of Use and Treatment

The present invention also provides methods of use of compounds of the present invention as described herein.

For example, in one aspect, provided are methods of treating a disease, disorder or condition selected from the group consisting of proliferative diseases (e.g., cancer, benign tumors), diabetic retinopathy, inflammatory diseases, autoimmune diseases, and infectious diseases (e.g., bacterial infections, fungal infections, parasitic infections) comprising administering an effective amount of a compound of Formula (I) to a subject.

In another aspect, provided is a compound of Formula (I) for use in the treatment of a disease, disorder or condition selected from the group consisting of proliferative diseases (e.g., cancer, benign tumors), diabetic retinopathy, inflammatory diseases, autoimmune diseases, or infectious diseases (e.g., bacterial infections, fungal infections, parasitic infections).

In certain embodiments, the inventive compound is useful in the treatment of a proliferative disease. Exemplary proliferative diseases include, but are not limited to, cancers and benign tumors. In certain embodiments, the proliferative disease is cancer.

Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above, e.g., mixed leukemia lymphoma (MLL); and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In certain embodiments, the inventive compound is useful in the treatment of diabetic retinopathy.

In certain embodiments, the inventive compound is useful in the treatment of an inflammatory disease. Exemplary inflammatory diseases include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatistis.

In certain embodiments, the inflammatory condition is an acute inflammatory condition (e.g. for example, inflammation resulting from infection), In certain embodiments, the inflammatory condition is a chronic inflammatory condition (e.g., conditions resulting from asthma, arthritis and inflammatory bowel disease), The compounds may also be useful in treating inflammation associated with trauma and noninflammatory myalgia. The compounds may also be useful in treating inflammation associated with cancer, In certain embodiments, the inventive compound is useful in the treatment of an autoimmune disease. Exemplary autoimmune diseases include, but are not limited to, arthritis (e.g., including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In certain embodiments, the inflammatory disorder and/or the immune disorder is a gastrointestinal disorder. In some embodiments, the gastrointestinal disorder is selected from gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease(IBD) (e.g., Crohn's disease, ulcerative colitis. collagenous colitis, lymphocytic colitis. ischaemic colitis, diversion colitis, Behcet's syndrome, indeterminate colitis) and inflammatory bowel syndrome (IBS)).

In certain embodiments, the inventive compound is useful in the treatment of an infectious disease (e.g., bacterial infection, fungal infection, and/or parasitic infection). In certain embodiments, the inventive compounds are useful in treating a parasitic infection (e.g., malaria). In certain embodiments, the inventive compounds are useful in treating a bacterial infection. In certain embodiments, the inventive compounds are useful in treating a fungal infection.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder (for example, a compound can be administered in combination with an anti-inflammatory agent, anti-cancer agent, etc.), and/or it may achieve different effects (e.g., control of adverse side-effects, e.g., emesis controlled by an anti-emetic).

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, cancer therapies, antibiotics, anti-viral agents, anesthetics, anti-coagulants, inhibitors of an enzyme, steroidal agents, steroidal or non-steroidal anti-inflammatory agents, antihistamine, immunosuppressant agents, anti-neoplastic agents, antigens, vaccines, antibodies, decongestant, sedatives, opioids, pain-relieving agents, analgesics, anti-pyretics, hormones, prostaglandins, progestational agents, anti-glaucoma agents, ophthalmic agents, anti-cholinergics, anti-depressants, anti-psychotics, hypnotics, tranquilizers, anti-convulsants/anti-epileptics (e.g., Neurontin, Lyrica, valproates (e.g., Depacon), and other neuro-stabilizing agents), muscle relaxants, anti-spasmodics, muscle contractants, channel blockers, miotic agents, anti-secretory agents, anti-thrombotic agents, anticoagulants, anti-cholinergics, β-adrenergic blocking agents, diuretics, cardiovascular active agents, vasoactive agents, vasodilating agents, anti-hypertensive agents, angiogenic agents, modulators of cell-extracellular matrix interactions (e.g. cell growth inhibitors and anti-adhesion molecules), or inhibitors/intercalators of DNA, RNA, protein-protein interactions, protein-receptor interactions, etc. Therapeutically active agents include small organic molecules such as drug compounds (e.g., compounds approved by the Food and Drugs Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

In certain embodiments, the additional therapeutically agent is a cancer therapy. Cancer therapies include, but are not limited to, surgery and surgical treatments, radiation therapy, and therapeutic cancer agents (e.g., biotherapeutic and chemotherapeutic cancer agents).

Exemplary biotherapeutic cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic cancer agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI- 571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In other embodiments, the additional therapeutically active agent is an anti-inflammatory agent. Exemplary anti-inflammatory agents include, but are not limited to, aspirin; ibuprofen; ketoprofen; naproxen; etodolac (LODINE®); COX-2 inhibitors such as celecoxib (CELEBREX®), rofecoxib (VIOXX®), valdecoxib (BEXTRA®), parecoxib, etoricoxib (MK663), deracoxib, 2-(4-ethoxy-phenyl)-3-(4-methanesulfonyl-phenyl)-pyrazolo[1,5-b] pyridazine, 4-(2-oxo-3-phenyl-2,3-dihydrooxazol-4-yl)benzenesulfonamide, darbufelone, flosulide, 4-(4-cyclohexyl-2-methyl-5-oxazolyl)-2-fluorobenzenesulfonamide), meloxicam, nimesulide, 1-Methylsulfonyl-4-(1,1-dimethyl-4-(4-fluorophenyl) cyclopenta-2,4-dien-3-yl)benzene, 4-(1,5-Dihydro-6-fluoro-7-methoxy-3-(trifluoromethyl)-(2)-benzothiopyrano(4,3-c) pyrazol-1-yl)benzenesulfonamide, 4,4-dimethyl-2-phenyl-3-(4-methylsulfonyl)phenyl)cyclo-butenone, 4-Amino-N-(4-(2-fluoro-5-trifluoromethyl)-thiazol-2-yl)-benzene sulfonamide, 1-(7-tert-butyl-2,3-dihydro-3,3-dimethyl-5-benzo-furanyl)-4-cyclopropyl butan-1-one, or their physiologically acceptable salts, esters or solvates; sulindac (CLINORIL®); diclofenac (VOLTAREN®); piroxicam (FELDENE®); diflunisal (DOLOBID®), nabumetone (RELAFEN®), oxaprozin (DAYPRO®), indomethacin (INDOCIN®); or steroids such as PEDIAPED® prednisolone sodium phosphate oral solution, SOLU-MEDROL® methylprednisolone sodium succinate for injection, PRELONE® brand prednisolone syrup.

Further examples of anti-inflammatory agents include naproxen, which is commercially available in the form of EC-NAPROSYN® delayed release tablets, NAPROSYN®, ANAPROX® and ANAPROX® DS tablets and NAPROSYN® suspension from Roche Labs, CELEBREX® brand of celecoxib tablets, VIOXX® brand of rofecoxib, CELESTONE® brand of betamethasone, CUPRAMINE® brand penicillamine capsules, DEPEN® brand titratable penicillamine tablets, DEPO-MEDROL brand of methylprednisolone acetate injectable suspension, ARAVA™ leflunomide tablets, AZULFIDIINE EN-Tabs® brand of sulfasalazine delayed release tablets, FELDENE® brand piroxicam capsules, CATAFLAM® diclofenac potassium tablets, VOLTAREN® diclofenac sodium delayed release tablets, VOLTAREN®-XR diclofenac sodium extended release tablets, or ENBREL® etanerecept products.

In certain embodiments, the additional therapeutically active agent is a pain-relieving agent. Exemplary pain relieving agents include, but are not limited to, analgesics such as non-narcotic analgesics [e.g., salicylates such as aspirin, ibuprofen (MOTRIN®, ADVIL®), ketoprofen (ORUDIS®), naproxen (NAPROSYN®), acetaminophen, indomethacin] or narcotic analgesics [e.g., opioid analgesics such as tramadol, fentenyl, sufentanil, morphine, hydromorphone, codeine, oxycodone, and buprenorphine]; non-steroidal anti-inflammatory agents (NSAIDs) [e.g., aspirin, acetaminophen, COX-2 inhibitors]; steroids or anti-rheumatic agents; migraine preparations such as beta adrenergic blocking agents, ergot derivatives; tricyclic antidepressants (e.g., amitryptyline, desipramine, imipramine); anti-epileptics (e.g., clonaxepam, valproic acid, phenobarbital, phenytoin, tiagaine, gabapentin, carbamazepine, topiramate, sodium valproate); $\alpha_2$ agonists; selective serotonin reuptake inhibitors (SSRIs), selective norepinepherine uptake inhibitors; benzodiazepines; mexiletine (MEXITIL); flecainide (TAMBOCOR); NMDA receptor antagonists [e.g., ketamine, detromethorphan, methadone]; and topical agents [e.g., capsaicin (Zostrix), EMLA cream, lidocaine, prilocaine].

Research Tools

In yet another aspect, provided are methods of using compounds of Formula (I) as research tools, e.g., by reacting a Formula (I), (II) or (III) with a polynucleotide in vivo or in vitro to provide a compound of Formula (IV), (V) and (VI), respectively.

In certain embodiments, $R^{12}$ is a polynucleotide or an amino group from a nucleic acid base (e.g., guanine).

In certain embodiments, the compound of Formula (I), (II) or (III) are labeled. In certain embodiments, any one of the atoms of the compounds of Formula (I), (II) or (III) carries a label. Thus, in certain embodiments, wherein the compound of Formula (I), (II) or (III) are labeled or carry a label, the compound of Formula (IV), (V) and (VI), formed therefrom, also are labeled or carry a label For example, in certain embodiments, provided is a method of labeling a polynucleotide comprising contacting a polynucleotide with a compound of Formula (I), (II) or (III) to provide a compound of Formula (IV), (V) and (VI). In certain embodiments, the polynucleotide is DNA or RNA. In certain embodiments, the polynucleotide is DNA.

It is understood that "labeling" means that the compounds of Formula (I), (II), (III), (IV), (V) and/or (VI) have at least one label to enable detection, and that the compound of Formula (I), (II) or (III), upon contact with the polynucleotide, covalently or non-covalently attaches to the polynucleotide. In certain embodiments, the compound of Formula (I), (II) or (III), upon contact with the polynucleotide, covalently attaches to (e.g., alkylates) the polynucleotide to provide a compound of Formula (IV), (V) and (VI), respectively.

In general, labels typically fall into five classes: a) isotopic labels, which may be radioactive or heavy isotopes, including, but not limited to, $^2$H, $^3$H, $^{13}$C, $^{14}$C, $^{15}$N, $^{31}$P, $^{32}$P, $^{35}$S, $^{67}$Ga, $^{99m}$Tc (Tc-99m), $^{111}$In, $^{123}$I, $^{125}$I, $^{169}$Yb, and $^{186}$Re; b) immune labels, which may be antibodies or antigens, which may be bound to enzymes (such as horseradish peroxidase) that produce detectable agents; c) colored, luminescent, phosphorescent, or fluorescent dyes; d) photoaffinity labels; and e) ligands with known binding partners (such as biotin-streptavidin, FK506-FKBP, etc.). It will be appreciated that the labels may be incorporated into the compound at any position that does not interfere with the biological activity or characteristic of the compound that is being detected. In certain embodiments, hydrogen atoms in the compound are replaced with deuterium atoms ($^2$H) to slow the degradation of the compound in vivo. Due to isotope effects, enzymatic degradation of the deuterated compounds may be slowed thereby increasing the half-life of the compound in vivo. In other embodiments such as in the identification of the biological target(s) of a natural product or derivative thereof, the compound is labeled with a radioactive isotope, preferably an isotope which emits detectable particles, such as 0 particles. In certain other embodiments of the invention, photoaffinity labeling is utilized for the direct elucidation of intermolecular interactions in biological systems. A variety of known photophores can be employed, most relying on photoconversion of diazo compounds, azides, or diazirines to nitrenes or carbenes (see, Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to, 4-azido-2,3,5,6-tetrafluorobenzoic acid. In other embodiments, biotin labeling is utilized.

In another aspect, provided is a method of cleaving a polynucleotide comprising contacting a polynucleotide with a compound of Formula (I). In certain embodiments, the polynucleotide is DNA or RNA. In certain embodiments, the polynucleotide is DNA. While not wishing to be bound by any theory, the cleavage may involve alkylation of the N7 position of a guanine residue in the polynucleotide by the epoxide functional group of a compound of Formula (I) to form a covalent complex. Cleavage of the covalent complex may occur through 1) a depurination process to yield a polynucleotide containing an abasic site or 2) depurination and cleavage of the polynucleotide to yield two or more smaller polynucleotide products, as exemplified in FIGS. 13 and 14.

EXAMPLES

In order that the invention described herein may be more fully understood, the following examples are set forth. It should be understood that these examples are for illustrative purposes only and are not to be construed as limiting this invention in any manner.

A Convergent, Fully Synthetic Route to Trioxacarcins

Figure 2A:
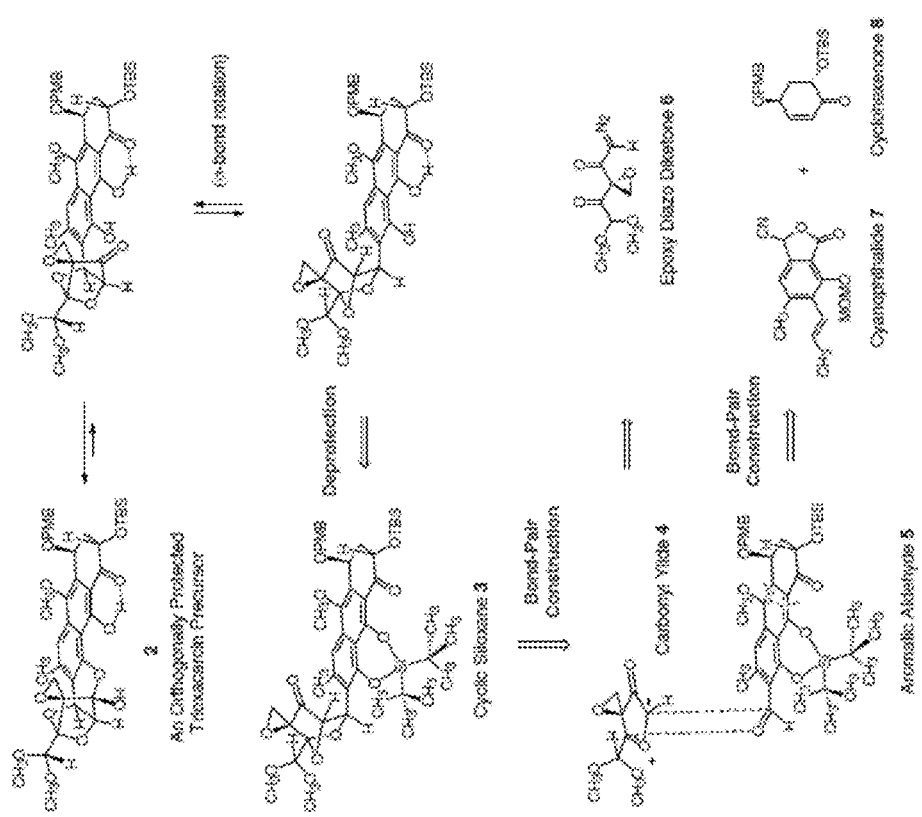
FIGS. 2A-2D depict the multiply convergent synthetic route to the trioxacarcin aglycone, DC-45-A$_2$.
Figure 2B:
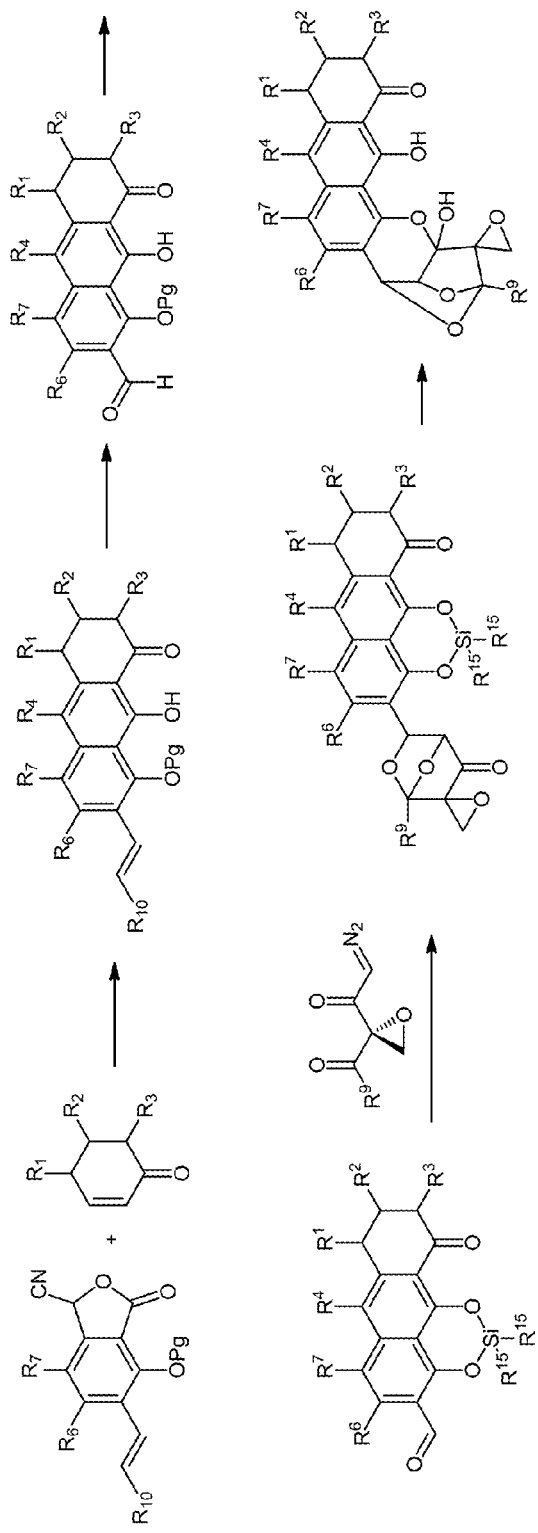

An enantioselective synthetic route to the natural product DC-45-A2 from a orthogonally protected trioxacarcin precursor (2), which in turn is the product of a late-stage assembly process using three components of similar complexity (diazo ketone 6, cyanophthalide 7, cyclohexenone 8) is presented (see, e.g., FIGS. 2A and 2B). Analogous routes to iso-DC-45-A2, chlorohydrin, dideoxy-DC-45-A2, and analogues thereof, are also presented.

As a strategic objective, we sought to develop a route that approached maximal convergence, which we specify as a requirement for strategic bond-pair constructions between components of equal structural complexity (determined by analysis of step-count) at or near the final step of the route. Although the importance of convergence in synthesis has long been appreciated, highly condensed polycyclic targets such as the trioxacarcins frequently do not lend themselves to convergent simplification of the type specified, and synthesis plans that might meet this objective can be stereochemically ambiguous and (partly as a consequence) may offer modest probability of success. As a sharp counterpoint; however, the end-value of a route that successfully achieves a high degree of convergence is made evident by the rapidity with which large numbers of structural analogs can be prepared and by the diversity of compounds that can be synthesized through variation of the coupling partners.

Figure 6:
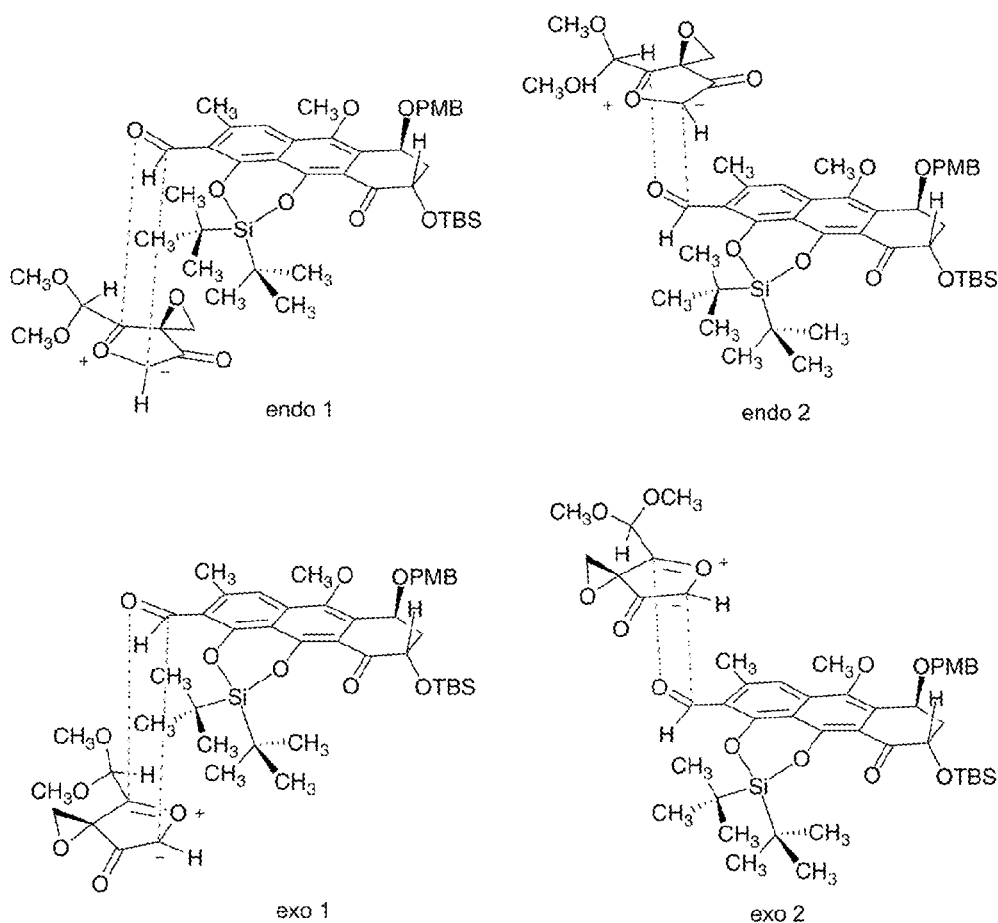
FIG. 6 shows the four possible combinations of the aldehyde and carbonyl ylide diastereofaces in the 1,3-dipolar cycloaddition reaction.

To address natural and non-natural trioxacarcins broadly, we targeted compound 2 and as its precursor the cyclic siloxane 3, differentially and orthogonally hydroxyl-protected derivatives of DC-45-A$_2$. We envisioned that target 3 could be disconnected through a powerfully simplifying 1,3-dipolar cycloaddition transform, producing the carbonyl ylide 4 and the aldehyde 5 as intermediates. FIG. 6 illustrates the diastereomeric products that arise from the four possible pairwise combinations of the two diastereofaces of each reactant.

Although we had no reasonable basis to predict the stereochemical outcome of the proposed cycloaddition, the extensive literature of carbonyl ylide-aldehyde additions suggested that quite different conditions could be explored as reaction variables (thermal versus metal-catalyzed processes, for example). In addition, the proposed route offered the ability to easily vary the hydroxyl protective groups within the coupling partners as a means to influence stereochemistry. Results discussed below make clear that both of these variables do in fact greatly influence the stereochemical outcome of each of the cycloaddition reactions we have studied.

The densely functionalized diazo ketone 6, the precursor to the carbonyl ylide 4, was synthesized in 8 steps, as shown in FIG. 2B, beginning with a highly diastereoselective auxiliary-controlled Baylis-Hillman reaction between the Oppolzer sultam-derived acrylimide 11 (1 equiv.) and anhydrous 2,2-dimethoxyacetaldehyde (3.0 equiv) using 1,4-diazabicyclo[2.2.2]octane (DABCO, 0.3 equiv) as catalyst in dichloromethane at 23° C. (16 h). The product of the reaction had incorporated two molecules of 2,2-dimethoxyacetaldehyde, and had expelled the Oppolzer sultam auxiliary by internal lactonization, as anticipated based on precedent (see, e.g., Brzezinski et al., *J. Am. Chem. Soc.* (1997) 119:4317-4318). Methanolysis of the resulting lactone (triethylamine in methanol, 30 min, 23° C.) afforded the corresponding methyl ester shown to be ≥98% enantiomerically pure as determined by capillary GC analysis. Hydroxyl protection with tert-butyldimethylsilyl trifluoromethanesulfonate (1.2 equiv) and N,N-diisopropylethylamine (1.5 equiv) then afforded the tert-butyldimethylsilyl ether 10 (48% over 3 steps). Nucleophilic epoxidation of 10 at 0° C. (4.5 h) in the presence of tert-butylhydroperoxide (2.0 equiv) and potassium tert-butoxide (0.1 equiv) provided selectively the anti epoxy ester 11 in 81% yield (2.4-g scale, anti:syn=13:1) (Švenda, J.; Myers, A. G. *Org. Lett.* 2009, 11, 2437-2440). Saponification of ester 11 (THF-MeOH—H$_2$O, LiOH, 0° C.) and activation of the resulting carboxylic acid by treatment with isobutylchloroformate (1.05 equiv) in the presence of Et$_3$N (1.1 equiv) at −20° C. with gradual warming to −10° C.) followed by addition of a solution of diazomethane in ether (~0.25 M, 2.0 equiv) and further warming to 23° C. provided after chromatographic purification on triethylamine-deactivated silica gel the epoxy diazo ketone 12 as a yellow oil (74% yield, 2 steps).

Exposure of this product to a 1:1 mixture (by volume) of triethylamine-trihydrofluoride and acetonitrile led to slow (44 h, 23° C.) but clean cleavage of the tert-butyldimethylsilyl protective group, affording the corresponding secondary alcohol in nearly quantitative yield. Oxidation with Dess-Martin periodinane (1.1 equiv) buffered with sodium bicarbonate (10.0 equiv, 23° C., 1 h) then afforded the corresponding epoxy diazo diketone 6 as a light yellow oil in 77% yield (2 steps) after chromatographic purification using triethylamine-deactivated silica gel. The diazo ketone 6 can be stored for several months without decomposition at −25° C., both neat or frozen in benzene, with care to exclude light.

The cyanophthalide 7 was synthesized in eight steps from 4-methyl salicylic acid following conventional lines, as depicted in FIG. 2B.

Two different routes were developed for the synthesis of the cyclohexenone fragment 8 (Kato, N.; Inada, M.; Sato. H.; Miyatake, R.; Kumagai, T.; Ueda, M. *Tetrahedron* 2006, 62, 7307-7318). The preferred route (depicted, see Experimentals below for alternative routes) employed L-malic acid as starting material and proceeded through a known, 4-step sequence to the lactone 17 (FIG. 2B) (Collum, D. B.; McDonald, J. H.; Still, W. C. *J. Am. Chem. Soc.* 1980, 102, 2118-2120; Schinzer, D.; Bauer, A.; Schieber, J. *Chem.-Eur. J.* 1999, 5, 2492-2500). The latter product was transformed into the aldehyde 18 in 70% yield (2 steps) by Weinreb amide formation (Williams, M. J.; Jobson, R. B.; Yasuda, N.; Marchesini, G.; Dolling U.-H.; Grabowski, E. J. *J. Tetrahedron Lett.* 1995, 36, 5461-5464) followed by oxidation with aqueous sodium hypochlorite (1.0 equiv) in the presence of 2,2,6,6-tetramethylpiperidine-1-oxyl (TEMPO) (0.01 equiv) and potassium bromide (0.1 equiv) (Anelli, P. L.; Biffi, C.; Montanari, F.; Quici, S. *J. Org. Chem.* 1987, 52, 2559-2562). Addition of aldehyde 18 to a 1:1 mixture of divinylzinc (2.0 equiv) and the amino alkoxide 19 (2.0 equiv) at −70° C. provided the 4S-alcohol 20 selectively (diastereomeric ratio 12:1), by which we infer that the substrate had reacted via bidendate coordination to the organometallic reagent (Oppolzer, W.; Radinov, R. N. *Tetrahedron Lett.* 1991, 32, 5777-5780). The product was susceptible to lactonization (Marshall, J. A.; Seletsky, B. M.; Luke, G. P. *J. Org. Chem.* 1994, 59, 3413-3420; Bondar. D.; Liu, J.; Muller, T.; Paquette, L. A. *Org. Lett.* 2005, 7, 1813-1816) and so was immediately protected as the 4-methoxybenzyl ether (21) using freshly prepared 4-methoxybenzyl trichloracetimidate (2.0 equiv) and Sc(OTf)$_3$ as catalyst (0.03 equiv, 57% yield over 2 steps, 12:1 mixture of C4 diastereomers, 17.8-g scale). Addition of vinylmagnesium bromide (3.0 equiv) to amide 21 with care to maintain an internal temperature of 0° C. provided cleanly the divinyl ketone, which underwent smooth ring-closing metathesis in the presence of the second-generation Hoveyda-Grubbs ruthenium alkylidene catalyst at 55° C. (0.09 M solution of substrate in deoxygenated benzene), providing after chromatographic isolation the diastereomerically pure cyclohexenone coupling component 8, in 75% yield over the 2 steps.

Figure 2C:
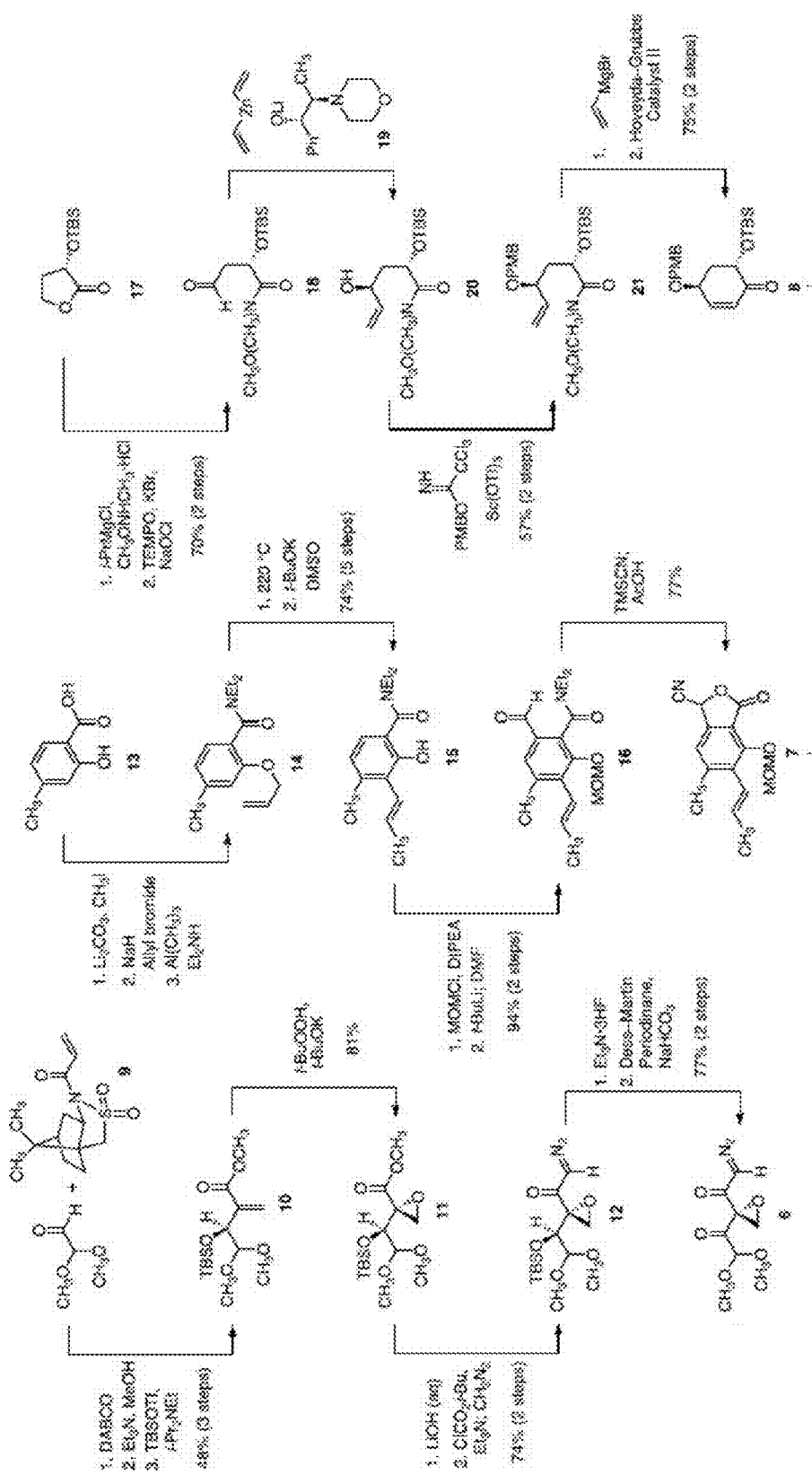
Figure 2D:
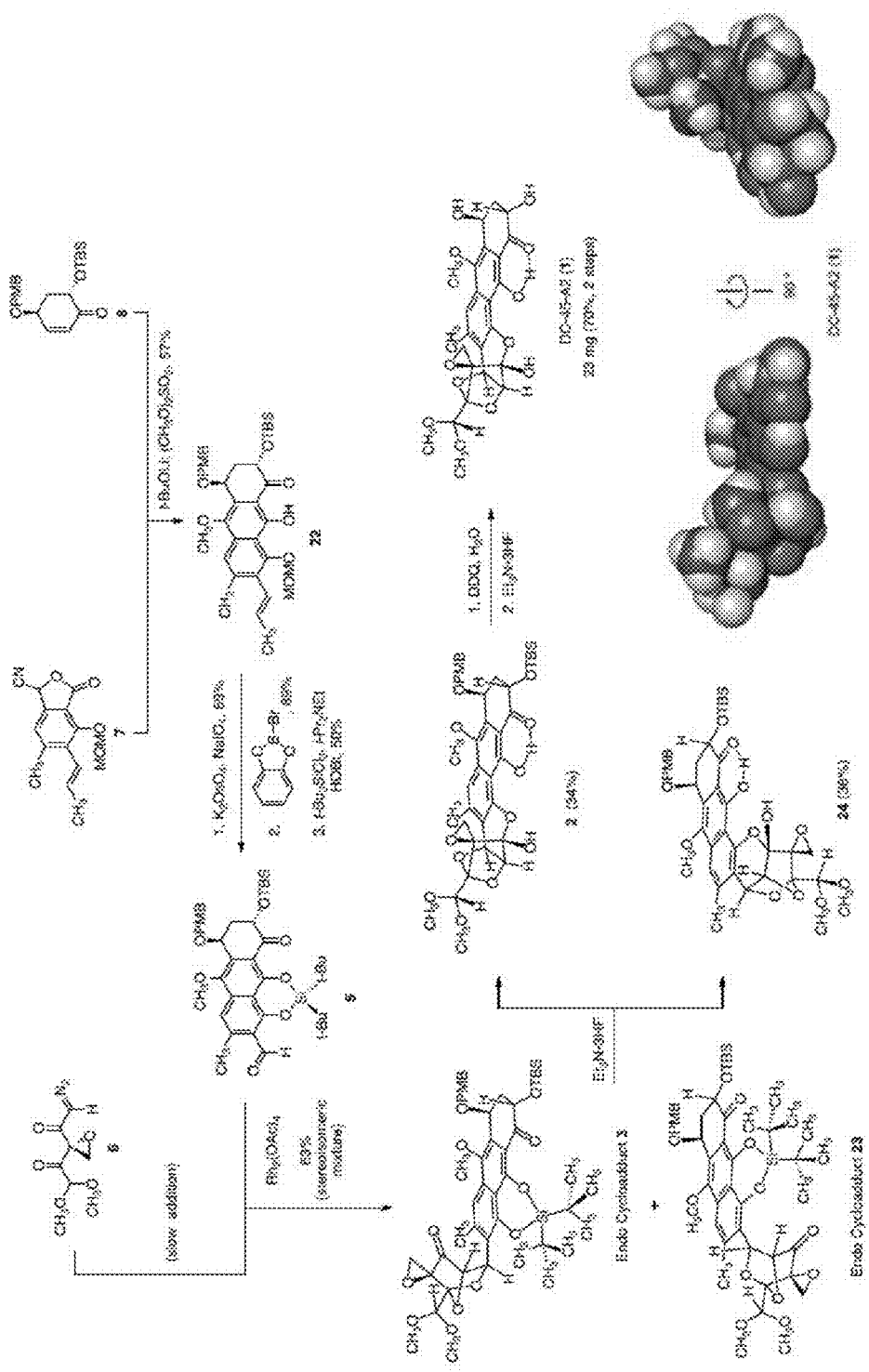

In the first of two late-stage ring-forming (bond-pair) coupling reactions, components 7 and 8 were combined in a Kraus-Sugimoto cyanophthalide annulation reaction (Kraus, G. A.; Sugimoto, H. *Tetrahedron Lett.* 1978, 19, 2266-2266) (FIG. 2C). Thus, addition of solution of enone 8 (1 equiv) to the cyanophthalide anion derived from deprotonation of 7 (3.0 equiv) with lithium tert-butoxide (3.0 equiv) in tetrahydrofuran at −78° C. led to rapid formation of Michael addition product(s) (based on tlc analysis, not characterized); upon warming to −40° C. these underwent cyclization to form a single dihydroquinone phenolate, which was trapped in situ by monomethylation with dimethylsulfate (9.0 equiv, −26→23° C.). The anthrone methyl ether 22 was obtained in 57% yield (3-g scale, yellow foam) after chromatographic purification, a process facilitated by the characteristic long-wavelength (365 nM) UV absorption of the product, with blue-green fluorescence, a characteristic of trioxacarcins. Oxidative cleavage of the alkenyl side-chain at 0° C. (4.0 equiv of NaIO$_4$; 0.1 equiv of K$_2$OsO$_4$.2H$_2$O; 2.0 equiv of 2,6-lutidine) then provided the corresponding aldehyde as an orange foam (69% yield) (Yu, W.; Mei, Y.; Kang, Y.; Hua, Z.; Jin, Z. *Org. Lett.* 2004, 6, 3217-3219). The methoxymethyl (MOM) protective group was cleanly and selectively removed by treatment of the latter product with B-bromocatecholborane (2.0 equiv), affording the bisphenol intermediate (89% yield) (Boeckman, R. K.; Potenza, J. C. *Tetrahedron Lett.* 1985, 26, 1411-1414) as a yellow foam. Protection of this moderately air-sensitive product (t-Bu$_2$SiCl$_2$, HOBt, DIPEA, 55° C.) provided the much more stable, di-tert-butylsiloxane derivative (5, 50% yield) for final coupling. Unprotected aldehyde was found to be unstable to silica gel chromatography and was incompatible with the subsequent cycloaddition reaction.

The fully oxygenated polycyclic skeleton of the trioxacarcins was assembled in one step by slow addition (syringe pump, 2 h) of a solution of the diazo ketone 6 (3.0 equiv, 2.26 M in dichloromethane) to a stirring suspension of aldehyde 5 (0.75 M, 1 equiv), rhodium(II) acetate (0.05 equiv), and powdered, activated 4 Å molecular sieves in dichloromethane at 23° C. After filtration through a pad of silica gel (4 cm, eluting with 30% ethyl acetate in hexanes) to remove the rhodium catalyst, the filtrate was concentrated, and the residue was purified by preparative RP-HPLC (C18 column, CH$_3$CN—H$_2$O) to provide in 63% yield a mixture of diastereomeric cycloadducts in which the two endo-diastereomers (3 and 23) greatly predominated. Pure samples of the individual diastereomers were obtained for spectroscopic analysis, but for preparative purposes it proved to be much more practical to separate the diastereomers after cleavage of the cyclic di-tert-butylsiloxane protective group (triethylamine-trihydrofluoride, 3.0 equiv, 23° C., 15 min), where the endo diastereomers alone underwent spontaneous hemiketalization; these products, both obtained as bright yellow oils, were easily separated by RP-HPLC [24, 52 mg, (36% yield) and 2, 48 mg (34% yield)]. Variation of the catalyst was indeed found to greatly influence the stereochemical outcome of the cycloaddition. For example, cycloaddition of 5 and 6 in the prescence of copper (I) tetrakis(acetonitrile) afforded as the major product an exo-diastereomer (46%) that represented only 14% of the diastereomeric product distribution when rhodium (II) acetate was used as catalyst. Although we believe it likely that the efficiency and stereoselectivity of formation of the desired endo-cycloadduct (3) may be improved by further exploration of different catalysts, in its present form the rhodium (II) acetate-catalyzed transformation provides more than sufficient quantities of the material for biological evaluation and mechanistic study. Two-step deprotection of endo-hemiketal 2 (DDQ; triethylamine-trihydrofluoride) afforded synthetic DC-45-A2 (1) (23 mg, 70% yield) (Shirahata, K; Iida, T., U.S. Pat. No. 4,459,291, issued Jul. 10, 1984, incorporated herein by reference). Both 1 and its immediate precursor exhibited appreciable water solubility, which was attenuated by saturation with sodium chloride. Synthetic DC-45-A$_2$ (1) is a bright yellow powder that is stable when stored neat at −25° C. with exclusion of light but undergoes slow decomposition over hours in solution at 23° C.

Crystallization of synthetic DC-45-A2 from ethyl acetate-hexanes provided a single crystal suitable for X-ray diffraction analysis; two representations of the three dimensional structure obtained are depicted in FIG. 2C. The structure conforms fully with that proposed for the natural product and shows that the spiro-epoxide is ideally aligned for opening by a G residue stacked upon the pi-face of the tricyclic core. It is revealing that similar two-step deprotection of the stereoisomeric endo-hemiketal 24 (with the more electrophilic carbon of the spiro-epoxide oriented away from the tricyclic aromatic core) gave rise to a chlorohydrin derivative (25%), presumably arising from ring-opening of the spiro-epoxide by chloride ion during workup, as well as the expected spiro-epoxide, iso-DC-450-A2 (25, 22%, depicted in FIG. 10A). No such opening was observed with DC-45-A2. In contrast, in experiments evaluating the reactions of DC-45-A2 (1) and iso-DC-45-A2 with the G residue of a known DNA substrate for alkylation by trioxacarcin A (Fitzner et al., Anal. Bioanal. Chem. (2008) 390:1139-1147), iso-DC-45-A2 (25) was found to be unreactive, whereas (1) readily alkylated the DNA duplex.

We measured $IC_{50}$ values of DC-45-A2, iso-DC-45-A2, and a fully synthetic analog, dideoxy-DC-45-A2 (26), which we prepared by the six-step route outlined in FIGS. 2B-2C without variation, save for the use of 2-cyclohexene-1-one as starting material in place of the substituted cyclohexeneone coupling component 8, in HeLa and H4609 cell lines. DC-45-A2 inhibited the growth of both cell lines at micromolar concentrations. DC-45-A2 was found to be a more potent growth inhibitor, with submicromolar IC50 values, and iso-DC-45-A2 was found to be inactive. Both DC-45-A2 and dideoxy-DC-45-A2 were found to modify a self-complementary 12-mer duplex oligonucleotide containing a single (central) G residue at 23° C., as determined by nondenaturing polyacrylamide gel electrophoresis with in-gel fluorescence detection as well as liquid chromatography-mass spectrometry (LC-MS) experiments, albeit with different rates and efficiencies of alkylation. Although alkylation of the DNA duplex by DC-45-A2 proceeds with a half life of hours at 23° C., the dideoxy-analog reacts with the DNA duplex within minutes at 23° C. and with apparently greater efficiency. Iso-DC-45-A2 was not observed to modify the same DNA duplex under any conditions examined.

Heretofore, antiproliferative effects of nonglycosylated trioxacarcins such as DC-45-A2 have not been reported, so far as we are aware, nor has their chemistry with deoxyribonucleic acids been studied. Our findings suggest that the nonglycosylated, rigid polycyclic framework of DC-45-A2, with a naturally configured spiro-epoxide function, comprises structural features necessary and sufficient to provide an electrophile capable of alkylating G residues of duplex DNA, and that substantial variation in the rate, efficiency, and sequence specificity of DNA alkylation might be achieved by substitution upon this framework, which need not necessarily involve glycosylation. Structural variations by the convergent route reported can be achieved in two distinct ways, which together should allow for multiplicative enhancement of the pool of synthetic trioxacarcins. First, selective derivatization of the hydroxyl groups should be feasible by virtue of their orthogonal protection. Second, more deep-seated structural changes can be achieved by variation of any of the three coupling components [exemplified by the synthesis of dideoxy-DC-45-A2 (26)]. We believe that the route to trioxacarcins described enables a comprehensive and broad evaluation of trioxacarcin-based structures as potential chemotherapeutic agents and provides a viable basis for their production on scales necessary to support clinical evaluation.

See also Svenda et al., "Organic Synthesis Toward Small-Molecule Probes and Drugs Special Feature: A multiply convergent platform for the synthesis of trioxacarcins" *PNAS* (2011) 1-6, incorporated herein by reference in its entirety.

General Experimental Procedures

All reactions were performed in round-bottom flasks fitted with rubber septa under a positive pressure of argon, unless otherwise noted. Air- and moisture-sensitive liquids were transferred via syringe or stainless steel cannula. Organic solutions were concentrated by rotary evaporation (house vacuum, ca. 25-40 Torr) at ambient temperature, unless otherwise noted. Analytical thin-layer chromatography (TLC) was performed using glass plates pre-coated with silica gel (0.25 mm, 60 Å pore-size, 230-400 mesh, Merck KGA) impregnated with a fluorescent indicator (254 nm). TLC plates were visualized by exposure to ultraviolet light, then were stained with either an aqueous sulfuric acid solution of ceric ammonium molybdate (CAM), an ethanol-aqueous sulfuric acid solution of 2,4-dinitrophenylhydrazine (DNP), or an aqueous sodium hydroxide-potassium carbonate solution of potassium permanganate ($KMnO_4$) then briefly heated on a hot plate. Flash-column chromatography was performed as described by Still, W. C.; Khan, M.; Mitra, A. *J. Org. Chem.* 1978, 43, 2923-2925 employing silica gel (60 Å, 32-63 µM, standard grade, Dynamic Adsorbents, Inc.).

Materials. Commercial solvents and reagents were used as received with the following exceptions. Triethylamine and tetramethylethylenediamine were distilled from calcium hydride under an atmosphere of dinitrogen. Tetrahydrofuran, dichloromethane, benzene, toluene, and ether were purified by the method of Pangborn, A. B.; Giardello, M. A.; Grubbs, R. H.; Rosen, R. K.; Timmers, F. *J. Organometallics* 1996, 15, 1518-1520. Anhydrous solutions of tert-butyl hydroperoxide in benzene were prepared and stored according to Sharpless (Sharpless, K. B.; Verhoeven, T. R. *Aldrichimica Acta* 1979, 12, 63-74; Hill, J. G.; Rossiter, B. E.; Sharpless, K. B. *J. Org. Chem.* 1983, 48, 3607-3608). All transfers of tert-butyl hydroperoxide solutions were conducted using calibrated plastic pipettes. Solutions of potassium tert-butoxide in tetrahydrofuran (1.0 M) were prepared in vials fitted with a syringe valve ("Mininert®") and were stored at ambient temperature in a desiccator for no more than seven days.

Instrumentation.

Proton magnetic resonance ($^1H$ NMR) spectra were recorded on Varian INOVA 500 (500 MHz) or 600 (600 MHz) NMR spectrometers at 23° C. Proton chemical shifts are expressed in parts per million (ppm, δ scale) and are referenced to residual protium in the NMR solvent ($CHCl_3$, δ 7.26; $C_6D_5H$, δ 7.15). Data are represented as follows: chemical shift, multiplicity (s=singlet, d=doublet, t=triplet, q=quartet, m=multiplet and/or multiple resonances, br=broad, app=apparent), integration, and coupling constant (J) in Hertz. Carbon nuclear magnetic resonance spectra ($^{13}C$ NMR) were recorded on Varian INOVA 500 (125 MHz) NMR spectrometers at 23° C. Carbon chemical shifts are expressed in parts per million (ppm, δ scale) and are referenced to the carbon resonances of the NMR solvent ($CDCl_3$, δ 77.0; $C_6D_6$, δ 128.0). Infrared (IR) spectra were obtained using a Shimadzu 8400S FT-IR spectrometer and were referenced to a polystyrene standard. Data are represented as follows: frequency of absorption ($cm^{-1}$), intensity of absorption (s=strong, m=medium, w=weak, br=broad). High-resolution mass spectra were obtained at the Harvard University Mass Spectrometry Facility. High performance liquid chromatography purifications were performed using an Agilent Technologies 1200 Series preparative HPLC system.

Synthetic Procedures

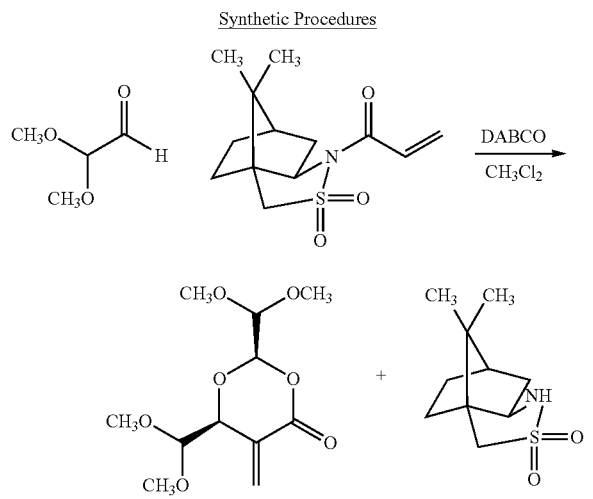

(2R,6S)-2,6-Bis(dimethoxymethyl)-5-methylidene-1,3-dioxan-4-one 1,4-Diazabicyclo[2.2.2]octane (275 mg, 2.45 mmol, 0.15 equiv) was added to a solution of 2,2-dimethoxyacetaldehyde (5.10 g, 49.0 mmol, 3.0 equiv) and sulfonyl imide (4.40 g, 16.3 mmol, 1 equiv) in dichloromethane (26 mL) at 23° C. After 2.5 h, a second portion of 1,4-diazabicyclo[2.2.2] octane (275 mg, 2.45 mmol, 0.15 equiv) was added. After 12.5 h, the reaction mixture was concentrated. The residue was purified by flash-column chromatography (30% ethyl acetate-hexanes initially, grading to 50% ethyl acetate-hexanes) to provide (2R,6S)-2,6-bis(dimethoxymethyl)-5-methylidene-1,3-dioxan-4-one (the product was obtained as a single diastereomer; the stereochemistry at C2 is inconsequential and is assigned tentatively as S; see Drewes, S. E.; Emslie, N. D.; Karodia, N.; Khan, A. A. *Chem. Ber.* 1990, 123, 1447-1448) contaminated with ~20% of the sultam auxiliary (total mass: 3.90 g). The bulk of the product was transformed as outlined in the following paragraph, without additional purification. Independently, an analytically pure sample of the product was obtained by further flash-column chromatography (30% ethyl acetate-hexanes initially, grading to 50% ethyl acetate-hexanes) and was characterized by $^1$H NMR, $^{13}$C NMR, IR, and HRMS. TLC: (30% acetone-hexanes) $R_f$=0.40 (KMnO$_4$); $^1$H NMR (500 MHz, CDCl$_3$) δ: 6.49 (m, 1H), 5.91 (dd, 1H, J=2.0, 1.0 Hz), 5.17 (d, 1H, J=4.5 Hz), 4.70 (m, 1H), 4.40 (d, 1H, J=4.5 Hz), 4.38 (d, 1H, J=5.0 Hz), 3.51 (s, 3H), 3.51 (s, 3H), 3.48 (s, 3H), 3.45 (s, 3H); $^{13}$C NMR (125 MHz, CDCl$_3$) δ: 163.6, 131.8, 129.2, 104.7, 102.6, 98.1, 77.7, 57.0, 55.9, 55.7, 54.9; FTIR (neat), cm$^{-1}$: 2944 (w), 2838 (w), 1746 (s), 1192 (s), 1074 (s); HRMS (ESI): Calcd for (C$_{11}$H$_{18}$O$_7$+Na)$^+$ 285.0945. found 285.0946.

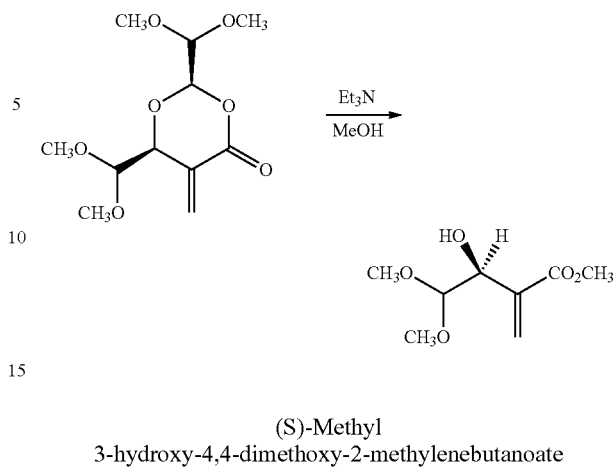

(S)-Methyl 3-hydroxy-4,4-dimethoxy-2-methylenebutanoate

Triethylamine (1.0 mL) was added to a solution of the dioxanone (1 equiv, see paragraph above) in methanol (80 mL) at 23° C. After 30 min, the reaction mixture was concentrated. The residue was purified by flash-column chromatography (30% ethyl acetate-hexanes initially, grading to 50% ethyl acetate-hexanes) to provide (S)-methyl 3-hydroxy-4,4-dimethoxy-2-methylenebutanoate contaminated with ~10% of the sultam auxiliary (total mass: 1.92 g). The bulk of the product was transformed as outlined in the following paragraph, without additional purification. Independently, an analytically pure sample of the product was obtained by further flash-column chromatography (30% ethyl acetate-hexanes initially, grading to 50% ethyl acetate-hexanes) and was characterized by $^1$H NMR, $^{13}$C NMR, IR, and HRMS. Chiral GC analysis of the purified alcohol ($t_R$=42.8 min) showed it to be >98% enantiomerically pure using for comparison a racemic sample ($t_R$=42.8 and 43.5 min; Restek Rt-bDEXsm column, length: 30 m, inner diameter: 0.25 mm, film thickness: 0.25 μm, temperature gradient: 40→160° C. at 2° C./min, flow rate: 5.9 mL/min). TLC: (40% ethyl acetate-hexanes) $R_f$=0.23 (KMnO$_4$); $^1$H NMR (500 MHz, CDCl$_3$) δ: 6.32 (s, 1H), 5.95 (s, 1H), 4.54 (dd, 1H, J=5.3, 5.0 Hz), 4.42 (d, 1H, J=5.0 Hz), 3.76 (s, 3H), 3.43 (s, 3H), 3.40 (s, 3H), 2.89 (d, 1H, J=5.5 Hz); $^{13}$C NMR (100 MHz, CDCl$_3$) δ: 166.7, 138.4, 127.1, 105.4, 71.1, 55.4, 55.0, 51.9. FTIR (neat), cm$^{-1}$: 3493 (br), 2953 (m), 1721 (s), 1438 (m), 1125 (s), 1073 (s); HRMS (ESI): Calcd for (C$_8$H$_{14}$O$_5$+Na)$^+$ 213.0733. found 213.0739.

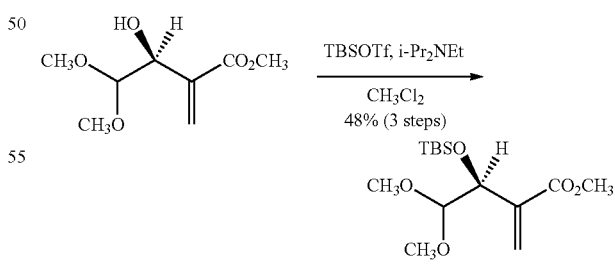

(S)-Methyl 3-tert-butyldimethylsilyloxy-4,4-dimethoxy-2-methylenebutanoate tert-Butyldimethylsilyltrifluoromethanesulfonate (2.78 mL, 12.1 mmol, 1.2 equiv) was added to an ice-cooled solution of alcohol (1 equiv, see paragraph above) and N,N-diisopropylethylamine (2.64 mL, 15.1 mmol, 1.5 equiv) in dichloromethane (100 mL) at 0° C. After 1 h, saturated aqueous sodium bicarbonate solution (30 mL) was added. The cooling bath was removed and the reaction flask was allowed to warm to 23° C. The layers were separated. The aqueous layer was extracted with dichloromethane (2×30 mL). The organic layers were combined. The combined solution was dried over sodium sulfate. The dried solution was filtered and the filtrate was concentrated. The residue was purified by flash-column chromatography (2% ethyl acetate-hexanes initially, grading to 6% ethyl acetate-hexanes) to provide 2.36 g of the product, (S)-methyl 3-tert-butyldimethylsilyloxy-4,4-dimethoxy-2-methylenebutanoate, as a colorless oil (48% over 3 steps) (Svenda, J.; Myers, A. G. Org. Lett. 2009, 11, 2437-2440). TLC: (40% ethyl acetate-hexanes) $R_f$=0.81 (KMnO$_4$); $^1$H NMR (500 MHz, CDCl$_3$) δ: 6.22 (s, 1H), 5.89 (s, 1H), 4.65 (d, 1H, J=5.0 Hz), 4.17 (d, 1H, J=6.0 Hz), 3.76 (s, 3H), 3.44 (s, 3H), 3.34 (s, 3H), 0.89 (s, 9H), 0.10 (s, 3H), 0.02 (s, 3H); $^{13}$C NMR (100 MHz, CDCl$_3$) δ: 166.9, 141.6, 125.1, 108.2, 71.5, 56.2, 55.6, 51.7, 25.7, 18.1-5.0, -5.0; FTIR (neat), cm$^{-1}$: 2953 (m), 2932 (m), 2859 (m), 2359 (m), 2344 (m), 1730 (s), 1260 (s), 1107 (s); HRMS (ESI): Calcd for (C$_{14}$H$_{28}$O$_5$Si+Na)$^+$ 327.1598. found 327.1610.

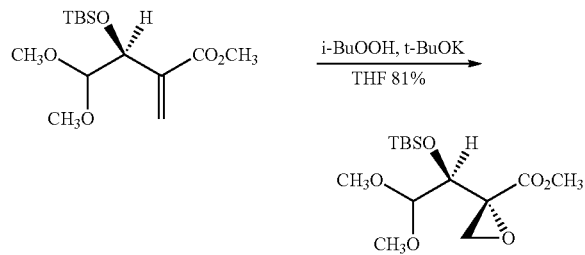

(2R,3S)-Methyl 3-tert-butyldimethylsilyloxy-2-epoxy-4,4-dimethoxybutanoate

Potassium tert-butoxide (1.0 M solution in tetrahydrofuran, 388 μL, 0.39 mmol, 0.050 equiv) was added to an ice-cooled solution of the alkene (2.36 g, 7.75 mmol, 1 equiv) and tert-butyl hydroperoxide (3.2 M solution in benzene, 4.85 mL, 15.5 mmol, 2.0 equiv) in tetrahydrofuran (77 mL) at 0° C. After 2.5 h, a second portion of potassium tert-butoxide (1.0 M solution in tetrahydrofuran, 388 μL, 0.39 mmol, 0.050 equiv) was added. After 2 h, solid sodium sulfite (4.88 g, 38.8 mmol, 5.0 equiv) was added in one portion. The cooling bath was removed and the reaction flask was allowed to warm to 23° C. After 30 min, the product mixture was filtered through a short plug of Celite, washing with ether (150 mL). The filtrate was concentrated. $^1$H NMR analysis of the residue revealed that the product comprised a 13:1 mixture of anti and syn epoxides, respectively. The mixture was separated by flash-column chromatography (10% ethyl acetate-hexanes initially, grading to 15% ethyl acetate-hexanes) to provide 2.01 g of the product, methyl 3-tert-butyldimethylsilyloxy-2-epoxy-4,4-dimethoxybutanoate,[4] as a colorless oil (81%). TLC: (20% ethyl acetate-hexanes) $R_f$=0.46 (CAM); $^1$H NMR (500 MHz, CDCl$_3$) δ: 4.40 (d, 1H, J=6.5 Hz), 4.07 (d, 1H, J=7.5 Hz), 3.76 (s, 3H), 3.48 (s, 3H), 3.46 (s, 3H), 3.09 (d, 1H, J=6.5 Hz), 2.88 (d, 1H, J=6.0 Hz), 0.88 (s, 9H), 0.10 (s, 3H), 0.09 (s, 3H); $^{13}$C NMR (125 MHz, CDCl$_3$) δ: 169.5, 107.4, 72.6, 59.2, 57.1, 56.9, 52.4, 50.1, 25.7, 18.2, -4.8, -5.0; FTIR (neat), cm$^{-1}$: 2953 (m), 2929 (m), 1740 (s), 1254 (s), 1105 (s); HRMS (ESI): Calcd for (C$_{14}$H$_{28}$O$_6$Si+K)$^+$ 359.1287. found 359.1291.

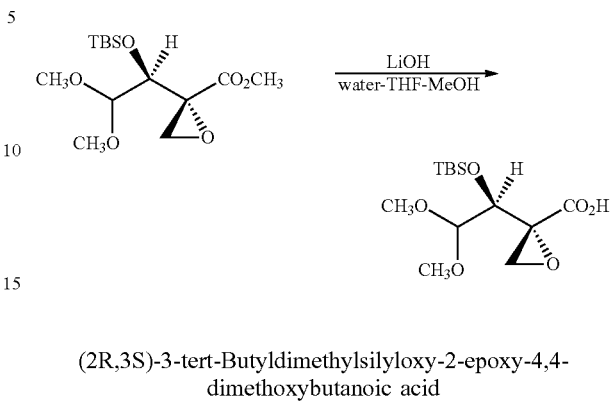

(2R,3S)-3-tert-Butyldimethylsilyloxy-2-epoxy-4,4-dimethoxybutanoic acid

Lithium hydroxide (1.0 M solution in water, 9.67 mL, 9.67 mmol, 2.0 equiv) was added to an ice-cooled solution of the ester (1.55 g, 4.84 mmol, 1 equiv) in a mixture of tetrahydrofuran (14 mL) and methanol (7.0 mL) at 0° C. After 9 h, the reaction mixture was diluted with ethyl acetate (60 mL). The diluted solution was acidified to pH ~3 by dropwise addition of 1.0 M aqueous hydrochloric acid solution (~10 mL). The reaction flask was allowed to warm to 23° C. The layers were separated. The aqueous layer was extracted with ethyl acetate (3×80 mL). The organic layers were combined. The combined solution was dried over sodium sulfate. The dried solution was filtered and the filtrate was concentrated to provide 1.48 g of the product, (2R,3S)-3-tert-butyldimethylsilyloxy-2-epoxy-4,4-dimethoxybutanoic acid, as a colorless oil. $^1$H NMR (500 MHz, CDCl$_3$) δ: 10.05 (br, 1H), 4.42 (d, 1H, J=6.0 Hz), 3.98 (d, 1H, J=6.0 Hz), 3.51 (s, 3H), 3.49 (s, 3H), 3.16 (d, 1H, J=5.5 Hz), 3.04 (d, 1H, J=6.0 Hz), 0.90 (s, 9H), 0.12 (s, 6H); $^{13}$C NMR (125 MHz, CDCl$_3$) δ: 171.8, 107.1, 72.7, 59.1, 57.1, 56.7, 50.5, 25.6, 18.1, -4.9, -5.0; FTIR (neat), cm$^{-1}$: 3150 (br), 2932 (w), 1742 (s), 1117 (s); HRMS (ESI): Calcd for (C$_{13}$H$_{26}$O$_6$Si+Na)$^+$ 329.1391. found 329.1394.

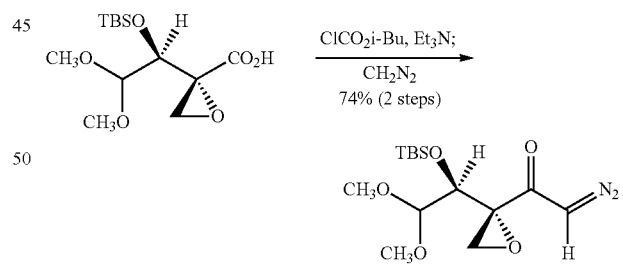

(2R,3S)-4-tert-Butyldimethylsilyloxy-1-diazo-3-epoxy-5,5-dimethoxypenta-2-one

Isobutylchloroformate (663 μL, 5.07 mmol, 1.05 equiv) was added dropwise to a solution of triethylamine (741 μL, 5.31 mmol, 1.1 equiv) in a mixture of ether (22 mL) and tetrahydrofuran (22 mL) at -20° C. After 20 min, a solution of the carboxylic acid (1.48 g, 4.83 mmol, 1 equiv, see paragraph above) in tetrahydrofuran (10 mL) was added dropwise over 10 min at -20° C. The reaction mixture was allowed to warm to -10° C. over 1 h. A freshly-distilled solution of diazomethane (0.25 M in ether, 39.0 mL, 9.66 mmol, 2.0 equiv) was added using a calibrated plastic pipette (CAUTION: diazomethane is an explosive and highly toxic gas and must be handled within a well-ventilated fume hood). The cooling bath was removed and the reaction flask was allowed to warm to 23° C. After 3 h, excess diazomethane was removed by passing a stream of nitrogen over the reaction mixture using a 22-gauge stainless steel needle and into an 8.75 M aqueous acetic acid solution. The reaction mixture was partitioned between saturated aqueous sodium bicarbonate solution (30 mL) and ether (200 mL). The layers were separated. The organic layer was washed with saturated aqueous sodium chloride solution (30 mL) and the washed solution was dried over sodium sulfate. The dried solution was filtered and the filtrate was concentrated. The residue was purified by flash-column chromatography on triethylamine-deactivated silica gel (5% ethyl acetate-hexanes initially, grading to 10% ethyl acetate-hexanes) to provide 1.18 g of the product, 4-tert-butyldimethylsilyloxy-1-diazo-3-epoxy-5,5-dimethoxypenta-2-one, as a yellow oil (74% over 2 steps). TLC: (40% ethyl acetate-hexanes) $R_f$=0.68 (CAM); $^1$H NMR (500 MHz, CDCl$_3$) δ: 5.59 (s, 1H), 4.49 (d, 1H, J=7.5 Hz), 4.04 (d, 1H, J=7.5 Hz), 3.45 (s, 3H), 3.42 (s, 3H), 3.12 (d, 1H, J=5.5 Hz), 2.76 (d, 1H, J=5.5 Hz), 0.88 (s, 9H), 0.09 (s, 6H); $^{13}$C NMR (125 MHz, CDCl$_3$) δ: 192.2, 106.4, 72.5, 63.4, 56.4, 56.0, 51.6, 50.8, 25.7, 18.1, −4.9, −5.1; FTIR (neat), cm$^{-1}$: 2932 (w), 2859 (w), 2106 (s), 1642 (s), 1360 (s), 1117 (s); HRMS (ESI): Calcd for $(C_{14}H_{26}N_2O_5Si+Na)^+$ 353.1503. found 353.1505.

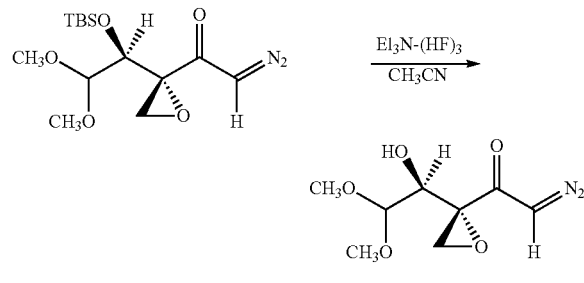

(2R,3S)-Diazo-3-epoxy-4-hydroxy-5,5-dimethoxypenta-2-one

The reaction was conducted under low lighting. The fume hood lights were turned off, and the reaction flask was wrapped in aluminum foil. Triethylamine-trihydrofluoride (1.8 mL) was added to a solution of alcohol (600 mg, 1.82 mmol, 1 equiv) in acetonitrile (1.8 mL) at 23° C. After 44 h, the reaction mixture was diluted with dichloromethane (50 mL). The diluted solution was added dropwise to saturated aqueous sodium bicarbonate solution (30 mL) (CAUTION: gas evolution). The layers were separated. The aqueous layer was extracted with dichloromethane (5×15 mL). The organic layers were combined. The combined solution was dried over sodium sulfate. The dried solution was filtered and the filtrate was concentrated to provide 392 mg of the product, (2R,3S)-diazo-3-epoxy-4-hydroxy-5,5-dimethoxypenta-2-one, as a yellow oil. The bulk of the product was transformed as outlined in the following paragraph, without additional purification. Independently, an analytically pure sample of the product was obtained by flash-column chromatography on triethylamine-deactivated silica gel (30% ethyl acetate-hexanes) and was characterized by $^1$H NMR, $^{13}$C NMR, IR, and HRMS. TLC: (40% ethyl acetate-hexanes) $R_f$=0.18 (CAM); $^1$H NMR (500 MHz, CDCl$_3$) δ: 5.63 (s, 1H), 4.56 (d, 1H, J=6.5 Hz), 4.27 (t, 1H, J=6.0 Hz), 3.44 (s, 3H), 3.43 (s, 3H), 3.22 (d, 1H, J=5.5 Hz), 2.75 (d, 1H, J=5.5 Hz), 2.32 (d, 1H, J=4.5 Hz); $^{13}$C NMR (125 MHz, CDCl$_3$) δ: 192.0, 104.2, 68.6, 61.9, 55.6, 54.5, 52.1, 49.8; FTIR (neat), cm$^{-1}$: 3441 (br), 2940 (s), 2106 (s), 1628 (s), 1364 (s), 1073 (s); HRMS (ESI): Calcd for $(C_8H_{12}N_2O_5+Na)^+$ 239.0638. found 239.0650.

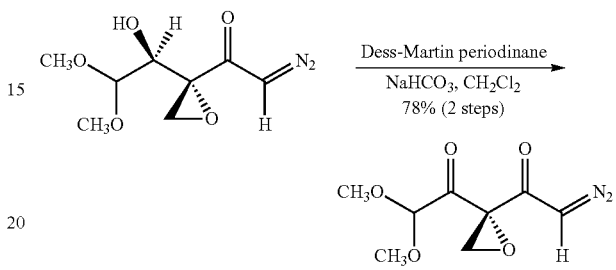

(3R)-1-Diazo-3-epoxy-5,5-dimethoxypenta-2,4-dione

Dess-Martin periodinane (847 mg, 2.00 mmol, 1.1 equiv) was added to a suspension of alcohol (392 mg, 1.81 mmol, 1 equiv, see paragraph above) and sodium bicarbonate (1.53 g, 18.2 mmol, 10 equiv) in dichloromethane (19 mL) at 23° C. After 1 h, the reaction mixture was diluted with ether (25 mL) and pentane (25 mL). The diluted mixture was filtered and the filtrate was concentrated. The residue was diluted with ether (25 mL) and pentane (25 mL). The diluted mixture was filtered and the filtrate was concentrated. The residue was purified by flash-column chromatography on triethylamine-deactivated silica gel (20% ethyl acetate-hexanes [containing 2% triethylamine] initially, grading to 40% ethyl acetate-hexanes [containing 2% triethylamine]) to provide 300 mg of the product, 1-diazo-3-epoxy-5,5-dimethoxypenta-2,4-dione, as a yellow oil (78% over two steps). TLC: (40% ethyl acetate-hexanes) $R_f$=0.30 (CAM); $^1$H NMR (600 MHz, C$_6$D$_6$) δ: 5.19 (s, 1H), 4.69 (s, 1H), 3.13 (s, 3H), 3.12 (s, 3H), 2.95 (d, 1H, J=6.0 Hz), 2.14 (d, 1H, J=6.0 Hz); $^{13}$C NMR (125 MHz, C$_6$D$_6$) δ: 196.5, 188.6, 101.7, 61.1, 54.2, 53.7, 51.5, 51.0; FTIR (neat), cm$^{-1}$: 3115 (w), 2926 (w), 2112 (s), 1746 (s), 1630 (s), 1371 (s), 1080 (s); HRMS (ESI): Calcd for $(C_8H_{10}N_2O_5+Na)^+$ 237.0482. found 237.0487.

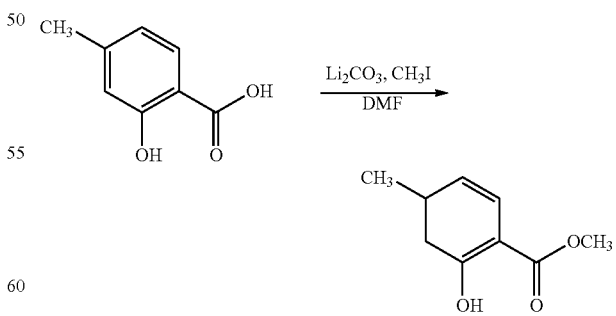

Methyl 2-hydroxy-4-methylbenzoate

Iodomethane (22.6 mL, 362 mmol, 1.1 equiv) was added to a suspension of 4-methylsalicylic acid (50.0 g, 329 mmol, 1 equiv) and lithium carbonate (26.8 g, 362 mmol, 1.1 equiv) in dimethylformamide (450 mL) at 23° C. The reaction flask was heated in an oil bath at 60° C. After 3.5 h, the warm suspension was partitioned carefully between ice water (500 mL) and ethyl acetate (800 mL). The layers were separated. The aqueous layer was extracted with ethyl acetate (800 mL). The organic layers were combined. The combined solution was washed sequentially with water (2×500 mL) then saturated aqueous sodium chloride solution (500 mL) and the washed solution was dried over sodium sulfate. The dried solution was filtered and the filtrate was concentrated. A small sample of the product (~50 mg) was purified by flash-column chromatography (2% ethyl acetate-hexanes) and was characterized by $^1$H NMR, $^{13}$C NMR, IR, and HRMS. The balance of the product, methyl 2-hydroxy-4-methylbenzoate, was used directly in the next reaction without purification. TLC: (2% ethyl acetate-hexanes) $R_f$=0.15 (CAM); $^1$H NMR (500 MHz, CDCl$_3$) δ: 10.70 (s, 1H), 7.70 (d, 1H, J=8.4 Hz), 6.79 (s, 1H), 6.69 (d, 1H, J=7.7 Hz), 3.92 (s, 3H), 2.34 (s, 3H); $^{13}$C NMR (125 MHz, CDCl$_3$) δ: 170.5, 161.5, 147.0, 129.6, 120.4, 117.7, 109.8, 52.0, 21.8; FTIR (neat), cm$^{-1}$: 3186 (m), 2956 (m), 1672 (s), 1623 (m), 1579 (m), 1504 (m), 1441 (s), 1338 (s), 1298 (s), 1250 (s), 1215 (s), 1157 (s), 1096 (s), 906 (s), 780 (s); HRMS (ESI): Calcd for (C$_9$H$_{10}$O$_3$+H)$^+$ 167.0703. found 167.0698.

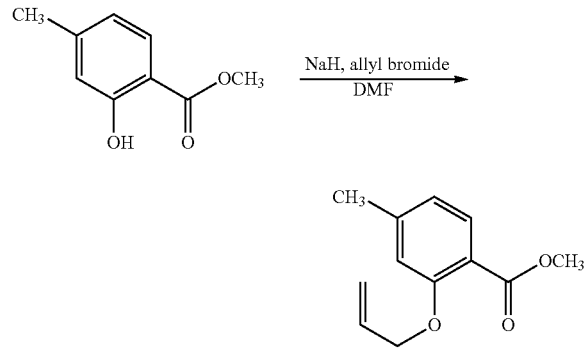

Methyl 2-(allyloxy)-4-methylbenzoate

The phenol (1 equiv, see paragraph above) was added to an ice-cooled suspension of sodium hydride (60% dispersion in mineral oil, 16.2 g, 405 mmol, 1.2 equiv) and allyl bromide (56.9 mL, 658 mmol, 2.0 equiv) in dimethylformamide (500 mL) at 0° C. After 10 min, the cooling bath was removed and the reaction flask was allowed to warm to 23° C. After 6 h, the reaction mixture was partitioned carefully between ice water (500 mL) and ether (500 mL). The layers were separated. The aqueous layer was extracted with ether (2×500 mL). The organic layers were combined. The combined solution was washed sequentially with water (3×400 mL) then saturated aqueous sodium chloride solution (400 mL) and the washed solution was dried over sodium sulfate. The dried solution was filtered and the filtrate was concentrated. A small sample of the product (~50 mg) was purified by flash-column chromatography (10% ethyl acetate-hexanes) and was characterized by $^1$H NMR, $^{13}$C NMR, IR, and HRMS. The balance of the product, methyl 2-(allyloxy)-4-methylbenzoate, was used directly in the next reaction without purification. TLC: (10% ethyl acetate-hexanes) $R_f$=0.16 (CAM); $^1$H NMR (500 MHz, CDCl$_3$) δ: 7.72 (d, 1H, J=7.8 Hz), 6.78 (d, 1H, J=8.0 Hz), 6.75 (s, 1H), 6.06 (ddt, 1H, J=17.4, 10.5, 4.9), 5.52 (ddt, 1H, J=17.2, 1.6, 1.6 Hz), 5.29 (ddt, 1H, J=9.3, 1.6, 1.6 Hz), 4.60 (m, 2H), 3.86 (s, 3H), 2.35 (s, 3H); $^{13}$C NMR (125 MHz, CDCl$_3$) δ: 166.6, 158.3, 144.4, 132.8, 131.8, 121.2, 117.4, 117.1, 114.3, 69.3, 61.7, 21.8; FTIR (neat), cm$^{-1}$: 2953 (w), 1719 (m), 1612 (m), 1503 (m), 1436 (m), 1299 (m), 1245 (m), 1088 (m) 905 (s), 728 (s); HRMS (ESI): Calcd for (C$_{12}$H$_{14}$O$_3$+H)$^+$ 207.1016. found 207.1024.

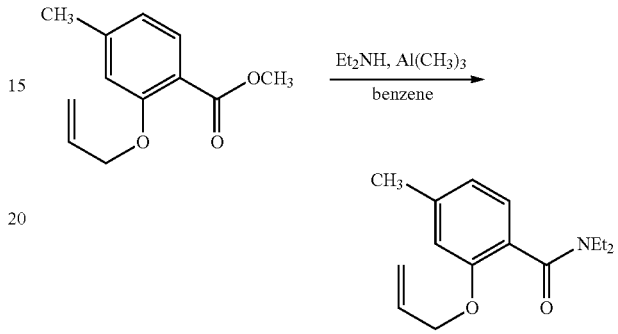

2-(Allyloxy)-N,N-diethyl-4-methylbenzamide

Trimethylaluminum (2.0 M solution in toluene, 300 mL, 600 mmol, 1.9 equiv) was added to an ice-cooled solution of diethylamine (124 mL, 1.20 mol, 3.8 equiv) in benzene (200 mL) at 0° C. After 10 min, the cooling bath was removed and the reaction flask was allowed to warm to 23° C. Ester (64.0 g, 311 mmol, 1 equiv, see paragraph above) was added dropwise to the reaction mixture over 45 min by cannula. The reaction mixture was heated at reflux in an oil bath at 120° C. (CAUTION: gas evolution). After 7 h, the heating bath was removed and the reaction flask was allowed to cool to 23° C. The reaction mixture was poured carefully into a mixture of ice water (1 L) and 12 M aqueous hydrochloric acid solution (20 mL). The layers were separated. The aqueous layer was extracted with ethyl acetate (3×1 L). The organic layers were combined. The combined solution was washed sequentially with water (1 L) then saturated aqueous sodium chloride solution (500 mL) and the washed solution was dried over sodium sulfate. The dried solution was filtered and the filtrate was concentrated. A small sample of the product (~50 mg) was purified by flash-column chromatography (30% ethyl acetate-hexanes) and was characterized by $^1$H NMR, $^{13}$C NMR, IR, and HRMS. The balance of the product, 2-(allyloxy)-N,N-diethyl-4-methylbenzamide, was used directly in the next reaction without purification. TLC: (20% ethyl acetate-hexanes) $R_f$=0.08 (CAM); $^1$H NMR (500 MHz, CDCl$_3$) δ: 7.08 (d, 1H, J=7.5 Hz), 6.77 (d, 1H, J=7.6 Hz), 6.68 (s, 1H), 5.98 (m, 1H), 5.36 (dd, 1H, J=17.2, 1.6 Hz), 5.21 (dd, 1H, J=10.5, 1.4 Hz), 4.51 (s, 2H), 3.71 (br s, 1H), 3.37 (br s, 1H), 3.15 (br s, 2H), 2.32 (s, 3H), 1.21 (t, 3H, J=7.3 Hz), 1.00 (t, 3H, J=7.1 Hz); $^{13}$C NMR (125 MHz, CDCl$_3$) δ: 168.8, 154.0, 139.9, 133.0, 127.3, 124.6, 121.6, 116.9, 113.1, 68.9, 42.6, 38.6, 21.6, 13.9, 12.8; FTIR (neat), cm$^{-1}$: 2978 (w), 2935 (w), 1611 (s), 1473 (m), 1460 (m), 1433 (m), 1293 (m), 1280 (m), 906 (s), 724 (s); HRMS (ESI): Calcd for (C$_{15}$H$_{21}$NO$_2$+Na)$^+$ 270.1464. found 270.1477.

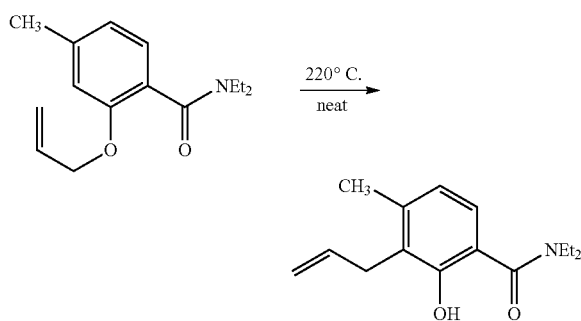

3-Allyl-N,N-diethyl-2-hydroxy-4-methylbenzamide

Amide (see paragraph above) was heated in an oil bath at 220° C. After 13 h, the heating bath was removed and the reaction flask was allowed to cool to 23° C. A small sample of the product (~50 mg) was purified by flash-column chromatography (10% ethyl acetate-hexanes) and was characterized by $^1$H NMR, $^{13}$C NMR, IR, and HRMS. The balance of the product, 3-allyl-N,N-diethyl-2-hydroxy-4-methylbenzamide, was used directly in the next reaction without purification. TLC: (16% ethyl acetate-hexanes) $R_f$=0.39 (CAM); $^1$H NMR (500 MHz, CDCl$_3$) δ: 10.16 (s, 1H), 7.06 (d, 1H, J=8.0 Hz), 6.66 (d, 1H, J=8.0 Hz), 5.95 (ddt, 1H, J=14.2, 10.3, 6.0 Hz), 5.00-4.94 (m, 2H), 3.51 (q, 4H, J=7.10 Hz), 3.46 (dt, 2H, J=6.0, 1.6), 2.29 (s, 3H), 1.27 (t, 6H, J=7.10); $^{13}$C NMR (125 MHz, CDCl$_3$) δ: 172.2, 157.0, 141.5, 135.7, 126.7, 124.9, 119.9, 115.2, 114.6, 42.2, 30.3, 19.6, 13.4; FTIR (neat), cm$^{-1}$: 3077 (w), 2975 (m), 2935 (m), 1591 (s), 1459 (s), 1446 (s), 1433 (s), 1350 (s), 1268 (s), 1255 (s), 1124 (s), 783 (s); HRMS (ESI): Calcd for (C$_{15}$H$_{21}$NO$_2$+H)$^+$ 248.1645. found 248.1645.

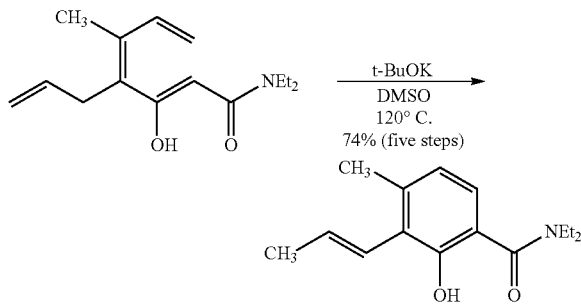

(E)-N,N-Diethyl-2-hydroxy-4-methyl-3-(prop-1-enyl)benzamide

Potassium tert-butoxide (175 g, 1.56 mol, 5.0 equiv) was added to a solution of olefin (1 equiv, see paragraph above) in dimethyl sulfoxide (300 mL) at 23° C. The reaction flask was heated in an oil bath at 120° C. After 70 min, the heating bath was removed and the reaction flask was allowed to cool to 23° C. The reaction mixture was diluted with water (200 mL). The diluted solution was acidified to pH ~2 with 6.0 M aqueous hydrochloric acid solution (~250 mL). The mixture was extracted with ethyl acetate (2×500 mL). The organic layers were combined. The combined solution was washed sequentially with water (5×500 mL) then saturated aqueous sodium chloride solution (500 mL) and the washed solution was dried over sodium sulfate. The dried solution was filtered and the filtrate was concentrated. The residue was purified by flash-column chromatography (10% ethyl acetate-hexanes) to provide 56.9 g of the product, (E)-N,N-diethyl-2-hydroxy-4-methyl-3-(prop-1-enyl)benzamide, as a yellow oil (74% over five steps). TLC: (20% ethyl acetate-hexanes) $R_f$=0.18 (CAM); $^1$H NMR (500 MHz, CDCl$_3$) δ: 9.94 (s, 1H), 7.01 (d, 1H, J=7.8 Hz), 6.67 (d, 1H, J=8.0 Hz), 6.42 (dq, 1H, J=16.0, 1.6 Hz), 6.24 (dq, 1H, J=16.2, 6.4 Hz), 3.50 (q, 4H, J=7.1 Hz), 2.33 (s, 3H), 1.94 (dd, 3H, J=6.6, 1.8 Hz), 1.25 (t, 6H, 7.1 Hz); $^{13}$C NMR (125 MHz, CDCl$_3$) δ: 171.9, 156.1, 140.2, 131.7, 126.1, 124.9, 124.3, 120.3, 115.9, 42.0, 21.0, 19.5, 13.4; FTIR (neat), cm$^{-1}$: 2979 (w), 1592 (m), 1460 (w), 1448 (w), 904 (s), 726 (s); HRMS (ESI): Calcd for (C$_{15}$H$_{21}$NO$_2$+H)$^+$ 248.1645. found 248.1650.

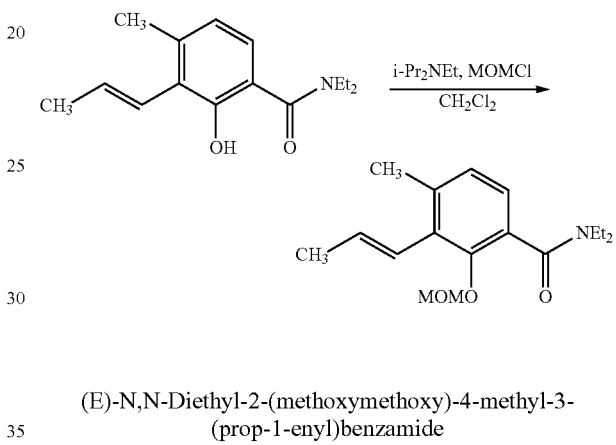

(E)-N,N-Diethyl-2-(methoxymethoxy)-4-methyl-3-(prop-1-enyl)benzamide

Chloromethylmethyl ether (34.7 mL, 457 mmol, 2.0 equiv) was added to a solution of the phenol (56.5 g, 228 mmol, 1 equiv) and N,N-diisopropylethylamine (79.6 mL, 457 mmol, 2.0 equiv) in dichloromethane (600 mL) at 23° C. After 24 h, the reaction mixture was diluted with water (200 mL). The layers were separated. The aqueous layer was extracted with dichloromethane (2×300 mL). The organic layers were combined. The combined solution was washed sequentially with water (100 mL) then saturated aqueous sodium chloride solution (100 mL) and the washed solution was dried over sodium sulfate. The dried solution was filtered and the filtrate was concentrated. A small sample of the product (~50 mg) was purified by flash-column chromatography (20% ethyl acetate-hexanes) and was characterized by $^1$H NMR, $^{13}$C NMR, IR and HRMS. The balance of the product, (E)-N,N-diethyl-2-(methoxymethoxy)-4-methyl-3-(prop-1-enyl)benzamide, was used directly in the next reaction without purification. TLC: (25% ethyl acetate-hexanes) $R_f$=0.21 (CAM); $^1$H NMR (500 MHz, CDCl$_3$) δ: 6.96 (m, 2H), 6.39 (dd, 1H, J=18.1, 2.0 Hz), 6.04 (qd, 1H, J=16.1, 6.3 Hz), 4.97 (br s, 1H), 4.94 (br s, 1H), 3.66 (br s, 1H), 3.47 (s, 3H), 3.41 (br s, 1H), 3.22 (br s, 1H), 3.14 (br s, 1H), 2.31 (s, 3H), 1.90 (dd, 3H, J=6.8, 2.0 Hz), 1.23 (t, 3H, J=7.3 Hz), 1.04 (t, 3H, J=7.3 Hz); $^{13}$C NMR (125 MHz, CDCl$_3$) δ: 169.0, 150.3, 138.2, 131.9, 129.7, 126.4, 125.2, 124.9, 99.5, 57.5, 43.0, 39.0, 20.9, 19.2, 13.9, 12.9; FTIR (neat), cm$^{-1}$: 2972 (m), 2935 (m), 1626 (s), 1428 (s), 1158 (s), 1123 (m), 1038 (m), 972 (s), 925 (s), 729 (s); HRMS (ESI): Calcd for (C$_{17}$H$_{25}$NO$_3$+H)$^+$ 292.1907. found 292.1918.

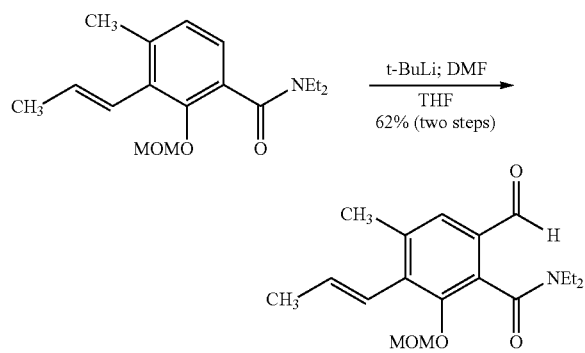

(E)-N,N-Diethyl-6-formyl-2-(methoxymethoxy)-4-methyl-3-(prop-1-enyl)benzamide tert-Butyllithium (1.7 M solution in pentane, 255 mL, 434 mmol, 2.0 equiv) was added to a solution of N,N,N,N-tetramethylethylenediamine (65.0 mL, 434 mmol, 2.0 equiv) in tetrahydrofuran (500 mL) at −78° C. After 15 min, a solution of the amide (1 equiv, see paragraph above) in tetrahydrofuran (300 mL) was added by cannula. After 1 h, dimethylformamide (191 mL, 2.60 mol, 12 equiv) was added. After 1.5 h, the cooling bath was removed and the reaction flask was allowed to warm to 23° C. After 16 h, the reaction mixture was diluted with saturated aqueous ammonium chloride solution (100 mL). After 20 min, the diluted solution was partially concentrated to remove the volatile organic solvents. The aqueous residue was partitioned between water (500 mL) and ethyl acetate (500 mL). The layers were separated. The aqueous layer was extracted with ethyl acetate (600 mL). The organic layers were combined. The combined solution was washed sequentially with water (3×400 mL) then saturated aqueous sodium chloride solution (400 mL) and the washed solution was dried over sodium sulfate. The dried solution was filtered and the filtrate was concentrated. The residue was purified by flash-column chromatography (35% ethyl acetate-hexanes) to provide 45.0 g of the product, (E)-N,N-diethyl-6-formyl-2-(methoxymethoxy)-4-methyl-3-(prop-1-enyl)benzamide, as a pale yellow oil (62% over two steps). TLC: (35% ethyl acetate-hexanes) $R_f$=0.19 (CAM); $^1$H NMR (500 MHz, CDCl$_3$) δ: 9.90 (s, 1H), 7.54 (s, 1H), 6.44 (dq, 1H, J=16.3, 1.6 Hz), 6.23 (dq, 1H, J=16.3, 6.6 Hz), 5.02 (d, 1H, J=5.3 Hz), 4.96 (d, 1H, J=5.3 Hz), 3.70-3.52 (m, 2H), 3.51 (s, 3H), 3.13 (m, 2H), 2.39 (s, 3H), 1.95 (dd, 3H, J=6.4, 1.6 Hz), 1.30 (t, 3H, J=7.1 Hz), 1.04 (t, 3H, J=7.1 Hz); $^{13}$C NMR (125 MHz, CDCl$_3$) δ: 190.1, 166.2, 150.7, 138.4, 138.3, 134.4, 132.3, 131.1, 127.1, 124.5, 99.8, 57.7, 43.1, 39.2, 21.0, 19.5, 13.7, 12.8; FTIR (neat), cm$^{-1}$: 2973 (m), 2935 (m), 2749 (w), 1695 (s), 1628 (s), 1591 (m), 1432 (m), 1280 (s), 1160 (s), 989 (s), 925 (s); HRMS (ESI): Calcd for (C$_{18}$H$_{25}$NO$_4$+H)$^+$ 320.1856. found 320.1862.

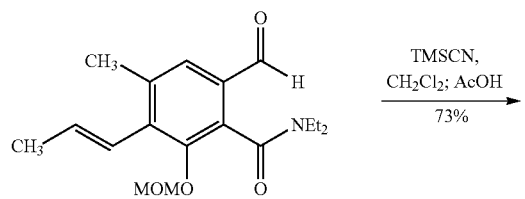

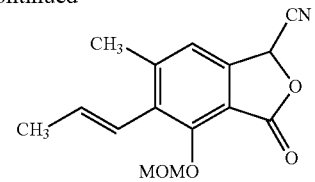

(E)-4-(Methoxymethoxy)-6-methyl-3-oxo-5-(prop-1-enyl)-1,3-dihydroisobenzofuran-1-carbonitrile Cyanotrimethylsilane (27.1 mL, 211 mmol, 1.5 equiv) was added to an ice-cooled solution of the aldehyde shown above (45.0 g, 141 mmol, 1 equiv) in dichloromethane (330 mL) at 0° C. After 30 min, the cooling bath was removed and the reaction flask was allowed to warm to 23° C. After 45 min, the solution was concentrated carefully. The residue was dissolved in glacial acetic acid (300 mL) (CAUTION: the highly toxic gas hydrogen cyanide may be generated upon treatment of the residue with acetic acid, this operation should be conducted in a well-ventilated fume hood). The acetic acid solution was stirred at 23° C. After 40 h, the solvent was removed as an azeotrope with heptane (four 300-mL portions). The residue was purified by flash-column chromatography (16% ethyl acetate-hexanes initially, grading to 25% ethyl acetate-hexanes) to provide 27.8 g of the product, (E)-4-(methoxymethoxy)-6-methyl-3-oxo-5-(prop-1-enyl)-1,3-dihydroisobenzofuran-1-carbonitrile, as a pale yellow solid (73%). TLC: (25% ethyl acetate-hexanes) $R_f$=0.31 (CAM); $^1$H NMR (500 MHz, CDCl$_3$) δ: 7.20 (s, 1H), 6.35 (d, 1H, J=16.1 Hz), 6.16 (dq, 1H, J=16.1, 6.4 Hz), 5.93 (s, 1H), 5.30 (m, 2H), 3.54 (s, 3H), 2.46 (s, 3H), 1.97 (d, 3H, J=6.35); $^{13}$C NMR (125 MHz, CDCl$_3$) δ: 165.7, 154.6, 147.7, 140.9, 134.8, 134.5, 123.1, 119.1, 114.1, 113.3, 100.8, 64.6, 57.9, 22.1, 19.3; FTIR (neat), cm$^{-1}$: 2936 (w), 1776 (s), 1607 (m), 1439 (m), 1281 (m), 1263 (m), 1159 (m), 1099 (m), 1028 (s), 982 (s), 908 (s); HRMS (ESI): Calcd for (C$_{15}$H$_{15}$NO$_4$+Na)$^+$ 296.0893. found 296.0896.

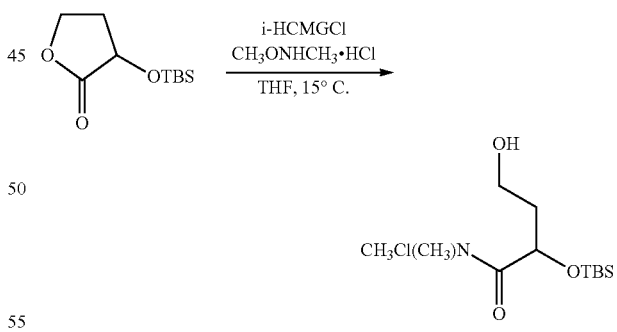

(2S)-2-(tert-Butyldimethylsilyloxy)-4-hydroxy-N-methoxy-N-methylbutanamide

A 1-L, three-necked, round-bottom flask was fitted with an addition funnel, a thermometer, and a rubber septum. The apparatus was flushed with argon for 20 min. (S)-3-(tert-Butyldimethylsilyloxy)dihydrofuran-2(3H)-one (Schinzer, D.; Bauer, A.; Schieber, J. Chem. Eur. J. 1999, 5, 2492-2500) (32.4 g, 150 mmol, 1 equiv), N,O-dimethylhydroxylamine hydrochloride (22.7 g, 233 mmol, 1.55 equiv), and tetrahydrofuran (300 mL) were added to the reaction flask at 23° C. The white slurry was cooled to an internal temperature of −15° C. in a dry ice-acetone bath. i-Propylmagnesium chloride (2 M solution in tetrahydrofuran, 225 mL, 450 mmol, 3.0 equiv) was added to the cooled slurry over 15 min through the addition funnel while maintaining the internal temperature of the reaction mixture between −15 and −8° C. by adding small portions of dry ice to the cooling bath. After the addition was complete, the internal temperature of the reaction mixture was maintained at −11° C. After 30 min, the cooling bath was removed and the reaction mixture was partitioned between saturated aqueous ammonium chloride solution (500 mL) and ethyl acetate (600 mL). The layers were separated. The aqueous layer was extracted with ethyl acetate (2×600 mL). The organic layers were combined. The combined solution was washed with saturated aqueous sodium chloride solution (200 mL) and the washed solution was dried over sodium sulfate. The dried solution was filtered and the filtrate was concentrated. A small sample of the product (~50 mg) was purified by flash-column chromatography (50% ethyl acetate-hexanes) and was characterized by $^1$H NMR, $^{13}$C NMR, IR, and HRMS. The balance of the product, (2S)-2-(tert-butyldimethylsilyloxy)-4-hydroxy-N-methoxy-N-methylbutanamide, was used directly in the next reaction without purification. TLC: (60% ethyl acetate-hexanes) $R_f$=0.14 (CAM); $^1$H NMR (500 MHz, CDCl$_3$) δ: 4.73 (br s, 1H), 3.75-3.64 (m, 5H), 3.14 (br s, 3H), 2.69 (br s, 1H), 1.89-1.80 (m, 2H), 0.84 (s, 9H), 0.03 (s, 3H), 0.01 (s, 3H); $^{13}$C NMR (125 MHz, CDCl$_3$) δ: 174.4, 68.0, 61.2, 59.0, 36.5, 32.5, 25.6, 18.1, −4.9, −5.5; FTIR (neat), cm$^{-1}$: 3441 (w, br), 2955 (m), 2930 (m), 2857 (m), 1663 (m), 1251 (m), 1096 (m), 995 (m), 835 (s), 777 (s); HRMS (ESI): Calcd for $(C_{12}H_{27}NO_4Si+H)^+$ 278.1782. found 278.1793.

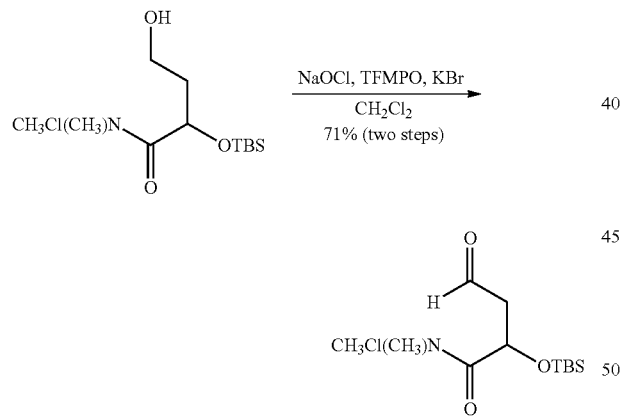

(2S)-2-(tert-Butyldimethylsilyloxy)-N-methoxy-N-methyl-4-oxobutanamide

Preparation of a sodium bicarbonate-buffered sodium hypochlorite stock solution: A Clorox bleach solution containing 6.15% sodium hypochlorite (150 mL) was combined with water (120 mL) in a 500 mL beaker. Sodium bicarbonate (18.0 g) was dissolved in the sodium hypochlorite solution immediately prior to use in the oxidation of primary alcohol.

A sodium bicarbonated-buffered sodium hypochlorite solution (355 mL, see paragraph above) was added to a water-bath cooled mixture of 2,2,6,6-tetramethylpiperidin-1-oxyl (247 mg, 1.58 mmol, 0.010 equiv), potassium bromide (1.88 g, 15.8 mmol, 0.10 equiv), and the alcohol above (1 equiv, see above) in dichloromethane (160 mL) at 23° C. After 15 min of vigorous stirring, the reaction mixture was partitioned between 1.0 M aqueous sodium hydroxide solution (500 mL) and dichloromethane (1 L). The layers were separated. The organic layer was washed sequentially with 1.0 M aqueous hydrochloric acid solution (500 mL), water (500 mL), then saturated aqueous sodium chloride solution (500 mL) and the washed solution was dried over sodium sulfate. The dried solution was filtered and the filtrate was concentrated. The residue was purified by flash-column chromatography (15% ethyl acetate-dichloromethane) to provide 29.2 g of the product, (2S)-2-(tert-butyldimethylsilyloxy)-N-methoxy-N-methyl-4-oxobutanamide, as a pale yellow oil (71% over two steps). TLC: (15% ethyl acetate-hexanes) $R_f$=0.45 (DNP); $^1$H NMR (500 MHz, CDCl$_3$) δ: 9.81 (s, 1H), 5.04 (m, 1H), 3.72 (s, 3H), 3.20 (br s, 3H), 2.83-2.73 (m, 2H), 0.88 (s, 9H), 0.11 (s, 9H), 0.08 (s, 3H); $^{13}$C NMR (125 MHz, CDCl$_3$) δ: 199.9, 172.4, 65.2, 61.4, 47.9, 32.5, 25.6, 18.1, −4.7, −5.3; FTIR (neat), cm$^{-1}$: 2930 (m), 2857 (m), 1724 (m), 1678 (s), 1136 (m), 1096 (m), 993 (m), 835 (s), 777 (s); HRMS (ESI): Calcd for $(C_{12}H_{25}NO_4Si+H)^+$ 276.1626. found 276.1630.

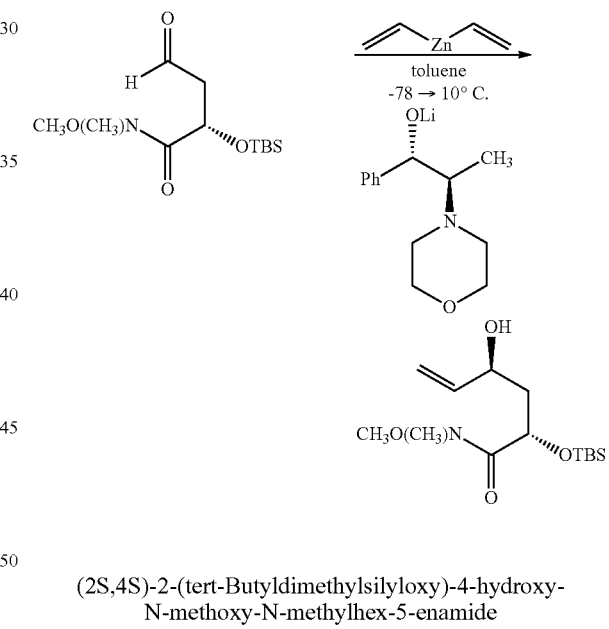

(2S,4S)-2-(tert-Butyldimethylsilyloxy)-4-hydroxy-N-methoxy-N-methylhex-5-enamide A 5-L, three-necked, round-bottom flask was fitted with a mechanical stirrer, a thermometer, and a rubber septum. The reaction apparatus was flushed with argon for 20 min. (1S,2R)-2-Morpholin-4-yl-1-phenylpropanol (Brubaker, J. D.; Myers, A. G. Org. Lett. 2007, 9, 3523-3525) (32.1 g, 145 mmol, 2.0 equiv) and toluene (1.40 L) were added to the reaction flask at 23° C. The reaction flask was cooled in an ice bath to 0° C. n-Butyllithium (2.5 M solution in hexanes, 58.0 mL, 145 mmol, 2.0 equiv) was added to the cooled solution by cannula over 10 min. After 35 min, divinyl zinc (0.28 M solution, 518 mL, 145 mmol, 2.0 equiv)[7] was added by cannula over 20 min. After 1 h, the reaction mixture was cooled to an internal temperature of −70° C. in a dry ice-acetone bath. A solution of the aldehyde shown above (20.0 g, 72.6 mmol, 1 equiv) in toluene (50 mL) was added to the cooled solution by cannula over 30 min. The reaction mixture was allowed to warm to an internal temperature of 10° C. over 5.5 h. The product solution was partitioned between 1.0 M aqueous hydrochloric acid solution (2 L) and ethyl acetate (1 L). The layers were separated. The organic layer was washed sequentially with 1.0 M aqueous hydrochloric acid solution (2 L), saturated aqueous sodium bicarbonate solution (1 L), then water (1 L) and the washed solution was dried over sodium sulfate. The dried solution was filtered and the filtrate was concentrated to provide (2S,4S)-2-(tert-butyldimethylsilyloxy)-4-hydroxy-N-methoxy-N-methyhex-5-enamide, which was used directly in the next reaction without purification. Attempts to purify the product by flash-column chromatography lead to silica gel-induced lactonization to furnish (3S,5S)-3-(tert-butyldimethylsilyloxy)-5-vinyldihydrofuran-2(3H)-one.

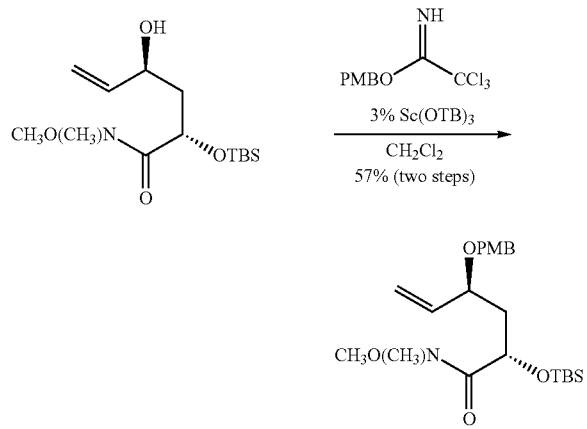

(2S,4S)-2-(tert-Butyldimethylsilyloxy)-N-methoxy-4[(4-methoxybenzyl)oxy]-N-methylhex-5-enamide Scandium triflate (1.07 g, 52.2 mmol, 0.03 equiv) was added to a solution of the alcohol above (1 equiv, see paragraph above) and 4-methoxybenzyl-2,2,2-trichloroacetimidate (30.2 mL, 145 mmol, 2.0 equiv) in dichloromethane (700 mL) at 23° C. After 30 min, the reaction mixture was partitioned between 1.0 M aqueous hydrochloric acid solution (1 L) and dichloromethane (1 L). The layers were separated. The organic layer was washed sequentially with 1.0 M aqueous hydrochloric acid solution (1 L), 1.0 M aqueous sodium hydroxide solution (2×1 L), water (1 L), then saturated aqueous sodium chloride solution (1 L) and the washed solution was dried over sodium sulfate. The dried solution was filtered and the filtrate was concentrated. The residue was purified by flash-column chromatography (11% ethyl acetate-hexanes initially, grading to 16% ethyl acetate-hexanes) to provide 17.8 g of the product, (2S,4S)-2-(tert-butyldimethylsilyloxy)-N-methoxy-4[(4-methoxybenzyl)oxy]-N-methylhex-5-enamide, as a pale yellow oil (57% over two steps). The product afforded in this procedure is a 12:1 mixture of diastereomers (C4 epimers); the major diastereomer is depicted in the equation above. The minor C4 epimer was carried through as an impurity to the stage of the ring-closing olefin-metathesis reaction (vide infra), where the diastereomeric products were easily separated. TLC: (20% ethyl acetate-hexanes) $R_f$=0.16 (KMnO$_4$); $^1$H NMR (500 MHz, CDCl$_3$) δ: 7.27 (d, 2H, J=8.2 Hz), 6.87 (d, 2H, J=8.7 Hz), 5.78 (ddd, 1H, J=17.9, 10.5, 7.8 Hz), 5.29 (d, 1H, J=17.4 Hz), 5.23 (d, 1H, J=10.1), 4.93 (br s, 1H), 4.54 (d, 1H, J=11.0 Hz), 4.26 (d, 1H, J=11.0 Hz), 3.81 (s, 3H), 3.64 (s, 3H), 3.17 (br s, 3H), 1.93-1.81 (m, 2H), 0.92 (s, 9H), 0.09 (s, 3H), 0.06 (s, 3H); $^{13}$C NMR (125 MHz, CDCl$_3$) δ: 158.9, 138.7, 131.0, 128.9, 117.0, 113.6, 77.0, 69.8, 66.4, 61.3, 55.2, 41.4, 32.7, 25.8, 18.3, −4.6, −5.2; FTIR (neat), cm$^{-1}$: 2955 (w), 2931 (w), 2857 (w), 1682 (m), 1514 (m), 1248 (s), 1086 (m), 831 (s); HRMS (ESI): Calcd for (C$_{22}$H$_{37}$NO$_5$Si+Na)$^+$ 446.2339. found 446.2303.

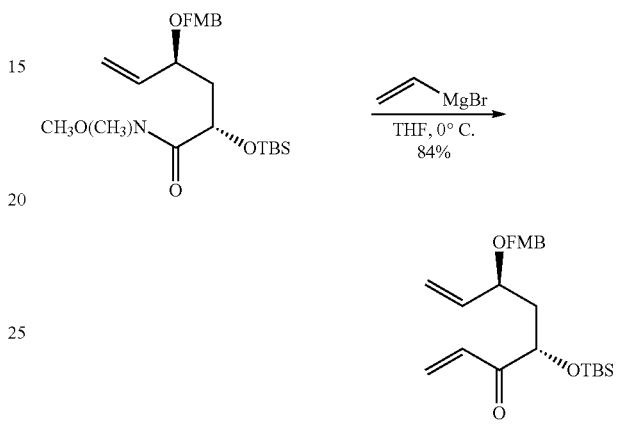

(4S,6S)-4-(tert-Butyldimethylsilyloxy)-6-(4-methoxybenzyloxy)octa-1,7-dien-3-one Vinylmagnesium bromide (1.0 M solution in tetrahydrofuran, 6.55 mL, 6.55 mmol, 1.5 equiv) was added to an ice-cooled solution of the amide (1.85 g, 4.37 mmol, 1 equiv) in tetrahydrofuran (43 mL) at 0° C. After 55 min, a second portion of vinylmagnesium bromide (1.0 M solution in tetrahydrofuran, 6.55 mL, 6.55 mmol, 1.5 equiv) was added. After 1 h, ethyl acetate (20 mL) was added. After 5 min, the reaction mixture was partitioned between saturated aqueous ammonium chloride solution (50 mL) and ethyl acetate (100 mL). The layers were separated. The organic layer was washed sequentially with water (20 mL) then saturated aqueous sodium chloride solution (20 mL) and the washed solution was dried over sodium sulfate. The dried solution was filtered and the filtrate was concentrated. The residue was purified by flash-column chromatography (5% ethyl acetate-hexanes) to provide 1.44 g of the product, (4S,6S)-4-(tert-butyldimethylsilyloxy)-6-(4-methoxybenzyloxy)octa-1,7-dien-3-one, as a colorless oil (84%). TLC: (10% ethyl acetate-hexanes) $R_f$=0.35 (CAM); $^1$H NMR (500 MHz, CDCl$_3$) δ: 7.24 (d, 2H, J=8.8 Hz), 6.87 (d, 2H, J=8.8 Hz), 6.70 (dd, 1H, J=17.6, 10.7 Hz), 6.35 (dd, 1H, J=17.6, 1.46), 5.78-5.71 (m, 2H), 5.28 (d, 1H, J=17.6 Hz), 5.24 (d, 1H, J=10.3), 4.51-4.47 (m, 2H), 4.22 (d, 1H, J=10.7 Hz), 3.99 (m, 1H), 3.80 (s, 3H), 1.92 (ddd, 1H, J=14.1, 9.8, 3.9 Hz), 1.72 (ddd, J=12.7, 9.3, 3.4 Hz), 0.91 (s, 9H), 0.03 (s, 3H), 0.02 (s, 3H); $^{13}$C NMR (125 MHz, CDCl$_3$) δ: 201.0, 159.0, 138.6, 131.4, 130.6, 129.2, 129.1, 117.6, 113.7, 76.6, 74.8, 69.8, 55.3, 41.2, 24.7, 18.2, −4.7, −5.2; FTIR (neat), cm$^{-1}$: 2930 (w), 2859 (w), 1701 (w), 1614 (m), 1248 (s), 1090 (m), 837 (s), 779 (s); HRMS (ESI): Calcd for (C$_{22}$H$_{34}$O$_4$Si+Na)$^+$ 413.2124. found 413.2134.

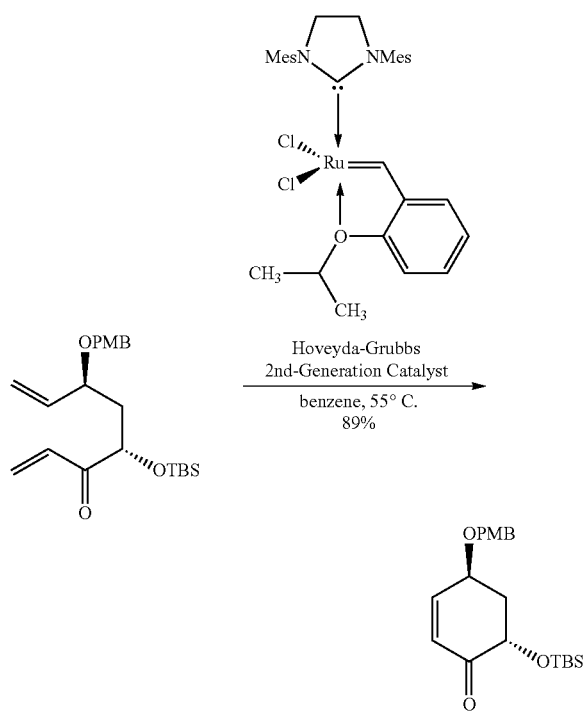

(4S,6S)-6-(tert-Butyldimethylsilyloxy)-4-(4-methoxybenzyloxy)cyclohex-2-enone ("Enone building block")

Hoveyda-Grubbs 2nd Generation Catalyst (45 mg, 72 μmol, 0.020 equiv) was added to a solution of the diene shown above (1.40 g, 3.58 mmol, 1 equiv) in benzene (40 mL, the solvent was degassed by sparging for 20 min with a slow stream of argon gas through a 22-gauge stainless steel needle) at 23° C. The reaction flask was heated in an oil bath at 55° C. After 40 min, the heating bath was removed and the reaction flask was allowed to cool to 23° C. The product solution was concentrated. The residue was purified by flash-column chromatography (5% ethyl acetate-hexanes initially, grading to 10% ethyl acetate-hexanes) to provide 1.16 g of the product, (4S,6S)-6-(tert-butyldimethylsilyloxy)-4-(4-methoxybenzyloxy)cyclohex-2-enone, as a colorless oil (89%). TLC: (20% ethyl acetate-hexanes) $R_f$=0.33 (CAM); $^1$H NMR (500 MHz, CDCl$_3$) δ: 7.28 (d, 2H, J=8.9 Hz), 6.90 (d, 2H, J=8.7 Hz), 6.88 (dd, 1H, J=10.3, 3.7 Hz), 5.94 (d, 1H, J=10.1 Hz), 4.61 (d, 1H, J=11.4 Hz), 4.55 (d, 1H, J=11.2 Hz), 4.40-4.34 (m, 2H), 3.81 (s, 3H), 2.30-2.20 (m, 2H), 0.88 (s, 9H), 0.10 (s, 3H), 0.09 (s, 3H); $^{13}$C NMR (125 MHz, CDCl$_3$) δ: 197.4, 159.5, 147.8, 129.8, 129.5, 128.2, 114.0, 71.2, 71.1, 70.3, 55.3, 37.7, 25.7, 18.3, −4.7, −5.4; FTIR (neat), cm$^{-1}$: 2955 (m), 2930 (m), 2857 (m), 1694 (s), 1514 (s), 1250 (s), 1078 (s), 907 (s); HRMS (ESI): Calcd for (C$_{20}$H$_{30}$O$_4$Si+H)$^+$ 363.1986. found 363.1991.

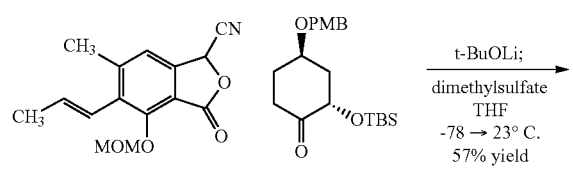

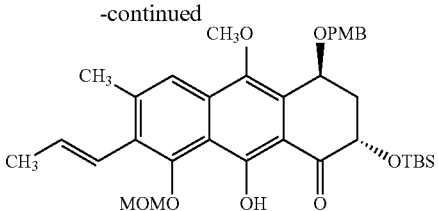

Tricyclic Olefin.

Lithium tert-butoxide (1.0 M solution in tetrahydrofuran, 24.8 mL, 24.8 mmol, 3.0 equiv) was added to a solution of the cyanophthalide above (2.26 g, 8.27 mmol, 1 equiv) in tetrahydrofuran (45 mL) at −78° C. After 5 min, a solution of the enone above (3.0 g, 8.27 mmol, 1.0 equiv) in tetrahydrofuran (45 mL) was added by cannula. The reaction flask was allowed to warm to −22° C. over 2.5 h, then dimethylsulfate (7.22 mL, 74.4 mmol, 9.0 equiv) was added. The reaction flask was allowed to warm to 23° C. over 2 h. After an additional 2.5 h, the reaction mixture was partitioned between saturated aqueous ammonium chloride solution (300 mL) and ethyl acetate (500 mL). The layers were separated. The organic layer was washed sequentially with water (300 mL) then saturated aqueous sodium chloride solution (300 mL) and the washed solution was dried over sodium sulfate. The dried solution was filtered and the filtrate was concentrated. The residue was purified by flash-column chromatography (hexanes initially, grading to 5% ethyl acetate-hexanes) to provide 2.95 g of the product, tricyclic olefin, as an orange foam (57%). TLC: (17% ethyl acetate-hexanes) $R_f$=0.36 (CAM); $^1$H NMR (500 MHz, CDCl$_3$) δ: 14.89 (s, 1H), 7.63 (s, 1H), 7.28 (d, 2H, J=8.5 Hz), 6.87 (d, 2H, J=8.2 Hz), 6.53 (d, 1H, J=16.3), 6.11 (dq, 1H, J=16.2, 6.4 Hz), 5.2 (m, 1H), 5.09 (d, 1H, J=6.2 Hz), 5.04 (d, 1H, J=6.2 Hz), 4.99 (dd, 1H, J=12.6, 5.3 Hz), 5.78 (d, 1H, J=11.0 Hz), 4.58 (d, 1H, J=11.0 Hz), 3.85 (s, 3H), 3.79 (s, 3H), 3.59 (s, 3H), 2.72 (ddd, 1H, J=13.3, 4.8, 3.2 Hz), 2.50 (s, 3H), 2.18 (m, 1H), 1.97 (d, 3H, J=6.4 Hz), 0.98 (s, 9H), 0.25 (s, 3H), 0.18 (s, 3H); $^{13}$C NMR (125 MHz, CDCl$_3$) δ: 203.7, 161.4, 159.2, 153.8, 144.8, 141.2, 133.1, 132.4, 131.7, 130.2, 129.5, 125.4, 125.1, 119.1, 188.8, 113.8, 108.4, 101.3, 70.8, 69.4, 68.8, 62.8, 57.9, 55.3, 36.6, 25.9, 22.2, 19.3, 18.6, −4.4, −5.3; FTIR (neat), cm$^{-1}$: 2951 (w), 2930 (w), 1611 (m), 1514 (w), 1443 (w), 1381 (w), 1362 (m), 1248 (m), 1155 (m), 1124 (m), 1040 (s), 1003 (m), 928 (m), 872 (m), 835 (m), 779 (m); HRMS (ESI): Calcd for (C$_{35}$H$_{46}$O$_8$Si+Na)$^+$ 645.2854. found 645.2854.

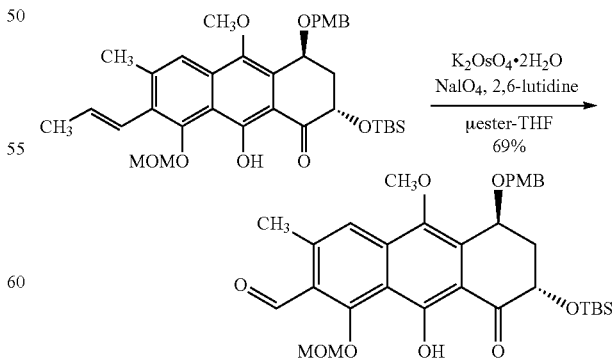

Tricyclic Aldehyde.

2,6-Lutidine (129 μL, 1.11 mmol, 2.0 equiv) was added to an ice-cooled solution of tricyclic olefin (345 mg, 0.55 mmol, 1 equiv), potassium osmate dihydrate (10 mg, 0.028 mmol, 0.05 equiv), and sodium periodate (474 mg, 2.22 mmol, 4.0 equiv) in a mixture of tetrahydrofuran (8 mL) and water (4 mL) at 0° C. After 5 min, the cooling bath was removed and the reaction flask was allowed to warm to 23° C. After 2 h, the reaction mixture was partitioned between water (30 mL), ethyl acetate (66 mL), and hexanes (33 mL). The layers were separated. The organic layer was washed with water (30 mL) then saturated aqueous sodium chloride solution (30 mL) and the washed solution was dried over sodium sulfate. The dried solution was filtered and the filtrate was concentrated. The residue was purified by flash-column chromatography (10% ethyl acetate-hexanes initially, grading to 15% ethyl acetate-hexanes) to provide 232 mg of the product, tricyclic aldehyde, as an orange foam (69%). TLC: (10% ethyl acetate-hexanes) $R_f$=0.18 (CAM); $^1$H NMR (500 MHz, CDCl$_3$) δ: 14.96 (s, 1H), 9.64 (s, 1H), 7.64 (s, 3H), 7.28 (d, 2H, J=8.5 Hz), 6.87 (d, 2H, J=8.5), 5.29-5.20 (m, 3H), 5.00 (dd, 1H, J=12.2, 5.1 Hz), 4.70 (d, 1H, J=11.0 Hz), 4.60 (d, 1H, J=11.0 Hz), 3.86 (s, 3H), 3.80 (s, 3H), 3.61 (s, 3H), 2.74 (s, 3H), 2.73 (m, 1H), 2.19 (m, 1H), 0.98 (s, 9H), 0.26 (s, 3H), 0.18 (s, 3H); $^{13}$C NMR (125 MHz, CDCl$_3$) δ: 204.2, 193.3, 163.2, 161.6, 159.4, 144.7, 141.8, 137.0, 129.9, 129.5, 127.6, 120.7, 118.1, 113.9, 109.2, 102.8, 71.1, 69.3, 68.6, 62.9, 58.4, 55.3, 36.3, 25.8, 22.3, 18.5, −4.5, −5.3; FTIR (neat), cm$^{-1}$: 2953 (w), 2930 (w), 2857 (w), 1686 (m), 1611 (s), 1514 (m), 1385 (m), 1364 (m), 1246 (s), 1153 (s), 1042 (s), 1011 (m), 930 (m), 872 (m), 837 (m), 779 (m); HRMS (ESI): Calcd for $(C_{33}H_{42}O_9Si+Na)^+$ 633.2490. found 633.2464.

provide 310 mg of the product, tricyclic aldehyde diol, as a yellow foam (89%). Attempts to purify the product by flash-column chromatography lead to decomposition. TLC: (30% ethyl acetate-hexanes) $R_f$=0.22 (CAM); $^1$H NMR (500 MHz, CDCl$_3$) δ: 15.58 (br s, 1H), 10.51 (s, 1H), 7.28 (d, 2H, J=8.7 Hz), 7.25 (s, 3H), 6.87 (d, 2H, J=8.7 Hz), 5.16 (m, 1H), 4.99 (dd, 1H, J=12.3, 5.2 Hz), 4.68 (d, 1H, J=11.1 Hz), 4.59 (d, 1H, J=10.7 Hz), 3.84 (s, 3H), 3.80 (s, 3H), 2.73 (s, 3H), 2.71 (m, 1H), 2.18 (m, 1H), 0.97 (s, 9H), 0.25 (s, 3H), 0.18 (s, 3H); $^{13}$C NMR (125 MHz, CDCl$_3$) δ: 203.9, 192.7, 166.5, 163.6, 159.4, 144.8, 142.7, 137.7, 130.7, 129.9, 129.5, 114.8, 114.2, 113.9, 108.5, 71.1, 69.0, 68.6, 62.8, 55.3, 36.5, 25.8, 21.0, 18.5, −4.5, −5.3; FTIR (neat), cm$^{-1}$: 3329 (w, br), 2953 (m), 2930 (m), 2857 (m), 1682 (m), 1614 (s), 1514 (m) 1391 (m) 1246 (s), 1153 (s), 1049 (m), 1034 (m) 870 (m), 837 (s); HRMS (ESI): Calcd for $(C_{31}H_{38}O_8Si+H)^+$ 567.2409. found 567.2398.

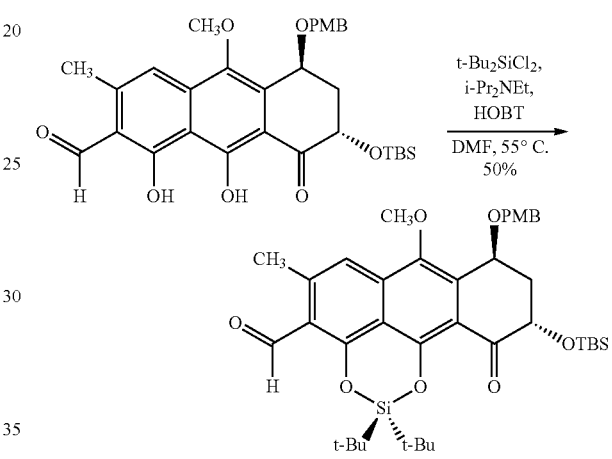

Tricyclic Aldehyde Silacycle.

Di-tert-butyldichlorosilane (151 μL, 0.72 mmol, 1.8 equiv) was added to a brown solution of the tricyclic aldehyde diol (225 mg, 0.40 mmol, 1 equiv), N,N-diisopropylethylamine (354 μL, 1.99 mmol, 5.0 equiv), and anhydrous 1-hydroxybenzotriazole (27 mg, 0.20 mmol, 0.5 equiv) in dimethylformamide (8.0 mL) at 23° C. The reaction flask was heated in an oil bath at 55° C. After 80 min, the heating bath was removed and the reaction flask was allowed to cool to 23° C. The reaction mixture was partitioned between saturated aqueous sodium bicarbonate solution (30 mL) and ether (150 mL). The layers were separated. The organic layer was washed with water (50 mL) and the washed solution was dried over sodium sulfate. The dried solution was filtered and the filtrate was concentrated. The residue was purified by flash-column chromatography (10% ethyl acetate-hexanes) to provide 140 mg of the product, tricyclic aldehyde silacycle, as a yellow oil (50%). TLC: (40% ethyl acetate in hexanes) $R_f$=0.87 (CAM); $^1$H NMR (500 MHz, CDCl$_3$) δ: 10.8 (s, 1H), 7.34 (s, 1H), 7.31 (d, 2H, J=6.5 Hz), 6.88 (d, 2H, J=7.0 Hz), 5.20 (dd, 1H, J=3.0, 3.0 Hz), 4.88 (dd, 1H, J=12.5, 5.0 Hz), 4.73 (d, 1H, J=11.0 Hz), 4.63 (d, 1H, J=10.5 Hz), 3.90 (s, 3H), 3.79 (s, 3H), 2.77-2.72 (m, 1H), 2.72 (s, 3H), 2.19-2.13 (m, 1H), 1.15 (s, 9H), 1.12 (s, 9H), 0.96 (s, 9H), 0.24 (s, 3H), 0.14 (s, 3H); $^{13}$C NMR (125 MHz, CDCl$_3$) δ: 194.2, 190.9, 160.4, 159.4, 150.2, 146.3, 140.3, 134.0, 133.2, 130.0, 129.8, 199.4, 116.5, 115.6, 115.3, 114.0, 71.4, 71.2, 69.8, 62.7, 55.3, 36.3, 26.1, 26.0, 26.0, 22.5, 21.4, 21.0, 18.7, −4.3, −5.4; FTIR (neat), cm$^{-1}$: 2936 (s), 1786 (s), 1684 (s), 1607 (s), 1373 (s),

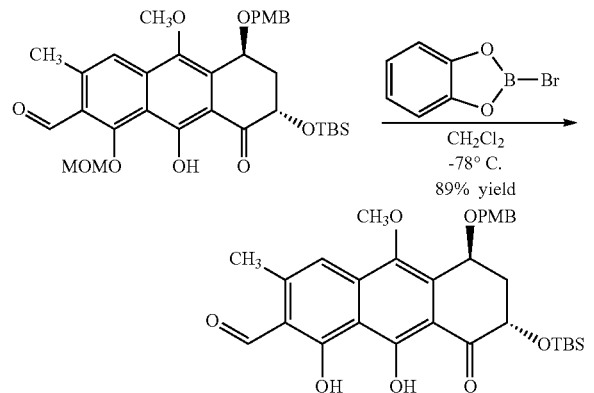

Tricyclic Aldehyde Diol.

A solution of B-bromocatecholborane (244 mg, 1.23 mmol, 2.0 equiv) in dichloromethane (9.0 mL) was added to a solution of the tricyclic aldehyde (275 mg, 0.61 mmol, 1 equiv) in dichloromethane (9.0 mL) at −78° C. After 45 min, the reaction mixture was diluted with saturated aqueous sodium bicarbonate solution (30 mL) and dichloromethane (50 mL). The cooling bath was removed, and the partially frozen mixture was allowed to warm to 23° C. The biphasic mixture was diluted with 0.2 M aqueous sodium hydroxide solution (125 mL). The layers were separated. The dark purple aqueous layer was extracted with dichloromethane (2×100 mL). The organic layers were combined. The combined solution was washed sequentially with 0.1 M aqueous hydrochloric acid solution (50 mL), water (3×50 mL), then saturated aqueous sodium chloride solution (50 mL) and the washed solution was dried over sodium sulfate. The dried solution was filtered and the filtrate was concentrated to 1247 (s), 1157 (s), 1034 (s); HRMS (ESI): Calcd for $(C_{39}H_{54}O_8Si_2+H)^+$ 707.3430. found 707.3422.

ducts, i.e.: Endocycloadduct 1 (44%), Eendocycloadduct 2 (40%), Exocycloadduct 1 (14%), and Exocycloadduct 2

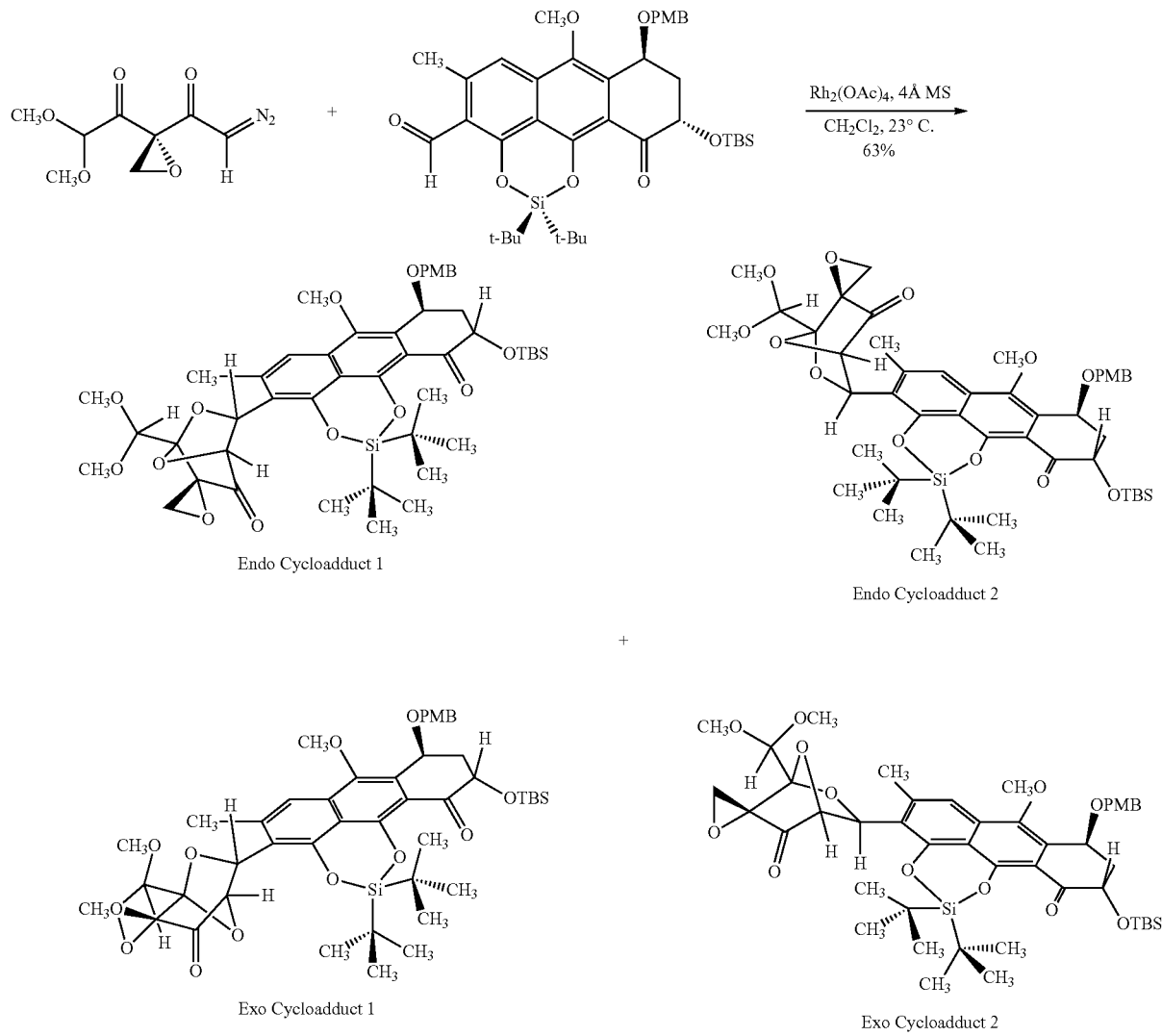

Endo Cycloadduct 1

Endo Cycloadduct 2

Exo Cycloadduct 1

Exo Cycloadduct 2

Endo-Selective Cycloadduct Formation.

A solution of the diazo ketone (194 mg, 0.90 mmol, 3.0 equiv) in dichloromethane (400 μL) was added by a motor-driven syringe pump over 120 min to a suspension of the tricyclic aldehyde silacycle (213 mg, 0.30 mmol, 1 equiv), rhodium(II) acetate dimer (6.6 mg, 20 μmol, 0.05 equiv), and powdered 4 Å molecular sieves (~50 mg) in dichloromethane (400 μL) at 23° C. After 10 min, the reaction mixture was concentrated. The residue was filtered through a short plug of silica gel (~5 cm), eluting with 30% ethyl acetate-hexanes to remove the rhodium(II) acetate dimer. The filtrate was concentrated. The residue was purified by preparatory HPLC (Agilent Prep-C18 column, 10 μm, 30×150 mm, UV detection at 254 nm, gradient elution with 90→100% acetonitrile in water, flow rate: 15 mL/min). The fractions eluting at 33-42 min were collected. The collected fractions were diluted with an equal volume of dichloromethane and the diluted solution was dried over sodium sulfate. The dried solution was filtered and the filtrate was concentrated to provide 170 mg of a mixture of cycload- (2%) in a ratio of 3.0:2.8:1:0.1 respectively (63% yield). Additionally, 12 mg of the starting material, tricyclic aldehyde silacycle, was recovered in the fractions eluting at 52-56 min (6%). Independently, analytically pure samples were obtained by preparatory HPLC purification of smaller batches (~10 mg) (Agilent Prep-C18 column, 10 μm, 30×150 mm, UV detection at 254 nm, gradient elution with 95→100% acetonitrile in water, flow rate: 15 mL/min) and were characterized by $^1$H NMR, $^{13}$C NMR, IR, and HRMS. An analytically pure sample of exo cycloadduct was prepared for characterization purposes using an alternate cycloaddition procedure which employed a copper catalyst in place of the rhodium catalyst; this alternate procedure was found to favor the formation of exo cycloadducts.

Endo cycloadduct 1 eluted at 23-25 min; TLC: (30% ethyl acetate-hexanes) $R_f$=0.46 (CAM); $^1$H NMR (500 MHz, CDCl$_3$) δ: 7.37 (s, 1H), 7.30 (d, 2H, J=9.0 Hz), 6.86 (d, 2H, J=8.5 Hz), 5.74 (d, 1H, J=3.0 Hz), 5.48 (d, 1H, J=3.5 Hz), 5.15 (dd, 1H, J=2.5, 3.0 Hz), 4.85 (dd, 1H, J=12.0, 4.5 Hz), 4.77 (s, 1H), 4.70 (d, 1H, J=11.0 Hz), 4.60 (d, 1H, J=11.0

Hz), 3.87 (s, 3H), 3.79 (s, 3H), 3.63 (d, 1H, J=6.0 Hz), 3.61 (s, 3H), 3.61 (s, 3H), 3.07 (d, 1H, J=7.0 Hz), 2.75 (s, 3H), 2.73-2.69 (m, 1H), 2.17-2.11 (m, 1H), 1.19 (s, 9H), 1.07 (s, 9H), 0.95 (s, 9H), 0.23 (s, 3H), 0.13 (s, 3H); $^{13}$C NMR (125 MHz, CDCl$_3$) δ: 201.0, 194.4, 159.3, 150.1, 149.1, 146.2, 139.6, 131.2, 130.3, 129.7, 129.4, 118.2, 116.8, 115.8, 114.5, 113.8, 107.0, 101.6, 83.4, 79.6, 71.3, 71.2, 69.6, 64.3, 62.6, 56.6, 55.9, 55.3, 50.9, 36.7, 26.4, 26.1, 26.0, 23.6, 21.2, 21.2, 18.7, −4.3, −5.3; FTIR (neat), cm$^{-1}$: 2928 (s), 2857 (s), 1784 (s), 1699 (s), 1611 (s), 1371 (s), 1250 (s); HRMS (ESI): Calcd for (C$_{47}$H$_{64}$O$_{13}$Si$_2$+H)$^+$ 893.3958. found 893.3932.

Endocycloadduct 2 eluted at 25-26 min; TLC: (30% ethyl acetate-hexanes) R$_f$=0.46 (CAM); $^1$H NMR (500 MHz, CDCl$_3$) δ: 7.33 (s, 1H), 7.29 (d, 2H, J=8.5 Hz), 6.86 (d, 2H, J=9.0 Hz), 5.62 (d, 1H, J=4.0 Hz), 5.44 (d, 1H, J=4.0 Hz), 5.19 (dd, 1H, J=3.0, 2.5 Hz), 4.86 (dd, 1H, J=12.0, 5.0 Hz), 4.85 (s, 1H), 4.70 (d, 1H, J=10.5 Hz), 4.60 (d, 1H, J=11.0 Hz), 3.87 (s, 3H), 3.79 (s, 3H), 3.69 (s, 3H), 3.58 (s, 3H), 3.39 (d, 1H, J=7.0 Hz), 3.10 (d, 1H, J=6.0 Hz), 2.74-2.70 (m, 1H), 2.59 (s, 3H), 2.16-2.10 (m, 1H), 1.17 (s, 9H), 1.09 (s, 9H), 0.95 (s, 9H), 0.23 (s, 3H), 0.13 (s, 3H); $^{13}$C NMR (125 MHz, CDCl$_3$) δ: 202.1, 194.5, 159.3, 150.3, 149.1, 146.1, 138.8, 131.0, 130.3, 129.7, 129.6, 118.0, 117.1, 115.3, 114.6, 113.8, 107.5, 99.9, 82.0, 78.0, 71.3, 71.1, 69.7, 62.8, 61.8, 57.1, 56.2, 55.3, 50.1, 36.4, 26.3, 26.2, 26.0, 23.8, 21.5, 20.9, 18.7, −4.3, −5.4; FTIR (neat), cm$^{-1}$: 2926 (s), 2855 (s), 1790 (s), 1701 (s), 1611 (s), 1373 (s), 1250 (s); HRMS (ESI): Calcd for (C$_{47}$H$_{64}$O$_{13}$Si$_2$+H)$^+$ 893.3958. found: 893.3982.

Exocycloadduct 1: TLC: (30% ethyl acetate-hexanes) R$_f$=0.11-0.28 (CAM); $^1$H NMR (600 MHz, CDCl$_3$) δ: 7.40 (s, 1H), 7.30 (d, 2H, J=8.4 Hz), 6.87 (d, 2H, J=8.4 Hz), 5.69 (s, 1H), 5.19 (dd, 1H, J=3.0, 2.4 Hz), 5.11 (s, 1H), 4.86 (dd, 1H, J=12.0, 4.8 Hz), 4.77 (s, 1H), 4.71 (d, 1H, J=11.4 Hz), 4.61 (d, 1H, J=10.8 Hz), 3.90 (s, 3H), 3.80 (s, 3H), 3.75 (d, 1H, J=6.6 Hz), 3.58 (s, 3H), 3.54 (s, 3H), 3.24 (d, 1H, J=6.6 Hz), 2.75-2.70 (m, 1H), 2.73 (s, 3H), 2.17-2.12 (m, 1H), 1.14 (s, 9H), 1.11 (s, 9H), 0.95 (s, 9H), 0.24 (s, 3H), 0.14 (s, 3H); $^{13}$C NMR (125 MHz, CDCl$_3$) δ: 202.2, 194.4, 159.3, 150.6, 149.5, 146.1, 139.7, 131.3, 130.2, 129.9, 129.7, 119.1, 117.0, 115.6, 114.7, 113.9, 107.3, 103.5, 84.8, 75.7, 71.3, 71.2, 69.8, 62.7, 61.5, 57.2, 57.0, 55.3, 50.9, 36.5, 26.2, 26.0, 23.0, 21.2, 21.0, 18.7, −4.3, −5.4; FTIR (neat), cm$^{-1}$: 2928 (s), 2857 (s), 1784 (s), 1703 (s), 1613 (s), 1515 (s), 1471 (s), 1371 (s), 1250 (s); HRMS (ESI): Calcd for (C$_{47}$H$_{64}$O$_{13}$Si$_2$+H)$^+$ 893.3958. found 893.3972.

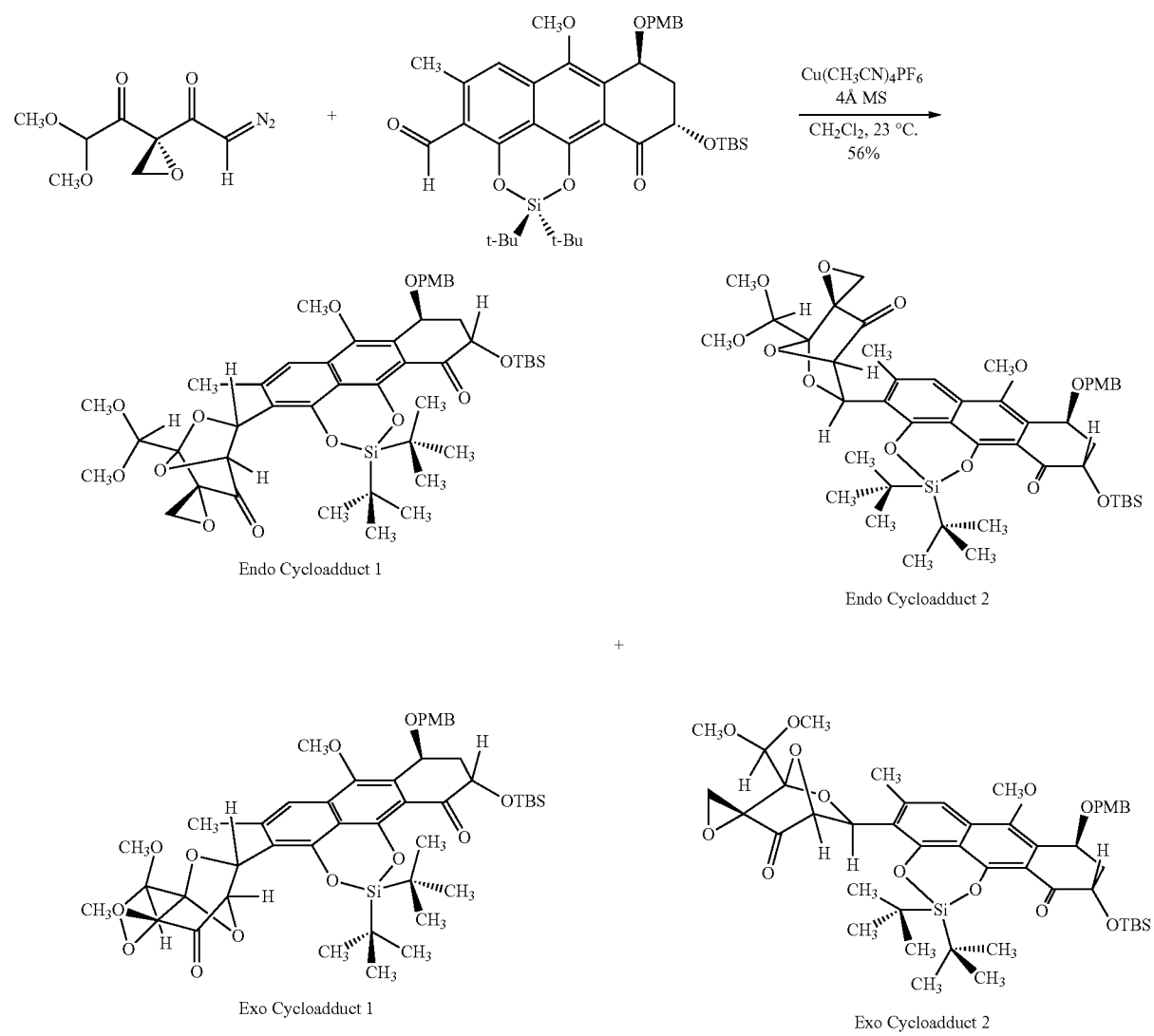

Exo-Selective Cycloadduct Formation.

A solution of (S)-1-diazo-3-epoxy-5,5-dimethoxypenta-2,4-dione (27 mg, 0.13 mmol, 3.0 equiv) in dichloromethane (100 μL) was added by a motor-driven syringe pump over 25 min to a suspension of the differentially protected aldehyde (30 mg, 0.04 mmol, 1 equiv), copper(I) tetrakis(acetonitrile) hexafluorophosphate (3.0 mg, 8.4 μmol, 0.2 equiv), and powdered 4-Å molecular sieves (~20 mg) in dichloromethane (150 μL) at 23° C. After 2 h and 40 min, triethylamine (10 μL) was added and the reaction mixture was concentrated. The residue was filtered through a short plug of silica gel (length: 3 cm; diameter: 1.5 cm), eluting with 30% ethyl acetate-hexanes to remove the copper complex and powdered 4-Å molecular sieves. The filtrate was concentrated. $^1$H NMR analysis of the residue established the following product distribution: Endocycloadduct 1 (27%), Endocycloadduct 2 (6%), Exocycloadduct 1 (48%), and Exocycloadduct 2 (19%). The residue was purified by rp-HPLC (Agilent Prep-C18 column, 10 μm, 30×150 mm, UV detection at 264 nm, gradient elution with 90→100% acetonitrile in water, flow rate: 20 mL/min). The fractions eluting at 30-34 min were collected. The collected fractions were concentrated to provide 21 mg of a mixture of purified cycloadducts with the following distribution: Endocycloadduct 1 (35%), Endocycloadduct 2 (5%), Exocycloadduct 1 (46%) and Exocycloadduct 2 (14%), as depicted above (56% yield). For characterization purposes, the purified product mixture was further separated by preparative TLC (the TLC plate was pre-treated with 5% triethylamine in hexanes; elution with 60% ethyl acetate-hexanes) to provide separately 5.2 mg (14%) of Endocycloadduct 1 ($R_f$=0.71, UV), 1.2 mg (3%) of Endocycloadduct 2 ($R_f$=0.77, UV), 5.2 mg (14%) of Exocycloadduct 1 ($R_f$=0.56, UV) and 3 mg (8%) of Exocycloadduct 2 ($R_f$=0.41, UV), each in ≥95% purity ($^1$H NMR analysis).

Exocycloadduct 1—TLC: (30% ethyl acetate-hexanes) $R_f$=0.11-0.28 (CAM); $^1$H NMR (600 MHz, CDCl$_3$) δ: 7.40 (s, 1H), 7.30 (d, 2H, J=8.4 Hz), 6.87 (d, 2H, J=8.4 Hz), 5.69 (s, 1H), 5.19 (dd, 1H, J=3.0, 2.4 Hz), 5.11 (s, 1H), 4.86 (dd, 1H, J=12.0, 4.8 Hz), 4.77 (s, 1H), 4.71 (d, 1H, J=11.4 Hz), 4.61 (d, 1H, J=10.8 Hz), 3.90 (s, 3H), 3.80 (s, 3H), 3.75 (d, 1H, J=6.6 Hz), 3.58 (s, 3H), 3.54 (s, 3H), 3.24 (d, 1H, J=6.6 Hz), 2.75-2.70 (m, 1H), 2.73 (s, 3H), 2.17-2.12 (m, 1H), 1.14 (s, 9H), 1.11 (s, 9H), 0.95 (s, 9H), 0.24 (s, 3H), 0.14 (s, 3H); $^{13}$C NMR (125 MHz, CDCl$_3$) δ: 202.2, 194.4, 159.3, 150.6, 149.5, 146.1, 139.7, 131.3, 130.2, 129.9, 129.7, 119.1, 117.0, 115.6, 114.7, 113.9, 107.3, 103.5, 84.8, 75.7, 71.3, 71.2, 69.8, 62.7, 61.5, 57.2, 57.0, 55.3, 50.9, 36.5, 26.2, 26.0, 23.0, 21.2, 21.0, 18.7, −4.3, −5.4; FTIR (neat), cm$^{-1}$: 2928 (s), 2857 (s), 1784 (s), 1703 (s), 1613 (s), 1515 (s), 1471 (s), 1371 (s), 1250 (s); HRMS (ESI): Calcd for (C$_{47}$H$_{64}$O$_{13}$Si$_2$+H)$^+$ 893.3958. found 893.3972.

Exocycloadduct 2—TLC: (30% ethyl acetate-hexanes) $R_f$=0.11-0.28 (CAM); $^1$H NMR (600 MHz, CDCl$_3$) δ: 7.39 (s, 1H), 7.31 (d, 2H, J=8.5 Hz), 6.86 (d, 2H, J=8.5 Hz), 5.59 (s, 1H), 5.19 (dd, 1H, J=3.0, 2.0 Hz), 5.14 (s, 1H), 4.86 (dd, 1H, J=13.0, 5.0 Hz), 4.82 (s, 1H), 4.72 (d, 1H, J=11.0 Hz), 4.61 (d, 1H, J=10.5 Hz), 3.89 (s, 3H), 3.79 (s, 3H), 3.56 (s, 3H), 3.56 (s, 3H), 3.38 (d, 1H, J=6.0 Hz), 3.22 (d, 1H, J=6.0 Hz), 2.74 (s, 3H), 2.74-2.70 (m, 1H), 2.18-2.12 (m, 1H), 1.18 (s, 9H), 1.07 (s, 9H), 0.95 (s, 9H), 0.24 (s, 3H), 0.13 (s, 3H); $^{13}$C NMR (125 MHz, CDCl$_3$) δ: 203.3, 194.5, 159.3, 150.5, 149.5, 146.1, 140.2, 131.4, 130.2, 130.0, 129.8, 119.1, 117.0, 115.5, 114.6, 113.9, 107.9, 101.6, 83.5, 74.4, 71.3, 71.2, 69.8, 62.7, 60.9, 57.6, 56.8, 55.3, 50.2, 36.5, 26.3, 26.0, 26.0, 22.9, 21.4, 20.9, 18.7, −4.3, −5.4; FTIR (neat), cm$^{-1}$: 2932 (s), 1786 (w), 1701 (s), 1613 (s), 1515 (s), 1371 (s), 1250 (s). HRMS (ESI): Calcd for (C$_{47}$H$_{64}$O$_{13}$Si$_2$+H)$^+$ 893.3958. found 893.3940.

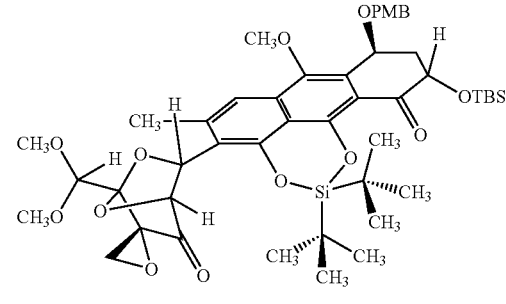

Endo Cycloadduct 1

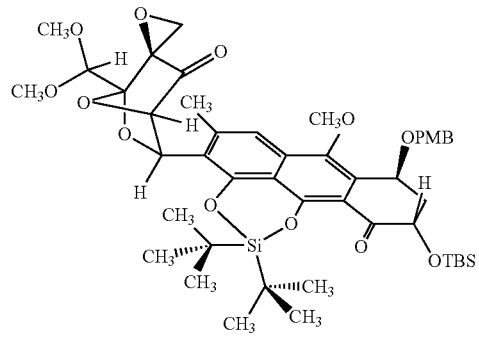

Endo Cycloadduct 2

+

$\xrightarrow{\text{Et}_3\text{N·3HF}}{\text{CH}_3\text{CN}}$ 70%

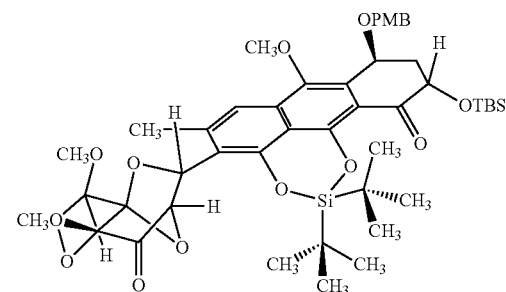

Exo Cycloadduct 1

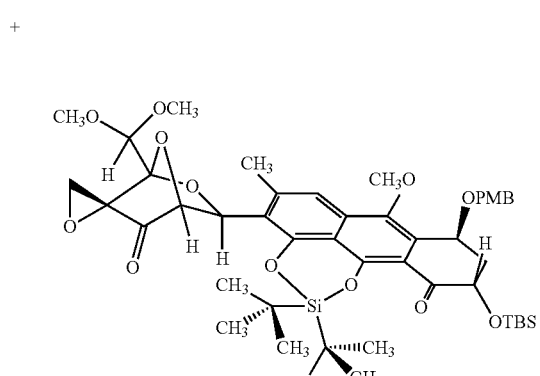

Exo Cycloadduct 2

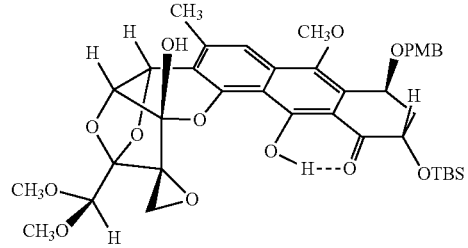

endo 1 hemiketal

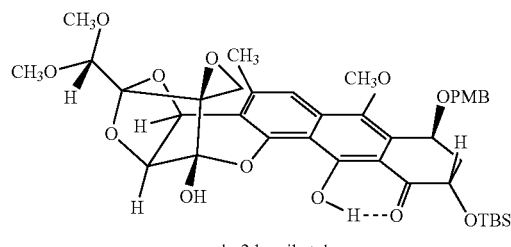

endo 2 hemiketal

Hemiketals.

Triethylamine-trihydrofluoride (93 μL, 0.57 mmol, 3.0 equiv) was added to a solution of cycloadducts (170 mg, 0.19 mmol, 1 equiv, see paragraph above) in acetonitrile (4.0 mL) at 23° C. After 15 min, the bright yellow solution was diluted with dichloromethane (100 mL). The diluted solution was washed sequentially with aqueous pH 7 phosphate buffer solution (20 mL) then saturated aqueous sodium chloride solution (15 mL) and the washed solution was dried over sodium sulfate. The dried solution was filtered and the filtrate was concentrated. The residue was purified by preparatory HPLC (Agilent Prep-C18 column, 10 μm, 30×150 mm, UV detection at 254 nm, gradient elution with 40→94% acetonitrile in water, flow rate: 15 mL/min). The fractions eluting at 36-40 min (endo 1 hemiketal) and 40-43 min (endo 2 hemiketal) were collected. The two sets of fractions were independently diluted with dichloromethane (~100 mL). The layers were separated. The organic layers were dried over sodium sulfate. The dried solutions were filtered and the filtrates were concentrated to provide 52 and 48 mg of the products, endo 1 hemiketal (36%) and endo 2 hemiketal (34%) respectively, as yellow-green oils.

Endo 1 hemiketal—TLC: (60% ethyl acetate-hexanes, TLC plate pre-treated with 5% Et$_3$N in hexanes) R$_f$=0.36 (CAM); $^1$H NMR (500 MHz, CDCl$_3$) δ: 14.7 (s, 1H), 7.35 (d, 2H, J=8.5 Hz), 7.25 (s, 1H), 6.90 (d, 2H, J=8.0 Hz), 5.14 (d, 1H, J=4.0 Hz), 5.04 (m, 1H), 4.94 (dd, 1H, J=12.5, 5.0 Hz), 4.86 (d, 1H, J=4.0 Hz), 4.72 (d, 1H, J=11.5 Hz), 4.64 (d, 1H, J=11.5 Hz), 4.60 (s, 1H), 3.80 (s, 3H), 3.67 (s, 3H), 3.51 (s, 3H), 3.47 (s, 3H), 3.29 (d, 1H, J=5.5 Hz), 3.17 (d, 1H, J=6.0 Hz), 2.66-2.62 (m, 1H), 2.47 (s, 3H), 2.12-2.06 (m, 1H), 0.96 (s, 9H), 0.24 (s, 3H), 0.18 (s, 3H); $^{13}$C NMR (125 MHz, CDCl$_3$) δ: 203.0, 162.7, 159.4, 151.9, 143.8, 141.6, 134.6, 130.0, 129.8, 126.8, 115.6, 114.3, 113.9, 113.8, 108.5, 103.3, 100.9, 97.3, 75.0, 70.7, 69.7, 69.2, 68.0, 66.5, 62.3, 56.3, 55.9, 55.3, 49.0, 36.4, 25.9, 20.1, 18.5, −4.3, −5.3; FTIR (neat), cm$^{-1}$: 3362 (br), 2930 (s), 1622 (s), 1572 (s), 1514 (s), 1445 (s), 1393 (s), 1250 (s), 1125 (s); HRMS (ESI): Calcd for (C$_{39}$H$_{48}$O$_{13}$Si+Na)$^+$ 775.2756. found 775.2721.

Endo 2 hemiketal—TLC: (60% ethyl acetate-hexanes, TLC plate pre-treated with 5% Et$_3$N in hexanes) R$_f$=0.31 (CAM); $^1$H NMR (500 MHz, CDCl$_3$) δ: 14.81 (s, 1H), 7.47 (s, 1H), 7.28 (d, 2H, J=8.5 Hz), 6.87 (d, 2H, J=9.0 Hz), 5.26 (d, 1H, J=4.0 Hz), 5.18 (dd, 1H, J=3.0, 2.0 Hz), 4.84 (d, 1H, J=4.0 Hz), 4.69 (d, 1H, J=10.5 Hz), 4.70 (s, 1H), 4.58 (d, 1H, J=11.5 Hz), 4.31 (s, 1H), 3.83 (s, 3H), 3.80 (s, 3H), 3.62 (s, 3H), 3.46 (s, 3H), 3.10 (d, 1H, J=5.0 Hz), 2.98 (d, 1H, J=5.5 Hz), 2.74-2.69 (m, 1H), 2.60 (s, 3H), 2.20-2.15 (m, 1H), 0.96 (s, 9H), 0.23 (s, 3H), 0.16 (s, 3H). $^{13}$C NMR (125 MHz, CDCl$_3$) δ: 203.2, 162.6, 159.3, 151.3, 144.0, 141.8, 135.0, 130.1, 129.5, 127.5, 116.3, 114.8, 114.7, 113.8, 108.5, 103.8, 100.1, 98.5, 73.2, 70.9, 69.7, 69.2, 69.2, 68.9, 62.7, 56.9, 56.6, 55.2, 50.3, 36.1, 25.9, 20.4, 18.6, −4.4, −5.4. FTIR (neat), cm$^{-1}$: 3414 (br), 2953 (s), 2857 (s), 1622 (s), 1391 (s), 1252 (s), 1125 (s), 1069 (s). HRMS (ESI): Calcd for (C$_{39}$H$_{48}$O$_{13}$Si+H)$^+$ 753.2937. found 753.2892.

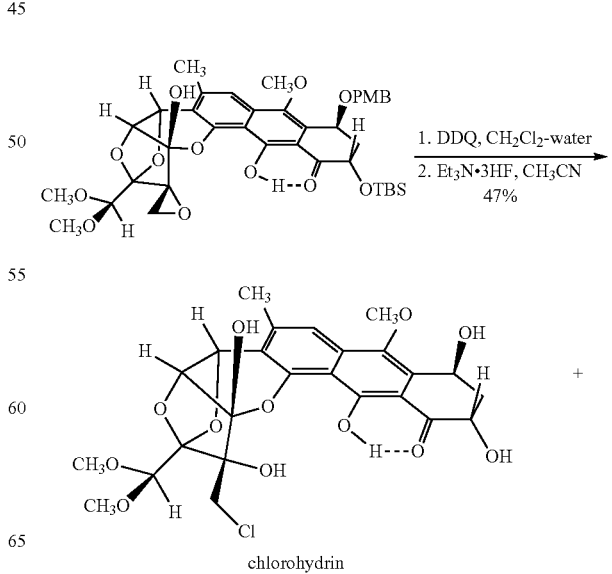

chlorohydrin

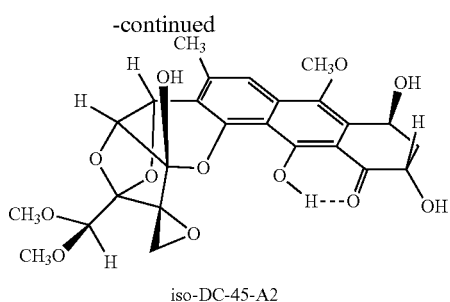

iso-DC-45-A2

11,12,13,15-tetraepi-DC-45-A2 and chlorohydrin 2,3-Dichloro-4,5-dicyanobenzoquinone (19 mg, 84 μmol, 1.2 equiv) was added to the hemiketal (52 mg, 70 μmol, 1 equiv) in a vigorously stirring, biphasic mixture of dichloromethane (1.5 mL) and water (150 μL) at 23° C. The reaction flask was covered with aluminum foil to exclude light. After 3 h, the green-colored mixture had become yellow. The product solution was partitioned between water (5 mL) and dichloromethane (50 mL). The layers were separated. The organic layer was dried over sodium sulfate. The dried solution was filtered and the filtrate was concentrated. $^1$H NMR analysis of the residue showed that the 4-methoxybenzyl protecting group was no longer present in the crude product mixture [TLC: (60% ethyl acetate-hexanes, TLC plate pre-treated with 5% Et$_3$N in hexanes) $R_f$=0.29 (CAM)]. The residue (1 equiv, see above) was dissolved in acetonitrile (1.5 mL), and triethylamine-trihydrofluoride (225 μL, 1.38 mmol, 20 equiv) was added at 23° C. The reaction flask was covered with aluminum foil to exclude light. After 10 h, the reaction mixture was partitioned between saturated aqueous sodium chloride solution (10 mL) and dichloromethane (50 mL). The layers were separated. The organic layer was dried over sodium sulfate. The dried solution was filtered and the filtrate was concentrated. The residue was purified by preparatory HPLC (Agilent Prep-C18 column, 10 μm, 30×150 mm, UV detection at 270 nm, gradient elution with 10→40% acetonitrile in water, flow rate: 20 mL/min) to provide 8 and 9 mg of the products, 11,12,13,15-tetraepi-DC-45-A$_2$ ("iso-DC-45-A$_2$") (22%, in fractions eluting at 17.5-18.5 min) and chlorohydrin (25%, in fractions eluting at 18.5-19.5 min) respectively, as bright yellow oils.

11,12,13,15-Tetraepi DC-45-A$_2$—TLC: (5% methanol-dichloromethane) $R_f$=0.23 (CAM); $^1$H NMR (500 MHz, CDCl$_3$) δ: 14.08 (s, 1H), 6.90 (s, 1H), 5.29 (app s, 1H), 5.16 (d, 1H, J=4.5 Hz), 5.02 (d, 1H, J=4.0 Hz), 5.01 (dd, 1H, J=12.5, 5.0 Hz), 4.62 (s, 3H), 3.76 (s, 3H), 3.52 (s, 3H), 3.48 (s, 3H), 2.29 (d, 1H, J=5.5 Hz), 3.21 (d, 1H, J=5.5 Hz), 2.81-2.76 (m, 1H), 2.47 (s, 3H), 2.06-2.01 (m, 1H); $^{13}$C NMR (100 MHz, CDCl$_3$) δ: 203.3, 161.6, 151.7, 143.6, 142.8, 134.5, 128.4, 115.6, 114.4, 113.6, 107.2, 103.7, 101.2, 97.7, 75.4, 69.3, 67.8, 66.5, 62.8, 61.6, 56.5, 56.2, 49.2, 37.1, 20.6; FTIR (neat), cm$^{-1}$: 3447 (br), 1620 (s), 1570 (s), 1445 (s), 1389 (s), 1086 (s), 978 (s); HRMS (ESI): Calcd for $(C_{25}H_{26}O_{12}+H)^+$ 519.1497. found 519.1494.

Chlorohydrin—TLC: (5% methanol-dichloromethane) $R_f$=0.23 (CAM); $^1$H NMR (500 MHz, CDCl$_3$) δ: 13.91 (s, 1H), 7.03 (s, 1H), 5.45 (br, 1H), 5.32 (s, 1H), 5.10 (d, 1H, J=4.0 Hz), 4.98 (br, 1H), 4.85 (d, 1H, J=3.0 Hz), 4.64 (s, 1H), 4.15 (d, 1H, J=12.0 Hz), 4.03 (d, 1H, J=12.0 Hz), 3.79 (s, 3H), 3.57 (s, 3H), 3.50 (s, 3H), 3.21 (br, 1H), 2.77 (app d, 1H, J=13.0 Hz), 2.58 (s, 1H), 2.46 (s, 3H), 2.05 (app t, 1H, J=12.5 Hz); $^{13}$C NMR (125 MHz, CDCl$_3$) δ: 203.2, 162.4, 153.0, 143.3, 142.0, 134.5, 129.0, 115.6, 113.4, 113.0, 107.3, 107.2, 103.3, 100.2, 82.6, 75.4, 69.3, 67.8, 62.8, 61.5, 57.3, 56.9, 47.7, 36.9, 20.2; FTIR (neat), cm$^{-1}$: 3475 (br), 1622 (s), 1570 (w), 1445 (s), 1391 (s), 1105 (s); HRMS (ESI): Calcd for $(C_{25}H_{27}ClO_{12}+H)^+$ 555.1269. found 555.1263.

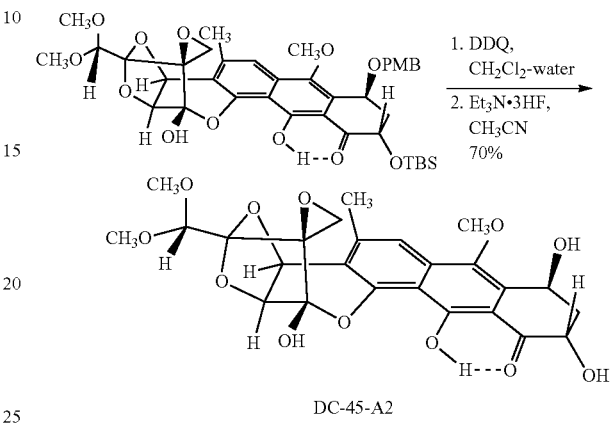

DC-45-A2

DC-45-A$_2$.

2,3-Dichloro-4,5-dicyanobenzoquinone (77 mg, 17 μmol, 1.2 equiv) was added to hemiketal (48 mg, 64 μmol, 1 equiv) in a vigorously stirring, biphasic mixture of dichloromethane (1.3 mL) and water (130 μL) at 23° C. The reaction flask was covered with aluminum foil to exclude light. After 5 h, the green-colored mixture had become yellow. The product solution was partitioned between saturated aqueous sodium chloride solution (5 mL) and dichloromethane (50 mL). The layers were separated. The organic layer was dried over sodium sulfate. The dried solution was filtered and the filtrate was concentrated. $^1$H NMR analysis of the residue showed that the 4-methoxybenzyl protecting group was no longer present in the crude product mixture [TLC: (60% ethyl acetate-hexanes, TLC plate pre-treated with 5% Et$_3$N in hexanes) $R_f$=0.27 (CAM)]. The residue (1 equiv, see above) was dissolved in acetonitrile (1.3 mL), and triethylamine-trihydrofluoride (209 μL, 1.28 mmol, 20 equiv) was added at 23° C. The reaction flask was covered with aluminum foil to exclude light. After 13.5 h, the reaction mixture was partitioned between saturated aqueous sodium chloride solution (10 mL) and dichloromethane (50 mL). The layers were separated. The organic layer was dried over sodium sulfate. The dried solution was filtered and the filtrate was concentrated. The residue was purified by preparatory HPLC (Agilent Prep-C18 column, 10 μm, 30×150 mm, UV detection at 270 nm, gradient elution with 10→40% acetonitrile in water, flow rate: 20 mL/min) to provide 23 mg of the product, DC-45-A$_2$, as a bright yellow powder (70%). TLC: (5% methanol-dichloromethane) $R_f$=0.23 (CAM); $^1$H NMR (600 MHz, CDCl$_3$) δ: 13.99 (s, 1H), 7.43 (s, 1H), 5.45 (app s, 1H), 5.25 (d, 1H, J=3.6 Hz), 4.91 (dd, 1H, J=12.6, 4.8 Hz), 4.85 (d, 1H, J=3.6 Hz), 4.71 (s, 1H), 4.58 (br, 1H), 3.92 (s, 3H), 3.62 (s, 3H), 3.47 (s, 3H), 3.13 (d, 1H, J=4.8 Hz), 3.02 (d, 1H, J=5.4 Hz), 2.74-2.70 (m, 1H), 2.61 (s, 3H), 2.33 (br, 1H), 2.21-2.17 (m, 1H); $^{13}$C NMR (125 MHz, CDCl$_3$) δ: 203.3, 162.2, 151.6, 144.4, 142.6, 135.6, 129.3, 116.3, 115.0, 114.5, 107.2, 103.9, 100.1, 98.7, 73.3, 69.5, 69.2, 67.7, 62.9, 61.8, 57.0, 56.6, 50.3, 37.0, 20.5; FTIR (neat), cm$^{-1}$: 3459 (br), 2944 (w), 1620 (s), 1567 (s), 1445 (s), 1387 (s), 1098 (s), 1069 (s); HRMS (ESI): Calcd for $(C_{25}H_{26}O_{12}+H)^+$ 519.1497. found 519.1494.

A Process for Preparing Dideoxy-DC-45-A2.

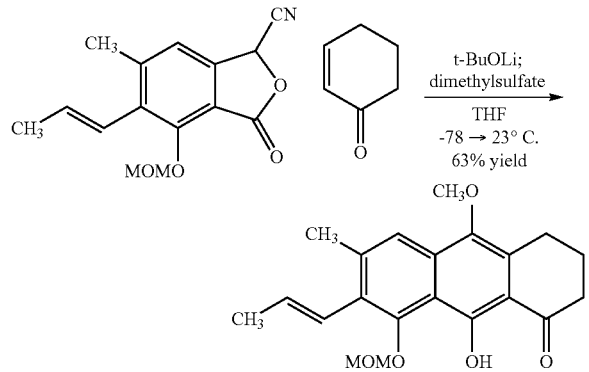

(E)-9-Hydroxy-10-methoxy-8-(methoxymethoxy)-6-methyl-7-(prop-1-enyl)-3,4-dihydroanthracen-1-one Lithium tert-butoxide (1.16 g, 14.5 mmol, 3.0 equiv) in tetrahydrofuran (15 mL) was added to a solution of cyanophthalide (1.32 g, 4.83 mmol, 1 equiv) in tetrahydrofuran (25 mL) at −78° C. After 5 min, a solution of cyclohex-2-enone (466 μL, 4.83 mmol, 1.0 equiv) in tetrahydrofuran (25 mL) was added by cannula. The reaction flask was allowed to warm to −25° C. over 2.5 h, then dimethylsulfate (4.12 mL, 43.5 mmol, 9.0 equiv) was added. The reaction flask was allowed to warm to 23° C. over 2 h. After an additional 1 h, the reaction mixture was diluted with 10% aqueous ammonium hydroxide solution (100 mL) and stirred for 10 min. The solution was partitioned between water (100 mL) and ethyl acetate (300 mL). The layers were separated. The organic layer washed with water (200 mL) and the washed solution was dried over sodium sulfate. The dried solution was filtered and the filtrate was concentrated. The residue was purified by flash-column chromatography (20% ethyl acetate-hexanes) to provide 1.09 g of the product, (E)-9-hydroxy-10-methoxy-8-(methoxymethoxy)-6-methyl-7-(prop-1-enyl)-3,4-dihydroanthracen-1-one as a yellow solid (63%). $^1$H NMR (500 MHz, CDCl$_3$): 14.93 (s, 1H), 7.59 (s, 1H), 6.53 (dd, 1H, J=16.1, 1.5 Hz), 6.09 (dq, 1H, J=16.1, 6.6 Hz), 5.08 (s, 2H), 3.79 (s, 3H), 3.60 (s, 3H), 3.03 (t, 2H, J=5.9 Hz), 2.73 (t, 2H, J=6.6 Hz), 2.48 (s, 3H), 2.08 (m, 2H), 1.96 (dd, 3H, J=6.6, 1.5 Hz). $^{13}$C NMR (125 MHz, CDCl$_3$): 204.8, 161.5, 153.6, 142.9, 141.1, 133.3, 132.0, 130.6, 127.7, 125.2, 118.4, 117.1, 110.7, 101.1, 60.9, 57.8, 38.9, 23.4, 22.2, 22.1, 19.3. FTIR, cm (thin film): 2945 (m), 1614 (s), 1560 (m), 1445 (m), 1377 (s), 1157 (m), 1037 (s). HRMS (ESI): Calcd for $(C_{21}H_{24}O_5+H)^+$ 357.1702. Found 357.1696. TLC: (20% ethyl acetate-hexanes): $R_f$=0.39 (CAM).

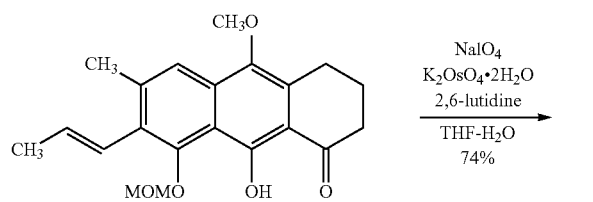

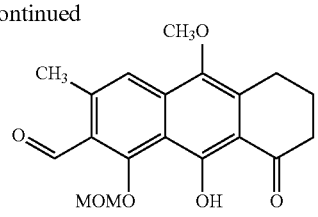

9-Hydroxy-10-methoxy-1-(methoxymethoxy)-3-methyl-8-oxo-5,6,7,8-tetrahydroanthracene-2-carbaldehyde 2,6-Lutidine (130 μL, 1.12 mmol, 2.0 equiv) was added to an ice-cooled mixture of (E)-9-hydroxy-10-methoxy-8-(methoxymethoxy)-6-methyl-7-(prop-1-enyl)-3,4-dihydroanthracen-1-one (200 mg, 0.56 mmol, 1 equiv), potassium osmate dihydrate (10 mg, 0.028 mmol, 0.05 equiv), and sodium periodate (480 mg, 2.24 mmol, 4.0 equiv) in a mixture of tetrahydrofuran (10 mL) and water (5 mL). After 10 min, the cooling bath was removed and the reaction flask was allowed to warm to 23° C. After 2.5 h, the reaction mixture was partitioned between water (50 mL) and ethyl acetate (100 mL). The layers were separated. The organic layer was dried over sodium sulfate. The dried solution was filtered and the filtrate was concentrated. The residue was purified by flash-column chromatography (15% ethyl acetate-hexanes initially, grading to 20% ethyl acetate-hexanes) to provide 142 mg of the product, 9-hydroxy-10-methoxy-1-(methoxymethoxy)-3-methyl-8-oxo-5,6,7,8-tetrahydroanthracene-2-carbaldehyde, as an orange foam (74%). $^1$H NMR (500 MHz, CDCl$_3$): 15.10 (s, 1H), 10.72 (s, 1H), 7.59 (s, 1H), 5.26 (s, 2H), 3.81 (s, 3H), 3.62 (s, 3H), 3.08 (t, 2H, J=6.6 Hz), 2.77 (t, 2H, J=6.6 Hz), 2.73 (s, 3H), 2.12 (m, 2H). $^{13}$C NMR (125 MHz, CDCl$_3$): 205.1, 193.2, 163.4, 161.7, 143.1, 141.6, 137.0, 132.4, 126.8, 120.0, 116.4, 111.4, 102.8, 61.1, 58.3, 38.8, 23.7, 22.3, 21.9. FTIR, cm$^{-1}$: (thin film) 2959 (m), 1674 (m), 1610 (s), 1560 (m), 1375 (s), 1246 (s), 1153 (m), 1038 (s), 1015 (s), 900 (s). HRMS (ESI): Calcd for $(C_{19}H_{20}O_6+H)^+$ 345.1333. Found 345.1329. TLC: (20% ethyl acetate-hexanes) $R_f$=0.22 (CAM).

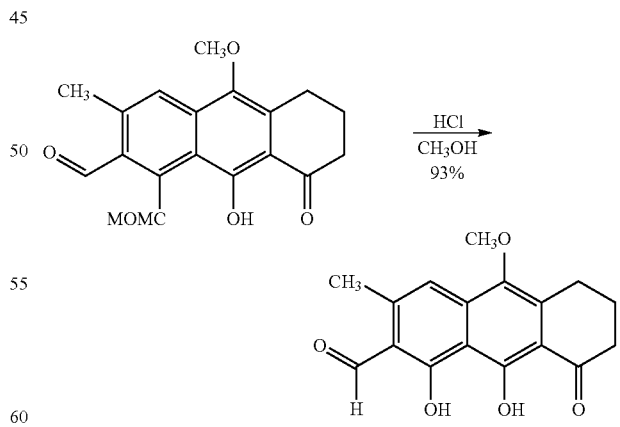

1,9-Dihydroxy-10-methoxy-3-methyl-8-oxo-5,6,7,8-tetrahydroanthracene-2-carbaldehyde 9-Hydroxy-10-methoxy-1-(methoxymethoxy)-3-methyl-8-oxo-5,6,7,8-tetrahydroanthracene-2-carbaldehyde (142 mg, 0.41 mmol, 1 equiv) was added to an ice-cooled solution of 2% aqueous hydrochloric acid in methanol (v/v, 4 mL). After 10 min, the cooling bath was removed and reaction flask was allowed to warm to 23° C. After 4 h, the yellow slurry was partitioned between saturated aqueous sodium bicarbonate solution (30 mL) and dichloromethane (60 mL). The layers were separated. The organic layer was dried over sodium sulfate. The dried solution was filtered and the filtrate was concentrated to provide 115 mg of the product, 1,9-dihydroxy-10-methoxy-3-methyl-8-oxo-5,6,7,8-tetrahydroanthracene-2-carbaldehyde, as a yellow powder (93%). $^1$H NMR (500 MHz, CDCl$_3$): 15.67 (br s, 1H), 10.43 (s, 1H), 7.20 (s, 1H), 3.79 (s, 3H), 3.05 (t, 2H, J=5.8 Hz), 2.76 (t, 2H, J=6.6 Hz), 2.70 (s, 3H), 2.12 (m, 2H). $^{13}$C NMR (125 MHz, CDCl$_3$): 204.8, 193.1, 167.3, 164.4, 143.3, 142.5, 138.1, 134.3, 115.6, 114.3, 112.8, 111.1, 61.2, 38.4, 23.9, 22.2, 21.0. FTIR, cm (thin film): 3285 (br), 2955 (m), 1670 (s), 1614 (m), 1497 (m), 1392 (s), 1373 (m), 1257 (s), 1248 (s), 1045 (s). HRMS (ESI): Calcd for $(C_{17}H_{16}O_5+Na)^+$ 323.0890. Found 323.0848. TLC: (100% ethyl acetate) $R_f$=0.12 (CAM).

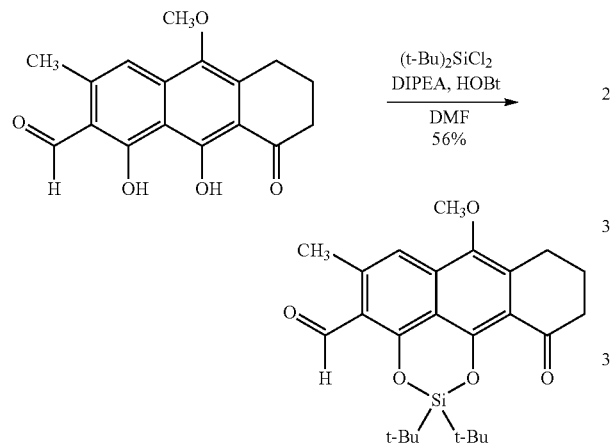

2,2-Di-tert-butyl-7-methoxy-5-methyl-11-oxo-8,9,10,11-tetrahydroanthra[9,1-de][1,3,2]dioxasiline-4-carbaldehyde Di-tert-butyldichlorosilane (29 μL, 0.14 mmol, 1.8 equiv) was added to a solution of 1,9-dihydroxy-10-methoxy-3-methyl-8-oxo-5,6,7,8-tetrahydroanthracene-2-carbaldehyde (23 mg, 0.077 mmol, 1 equiv), hydroxybenzotriazole (5.2 mg, 0.038 mmol, 0.50 equiv), and diisoproylethylamine (67 μL, 0.38 mmol, 5.0 equiv) in diethylformamide (1.0 mL) at 23° C. The reaction flask was heated in an oil bath at 55° C. After 3 h, the reaction flask was allowed to cool to 23° C. The mixture was partitioned between water (10 mL) and ethyl acetate (30 mL). The layers were separated. The organic layer was washed with brine (5 mL) and the washed solution was dried over sodium sulfate. The dried solution was filtered and the filtrate was concentrated. The residue was purified by flash-column chromatography (10% ethyl acetate-hexanes) to provide 19 mg of the product, 2,2-di-tert-butyl-7-methoxy-5-methyl-11-oxo-8,9,10,11-tetrahydroanthra[9,1-de][1,3,2]dioxasiline-4-carbaldehyde, as a pale yellow foam (56%). $^1$H NMR (500 MHz, CDCl$_3$): 10.82 (s, 1H), 7.31 (s, 1H), 3.83 (s, 3H), 3.07 (m, 2H), 2.71 (s, 3H), 2.66 (m, 2H), 2.10 (m, 2H), 1.15 (app s, 18H). $^{13}$C NMR (125 MHz, CDCl$_3$): 196.1, 190.9, 160.7, 150.8, 144.6, 140.5, 136.1, 133.9, 118.8, 116.9, 115.9, 113.8, 61.1, 41.0, 26.1, 24.4, 22.5, 22.1, 21.2. FTIR, cm$^{-1}$ (thin film): 2938 (m), 2863 (m), 1682 (s), 1607 (s), 1371 (s). HRMS (ESI): Calcd for $(C_{25}H_{32}O_5Si+H)^+$ 441.2092. Found 441.1980. TLC (10% ethyl acetate-hexanes): $R_f$=0.24 (CAM).

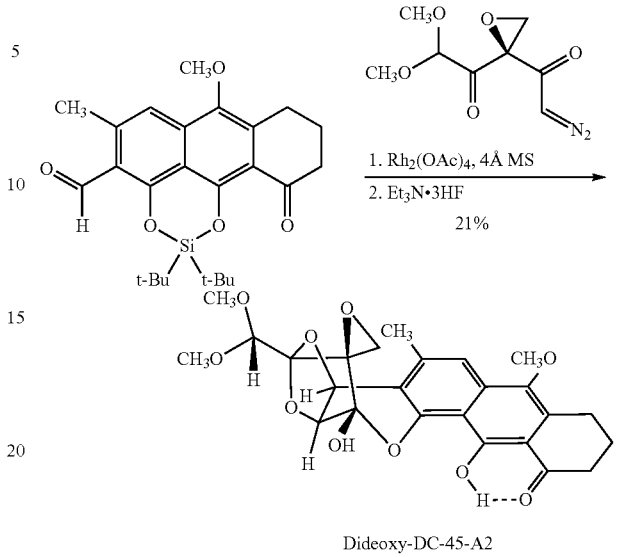

Dideoxy-DC-45-A2

Dideoxy-DC-45-A2.

A solution of diazo compound (570 mg, 2.66 mmol, 1.5 equiv) in dichloromethane (700 μL) was added by a motor-driven syringe pump over 8 h to a suspension of 2,2-di-tert-butyl-7-methoxy-5-methyl-11-oxo-8,9,10,11-tetrahydroanthra[9,1-de][1,3,2]dioxasiline-4-carbaldehyde (782 mg, 1.77 mmol, 1 equiv), rhodium acetate dimer (39.2 mg, 0.089 mmol, 0.05 equiv), and powdered 4 angstrom molecular sieves (~250 mg) in dichloromethane (3.0 mL) at 23° C. The flask and the syringe containing the diazo compound were covered with aluminum foil. After the addition was complete, the mixture was loaded onto a plug of silica gel and eluted with 30% ethyl acetate-hexanes to remove the solids. The filtrate was concentrated. The crude product was purified by flash column chromatography (5% ethyl acetate-hexanes initially, grading to 30% ethyl acetate-hexanes) to provide a mixture of cycloadducts (517 mg, structures not shown).

Triethylamine-trihydrofluoride was added to a solution of a mixture of cycloadducts in acetonitrile (0.05 M, 16.5 mL) at 23° C. After 20 min, the reaction mixture was diluted with dichloromethane (400 mL) and washed sequentially with pH 7 buffer (100 mL) then saturated aqueous sodium chloride solution (100 mL). The washed solution was dried over magnesium sulfate and concentrated. The residue was purified by flash-column chromatography (30% ether-hexanes initially, grading to ethyl acetate) on silica gel deactivated with triethylamine, to provide 178 mg of the desired product, dideoxy-DC-45-A2, as a yellow solid (21% over two steps). TLC: (50% ethyl acetate-hexanes) $R_f$=0.14 (CAM); $^1$H NMR (500 MHz, CDCl$_3$) δ: 14.9 (s, 1H), 7.44 (s, 1H), 5.26 (d, 1H, J=3.5 Hz), 4.83 (d, 1H, J=4.0 Hz), 4.71 (s, 1H), 4.37 (br s, 1H), 3.78 (s, 3H), 3.62 (s, 3H), 3.47 (s, 3H), 3.14 (d, 1H, J=5.0 Hz), 3.06 (d, 1H, J=5.0 Hz), 3.05-3.02 (m, 2H), 2.74-2.72 (m, 2H), 2.59 (s, 3H), 2.11-2.06 (m, 2H); $^{13}$C NMR (125 MHz, CDCl$_3$) δ: 204.4, 162.8, 151.5, 142.4, 141.7, 135.2, 130.2, 115.8, 113.5, 113.2, 111.0, 103.8, 100.1, 98.4, 73.3, 69.8, 69.3, 60.9, 57.0, 56.6, 50.5, 38.7, 23.5, 22.0, 20.4; FTIR (neat), cm$^{-1}$: 3424 (br), 2926 (s), 1620 (s), 1445 (w), 1389 (s), 1092 (s); HRMS (ESI): Calcd for $(C_{25}H_{26}O_{10}+H)^+$ 487.1599. found 487.1597.

A Process for Preparing an Intermediate Useful in the Synthesis of 2-Deoxy-Trioxacarcin Analogues

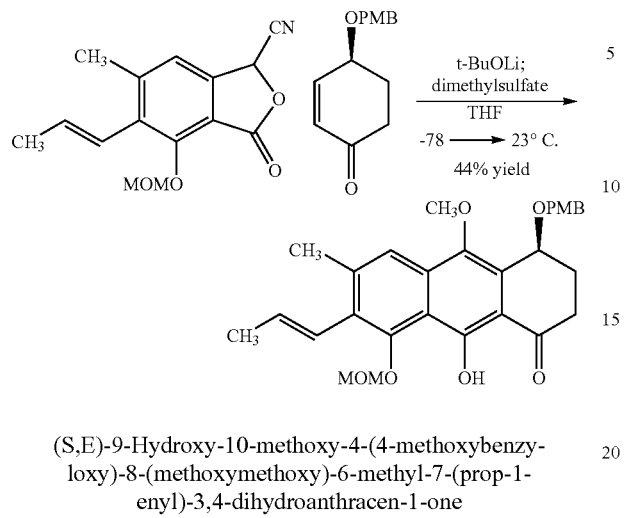

(S,E)-9-Hydroxy-10-methoxy-4-(4-methoxybenzyloxy)-8-(methoxymethoxy)-6-methyl-7-(prop-1-enyl)-3,4-dihydroanthracen-1-one

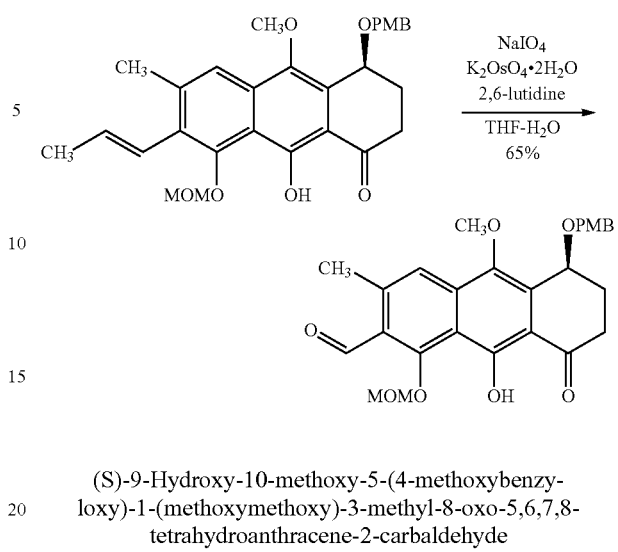

(S)-9-Hydroxy-10-methoxy-5-(4-methoxybenzyloxy)-1-(methoxymethoxy)-3-methyl-8-oxo-5,6,7,8-tetrahydroanthracene-2-carbaldehyde Lithium tert-butoxide (879 mg, 11.0 mmol, 3.0 equiv) in tetrahydrofuran (10 mL) was added to a solution of cyanophthalide (1.0 g, 3.66 mmol, 1 equiv) in tetrahydrofuran (20 mL) at −78° C. After 5 min, a solution of S-(4-methoxybenzyloxy)cyclohex-2-enone (850 mg, 3.66 mmol, 1.0 equiv) in tetrahydrofuran (10 mL) was added by cannula. The reaction flask was allowed to warm to −20° C. over 1 h, then dimethylsulfate (3.15 mL, 32.9 mmol, 9.0 equiv) was added. The reaction flask was allowed to warm to 23° C. After an additional 4.5 h, the reaction mixture was partitioned between saturated aqueous ammonium chloride solution (100 mL) and ethyl acetate (200 mL). The layers were separated. The organic layer was washed with saturated aqueous ammonium chloride solution (100 mL) and the washed solution was dried over sodium sulfate. The dried solution was filtered and the filtrate was concentrated. The residue was diluted with 3.0 M aqueous ammonium hydroxide solution (100 mL) and dichloromethane (10 mL). The biphasic mixture was stirred vigorously. After 20 min, the mixture was partitioned between saturated aqueous ammonium chloride solution (150 mL) and ethyl acetate (250 mL). The layers were separated. The organic layer was washed with saturated aqueous ammonium chloride solution (150 mL) and the washed solution was dried over sodium sulfate. The dried solution was filtered and the filtrate was concentrated. The residue was purified by flash-column chromatography (10% ethyl acetate-hexanes) to provide 791 mg of the product, (S,E)-9-hydroxy-10-methoxy-4-(4-methoxybenzyloxy)-8-(methoxymethoxy)-6-methyl-7-(prop-1-enyl)-3,4-dihydroanthracen-1-one, as a yellow oil (44%). $^1$H NMR (500 MHz, CDCl$_3$): 15.10 (s, 1H), 7.65 (s, 1H), 7.26 (d, 2H, J=8.8 Hz), 6.85 (d, 2H, J=8.8 Hz), 6.53 (d, 1H, J=16.1 Hz), 6.12 (dq, 1H, J=16.1, 6.5 Hz), 5.21 (br s, 1H), 5.10 (d, 1H, J=6.6 Hz), 5.07 (d, 1H, J=6.6 Hz), 4.61 (d, 1H, J=11.0 Hz), 4.49 (d, 1H, J=11.7 Hz), 3.85 (s, 3H), 3.78 (s, 3H), 3.60 (s, 3H), 3.20 (m, 1H), 2.59 (m, 1H), 2.52 (m, 1H), 2.51 (s, 3H), 2.05 (m, 1H), 1.98 (dd, 3H, J=6.6, 1.5 Hz). $^{13}$C NMR (125 MHz, CDCl$_3$): 204.7, 161.6, 159.2, 153.8, 144.5, 141.2, 133.1, 132.4, 131.6, 130.5, 129.4, 125.9, 125.2, 119.2, 118.6, 113.7, 109.4, 101.2, 70.2, 67.4, 62.8, 57.9, 55.2, 32.4, 26.7, 22.2, 19.3. FTIR, cm$^{-1}$ (thin film): 2936 (m), 1611 (s), 1512 (m), 1377 (s), 1246 (s), 1036 (s). HRMS (ESI): Calcd for (C$_{29}$H$_{32}$O$_7$+Na)$^+$ 515.2040. Found 515.1954. TLC (20% ethyl acetate-hexanes): R$_f$=0.27 (CAM).

Potassium osmate dihydrate (29 mg, 0.079 mmol, 0.05 equiv) was added to an ice-cooled mixture of (S,E)-9-hydroxy-10-methoxy-4-(4-methoxybenzyloxy)-8-(methoxymethoxy)-6-methyl-7-(prop-1-enyl)-3,4-dihydroanthracen-1-one (780 mg, 1.58 mmol, 1 equiv), 2,6-lutidine (369 µL, 3.17 mmol, 2.0 equiv), and sodium periodate (1.36 g, 6.33 mmol, 4.0 equiv) in a mixture of tetrahydrofuran (20 mL) and water (10 mL). After 10 min, the cooling bath was removed and the reaction flask was allowed to warm to 23° C. After 1.5 h, the reaction mixture was partitioned between water (100 mL) and ethyl acetate (150 mL). The layers were separated. The organic layer was washed with aqueous sodium chloride solution (50 mL) and the washed solution was dried over sodium sulfate. The dried solution was filtered and the filtrate was concentrated. The residue was purified by flash-column chromatography (20% ethyl acetate-hexanes) to provide 498 mg of the product, (S)-9-hydroxy-10-methoxy-5-(4-methoxybenzyloxy)-1-(methoxymethoxy)-3-methyl-8-oxo-5,6,7,8-tetrahydroanthracene-2-carbaldehyde, as an orange foam (65%). $^1$H NMR (500 MHz, CDCl$_3$): 15.17 (s, 1H), 10.74 (s, 1H), 7.66 (s, 1H), 7.27 (d, 2H, J=8.5 Hz), 6.86 (d, 2H, J=8.6 Hz), 5.30-5.18 (m, 3H), 4.63 (d, 1H, J=11.1 Hz), 4.52 (d, 1H, J=12.0 Hz), 3.86 (s, 3H), 3.79 (s, 3H), 3.62 (s, 3H), 3.22 (m, 1H), 2.75 (s, 3H), 2.63 (m, 1H), 2.54 (m, 1H), 2.08 (m, 1H). $^{13}$C NMR (125 MHz, CDCl$_3$): 204.9, 193.2, 163.2, 161.7, 159.2, 144.4, 141.7, 137.0, 130.1, 129.4, 120.7, 117.9, 113.8, 110.0, 102.8, 70.4, 67.2, 62.9, 58.3, 55.2, 32.3, 26.3, 22.2. FTIR, cm$^{-1}$ (thin film): 2936 (m), 2907 (m), 1684 (s), 1611 (s), 1377 (s), 1246 (s). HRMS (ESI): Calcd for (C$_{27}$H$_{28}$O$_8$+K)$^+$: 519.1416. Found 519.1368. TLC (20% ethyl acetate-hexanes): R$_f$=0.17 (CAM).

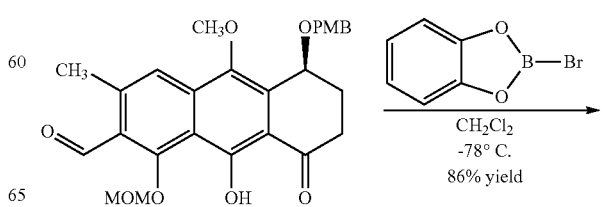

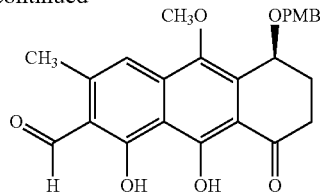

(S)-1,9-Dihydroxy-10-methoxy-5-(4-methoxybenzyloxy)-3-methyl-8-oxo-5,6,7,8-tetrahydroanthracene-2-carbaldehyde A solution of B-bromocatecholborane (418 mg, 2.10 mmol, 2.0 equiv) in dichloromethane (15 mL) was added to a solution of (S)-9-hydroxy-10-methoxy-5-(4-methoxybenzyloxy)-1-(methoxymethoxy)-3-methyl-8-oxo-5,6,7,8-tetrahydroanthracene-2-carbaldehyde (490 mg, 1.05 mmol, 1 equiv) in dichloromethane (15 mL) at −78° C. After 50 min, the reaction mixture was diluted with saturated aqueous sodium bicarbonate solution (25 mL) and dichloromethane (100 mL). The cooling bath was removed, and the partially frozen mixture was allowed to warm to 23° C. The biphasic mixture was diluted with 0.2 M aqueous sodium hydroxide solution (100 mL). The layers were separated. The aqueous layer was extracted with dichloromethane (100 mL). The organic layers were combined. The combined solution was washed sequentially with 0.1 M aqueous hydrochloric acid solution (100 mL), water (2×100 mL), then saturated aqueous sodium chloride solution (100 mL) and the washed solution was dried over sodium sulfate. The dried solution was filtered and the filtrate was concentrated to provide 380 mg of the product, (S)-1,9-dihydroxy-10-methoxy-5-(4-methoxybenzyloxy)-3-methyl-8-oxo-5,6,7,8-tetrahydroanthracene-2-carbaldehyde, as a yellow foam (86%). $^1$H NMR (500 MHz, CDCl$_3$): 15.89 (br s, 1H), 12.81 (br s, 1H), 10.51 (s, 1H), 7.27-7.26 (m, 3H), 6.86 (d, 2H, J=9.2 Hz), 5.14 (app s, 1H), 4.62 (d, 1H, J=11.0 Hz), 4.51 (d, 1H, J=11.0 Hz), 3.85 (s, 3H), 3.80 (s, 3H), 3.21 (m, 1H), 2.73 (s, 3H), 2.62 (m, 1H), 2.54 (m, 1H), 2.07 (m, 1H). $^{13}$C NMR (125 MHz, CDCl$_3$): 204.4, 192.7, 166.6, 164.3, 159.3, 144.4, 142.7, 137.9, 130.4, 130.2, 129.4, 114.9, 114.2, 113.9, 113.8, 109.4, 70.4, 67.1, 62.8, 55.3, 31.8, 26.5. FTIR, cm$^{-1}$ (thin film): 3316 (br w), 2938 (m), 1678 (m), 1610 (s), 1514 (m), 1393 (m), 1246 (s). HRMS (ESI): Calcd for (C$_{25}$H$_{24}$O$_7$+Na)$^+$ 459.1414. Found 459.1354. TLC (50% ethyl acetate-hexanes): R$_f$=0.30 (CAM).

(S)-2,2-Di-tert-butyl-7-methoxy-8-(4-methoxybenzyloxy)-5-methyl-11-oxo-8,9,10,11-tetrahydroanthra[9,1-de][1,3,2]dioxasiline-4-carbaldehyde Di-tert-butyldichlorosilane (342 µL, 1.62 mmol, 1.8 equiv) was added to a solution of (S)-1,9-dihydroxy-10-methoxy-5-(4-methoxybenzyloxy)-3-methyl-8-oxo-5,6,7,8-tetrahydroanthracene-2-carbaldehyde (380 mg, 0.90 mmol, 1 equiv), hydroxybenzotriazole (60.8 mg, 0.45 mmol, 0.50 equiv) and diisopropylethylamine (786 µL, 4.50 mmol, 5.0 equiv) in dimethylformamide (30 mL). The reaction flask was heated in an oil bath at 55° C. After 2 h, the reaction flask was allowed to cool to 23° C. The reaction mixture was partitioned between saturated aqueous sodium bicarbonate solution (100 mL) and ethyl acetate (150 mL). The layers were separated. The organic layer was washed sequentially with water (2×100 mL) then saturated aqueous sodium chloride solution (100 mL) and the washed solution was dried over sodium sulfate. The dried solution was filtered and the filtrate was concentrated. The residue was purified by flash-column chromatography (10% ethyl acetate-hexanes) to provide 285 mg of the product, (S)-2,2-di-tert-butyl-7-methoxy-8-(4-methoxybenzyloxy)-5-methyl-11-oxo-8,9,10,11-tetrahydroanthra[9,1-de][1,3,2]dioxasiline-4-carbaldehyde, as a yellow foam (56%). The enantiomeric compound (R)-2,2-di-tert-butyl-7-methoxy-8-(4-methoxybenzyloxy)-5-methyl-11-oxo-8,9,10,11-tetrahydroanthra[9,1-de][1,3,2]dioxasiline-4-carbaldehyde has been prepared using the same route by utilizing R-(4-methoxybenzyloxy)cyclohex-2-enone as starting material. $^1$H NMR (500 MHz, CDCl$_3$): 10.84 (s, 1H), 7.37 (s, 1H), 7.25 (d, 2H, J=8.8 Hz), 6.85 (d, 2H, J=8.7 Hz), 5.20 (app s, 1H), 4.62 (d, 1H, J=10.0 Hz), 4.51 (d, 1H, J=11.4 Hz), 3.88 (s, 3H), 3.78 (s, 3H), 3.03 (m, 1H), 2.73 (s, 3H), 2.57-2.53 (m, 2H), 2.07 (m, 1H), 1.16 (s, 9H), 1.14 (s, 9H). $^{13}$C NMR (125 MHz, CDCl$_3$): 195.6, 190.9, 160.5, 159.2, 150.4, 145.7, 140.4, 134.0, 133.9, 130.3, 129.4, 119.5, 116.6, 115.8, 115.3, 113.8, 70.4, 67.8, 62.9, 55.2, 34.0, 26.0, 26.0, 22.5, 21.3, 21.1. FTIR, cm$^{-1}$ (thin film): 2936 (m), 2862 (m), 1682 (s), 1607 (s), 1371 (s), 1244 (s) 1057 (s). HRMS (ESI): Calcd for (C$_{33}$H$_{40}$O$_7$Si+H)$^+$ 577.2616. Found 577.2584. TLC (10% ethyl acetate-hexanes): R$_f$=0.19 (CAM).

Alternative Routes to (4S,6S)-6-(tert-Butyldimethylsilyloxy)-4-(4-methoxybenzyloxy)cyclohex-2-enone

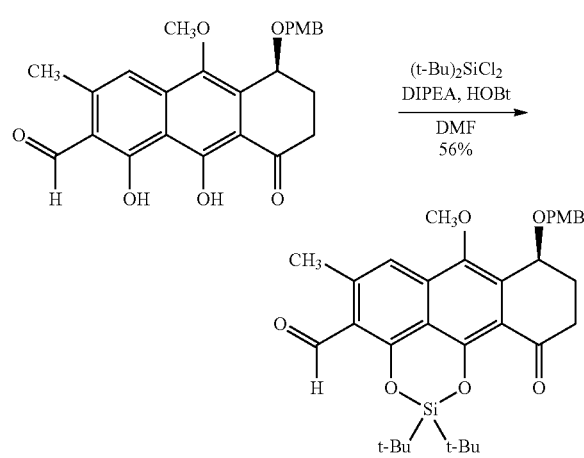

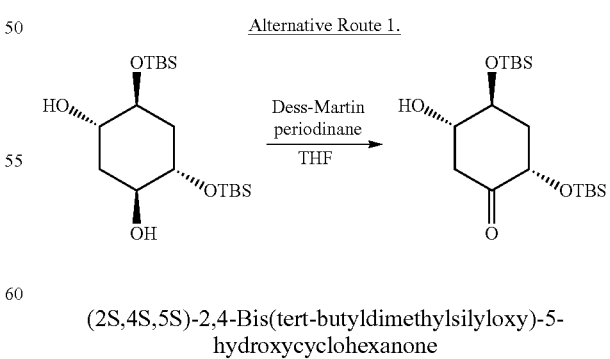

(2S,4S,5S)-2,4-Bis(tert-butyldimethylsilyloxy)-5-hydroxycyclohexanone

Dess-Martin periodinane (6.11 g, 14.4 mmol, 1.1 equiv) was added to a solution of diol (5.00 g, 13.3 mmol, 1 equiv) in tetrahydrofuran (120 mL) at 23° C. (Lim, S. M.; Hill, N.; Myers, A. G. *J. Am. Chem. Soc.* 2009, 131, 5763-5765).

After 40 min, the reaction mixture was diluted with ether (300 mL). The diluted solution was filtered through a short plug of silica gel (~5 cm) and eluted with ether (300 mL). The filtrate was concentrated. The bulk of the product was transformed as outlined in the following paragraph, without purification. Independently, an analytically pure sample of the product was obtained by flash-column chromatography (20% ethyl acetate-hexanes) and was characterized by $^1$H NMR, $^{13}$C NMR, IR, and HRMS. TLC: (17% ethyl acetate-hexanes) R$_f$=0.14 (CAM); $^1$H NMR (500 MHz, CDCl$_3$) δ: 4.41 (dd, 1H, J=9.8, 5.5 Hz), 4.05 (m, 1H), 4.00 (m, 1H), 2.81 (ddd, 1H, J=14.0, 3.7, 0.9 Hz), 2.52 (ddd, 1H, J=14.0, 5.3, 0.9 Hz), 2.29 (br s, 1H), 2.18 (m, 1H), 1.98 (m, 1H), 0.91 (s, 9H), 0.89 (s, 9H), 0.13 (s, 3H), 0.11 (s, 3H), 0.09 (s, 3H), 0.04 (s, 3H); $^{13}$C NMR (125 MHz, CDCl$_3$) δ: 207.9, 73.9, 73.3, 70.5, 43.3, 39.0, 25.7, 25.6, 18.3, 17.9, −4.7, −4.8, −4.9, −5.4; FTIR (neat), cm$^{-1}$: 3356 (br), 2954 (m), 2930 (m), 2857 (m), 1723 (m), 1472 (m), 1253 (s), 1162 (m), 1105 (s), 1090 (s), 1059 (s), 908 (s), 834 (s), 776 (s), 731 (s); HRMS (ESI): Calcd for (C$_{18}$H$_{38}$O$_4$Si$_2$+H)$^+$ 375. 2381. found 375.2381.

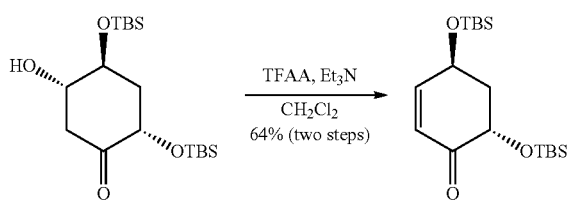 [SMILES: CC(C)(C)[Si](C)(C)O[C@H]1C[C@H](O[Si](C)(C)C(C)(C)C)[C@@H](O)CC1=O ; CC(C)(C)[Si](C)(C)O[C@@H]1C=CC(=O)[C@@H](O[Si](C)(C)C(C)(C)C)C1]

(4S,6S)-4,6-Bis(tert-butyldimethylsilyloxy)cyclohex-2-enone

Trifluoroacetic anhydride (6.06 mL, 43.6 mmol, 3.3 equiv) was added to an ice-cooled solution of the alcohol (1 equiv, see paragraph above) and triethylamine (18.2 mL, 131 mmol, 9.9 equiv) in dichloromethane (250 mL) at 0° C. After 20 min, the cooling bath was removed and the reaction flask was allowed to warm to 23° C. After 18 h, the reaction flask was cooled in an ice bath at 0° C., and the product solution was diluted with water (100 mL). The cooling bath was removed and the reaction flask was allowed to warm to 23° C. The layers were separated. The aqueous layer was extracted with dichloromethane (2×200 mL). The organic layers were combined. The combined solution was washed with saturated aqueous sodium chloride solution (100 mL) and the washed solution was dried over sodium sulfate. The dried solution was filtered and the filtrate was concentrated. The residue was purified by flash-column chromatography (6% ethyl acetate-hexanes) to provide 3.02 g of the product, (4S,6S)-4,6-bis(tert-butyldimethylsilyloxy)cyclohex-2-enone, as a colorless oil (64% over two steps). TLC: (20% ethyl acetate-hexanes) R$_f$=0.56 (CAM); $^1$H NMR (500 MHz, CDCl$_3$) δ: 6.76 (dd, 1H, J=10.1, 3.6 Hz), 5.88 (d, 1H, J=10.1 Hz), 4.66 (ddd, 1H, J=5.6, 4.1, 3.6 Hz), 4.40 (dd, 1H, J=8.1, 3.7 Hz), 2.26 (ddd, 1H, J=13.3, 8.0, 4.1 Hz), 2.11 (ddd, 1H, J=13.2, 5.6, 3.8 Hz), 0.91 (s, 9H), 0.89 (s, 9H), 0.12 (s, 3H), 0.11 (s, 3H), 0.10 (s, 3H), 0.10 (s, 3H); $^{13}$C NMR (125 MHz, CDCl$_3$) δ: 197.5, 150.3, 127.0, 71.0, 64.8, 41.6, 25.7, 25.7, 18.3, 18.1, −4.7, −4.8, −4.8, −5.4; FTIR (neat), cm$^{-1}$: 3038 (w), 2955 (m), 2930 (m), 1705 (m), 1472 (m), 1254 (m), 1084 (m), 835 (s), 777 (s), 675 (s); HRMS (ESI): Calcd for (C$_{18}$H$_{36}$O$_2$Si$_2$+Na)$^+$ 379. 2095. found 379. 2080.

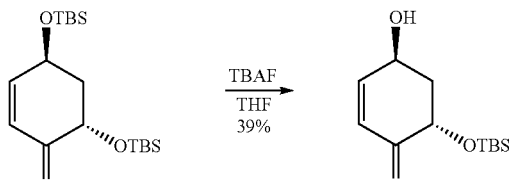

(4S,6S)-6-(tert-Butyldimethylsilyloxy)-4-hydroxycyclohex-2-enone

Tetra-n-butylammonium fluoride (1.0 M solution in tetrahydrofuran, 8.00 mL, 8.00 mmol, 1.0 equiv) was added to an ice-cooled solution of the enone (2.85 g, 8.00 mmol, 1 equiv) and acetic acid (485 μL, 8.00 mmol, 1.0 equiv) in tetrahydrofuran (80 mL) at 0° C. After 2 h, the cooling bath was removed and the reaction flask was allowed to warm to 23° C. After 22 h, the reaction mixture was partitioned between water (100 mL) and ethyl acetate (300 mL). The layers were separated. The aqueous layer was extracted with ethyl acetate (2×300 mL). The organic layers were combined. The combined solution was washed sequentially with saturated aqueous sodium bicarbonate solution (100 mL) then saturated aqueous sodium chloride solution (100 mL) and the washed solution was dried over sodium sulfate. The dried solution was filtered and the filtrate was concentrated. The residue was purified by flash-column chromatography (25% ethyl acetate-hexanes) to provide 760 mg of the product, (4S,6S)-6-(tert-butyldimethylsilyloxy)-4-hydroxycyclohex-2-enone, as a white solid (39%). TLC: (20% ethyl acetate-hexanes) R$_f$=0.20 (CAM); $^1$H NMR (500 MHz, CDCl$_3$) δ: 6.87 (dd, 1H, J=10.2, 3.2 Hz), 5.95 (dd, 1H, J=10.3, 0.9 Hz), 4.73 (m, 1H), 4.35 (dd, 1H, J=7.6, 3.7 Hz), 2.39 (m, 1H), 2.13 (ddd, 1H, J=13.3, 6.2, 3.4 Hz), 1.83 (d, 1H, J=6.2), 0.89 (s, 9H), 0.10 (s, 3H), 0.10 (s, 3H); $^{13}$C NMR (125 MHz, CDCl$_3$) δ: 197.3, 150.0, 127.5, 70.9, 64.2, 41.0, 25.7, 18.2, −4.8, −5.4; FTIR (neat), cm$^{-1}$: 2956 (w), 2931 (w), 2858 (w), 1694 (m); HRMS (ESI): Calcd for (C$_{12}$H$_{22}$O$_3$Si+H)$^+$ 243.1411. found 243.1412.

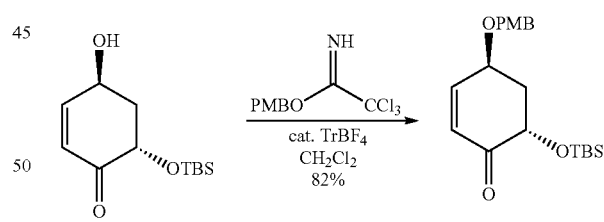

(4S,6S)-6-(tert-Butyldimethylsilyloxy)-4-(4-methoxybenzyloxy)cyclohex-2-enone

Triphenylmethyl tetrafluoroborate (16 mg, 50 μmol, 0.050 equiv) was added to a solution of 4-methoxybenzyl-2,2,2-trichloroacetimidate (445 μL, 2.5 mmol, 2.5 equiv) and alcohol (242 mg, 1.0 mmol, 1 equiv) in ether (10 mL) at 23° C. After 4 h, the reaction mixture was partitioned between saturated aqueous sodium bicarbonate solution (15 mL) and ethyl acetate (50 mL). The layers were separated. The aqueous layer was extracted with ethyl acetate (50 mL). The organic layers were combined. The combined solution was washed with water (2×20 mL) and the washed solution was dried over sodium sulfate. The dried solution was filtered and the filtrate was concentrated. The residue was purified by flash column chromatography (5% ethyl acetate-hexanes initially, grading to 10% ethyl acetate-hexanes) to provide 297 mg of the product, (4S,6S)-6-(tert-butyldimethylsilyloxy)-4-(4-methoxybenzyloxy)cyclohex-2-enone, as a colorless oil (82%).

Alternate Route 2

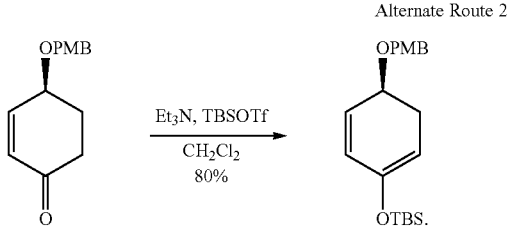

(S)-tert-Butyl(4-(4-methoxybenzyloxy)cyclohexa-1,5-dienyloxy)dimethylsilane tert-Butyldimethylsilyl trifluoromethanesulfonate (202 μL, 0.94 mmol, 2.0 equiv) was added to an ice-cooled solution of triethylamine (262 μL, 1.88 mmol, 4.0 equiv) and enone (109 mg, 0.47 mmol, 1 equiv) in dichloromethane (5.0 mL). After 30 min, the reaction mixture was partitioned between saturated aqueous sodium bicarbonate solution (10 mL), water (30 mL), and dichloromethane (40 mL). The layers were separated. The organic layer was washed sequentially with saturated aqueous ammonium chloride solution (20 mL) then saturated aqueous sodium chloride solution (20 mL) and the washed solution was dried over sodium sulfate. The dried solution was filtered and the filtrate was concentrated. The residue was purified by flash-column chromatography with triethylamine-treated silica gel (5% ethyl acetate-hexanes), to provide 130 mg of the product, (S)-tert-butyl(4-(4-methoxybenzyloxy)cyclohexa-1,5-dienyloxy)dimethylsilane, as a colorless oil (80%). $^1$H NMR (500 MHz, CDCl$_3$): 7.27 (d, 2H, J=8.7 Hz), 6.88 (d, 2H, J=8.6 Hz), 5.96 (dd, 1H, J=9.9, 3.5 Hz), 5.87 (d, 1H, J=9.6 Hz), 4.94 (m, 1H), 4.46 (s, 2H), 4.14 (m, 1H), 3.81 (s, 3H), 2.49 (m, 2H), 0.93 (s, 9H), 0.16 (s, 3H), 0.15 (s, 3H). $^{13}$C NMR (125 MHz, CDCl$_3$): 159.1, 147.5, 130.9, 129.2, 128.6, 128.1, 113.8, 101.4, 70.2, 69.0, 55.3, 28.5, 25.7, 18.0, −4.5, −4.5. FTIR, cm$^{-1}$ (thin film): 2957 (m), 2931 (m), 2859 (m), 1655 (w), 1613 (w), 1515 (s), 1248 (s), 1229 (s), 1037 (m), 910 (s). HRMS (ESI): Calcd for $(C_{20}H_{30}O_3Si+H)^+$ 347.2037. Found 347.1912. TLC (20% ethyl acetate-hexanes): R$_f$=0.74 (CAM).

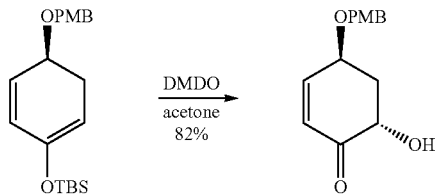

(4S,6S)-6-Hydroxy-4-(4-methoxybenzyloxy)cyclohex-2-enone

A solution of dimethyldioxirane (0.06 M solution in acetone, 2.89 mL, 0.17 mmol, 1.2 equiv) was added to an ice-cooled solution of (S)-tert-butyl(4-(4-methoxybenzyloxy)cyclohexa-1,5-dienyloxy)dimethylsilane (50 mg, 0.14 mmol, 1 equiv). After 10 min, the reaction mixture was partitioned between dichloromethane (15 mL) and 0.5 M aqueous hydrochloric acid (10 mL). The layers were separated. The organic layer was washed sequentially with saturated aqueous sodium bicarbonate solution (10 mL) then water (10 mL) and the washed solution was dried over sodium sulfate. The dried solution was filtered and the filtrate was concentrated. The residue was purified by flash-column chromatography to provide 30 mg of the product, (4S,6S)-6-hydroxy-4-(4-methoxybenzyloxy)cyclohex-2-enone, as a colorless oil (82%). $^1$H NMR (500 MHz, CDCl$_3$): 7.28 (d, 2H, J=8.2 Hz), 6.89 (m, 3H), 6.09 (d, 1H, J=10.1 Hz), 4.64 (m, 2H), 4.53 (d, 1H, J=11.4 Hz), 4.24 (m, 1H), 3.81 (s, 3H), 3.39 (d, 1H, J=1.4 Hz), 2.67 (m, 1H), 1.95 (ddd, 1H, J=12.8, 12.8, 3.6 Hz). $^{13}$C NMR (125 MHz, CDCl$_3$): 200.4, 159.5, 146.6, 129.7, 129.4, 127.8, 114.0, 71.6, 69.8, 68.9, 55.3, 35.1. FTIR, cm$^{-1}$ (thin film): 3474 (br), 2934 (m), 2864 (m), 1692 (s), 1613 (m), 1512 (s), 1246 (s), 1059 (s), 1032 (s). HRMS (ESI): Calcd for $(C_{14}H_{16}O_4+Na)^+$ 271.0941. Found 271.0834. TLC (50% ethyl acetate-hexanes): R$_f$=0.57 (CAM).

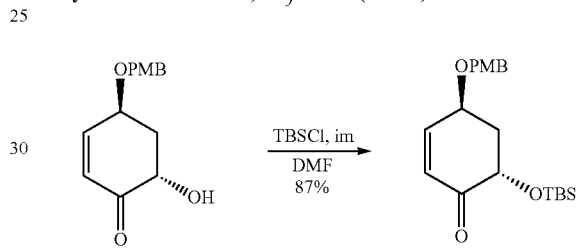

(4S,6S)-6-(tert-Butyldimethylsilyloxy)-4-(4-methoxybenzyloxy)cyclohex-2-enone tert-Butyldimethychlorosilane (26 mg, 0.18 mmol, 1.5 equiv) was added to an ice-cooled solution of (4S,6S)-6-hydroxy-4-(4-methoxybenzyloxy)cyclohex-2-enone (29 mg, 0.12 mmol, 1 equiv) and imidazole (24 mg, 0.35 mmol, 3 equiv) in dimethylformamide (0.5 mL). After 45 min, the reaction mixture was partitioned between water (15 mL), saturated aqueous sodium chloride solution (15 mL), and ethyl acetate (20 mL). The layers were separated. The organic layer was washed with water (2×20 mL) and the washed solution was dried over sodium sulfate. The dried solution was filtered and the filtrate was concentrated. The residue was purified by flash-column chromatography to provide 29 mg of the product, (4S,6S)-6-(tert-butyldimethylsilyloxy)-4-(4-methoxybenzyloxy)cyclohex-2-enone, as a colorless oil (87%).

Glycosylation Experiments

Glycosylation experiments demonstrate that the chemical process developed allows for the preparation of synthetic, glycosylated trioxacarcins. Specifically, the C4 or C13 hydroxyl group may be selectively glycosylated with a glycosyl donor (for example, a glycosyl acetate) and an activating agent (for example, TMSOTf), which enables preparation of a wide array of trioxacarcin analogues.

Selective Glycosylation of the C4 Hydroxyl Group
Glycosylation of a Differentially-Protected Trioxacarcin Precursor

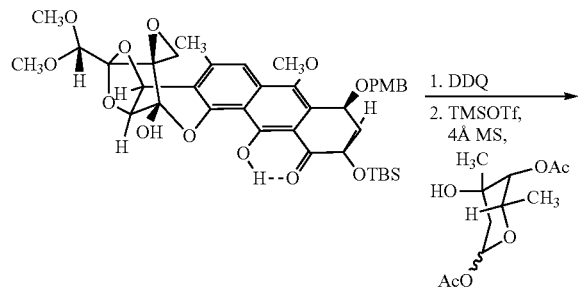

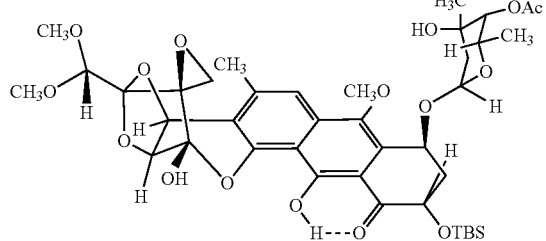

2,3-Dichloro-5,6-dicyanoenzoquinone (19.9 mg, 88 mol, 1.1 equiv) was add to a vigorously stirring, biphasic solution of differentially protected trioxacarcin precursor (60 mg, 80 μmol, 1 equiv) in dichloromethane (1.1 mL) and pH 7 phosphate buffer (220 μL) at 23° C. The reaction flask was covered with aluminum foil to exclude light. Over the course of 3 h, the reaction mixture was observed to change from myrtle green to lemon yellow. The product solution was partitioned between water (5 mL) and dichloromethane (50 mL). The layers were separated. The organic layer was dried over sodium sulfate. The dried solution was filtered and the filtrate was concentrated. The residue was purified by preparatory HPLC (Agilent Prep-C18 column, 10 μm, 30×150 mm, UV detection at 270 nm, gradient elution with 40→90% acetonitrile in water, flow rate: 15 mL/min) to provide 33 mg of the product as a yellow-green powder (65%).

Trimethylsilyl triflate (10% in dichloromethane, 28.3 μL, 16 μmol, 0.3 equiv) was added to a suspension of deprotected trioxacarcin precursor (33 mg, 52 μmol, 1 equiv), 1-O-acetyltrioxacarcinose A (14.1 mg, 57 mol, 1.1 equiv), and powdered 4-Å molecular sieves (~50 mg) in dichloromethane (1.0 mL) at −78° C. After 5 min, the mixture was diluted with dichloromethane containing 10% triethylamine and 10% methanol (3 mL). The reaction flask was allowed to warm to 23° C. The mixture was filtered and partitioned between dichloromethane (40 mL) and saturated aqueous sodium chloride solution (5 mL). The layers were separated. The organic layer was dried over sodium sulfate. The dried solution was filtered and the filtrate was concentrated. The residue was purified by preparatory HPLC (Agilent Prep-C18 column, 10 μm, 30×150 mm, UV detection at 270 nm, gradient elution with 40→90% acetonitrile in water, flow rate: 15 mL/min) to provide 20 mg of the product as a yellow-green powder (47%). TLC: (5% methanol-dichloromethane) $R_f$=0.40 (CAM); $^1$H NMR (500 MHz, CDCl$_3$) δ: 7.47 (s, 1H), 5.38 (d, 1H, J=3.6 Hz), 5.35 (app s, 1H), 5.26 ppm (d, 1H, J=4.0 Hz), 4.84 (d, 1H, J=4.0 Hz), 4.78 (dd, 1H, J=12.3, 5.2 Hz), 4.75 (s, 1H), 4.71 (s, 1H), 4.52 (q, 1H, J=6.6 Hz), 3.86 (s, 1H), 3.83 (s, 3H), 3.62 (s, 3H), 3.47 (s, 3H), 3.15 (d, 1H, J=5.3 Hz), 3.05 (d, 1H, J=5.3 Hz), 2.60 (s, 3H), 2.58 (m, 1H), 2.35 (m, 1H), 2.14 (s, 3H), 1.96 (dd, 1H, J=14.6, 4.1 Hz), 1.62 (d, 1H, J=14.6 Hz), 1.26 (s, 1H), 1.23 (d, 3H, J=6.6 Hz), 1.08 (s, 3H), 0.95 (s, 9H), 0.24 (s, 3H), 0.16 (s, 3H); $^{13}$C NMR (125 MHz, CDCl$_3$) δ: 202.8, 170.5, 163.2, 151.8, 144.4, 142.4, 135.2, 126.6, 116.8, 115.2, 115.1, 108.3, 104.0, 100.3, 98.6, 98.3, 74.6, 73.4, 69.8, 69.5, 69.5, 68.9, 69.5, 69.5, 68.9, 68.4, 62.9, 62.7, 57.2, 56.8, 50.7, 38.8, 36.8, 26.0, 25.9, 21.1, 20.6, 18.6, 17.0, −4.2, −5.3; FTIR (neat), cm$^{-1}$: 2953 (w), 2934 (w), 2857 (w), 1749 (w), 1622 (m), 1570 (w), 1447 (w), 1391 (m), 1321 (w), 1294 (w), 1229 (m), 1159 (m), 1121 (s), 1084 (s), 1071 (m), 1020 (m), 995 (s), 943 (s), 868 (m), 837 (m), 779 (m); HRMS (ESI): Calcd for (C$_{40}$H$_{54}$O$_{16}$Si+Na)$^+$ 841.3073. found 841.3064.

Glycosylation of a Cycloaddition Coupling Partner

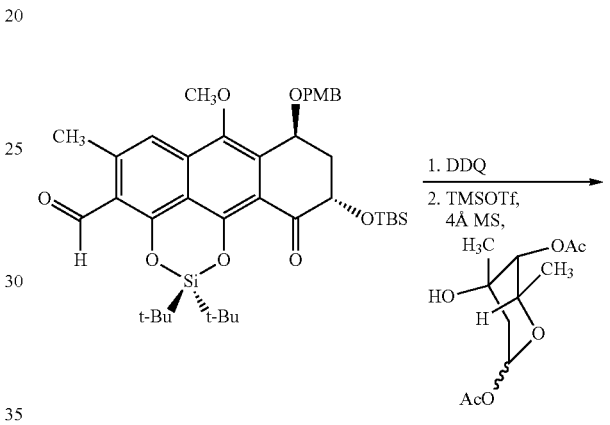

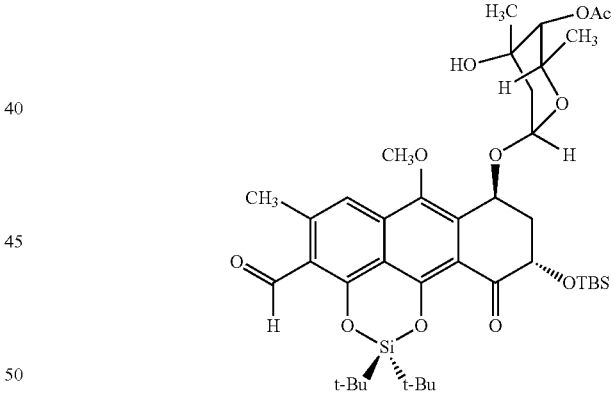

2,3-Dichloro-5,6-dicyanobenzoquinone (14.3 mg, 63 μmol, 1.2 equiv) was added to a vigorously stirring, biphasic solution of differentially protected aldehyde (37 mg, 52 μmol, 1 equiv) in dichloromethane (870 μL) and water (175 μL) at 23° C. The reaction flask was covered with aluminum foil to exclude light. Over the course of 2 h, the reaction mixture was observed to change from myrtle green to lemon yellow. The product solution was partitioned between water (5 mL) and dichloromethane (40 mL). The layers were separated. The organic layer was dried over sodium sulfate. The dried solution was filtered and the filtrate was concentrated. The residue was purified by flash-column chromatography (5% ethyl acetate-hexanes initially, grading to 10% ethyl acetate-hexanes) to provide 28 mg of the product as a yellow powder (91%). TLC: (20% ethyl acetate-hexanes) $R_f$=0.37 (CAM); $^1$H NMR (500 MHz, CDCl$_3$) δ: 10.83 (s, 1H), 7.30 (s, 1H), 5.45 (m, 1H), 4.68 (dd, 1H, J=10.3, 4.2 Hz), 3.97 (s, 3H), 3.31 (brs, 1H), 2.72 (s, 3H), 2.51-2.45 (m, 1H), 2.41-2.37 (m, 1H), 1.15 (s, 9H), 1,13 (s, 9H), 0.88 (s, 9H), 0.15 (s, 3H), 0.11 (s, 3H); $^{13}$C NMR (125 MHz, CDCl$_3$) δ: 194.6, 191, 160.5, 150.2, 146, 140.8, 135.8, 134, 119.6, 116.2, 115.4, 114.7, 72.7, 63.7, 62.4, 38.8, 29.9, 62.4, 38.8, 63.7, 62.4, 38.8, 63.7, 62.4, 38.8, 29.9, 26.2, 26.1, 26, 22.7, 21.4; FTIR (neat), cm$^{-1}$: 3470 (br, w), 2934 (w), 2888 (w), 1684 (s), 1607 (s), 1560 (w), 1472 (m), 1445 (w), 1392 (m), 1373 (s), 1242 (s), 1153 (s), 1119 (w), 1074 (m), 1044 (s), 1013 (s), 982 (w), 934 (m), 907 (w), 870 (m), 827 (s), 795 (s), 779 (s), 733 (s), 664 (s); HRMS (ESI): Calcd for $(C_{31}H_{46}O_7Si_2+H)^+$ 587.2855. found 587.2867.

Trimethylsilyl triflate (10% in dichloromethane, 25.9 μL, 14 μmol, 0.3 equiv) was added to a suspension of deprotected aldehyde (28 mg, 48 μmol, 1 equiv), 1-O-acetyltrioxacarcinose A (12.9 mg, 52 μmol, 1.1 equiv), and powdered 4-Å molecular sieves (~50 mg) in dichloromethane (1.0 mL) at −78° C. After 5 min, the mixture was diluted with dichloromethane containing 10% triethylamine and 10% methanol (3 mL). The reaction flask was allowed to warm to 23° C. The mixture was filtered and partitioned between dichloromethane (40 mL) and saturated aqueous sodium chloride solution (5 mL). The layers were separated. The organic layer was dried over sodium sulfate. The dried solution was filtered and the filtrate was concentrated. The residue was purified by preparatory HPLC (Agilent Prep-C18 column, 10 μm, 30×150 mm, UV detection at 270 nm, gradient elution with 80→98% acetonitrile in water, flow rate: 15 mL/min) to provide 15 mg of the product as a yellow powder (41%). TLC: (20% ethyl acetate-hexanes) $R_f$=0.29 (CAM); $^1$H NMR (500 MHz, CDCl$_3$) δ: 10.83 (s, 1H), 7.32 (s, 1H), 5.43 (d, 1H, J=3.9 Hz), 5.32 (m, 1H), 4.74 (s, 1H), 4.67 (dd, 1H, J=12.3, 5.0 Hz), 4.54 (q, 1H, J=6.6 Hz), 3.91 (s, 1H), 3.88 (s, 3H), 2.72 (s, 3H), 2.59 (ddd, 1H, J=13.8, 5.0, 3.2 Hz), 2.34 (m, 1H), 2.14 (s, 3H), 1.97 (dd, 1H, J=14.2, 4.2 Hz), 1.71 (d, 1H, J=14.6 Hz), 1.22 (d, 3H, J=6.3 Hz), 1.15 (s, 9H), 1.15 (s, 9H), 1.08 (s, 3H), 0.93 (s, 9H), 0.23 (s, 3H), 0.13 (s, 3H); $^{13}$C NMR (125 MHz, CDCl$_3$) δ: 193.9, 191.0, 170.5, 146.4, 140.9, 134.0, 132.4, 119.8, 116.8, 115.8, 115.0, 110.8, 99.6, 74.6, 71.5, 70.4, 68.9, 62.9, 62.7, 39.1, 36.9, 26.2, 26.1, 26.1, 25.9, 24.1, 22.7, 21.5, 21.3, 21.1, 18.7, 16.9, −4.1, −5.3; FTIR (neat), cm$^{-1}$: 3524 (br, w), 2934 (m), 2861 (m), 1749 (m), 1686 (s), 1607 (s), 1560 (m), 1474 (m), 1447 (m), 1424 (w), 1375 (s), 1233 (s), 1159 (s), 1117 (m), 1080 (m), 1049 (s), 1015 (s), 997 (s), 937 (m), 883 (m), 872 (m), 827 (s), 797 (m), 781 (m), 737 (w), 677 (w), 667 (m); HRMS (ESI): Calcd for $(C_{40}H_{60}O_{11}Si_2+H)^+$ 773.3747. found 773.3741.

General Glycosylation Procedure of the C13 Hydroxyl Group

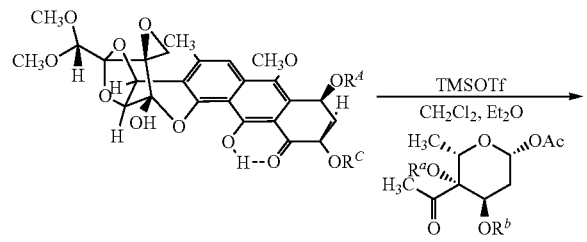

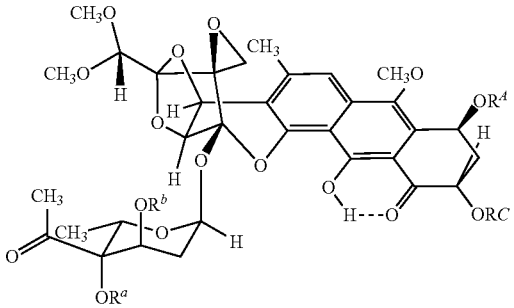

Crushed 4-Å molecular sieves (~570 mg/1 mmol sugar donor) was added to a stirring solution of the sugar acceptor (1 equiv.) and the sugar donor (30.0 equiv.) in dichloromethane (1.6 mL/1 mmol sugar donor) and diethylether (0.228 mL/1 mmol sugar donor) at 23° C. The bright yellow mixture was stirred for 90 min at 23° C. and finally cooled to −78° C. TMSOTf (10.0 equiv.) was added over the course of 10 min at −78° C. After 4 h, a second portion of TMSOTf (5.0 equiv.) was added at −78° C. and stirring was continued for 1 h. The last portion of TMSOTf (5 equiv.) was added. After 1 h, triethylamine (20 equiv.) was added and the reaction the product mixture was filtered through a short column of silica gel deactivated with triethylamine (30% ethyl acetate-hexanes initially, grading to 50% ethyl acetate-hexanes). $^1$H NMR analysis of the residue showed minor sugar donor remainings and that the sugar acceptor had been glycosylated. The residue was purified by preparatory HPLC (Agilent Prep-C18 column, 10 μm, 30×150 mm, UV detection at 270 nm, gradient elution with 40→100% acetonitrile in water, flow rate: 15 mL/min) to provide the glycosylation product as a bright yellow oil Three Specific Compounds Prepared by the General Glycosylation Procedure for the C13 Hydroxyl Group:

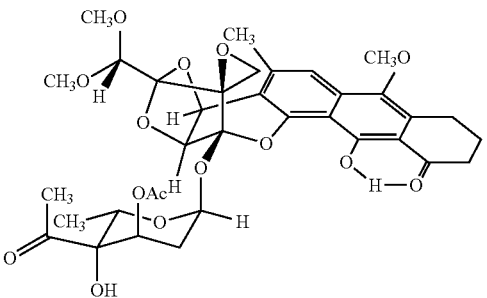

10% yield; TLC: (50% ethyl acetate-hexane) $R_f$=0.58 (UV, CAM); $^1$H NMR (600 MHz, CDCl$_3$) δ: 7.43 (s, 1H), 5.84 (t, J=3.6 Hz, 1H), 5.29 (d, J=4.2 Hz, 1H), 5.19 (d, J=4.2 Hz, 1H), 5.01 (q, J=6.6 Hz, 1H), 4.75 (t, J=3.6 Hz, 1H), 4.73 (s, 1H), 3.88 (s, OH), 3.77 (s, 3H), 3.63 (s, 3H), 3.47 (s, 3H), 3.03 (app q, J=5.4 Hz, 2H), 2.84 (d, J=6.0 Hz, 1H), 2.77 (d, J=6.0 Hz, 1H), 2.72 (t, J=6.6 Hz, 2H), 2.58 (s, 3H), 2.36 (s, 3H), 2.33 (t, J=3.0 Hz, 2H), 2.23 (s, 3H), 2.11-2.06 (m, 2H), 1.08 (d, J=6.0 Hz, 3H).

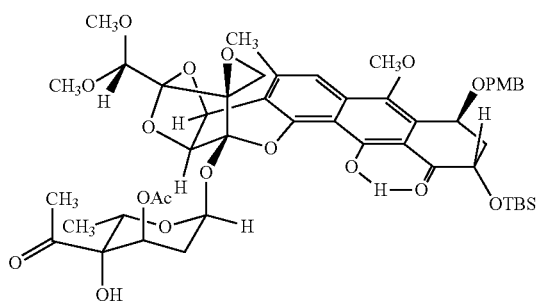

81% yield, TLC: (50% ethyl acetate-hexane) $R_f$=0.30 (UV, CAM); $^1$H NMR (600 MHz, CDCl$_3$) δ: 7.46 (s, 1H), 7.28 (d, J=9 Hz, 2H), 6.87 (d, J=8.4 Hz, 2H), 5.83 (dd, J=3.6, 1.8 Hz, 1H), 5.30 (d, J=4.2 Hz, 1H), 5.19 (d, J=4.2 Hz, 1H), 5.19 (m, 1H), 5.00 (q, J=6.0 Hz, 1H), 4.96 (dd, J=12.0, 4.8 Hz, 1H), 4.75 (t, J=3.6 Hz, 1H), 4.74 (s, 1H), 4.70 (d, J=10.8 Hz, 1H), 4.59 (d, J=10.8 Hz, 1H), 3.86 (s, OH), 3.83 (s, 3H), 3.80 (s, 3H), 3.63 (s, 3H), 3.47 (s, 3H), 2.81 (d, J=6.0 Hz, 1H), 2.73-2.68 (m, 1H), 2.70 (d, J=6.0 Hz, 1H), 2.59 (s, 3H), 2.35 (s, 3H), 2.33-2.28 (m, 2H), 2.22 (s, 3H), 2.19-2.13 (m, 1H), 1.08 (d, J=6.0 Hz, 3H), 0.97 (s, 9H), 0.25 (s, 3H), 0.17 (s, 3H); HRMS (ESI): Calcd for $(C_{49}H_{62}O_{18}Si+H)^+$ 967.3778. found 967.3795; HRMS (ESI): Calcd for $(C_{49}H_{62}O_{18}Si+Na)^+$ 989.3598. found 989.3585.

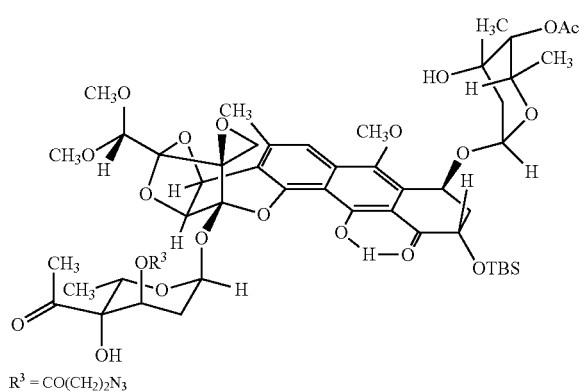

$R^3$ = CO(CH$_2$)$_2$N$_3$

Compound Detected by ESI Mass Spectrometry: Calculated Mass for $[C_{52}H_{71}N_3O_{21}Si-H]^{-1}$=1100.4277, Measured Mass=1100.4253.

Measurement of IC$_{50}$ Values

Cell Culture. H460 cells and HeLa S3 cells were purchased from American Type Culture Collection (ATCC). H460 cells were maintained in RPMI-1640 medium supplemented with 10% fetal bovine serum (FBS). HeLa S3 cells were maintained in Dulbecco's Modified Eagle's Medium supplemented with 10% fetal bovine serum (FBS).

Cell Proliferation Assay.

A solution of H460 or HeLa S3 cells (3000 cells/well) in growth medium was seeded onto a 96-well plate. The 96-well plate was incubated for 24 h at 37° C. Stock solutions of each compound were serially diluted and administrated to cells to achieve final concentrations of 38 nM to 83 µM (DC-45-A2 and iso-DC-45-A2) or 3.4 nM to 7.5 µM (dideoxy-DC-45-A2). After incubating at 37° C. for 72 h, 20 µL of MTS/PMS solution (Promega CellTiter 96® Aqueous Non-Radioactive Cell Proliferation Assay) was added to each well. After incubating at 37° C. for 3.5 h, the absorbance at 490 nm was recorded using a microplate reader (SpectraMax PLUS384) as a measure of viable cells. Percent growth inhibition was calculated for each well based upon the following formula: percent growth inhibition=100×(C−T)/C, where T is the absorbance of the well containing the test compound minus the average absorbance of wells containing media alone, and C is the average absorbance of wells containing vehicle control-treated cells minus the average absorbance of wells containing media alone. The average percent inhibition at each concentration was plotted against log (concentration) and the IC$_{50}$ values were computed.

DNA Alkylation Studies

DNA-Gel and LC/MS Experiments Demonstrating that DC-45-A2 and Dideoxy-DC-45-A2 Form a Covalent Complex with the DNA Oligonucleotide d(AATTACGTAATT). DC-45-A2, dideoxy-DC-45-A2, and iso-DC-45-A2 fluoresce with a blue-green wavelength under long-wave (365 nm) ultraviolet light, which was evident from irradiation of the compounds using a hand-held two-wavelength UV lamp. The absorption and emission spectra ($\lambda_{max}/\lambda_{em}$) of DC-45-A2, dideoxy-DC-45-A2, and iso-DC-45-A2 were measured in alkylation buffer to be 405/500 nm, 407/490 nm, and 405/505 nm, respectively (the buffer used in this experiment and in all subsequent alkylation experiments was comprised of pH 7 phosphate buffer (1 mM) and sodium chloride (100 mM)).

We compared the reactivity of DC-45-A2, dideoxy-DC-45-A2, and iso-DC-45-A2 toward the self-complementary DNA 12-mer d(AATTACGTAATT). This oligonucleotide had previously been shown to react with trioxacarcin A, which underwent an epoxide-opening reaction with the N7 atom of the central guanine residue to form a covalent complex (A. Fitzner, H. Frauendorf, H. Laatsch, U. Diederichsen, Anal. Bioanal. Chem. 390, 1139 (2008)). However, previous to this work there have been no reported studies on the reactivity of non-glycosylated trioxacarcins towards duplex DNA.

Two independent techniques were used to evaluate the reactivity of the synthesized trioxacarcins towards d(AATTACGTAATT). The first technique involved detecting alkylated DNA oligonucleotides by in-gel fluorescence with non-denaturing DNA-gel electrophoresis. The second technique involved detecting alkylated DNA oligonucleotides using a liquid chromatography-mass spectrometry method.

Identification of DNA-Trioxacarcin Adducts by DNA Gel Electrophoresis.

Figure 10:
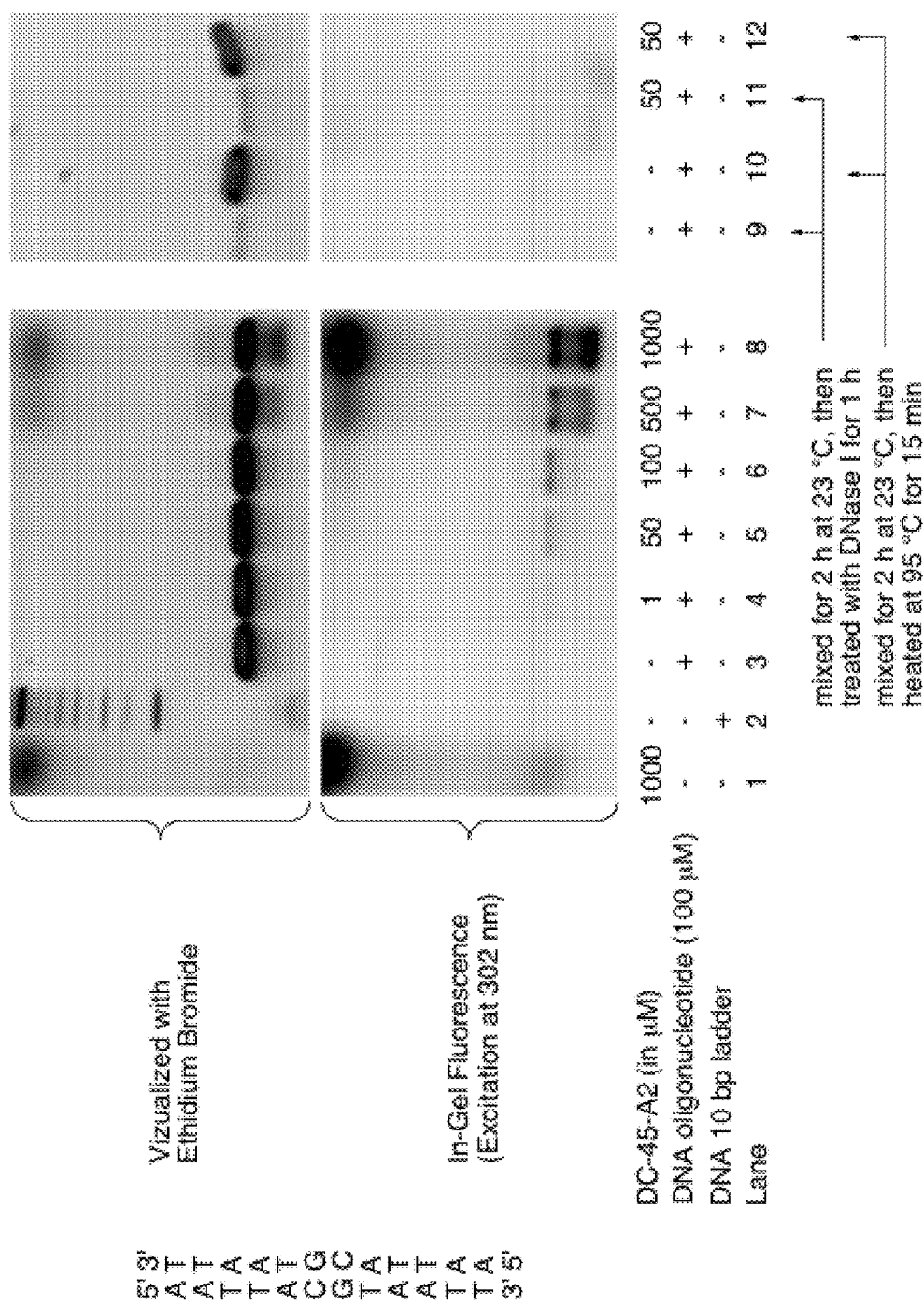
FIG. 10. Formation of a DC-45-A2-Duplex DNA Covalent Complex, as Detected by DNA-Gel Electrophoresis.

We began the DNA-alkylation studies by evaluating the activity of DC-45-A2 towards the self-complementary 12-mer d(AATTACGTAATT) in pH 7 phosphate buffer at different concentrations (FIG. 10). The concentration of the oligonucleotide was held constant at 100 µM while DC-45-A2 was used at five different concentrations ranging from 1 µM to 1000 µM (lanes 4-8) in five separate reactions. At the highest concentrations of DC-45-A2 (500 µM and 1000 µM), a second and distinct fluorescent complex was observed by in-gel fluorescence. This signal might be attributed to alkylation at multiple sites on the oligonucleotide (i.e. at the N$_7$ positions of both guanine residues in the duplex); this was observed to be the case when duplex oligonucleotides containing more than one guanine residue were treated with an excess of trioxacarcin A, see, e.g., A. Fitzner, H. Frauendorf, H. Laatsch, U. Diederichsen, Anal. Bioanal. Chem. 390, 1139 (2008). After incubation for 3 h at 23° C., aliquots of the reactions mixtures were loaded onto a 20% crosslinked polyacrylamide gel. After electrolution, the gels were visualized using an alpha imager, first by irradiating the gel at 302 nm to image fluorescent species in the gel (in-gel fluorescence) and then by treating the gel with ethidium bromide and again irradiating at 302 nm to image fluorescent species in the treated gel. The fluorescence quantum efficiency of an ethidium bromide molecule increases 20- to 25-fold upon intercalation into duplex DNA: J.-B. Le Pecq, C. Paoletti, *Anal. Biochem.* 17, 100 (1966). The fluorescent DC-45-A2-DNA complex was clearly observed (prior to ethidium bromide staining) even at the lowest concentration of DC-45-A2 (1 mM). When the reaction mixture used in lane 5 (50 μM in DC-45-A2) was treated with DNase I for 1 h, the fluorescent species was destroyed (lane 11), indicating that the fluorescent species contained DNA. We also found that the fluorescent complex could be destroyed by heating the reaction mixture at 95° C. for 15 min (lane 12).

Figure 11:
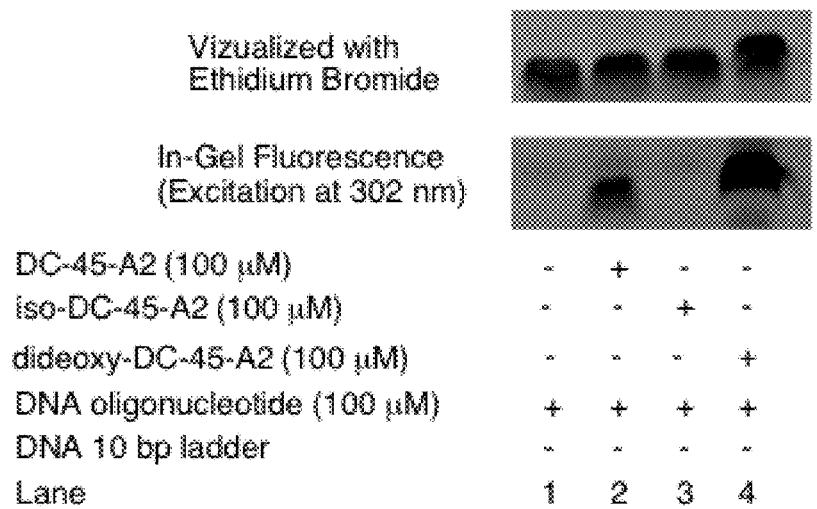
FIG. 11 depicts the comparison of the reactivity of DC-45-12, iso-DC-45-A2, and dideoxy-DC-45-A2 towards a self-complementary duplex DNA oligonucleotide (12-mer d(AATTACGTAATT)); TBE 20% polyacrylamide gel visualized with ethidium bromide and by in-gel fluorescence.

Next, we compared the reactivity of DC-45-A2 to both iso-DC-45-A2 and dideoxy-DC-45-A2 towards the same oligonucleotide in three separate alkylation experiments (FIG. 11). At compound and DNA concentrations of 100 μM, DC-45-A2, and dideoxy-DC-45-A2 fluorescent complexes with the oligonunucleotide were clearly detected after a two-hour reaction time at 23° C., while an iso-DC-45-A2 complex was not. We note that the dideoxy-DC-45-A2 complex displayed a more intense signal, possibly indicative of a greater reactivity of the structurally simpler compound.

Figure 12:
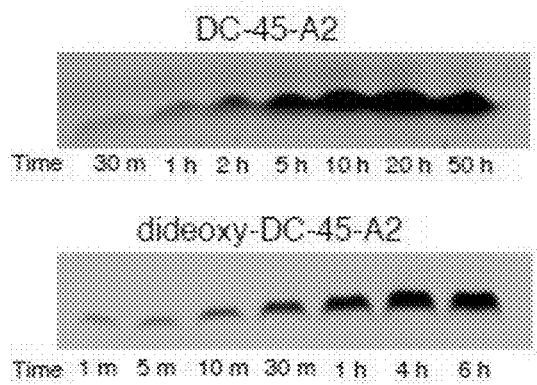
FIG. 12 depicts images of TBE gels of the products of the reaction of the self-complementary duplex 12-mer d(AATTACGTAATT) (100 μM) with DC-45-A2 or dideoxy-DC-45-A2 (25 μM) at 23° C. for the indicated times; visualized by in-gel fluorescence.

Having noted the apparent differential reactivity between DC-45-A2 and dideoxy-DC-45-A2, we performed an experiment to visualize the formation of the fluorescent complex at different reaction times (FIG. 12). The reaction of the oligonucleotide with DC-45-A2 reached an approximate maximum of fluorescence intensity between 5 and 10 h, while the reaction of the oligonucleotide with dideoxy-DC-45-A2 reached a maximum fluorescence intensity between 1 and 4 h.

Identification of DNA-Trioxacarcin Adducts by LC/MS

Next, we performed a set of experiments to determine whether the DC-45-A2 and dideoxy-DC-45-A2 complexes observed by DNA-gel electrophoresis were covalent or not. A liquid chromatography-mass spectrometry (LC/MS) method was developed for the detection of DNA oligonucleotides and covalent DNA-small molecule complexes. The mass spectrometer was used in a negative ion mode under conditions that had been optimized for the detection of single-stranded nucleic acids.

Figure 13:
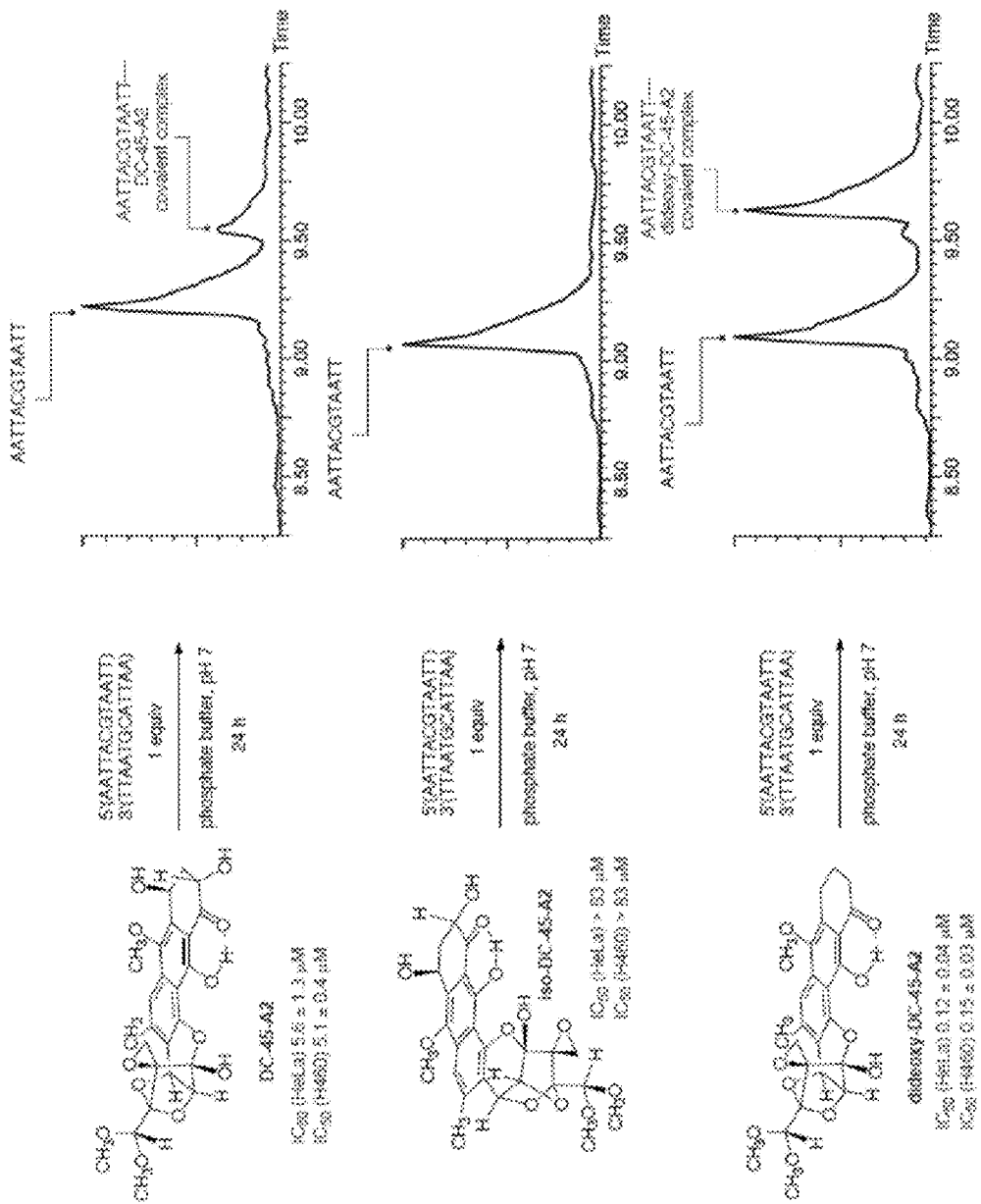
FIG. 13 provides IC$_{50}$ values for DC-45-A2, iso-DC-45-A2, and dideoxy-DC-45-A2 measured in HeLa (cervical cancer) and H460 (lung cancer) cells lines, and depicts LC/MS chromatograms of reaction mixtures of the self-complementary duplex 12-mer d(AATTACGTAATT) (100 μM) and i) DC-45-A2 (100 μM), ii) Iso-DC-45-A2 (100 μM), and iii) Dideoxy-DC-45-A2 (100 μM) after 24 h at 23° C.

To solutions of the oligonucleotide d(AATTACGTAATT) (100 μM) in pH 7 buffer were added, in three separate reaction vials, 1 equiv of DC-45-A2, 1 equiv of iso-DC-45-A2, or 1 equiv of dideoxy-DC-45-A2. After incubation for 24 h at 23° C., it was evident from the LC/MS chromatogram that a covalent DNA-small molecule complex had formed in both the DC-45-A2 and dideoxy-DC-45-A2 reaction mixtures but not in the iso-DC-45-A2 reaction mixture (FIG. 13). The alkylated single-stranded oligonucleotide eluted as a signal that was separate from the non-alkylated oligonucleotide. The apparently greater relative abundance of the dideoxy-DC-45-A2 complex compared to the abundance of the DC-45-A2 complex supports the hypothesized greater reactivity of dideoxy-DC-45-A2, as noted in the section above. The absence of an iso-DC-45-A2 complex is consistent with the absence of reactivity of this compound towards the oligonucleotide under the alkylation conditions in the DNA-gel experiment described in the section above. The $IC_{50}$ values of the three compounds in antiproliferative assays are also depicted in FIG. 13.

Figure 14:
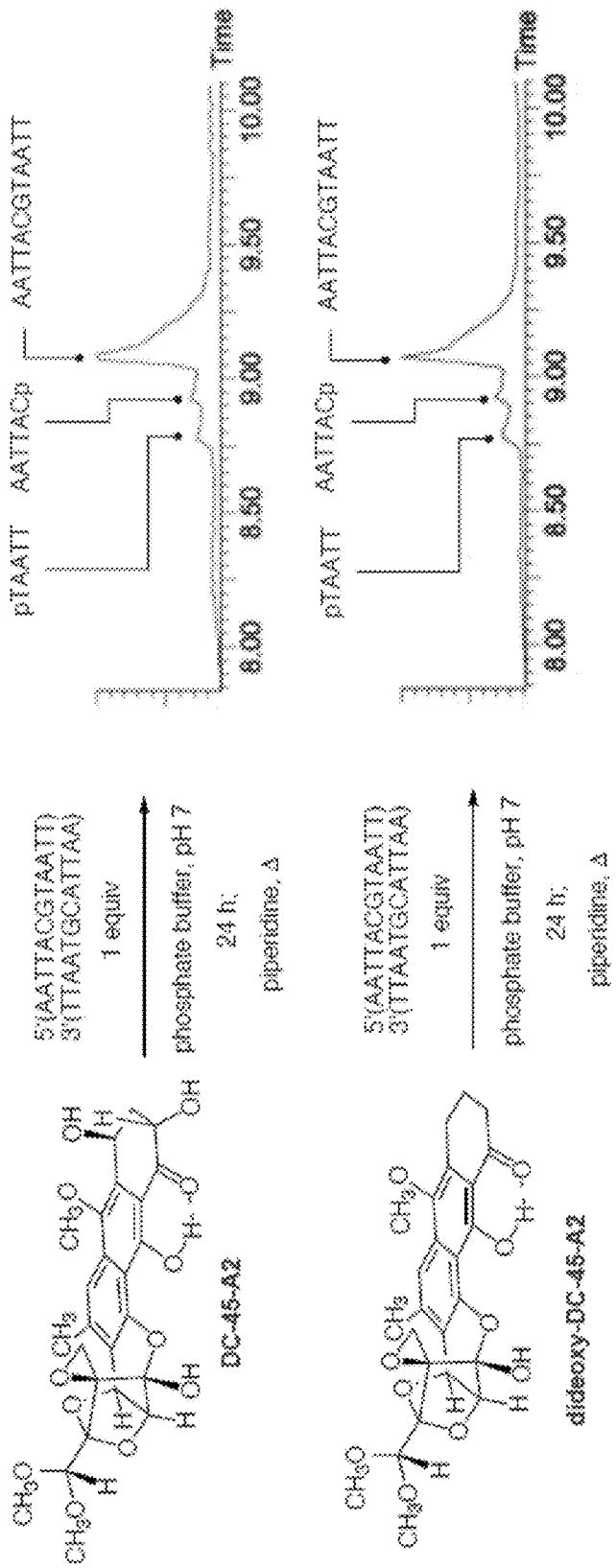
FIG. 14 depicts LC/MS chromatogram of reaction mixtures of the self-complementary duplex 12-mer d(AATTACGTAATT) with DC-45-A2 or Dideoxy-DC-45-A2 after 24 h at 23° C., followed by treatment with piperidine and heating for 30 min at 95° C.; pTAATT (SEQ ID NO 2); AATTACp (SEQ ID NO 3).

To test whether or not alkylation by DC-45-A2 and dideoxy-DC-45-A2 occurs at the N7 guanine site via the same epoxide opening mechanism observed for trioxacarcin A, we treated samples of alkylated oligonucleotide with piperidine to provide a product solution with a final concentration of 1.0 M in piperidine. Heating the resulting solutions for 30 minutes at 95° C. led to the disappearance of the LC/MS peak corresponding to the alkylated strand with concomitant formation of two additional products, corresponding to the masses of pTAATT and AATTACp (FIG. 14). This fragmentation is consistent with induced single strand cleavage of the type observed in the Maxam-Gilbert G-specific reaction that is associated with N7 guanine alkylation. In the present case, the guanine residue has been excised and the phosphates at the 3' and 5' positions have been eliminated to give the two fragment strands.

Strand cleavage to form the fragments pTAATT and AATTACp from the G-alkylated oligonucleotide upon treatment with piperidine and heating is consistent with the Maxam-Gilbert G-specific reaction. While the two fragments are less abundant than would be expected from quantitative alkylation and quantitative strand cleavage, the presence of the two fragments is suggestive of alkylation of guanine at the $N_7$ position (A. M. Maxam, W. Gilbert, *Proc. Natl. Acad. Sci* 74, 560 (1977); W. B. Mattes, J. A. Hartley, K. W. Kohn, *Biochim. Biophys. Acta* 686, 71 (1986)).

Experiments have been presented demonstrating that the non-glycosylated trioxacarcins DC-45-A2 and dideoxy-DC-45-A2 form covalent adducts with duplex DNA. The fluorescent DNA-small molecule adducts may be visualized by in-gel fluorescence or detected by LC/MS. The covalent adducts are thermally unstable; heat treatment destroys the fluorescent complex. Furthermore, treatment with piperidine and heat yields oligonucleotide fragments that are consistent with DNA alkylation and strand cleavage at a guanine residue.

Experimental Details for DNA-Gel and LC/MS Experiments

Preparation of Solutions.

Preparation of Alkylation Buffer (10 mM potassium phosphate buffer [pH 7.0], 100 mM sodium chloride): A stock solution of alkylation buffer was prepared by combining 1.0 M aqueous dipotassium hydrogen phosphate solution (61.5 μL), 1.0 M aqueous potassium dihydrogen phosphate solution (38.5 μL), and 5.0 M aqueous sodium chloride solution (200 μL) then adjusting the total volume to 10 mL with water.

Preparation of DNA Loading Buffer (50 mM Tris buffer [pH 8.0], 25% glycerol, 5 mM EDTA, 0.025% bromophenol blue, 0.025% xylene cyanol FF): A stock solution of 50 mM, pH 8.0 Tris buffer was prepared by combining 0.1 M aqueous tris(hydroxymethyl)aminomethane solution (50 mL) and 0.1 M aqueous hydrochloric acid solution (29.2 mL) then adjusting the total volume to 100 mL with water. A stock solution of DNA loading buffer was prepared by combining glycerol (2.5 mL), ethylenediaminetetraacetic acid (15 mg), bromophenol blue (2.5 mg), and xylene cyanol FF (2.5 mg) then adjusting the total volume to 10 mL with the previously prepared 50 mM, pH 8.0 Tris buffer.

Detection of a DC-45-A2-Alkylated DNA Oligonucleotide.

General Method: To a solution of dsDNA [ds(AATTACGTAATT), 1.07 mM] in alkylation buffer (86.7 μL, see above for preparation of solutions) in a 1.7-mL centrifuge tube was added a solution of DC-45-A2 in DMSO (2.00 μL, 5 mM). The sample was votexed, then rotated end-over-end at 23° C. for 2 h. The sample was stored at 4° C. for 16 h. The sample was diluted to a concentration of 5 μM of dsDNA. A 10 μL sample of the diluted solution was injected into a short oligonucleotide column (gradient elution with 6 nM TEAB buffer and methanol, flow rate 150 μL/min) and the column output was monitored by mass spectrometry in a negative ionization mode. The doubly deionized DC-45-A2-alkylated single-stranded DNA oligonucleotide (mass/charge=2079.4) was detected at 9.32 min.

Figure 7:
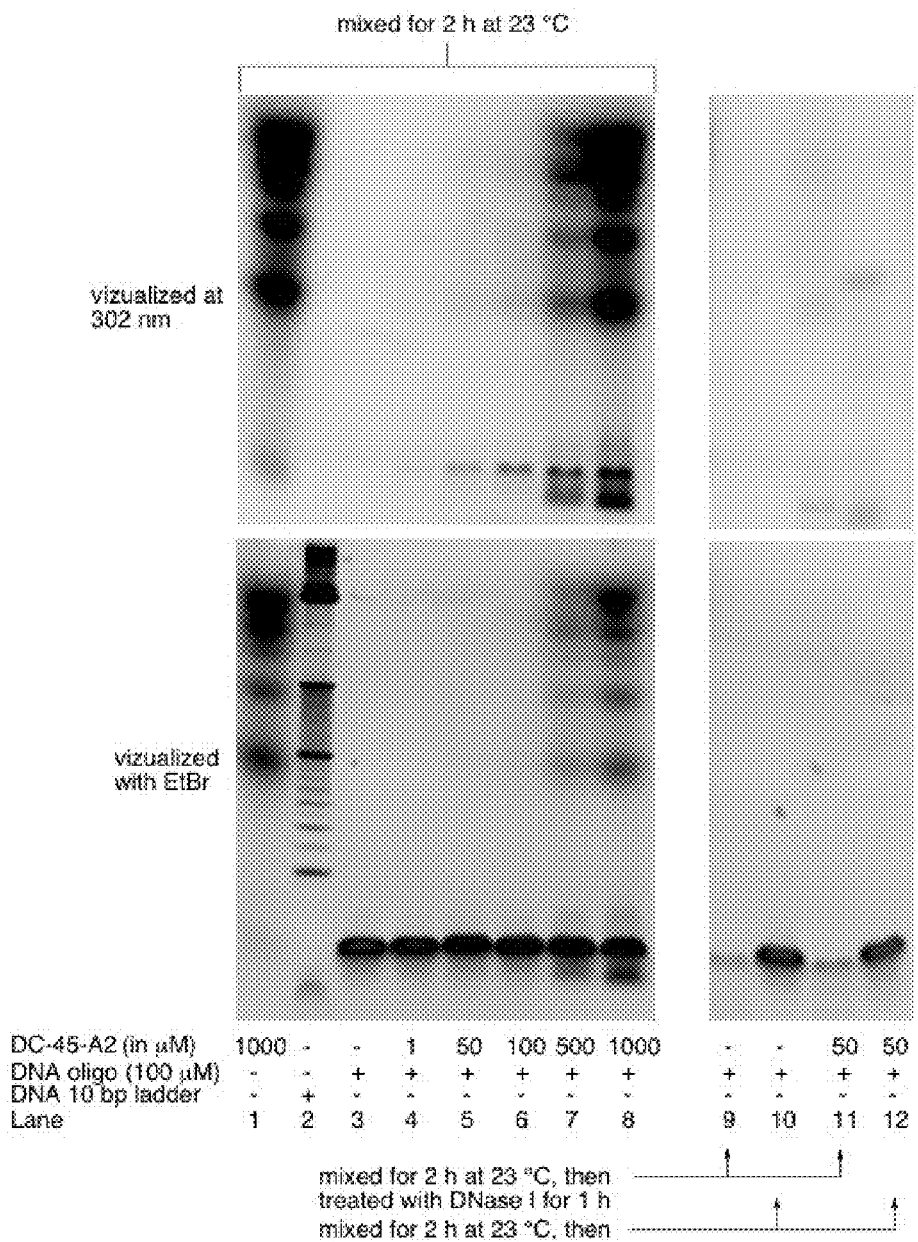
FIG. 7 shows alkylation of the DNA oligonucleotide ds(AATTACGTAATT) (SEQ ID NO 1) with DC-45-A$_2$.
Figure 8:
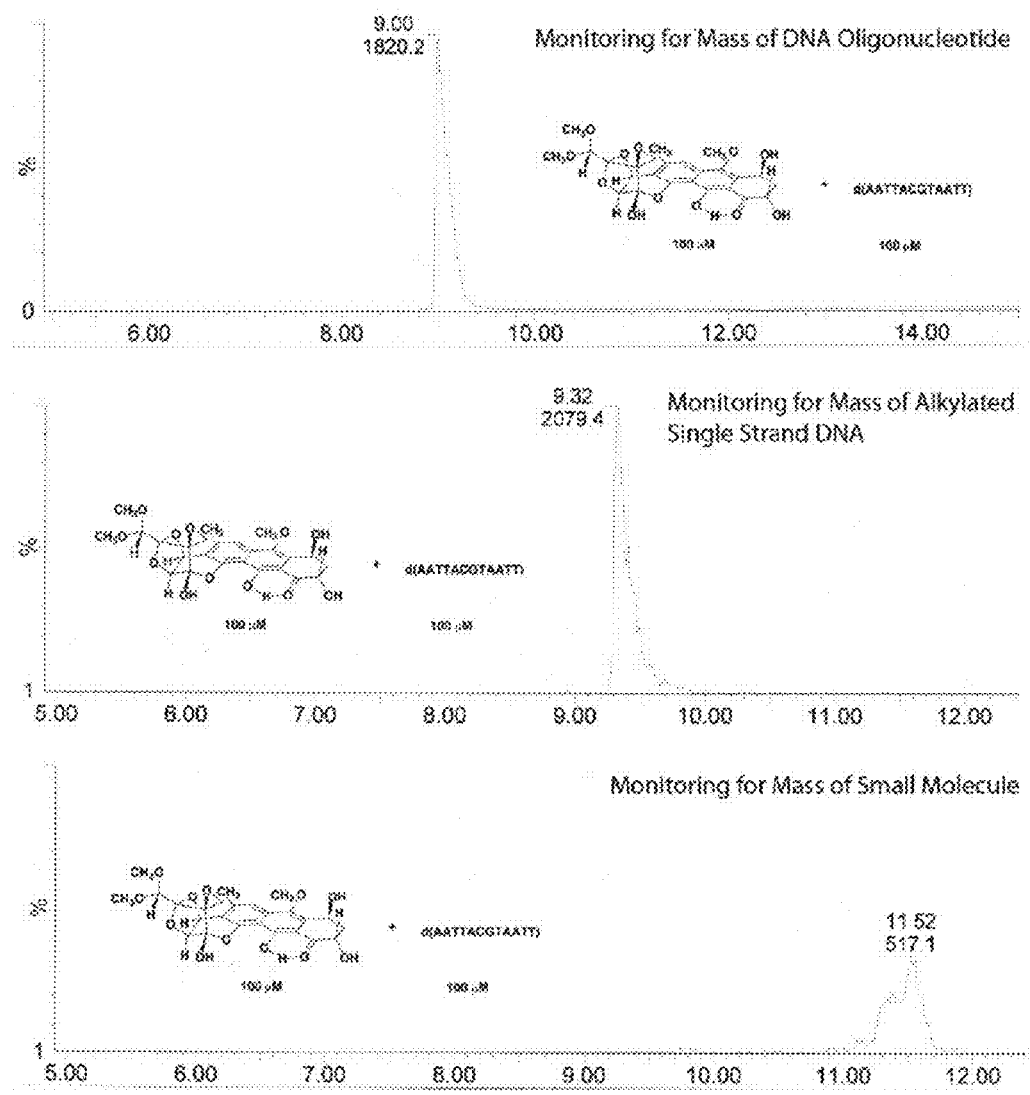
FIG. 8 shows an LC/MS analysis of a reaction mixture of the DNA oligonucleotide ds(AATTACGTAATT) and DC-45-A$_2$.
Figure 9:
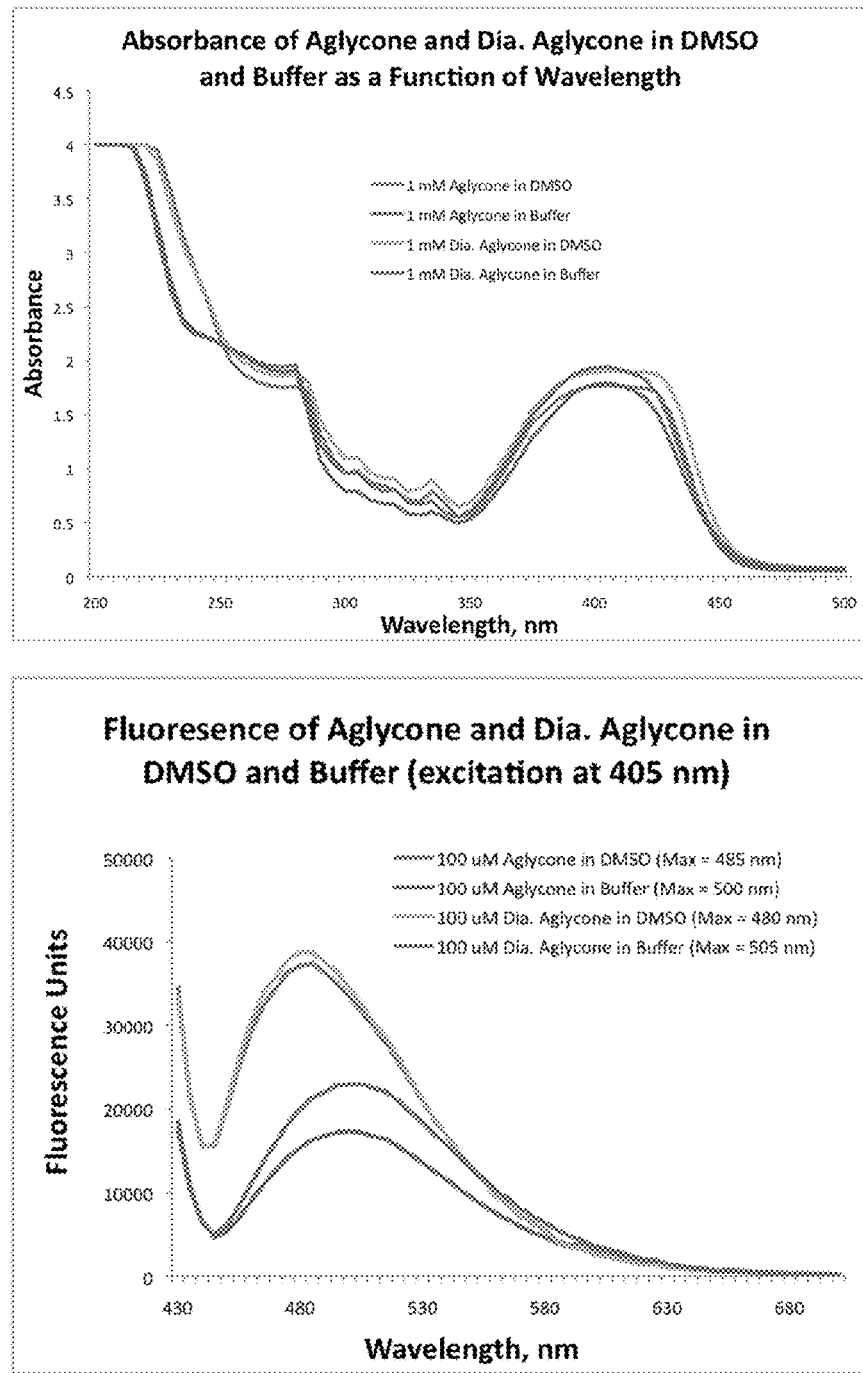
FIG. 9 depicts the fluorescence and absorbance spectra of DC-45-A$_2$ and iso-DC-45-A$_2$.

FIG. 7 Experiment:

To solutions of dsDNA [ds(AATTACGTAATT), lanes 3-8: 9.34 μL, 1.07 mM] in alkylation buffer (86.7 μL, see above for preparation of solutions) in 1.7 mL centrifuge tubes were added the indicated solutions of DC-45-A2 in DMSO (lane 1: 4.00 μL, 25 mM; lane 4: 0.20 μL, 4 mM; lane 5: 1.00 μL, 5 mM; lane 6: 2.00 μL, 5 mM; lane 7: 2.00 μL, 25 mM; lane 8: 4.00 μL, 25 mM) and DMSO (lane 3: 4.00 μL; lane 4: 3.80 μL; lane 5: 3.00 μL; lane 6: 2.00 μL; lane 7: 2.00 μL). The samples were votexed, then rotated end-over-end at 23° C. for 2 h. A 10-μL aliquot was removed from each centrifuge tube and diluted with 5× loading buffer (2.50 μL, see above for preparation of solutions). A tris-borate EDTA mini gel (20%, 12 well) was loaded with samples (10 μL). Lane 2 was loaded with 10 μL of a solution containing 2.00 μL 10 bp DNA Ladder (Invitrogen, Cat. No. 10821-015), 8.00 μL of alkylation buffer, and 2.50 μL of loading buffer. 20.0 μL aliquots were removed from centrifuge tubes corresponding to lanes 3 and 5 and transferred to fresh 1.7 mL centrifuge tubes. The new reactions were independently heated at 95° C. for 15 min. After centrifugation-promoted cooling, the reactions were diluted with 5× loading buffer (5.00 μL). Lanes 10 and 12 were loaded with the samples (10.0 μL, corresponding to samples associated with lanes 3 and 5, respectively). A second pair of 18.0 μL aliquots were removed from centrifuge tubes corresponding to lanes 3 and 5 and transferred to fresh 1.7 mL centrifuge tubes. To each tube was added DNase I (2.00 μL, Invitrogen) and the samples were rotated end-over-end at 23° C. for 1 h. The digestion was stopped by the addition of 5× loading buffer (5 μL). Lanes 9 and 11 were loaded with the samples (10.0 μL, corresponding to samples associated with lanes 3 and 5, respectively). The samples were electroluted (165 V, 2 h, 23° C.) and visualized by in-gel fluorescence scanning (302 nm) and by staining with ethidium bromide to provide the images in FIG. 7.

Detection of DNA-DC-45-A2 at Different Concentrations of DC-45-A2 Using In-Gel Fluorescence.

Seven vials (designated vials 1 and vials 3-8) were loaded with alkylation buffer (86.7 μL, see above for preparation). A solution of duplex oligonucleotide d(AATTACGTAATT) (1.07 mM [concentration of the DNA duplex] in alkylation buffer [see above for preparation], 9.34 μL, 10 nmol, 1 equiv) was added to vials 3-8. Dimethylsulfoxide was added in the following amounts to vials 3-7 (vial 3, 4.00 μL; vial 4, 3.80 μL; vial 5, 3.00 μL; vials 6-7, 2.00 μL). Solutions of DC-45-A2 in dimethylsulfoxide was added to vial 1 and vials 4-8 at the following concentrations and amounts (vial 1, 25 mM solution of DC-45-A2, 4.00 μL; vial 4, 5 mM solution of DC-45-A2, 0.20 μL; vial 5, 5 mM solution of DC-45-A2, 1.00 μL; vial 6, 5 mM solution of D-45-A2, 2.00 μL; vial 7, 25 mM solution of DC-45-A2, 2.00 μL; vial 8, 25 mM solution of DC-45-A2, 4.00 μL). The samples were vortexed, then rotated end-over-end at 23° C. After 2 h, four vials (designated vials 9-12) were prepared containing the following (vial 9, an aliquot of the solution from vial 3 [18.0 μL], DNase I enzyme solution [2.00 μL, Invitrogen 18047-019]; vial 10, an aliquot of the solution from vial 3 [20.0 μL]; vial 11, an aliquot of the solution from vial 5 [18.0 μL], DNase I enzyme [2.00 μL, Invitrogen 18047-019]; vial 12, an aliquot of the solution from vial 5 [20.0 μL]. Vials 9 and 11 were rotated end-over-end at 23° C. for 1 h. Vials 10 and 12 were heated at 95° C. for 15 min. To a final vial (designated vial 2) was added a 10-bp DNA ladder (4 μL, Invitrogen 10821-015) and alkylation buffer (16.0 μL). Vials 2 and 9-12 were diluted with loading buffer (5.00 μL, see above for preparation). A 20-μL aliquot was removed from vials 1 and 3-8. Each aliquot was diluted with loading buffer (5.00 μL, see above for preparation). The resulting solutions were vortexed, and 10-μL samples from each of the four vortexed solutions were loaded onto a non-denaturing, polyacrylamide tris-borate EDTA mini gel (20% crosslinked, 12-well) in lanes 1-12. The samples were electroluted (165 V, 2 h, 23° C.) and visualized by in-gel fluorescence scanning (excitation at 302 nm) and with ethidium bromide to provide the images presented in FIG. 10.

Detection of DNA-DC-45-A2 and DNA-Dideoxy-DC-45-A2 Complexes Using In-Gel Fluorescence.

To four solutions (designated as vials 1-4) of duplex DNA oligonucleotide d(AATTACGTAATT) (0.72 mM [concentration of the DNA duplex] in alkylation buffer [see above for preparation], 13.9 μL, 10 nmol, 1 equiv) in alkylation buffer (84.1 μL) were added, respectively, dimethylsulfoxide (2.0 μL, vial 1), DC-45-A2 (5.0 mM solution in dimethylsulfoxide, 2.0 μL, 10 nmol, 1.0 equiv, vial 2), iso-DC-45-A2 (5.0 mM solution in dimethylsulfoxide, 2.0 μL, 10 nmol, 1.0 equiv, vial 3), and dideoxy-DC-45-A2 (5.0 mM solution in dimethylsulfoxide, 2.0 μL, 10 nmol, 1.0 equiv, vial 4). The samples were vortexed, then rotated end-over-end at 23° C. for 2 h. A 10-μL aliquot was removed from each reaction mixture. Each aliquot was diluted with loading buffer (2.50 μL, see above for preparation). The resulting solutions were vortexed, and 10-μL samples from each of the four vortexed solutions were loaded onto a non-denaturing, polyacrylamide tris-borate EDTA mini gel (20% crosslinked, 12-well) in lanes 1-4. The samples were electroluted (165 V, 2 h, 23° C.) and visualized by in-gel fluorescence scanning (excitation at 302 nm) and with ethidium bromide to provide the images presented in FIG. 11.

Time-Course Study of the Reaction Between a Self-Complementary DNA 12-Mer with DC-45-A2.

To seven solutions of duplex DNA oligonucleotide d(AATTACGTAATT) (0.72 mM [concentration of the DNA duplex] in alkylation buffer [see above for preparation], 13.9 μL, 10 nmol, 1 equiv) in alkylation buffer (85.6 μL) was added DC-45-A2 (4, 5 mM solution in dimethylsulfoxide, 0.50 μL, 2.5 nmol, 0.25 equiv) at times 0, 30 h, 40 h, 45 h, 48 h, 49 h, and 49 h 30 min. The samples were vortexed, then rotated end-over-end at 23° C. At time 50 h, a 10-μL aliquot was removed from each reaction mixture. Each aliquot was diluted with loading buffer (2.50 μL, see above for preparation). The resulting solutions were vortexed, and a 10-μL sample from each of the seven vortexed solutions was loaded onto a non-denaturing, polyacrylamide tris-borate EDTA mini gel (20% crosslinked, 12-well). The samples were electroluted (165 V, 2 h, 23° C.) and visualized by in-gel fluorescence scanning (excitation at 302 nm) to provide the image presented in FIG. 12.

Time-Course Study of the Reaction of a Self-Complementary DNA 12-Mer with Dideoxy-DC-45-A2.

To seven solutions of duplex DNA oligonucleotide d(AATTACGTAATT) (0.72 mM [concentration of the DNA duplex] in alkylation buffer [see above for preparation], 13.9 μL, 10 nmol, 1 equiv) in alkylation buffer (85.6 μL) was added dideoxy-DC-45-A2 (5 mM solution in dimethylsulfoxide, 0.50 μL, 2.5 nmol, 0.25 equiv) at times 0, 2 h, 5 h, 5 h 30 min, 5 h 50 min h, 5 h 55 min, and 5 h 59 min. The samples were vortexed, then rotated end-over-end at 23° C. At time 6 h, a 10-μL aliquot was removed from each reaction mixture. Each aliquot was diluted with loading buffer (2.50 µL, see above for preparation). The resulting solutions were vortexed, and a 10-µL sample from each of the seven vortexed solutions was loaded onto a non-denaturing, polyacrylamide tris-borate EDTA acid mini gel (20% cross-linked, 12-well). The samples were electroluted (165 V, 2 h, 23° C.) and visualized by in-gel fluorescence scanning (excitation at 302 nm) to provide the image presented in FIG. 12.

Liquid Chromatography/Mass Spectrometric Analysis of Oligonucleotide-Alkylation Reaction Mixtures.

To five separate solutions (designated as vials 1-5) of duplex DNA oligonucleotide d(AATTACGTAATT) (0.72 mM [concentration of the DNA duplex] in alkylation buffer [see paragraph above for preparation], 13.9 µL, 10 nmol, 1 equiv) in alkylation buffer (84.1 µL) were added, respectively, DC-45-A2 (5.0 mM solution in dimethylsulfoxide, 2.0 µL, 10 nmol, 1.0 equiv, vials 1 and 2), iso-DC-45-A2 (5.0 mM solution in dimethylsulfoxide, 2.0 µL, 10 nmol, 1.0 equiv, vial 3), and dideoxy-DC-45-A2 (5.0 mM solution in dimethylsulfoxide, 2.0 µL, 10 nmol, 1.0 equiv, vials 4 and 5). The samples were vortexed, then rotated end-over-end at 23° C. After 23 h 30 min, vials 2 and 5 were diluted with piperidine (10 µL) and placed in a heating block at 95° C. After 30 min, vials 2 and 5 were cooled by centrifugation for 30 seconds (VWR Labnet C-1200 Minicentrifuge). After a total reaction time of 24 h, a 5-µL aliquot was removed from each of the five reaction mixtures. Each aliquot was diluted with alkylation buffer (95 µL, see above for preparation). A 10-µL sample from each of the diluted solutions was injected onto an Acquity UPLC BEH C18 1.7 µm 2.1×50 mm column (gradient elution with 6 nM triethylammonium bicarbonate buffer and methanol, flow rate 150 µL/min) fitted to a Waters Alliance 2695 HPLC pump, and the column output was monitored by ESI-TOF mass spectrometry in negative ionization mode. FIG. 13 illustrates the LC/MS chromatograms from obtained from vials 1, 3, and 4. The oligonucleotide alkylated by DC-45-A2 was detected at 9.55 min in the trace obtained from the sample removed from vial 1: [single-strand oligonucleotide • DC-45-A2-2 protons]$^{-2}$=2078.89; measured=2078.85). The oligonucleotide alkylated by dideoxy-DC-45-A2 was detected at 9.63 in the trace obtained from the sample removed from vial 4: [single-strand oligonucleotide • dideoxy-DC-45-A2-2 protons]$^{-2}$=2062.90; measured=2062.85. FIG. 14 illustrates the LC/MS chromatograms obtained from the samples removed from vials 2 and 5.

Fluorescence Microscopy

Figure 15:
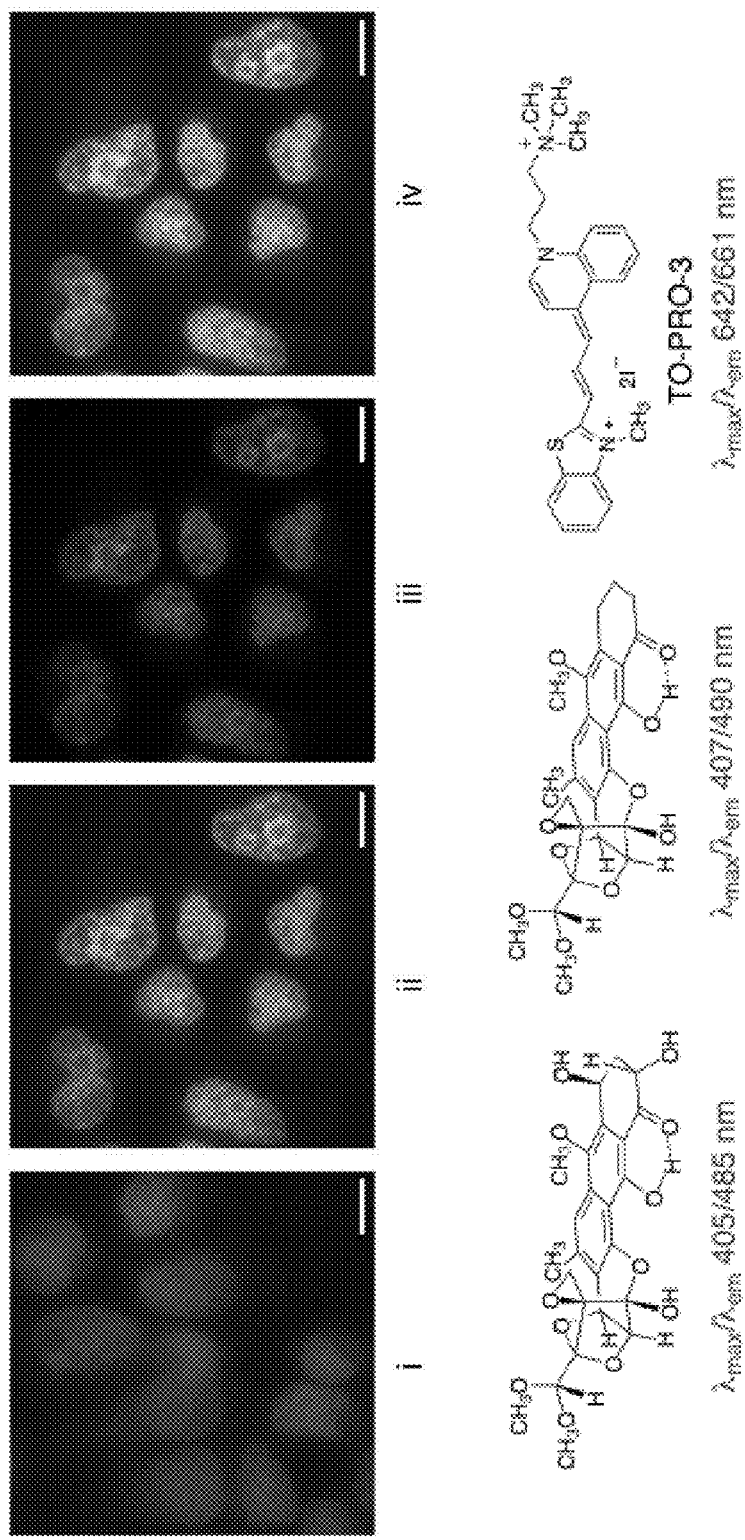
FIG. 15. Fluorescence images of nuclei of H460 cells labeled with DC-45-A2 [4.0 μM] or dideoxy-DC-45-A2 [0.4 μM] for 5 h at 37° C. Green channel [$\lambda_{abs}/\lambda_{em}$ 387/510 nm] of DC-45-A2 treated cells (panel i) and dideoxy-DC-45-A2 treated cells (panel ii). Near-IR channel shows simultaneous binding of the known nucleic acid stain TO-PRO-3 (panel iii), and merged channel shows excellent colocalization (panel iv). The scale bar represents 10 μm. When

Fluorescence images of nuclei of H460 cells labeled with DC-45-A2 [4.0 µM] or dideoxy-DC-45-A2 [0.4 µM] for 5 h at 37° C. is provided in FIG. 15. Green channel [$\lambda_{abs}/\lambda_{em}$ 387/510 nm] of i) DC-45-A2 treated cells and ii) dideoxy-DC-45-A2 treated cells. iii) Near-IR channel shows simultaneous binding of the known nucleic acid stain TO-PRO-3, and iv) Merged channel shows excellent colocalization. The scale bar represents 10 µm. The experiments demonstrate that i) the inherent fluorescence of DC-45-A2 and dideoxy-DC-45-A2 allow the compounds to be imaged within cells using fluorescence microscopy and ii) dideoxy-DC-45-A2 co-localizes with nuclear DNA in H460 cells.

Experimental Details for Fluorescence Microscopy:

H460 cells were grown on 22 mm glass coverslips and allowed to attach for 24 h. Subconfluent H460 cells (50-60% confluency) were treated with drugs of desired concentration and incubated at 37° C. for 5 h. The coverslips were washed three times with warm PBS. The cells were then fixed with 4% paraformaldehyde in PBS at 23° C. for 15 min. At 23° C., the cells were permeablized with 0.1% Triton-X100 in PBS for 15 min and blocked with 5% BSA for 40 min. After two washes with PBS, the cells were incubated with 0.2 µM TO-PRO-3 (Invitrogen) in PBS at 23° C. for 15 min. The coverslips were washed three times with PBS and mounted with Mowiol on microscope slides. Fluorescent images were captured on an Olympus IX71 inverted microscope equipped with a 60× water-immersion objective, a Nikon Intensilight Illuminator, and an Andor iXon EMCCD camera. Imaging data of DC-45-A2 and dideoxy DC-45-A2 were collected with a 387/11 nm excitation filter and a 510/84 nm emission filter purchased from Semrock. TO-PRO-3 dye was imaged using Cy5 channels. The images were complied and colorized using ImageJ software.

OTHER EMBODIMENTS

All patents, patent applications, and literature references cited herein are incorporated herein by reference.

Those skilled in the art will recognize, or be able to ascertain using no more than routine experimentation, many equivalents to the specific embodiments, described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any compound; any method of synthesis; any method of use; etc.) can be excluded from any one or more claims, for any reason, whether or not related to the existence of prior art.

The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:

1. A compound of the Formula (I):

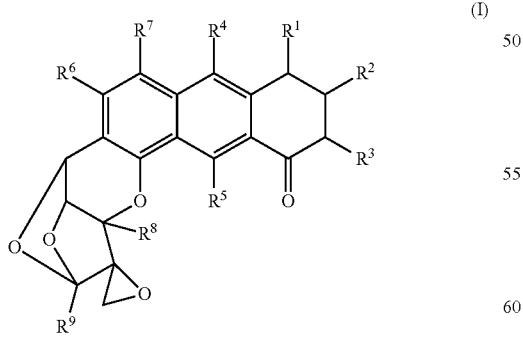

(I)

or a pharmaceutically acceptable form thereof; wherein:

$R^1$ is —$OR^{A1}$; wherein $R^{A1}$ is hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl;

each occurrence of $R^2$ and $R^3$ is hydrogen;

$R^4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{D1}$; —$C(=O)R^{D2}$; —$CO_2R^{D2}$; —CN; —SCN; —$SR^{D1}$; —$SOR^{D1}$; —$SO_2R^{D2}$; —$NO_2$; —$N_3$; —$N(R^{D2})_2$; —$NR^{D2}C(=O)R^{D2}$; —$NR^{D2}C(=O)N(R^{D2})_2$; —$OC(=O)OR^{D1}$; —$OC(=O)R^{D2}$; —$OC(=O)N(R^{D2})_2$; —$NR^{D2}C(=O)OR^{D1}$; or —$C(R^{D2})_3$; wherein each occurrence of $R^{D1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{D2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiolamino; or substituted amino; or two $R^{D2}$ groups are optionally joined to form a heterocyclyl or heteroaryl ring;

$R^5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^{E1}$; —$C(=O)R^{E2}$; —$CO_2R^{E1}$; —CN; —SCN; —$SR^{E1}$; —$SOR^{E1}$; —$SO_2R^{E2}$; —$NO_2$; —$N_3$; —$N(R^{E2})_2$; —$NR^{E2}C(=O)R^{E2}$; —$NR^{E2}C(=O)N(R^{E2})_2$; —$OC(=O)OR^{E1}$; —$OC(=O)R^{E2}$; —$OC(=O)N(R^{E2})_2$; —$NR^{E2}C(=O)OR^{E1}$; or —$C(R^{E2})_3$; wherein each occurrence of $R^{E1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{E2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{E2}$ groups are optionally joined to form a heterocyclyl or heteroaryl ring;

$R^6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $-OR^{F1}$; $-C(=O)R^{F2}$; $-CO_2R^{F1}$; $-CN$; $-SCN$; $-SR^{F1}$; $-SOR^{F1}$; $-SO_2R^{F2}$; $-NO_2$; $-N_3$; $-N(R^{F2})_2$; $-NR^{F2}C(=O)R^{F2}$; $-NR^{F2}C(=O)N(R^{F2})_2$; $-OC(=O)OR^{F1}$; $-OC(=O)R^{F2}$; $-OC(=O)N(R^{F2})_2$; $-NR^{F2}C(=O)OR^{F1}$; or $-C(R^{F2})_3$; wherein each occurrence of $R^{F1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{F2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{F2}$ groups are optionally joined to form a heterocyclyl or heteroaryl ring;

$R^7$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $-OR^{G1}$; $-C(=O)R^{G2}$; $-CO_2R^{G1}$; $-CN$; $-SCN$; $-SR^{G1}$; $-SOR^{G1}$; $-SO_2R^{G2}$; $-NO_2$; $-N_3$; $-N(R^{G2})$; $-NR^{G2}C(=O)R^{G2}$; $-NR^{G2}C(=O)N(R^{G2})_2$; $-OC(=O)OR^{G1}$; $-OC(=O)R^{G2}$; $-OC(=O)N(R^{G2})_2$; $-NR^{G2}C(=O)OR^{G1}$; or $-C(R^{G2})_3$; wherein each occurrence of $R^{G1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{G2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; amino; or substituted amino; or two $R^{G2}$ groups are optionally joined to form a heterocyclyl or heteroaryl ring;

$R^8$ is $-OR^{H1}$, wherein $R^{H1}$ is hydrogen, carbohydrate, an oxygen-protecting group, cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; or acyl;

$R^9$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; $-OR^{I1}$; $-C(=O)R^{I2}$; $-CO_2R^{I1}$; $-CN$; $-SCN$; $-SR^{I1}$; $-SOR^{I1}$; $-SO_2R^{I2}$; $-NO_2$; $-N_3$; $-N(R^{I2})_2$; $-NR^{I2}C(=O)R^{I2}$; $-NR^{I2}C(=O)N(R^{I2})_2$; $-OC(=O)OR^{I1}$; $-OC(=O)R^{I2}$; $-OC(=O)N(R^{I2})_2$; $-NR^{I2}C(=O)OR^{I1}$; or $-C(R^{I2})_3$; wherein each occurrence of $R^{I1}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl; and wherein each occurrence of $R^{I2}$ is independently hydrogen; carbohydrate; a protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; substituted or unsubstituted heteroaryl; substituted hydroxyl; substituted thiol; or substituted amino; or two $R^{I2}$ groups are optionally joined to form a heterocyclyl or heteroaryl ring;

or $R^1$ and $R^4$ are optionally taken together with the intervening carbon atoms to form an optionally substituted cyclic moiety;

or $R^4$ and $R^7$ are optionally be taken together with the intervening carbon atoms to form an optionally substituted cyclic moiety;

or $R^6$ and $R^7$ are optionally be taken together with the intervening carbon atoms to form an optionally substituted cyclic moiety.

2. The compound of claim 1, wherein the compound is of the formula:

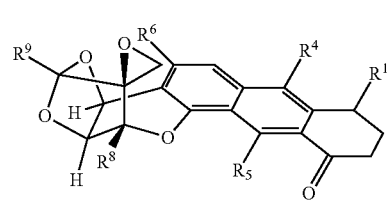

(II-c)

or a pharmaceutically acceptable form thereof.

3. The compound of claim 1, wherein the compound is of the formula:

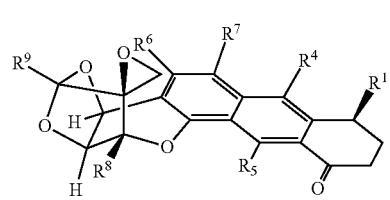

(II-g)

or a pharmaceutically acceptable form thereof.

4. The compound of claim 1, wherein $R^1$ is —OH.

5. The compound of claim 1, wherein $R^1$ is —$OR^{A1}$, wherein $R^{A1}$ is a carbohydrate; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl.

6. The compound of claim 1, wherein $R^1$ is —$OR^{A1}$, wherein $R^{A1}$ is a carbohydrate.

7. The compound of claim 6, wherein the carbohydrate is:

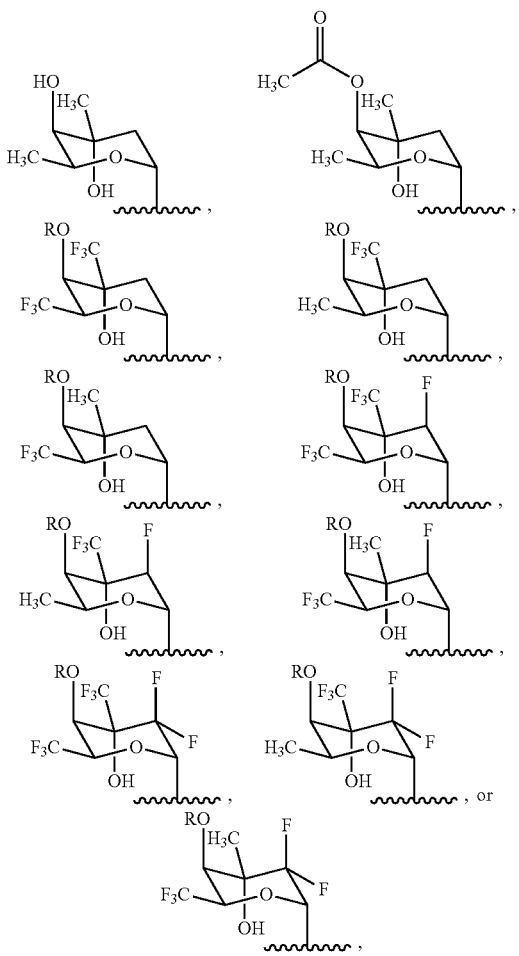

wherein each occurrence of R is independently hydrogen, acyl, or $C_{1-6}$ alkyl.

8. The compound of claim 1, wherein $R^4$ is —$OR^{D1}$, wherein $R^{D1}$ is a carbohydrate; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl.

9. The compound of claim 1, wherein $R^4$ is —OH.

10. The compound of claim 1, wherein $R^5$ is —$OR^{E1}$, wherein $R^{E1}$ is a carbohydrate; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl.

11. The compound of claim 1, wherein $R^5$ is —OH.

12. The compound of claim 1, wherein $R^6$ is $C_{1-6}$ alkyl.

13. The compound of claim 1, wherein $R^7$ is hydrogen.

14. The compound of claim 1, wherein $R^8$ is —$OR^{H1}$, wherein $R^{H1}$ is a carbohydrate, an oxygen-protecting group, cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; or acyl.

15. The compound of claim 1, wherein $R^{H1}$ is hydrogen, a carbohydrate, or $C_{1-6}$alkyl.

16. The compound of claim 15, wherein the carbohydrate is:

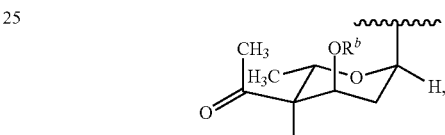

wherein $R^a$ and $R^b$ are independently selected from the group consisting of hydrogen; carbohydrate; an oxygen protecting group; cyclic or acyclic, substituted or unsubstituted, branched or unbranched aliphatic; cyclic or acyclic, substituted or unsubstituted, branched or unbranched heteroaliphatic; acyl; substituted or unsubstituted aryl; or substituted or unsubstituted heteroaryl.

17. The compound of claim 1, wherein $R^9$ is —CH$(OR^{I3})_2$; and each occurrence of $R^{I3}$ is independently hydrogen, substituted or unsubstituted alkyl, substituted or unsubstituted aryl, substituted or unsubstituted heteroaryl, or a carbohydrate.

18. The compound of claim 1, wherein $R^9$ is —CH$(OCH_3)_2$.

19. A pharmaceutical composition comprising a compound of claim 1 or a pharmaceutically acceptable form thereof, and a pharmaceutically acceptable excipient.

20. A method of treating a disease, disorder or condition selected from the group consisting of proliferative diseases, diabetic retinopathy, inflammatory diseases, autoimmune diseases, and infectious diseases, comprising administering to a subject an effective amount of a compound of claim 1 or pharmaceutically acceptable form thereof.

* * * * *